(12) United States Patent
Cociorva et al.

(10) Patent No.: US 8,063,221 B2
(45) Date of Patent: Nov. 22, 2011

(54) AMINOQUINOLONES AS GSK-3 INHIBITORS

(75) Inventors: Oana Cociorva, San Diego, CA (US); Bei Li, San Diego, CA (US); Anna Katrin Szardenings, Torrance, CA (US); Yasumichi Fukuda, Shimotsuga-gun (JP); Masahiro Nomura, Shimotsuga-gun (JP); Shigeki Seto, Shimotsuga-gun (JP); Kazuhiro Yumoto, Shimotsuga-gun (JP); Kyoko Okada, Shimotsuga-gun (JP); Ayako Nakamura, Shimotsuga-gun (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 11/718,000

(22) Filed: Mar. 13, 2007

(65) Prior Publication Data

US 2007/0254866 A1 Nov. 1, 2007

Related U.S. Application Data

(60) Provisional application No. 60/781,628, filed on Mar. 13, 2006.

(51) Int. Cl.
*C07D 215/00* (2006.01)
*A01N 43/42* (2006.01)
*A61K 31/47* (2006.01)

(52) U.S. Cl. ......... 546/156; 514/312; 514/277; 546/152
(58) Field of Classification Search ................... 514/183
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni et al. |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,044,126 A | 8/1977 | Cook et al. |
| 4,364,923 A | 12/1982 | Cook et al. |
| 4,414,209 A | 11/1983 | Cook et al. |
| 4,762,831 A | 8/1988 | Grohe et al. |
| 4,847,375 A | 7/1989 | Grohe et al. |
| 4,990,508 A | 2/1991 | Narita et al. |
| 5,033,252 A | 7/1991 | Carter |
| 5,052,558 A | 10/1991 | Carter |
| 5,059,595 A | 10/1991 | Le Grazie |
| 5,073,543 A | 12/1991 | Marshall et al. |
| 5,120,548 A | 6/1992 | McClelland et al. |
| 5,153,203 A * | 10/1992 | Yatsunami et al. ........... 514/312 |
| 5,190,923 A | 3/1993 | Vincent et al. |
| 5,323,907 A | 6/1994 | Kalvelage |
| 5,354,556 A | 10/1994 | Sparks et al. |
| 5,387,748 A | 2/1995 | Demuth, Jr. et al. |
| 5,430,152 A | 7/1995 | Saukaitis et al. |
| 5,591,767 A | 1/1997 | Mohr et al. |
| 5,612,059 A | 3/1997 | Cardinal et al. |
| 5,639,476 A | 6/1997 | Oshlack et al. |
| 5,639,480 A | 6/1997 | Bodmer et al. |
| 5,674,533 A | 10/1997 | Santus et al. |
| 5,709,874 A | 1/1998 | Hanson et al. |
| 5,733,566 A | 3/1998 | Lewis |
| 5,739,108 A | 4/1998 | Mitchell |
| 5,759,542 A | 6/1998 | Gurewich |
| 5,798,119 A | 8/1998 | Herbig et al. |
| 5,840,674 A | 11/1998 | Yatvin et al. |
| 5,891,474 A | 4/1999 | Busetti et al. |
| 5,900,252 A | 5/1999 | Calanchi et al. |
| 5,922,356 A | 7/1999 | Koseki et al. |
| 5,972,366 A | 10/1999 | Haynes et al. |
| 5,972,891 A | 10/1999 | Kamei et al. |
| 5,980,945 A | 11/1999 | Ruiz |
| 5,985,307 A | 11/1999 | Hanson et al. |
| 5,993,855 A | 11/1999 | Yoshimoto et al. |
| 6,004,534 A | 12/1999 | Langer et al. |
| 6,039,975 A | 3/2000 | Shah et al. |
| 6,045,830 A | 4/2000 | Igari et al. |
| 6,048,736 A | 4/2000 | Kosak |
| 6,060,082 A | 5/2000 | Chen et al. |
| 6,071,495 A | 6/2000 | Unger et al. |
| 6,087,324 A | 7/2000 | Igari et al. |
| 6,113,943 A | 9/2000 | Okada et al. |
| 6,120,751 A | 9/2000 | Unger |
| 6,131,570 A | 10/2000 | Schuster et al. |
| 6,139,865 A | 10/2000 | Friend et al. |
| 6,197,350 B1 | 3/2001 | Yamagata et al. |
| 6,221,633 B1 | 4/2001 | Ertl et al. |
| 6,221,897 B1 | 4/2001 | Frick et al. |

(Continued)

FOREIGN PATENT DOCUMENTS

CN 1181381 11/1997

(Continued)

OTHER PUBLICATIONS

Singh et al., Synthesis and antibacterial activity of 7-hydrazinoquinolones, 1998, Eur. J. Med. Chem., vol. 33, pp. 697-703.*
Wentland, et al., Synthesis and Bacterial DNA Gyrase Inhibitory Properties of a Spirocyclopropylquinolone Derivative, J. Med. Chem. 31:1694-1697, 1988.
Kiely, et al., New "Ofloxacin" Type Antibacterial Agents. Incorporation of the Spiro Cyclopropyl Group at N-1. J. Med. Chem. 31:2004-2008, 1988.
Calas, et al., Relation structure-activité dans la série des quinolones, Eur. J. Med. Chem. 26:279-290, 1991.
Wentland, et al, Relationship of Structure of Bridged (2,6-Dimethyl-4-Pyridinyl)-Quinolones to Mammalian Topoisomerase II Inhibition, Bioorg. Med. Chem Lett. 3 (8) 1711-1716, 1993.
Toda, et al., Pyridonecarboxylic Acids as Antibacterial Agents IX[1a] Synthesis and Structure—Activity Relationship of 3-Substituted 10-(1-Aminocyclopropyl)-9-fluoro-7-oxo-2,3-dihydro-7H-pyrido[1,2,3-de]-1,4-benzoxazine-6-carboxylic Acids and Their 1-Thio and 1-Aza Analogues[2], Chem. Pharm. Bull 42 (12) 2569-2574, 1994.

(Continued)

*Primary Examiner* — Leslie A. Royds Draper
*Assistant Examiner* — Meghan Finn
(74) *Attorney, Agent, or Firm* — Jones Day

(57) ABSTRACT

Provided herein are aminoquinolones and pharmaceutically acceptable derivatives thereof. In certain embodiments, provided herein are compounds, compositions and methods for treating, preventing or ameliorating GSK-3 mediated diseases.

60 Claims, 1 Drawing Sheet

U.S. PATENT DOCUMENTS

| | | | |
|---|---|---|---|
| 6,245,744 | B1 | 6/2001 | Frick et al. |
| 6,248,363 | B1 | 6/2001 | Patel et al. |
| 6,253,872 | B1 | 7/2001 | Neumann |
| 6,264,970 | B1 | 7/2001 | Hata et al. |
| 6,267,981 | B1 | 7/2001 | Okamoto et al. |
| 6,271,359 | B1 | 8/2001 | Norris et al. |
| 6,274,552 | B1 | 8/2001 | Tamarkin et al. |
| 6,316,652 | B1 | 11/2001 | Steliou |
| 6,342,512 | B1 | 1/2002 | Kirsch et al. |
| 6,350,458 | B1 | 2/2002 | Modi |
| 6,376,461 | B1 | 4/2002 | Igari et al. |
| 6,419,961 | B1 | 7/2002 | Igari et al. |
| 6,589,548 | B1 | 7/2003 | Oh et al. |
| 6,613,358 | B2 | 9/2003 | Randolph et al. |
| 6,699,500 | B2 | 3/2004 | Okada et al. |
| 6,740,634 | B1 | 5/2004 | Saikawa et al. |
| 6,825,353 | B2 | 11/2004 | Saito et al. |
| 6,967,205 | B1 | 11/2005 | Abdul-Rahman |
| 2004/0132764 | A1 | 7/2004 | Locher |
| 2005/0054663 | A1 | 3/2005 | Bennett et al. |
| 2005/0182085 | A1 | 8/2005 | Defossa et al. |

FOREIGN PATENT DOCUMENTS

| | | |
|---|---|---|
| CN | 1491944 A | 4/2004 |
| EP | 0 265 230 A1 | 4/1988 |
| EP | 0 390 215 A2 | 10/1990 |
| EP | 0 945 435 A1 | 9/1999 |
| EP | 1 486 488 A1 | 12/2004 |
| EP | 1 650 192 A1 | 4/2006 |
| ES | 206819 | 5/1992 |
| JP | S59-1489 | 1/1984 |
| JP | 62198685 | 2/1986 |
| JP | S62-53987 | 5/1986 |
| JP | S62-167769 | 1/1987 |
| JP | S62-252772 | 4/1987 |
| JP | S63-264439 | 1/1988 |
| JP | S63-132891 | 6/1988 |
| JP | 03133983 | 10/1989 |
| JP | H1-268679 | 10/1989 |
| JP | H5-25162 | 2/1993 |
| WO | WO 97/26265 | 7/1997 |
| WO | WO 97/41097 | 11/1997 |
| WO | WO 98/08871 | 3/1998 |
| WO | WO 99/15525 | 4/1999 |
| WO | WO 99/65897 | 12/1999 |
| WO | WO 00/38675 | 7/2000 |
| WO | WO 00/40569 | 7/2000 |
| WO | WO 00/63208 | 10/2000 |
| WO | WO 00/66585 | 11/2000 |
| WO | WO 00/71549 A1 | 11/2000 |
| WO | WO 00/78312 A1 | 12/2000 |
| WO | WO 01/09111 A1 | 2/2001 |
| WO | WO 01/83451 A1 | 11/2001 |
| WO | WO 01/85695 A1 | 11/2001 |
| WO | WO 02/04462 A1 | 1/2002 |
| WO | WO 02/09758 A2 | 2/2002 |
| WO | WO 02/17918 | 3/2002 |
| WO | 02/04462 | 6/2002 |
| WO | WO 02/092571 A1 | 11/2002 |
| WO | 2004/019932 | 8/2003 |
| WO | WO 2004/089930 | 10/2004 |
| WO | WO 2004/096221 A1 | 11/2004 |
| WO | WO 2005/007111 A2 | 1/2005 |
| WO | WO 2009/035634 | 3/2009 |
| WO | WO 2009/035684 | 3/2009 |

OTHER PUBLICATIONS

Golub, et al., Evaluation of 3-carbooxy-4(1H)-quinolones as inhibitors of human protein kinase CK2, J. Med. Chem 49: 6443, 2006.

Asakawa, et al., Cocaine-Amphetamine-Regluated Transcript Influences Energy Metabolism, Anxiety and Gastric Emptying in Mice, Horm. Metab.Re. 33(9):554-58, 2001.

Atarashi, et al., Synthesis and Antibacterial Activities of Optically Active Ofloxacin and Its Fluoromethyl Derivative, Chem. Pharm. Bull. 35(5):1896-902, 1987.

Buchwald, et al., Long-Term, Continuous Intravenous Heparin Administration by an Implantable Infusion Pump in Ambulatory Patients with Recurrent Venous Thrombois, Surgery 88(4):507-16, 1980.

Coghlan, et al., Selective Small Molecule Inhibitors of Glycogen Synthase Kinase-3 Modulate Glycogen Metabolism and Gene Transcription, Chemistry & Biology 7(10):793-03, 2000.

Doyle, et al., Alkyl Nitrite-Metal Halide Deamination Reactions. 2. Substitutive Deamination of Arylamines by Alkyl Nitrites and Copper (II) Halides. A Direct and Remarkably Efficient Conversion of Arylamines to Aryl Halides, J. Org. Chem. 42(14): 2426-31, 1977.

Fujita, et al., 5-Alkoxyimidazoquinolones as Potential Antibacterial Agents. Synthesis and Structure—Activity Relationships, Chem. Pharm. Bull. 44(5):987-90, 1996.

Guo, H., et al., 5-amino-S-methoxy Quinolone Carboxylic Acid Derivatives and Its Preparation, Inst. Med. Biol. Tech. Chin, Abstract, 2004.

Haq, et al., Glycogen Synthase Kinase-3β is a Negative Regulator of Cardiomyocyte Hypertrophy, J. Cell. Biol. 151(1):117-29, 2000.

Havlicek, et. al., Cytokinin-Derived Cyclin-Dependent Kinase Inhibitors: Synthesis and cdc2 Inhibitory Activity of Olomoucine and Related Compounds, J. Med. Chem. 40:408-12, 1997.

Kiely, et al., A General Method for the Preparation of 2-Substituted-4-oxo-3-Quinolinecarboxylic Acids, J. Heterocyclic Chem. 26(6):1675-81, 1989.

Kim, et al., GSK3, a Master Switch Regulating Cell-Fate Specification and Tumorigenesis, Curr. Opin. Genetics & Dev. 10:508-14, 2000.

Kondo, et al., Studies on Prodrugs. 7. Synthesis and Antimicrobial Activity of 3-Formylquinolone Derivatives, J. Med. Chem. 31:221-25, 1988.

Langer, New Methods of Drug Delivery, Science 249(4976):1527-33, 1990.

Lee, et al., Leptin Agonists as a Potential Approach to the Treatment of Obesity, Drugs of the Future 26(9):873-81, 2001.

Miyamoto, et al., Synthesis and Structure-Activity Relationships of 5-Substituted 6,8-Difluoroquinolones, Including Sparfloxacin, a New Quinolone Antibacterial Agent with Improved Potency, J. Med. Chem. 33:1645-56, 1990.

Saloutin, et al., Novel Fluorinated Chromones, J. Fluoerine Chem. 65:37-41, 1993.

Salvador, et al., Perspectives in the Therapeutic Use of Leptin, Expert Opinion on Pharmacotherapy 2(l0):1615-22,2001.

Saudek, et al., A Preliminary Trial of the Programmable Implantable Medication System for Insulin Delivery, N. Engl. J. Med. 321(9):574-79, 1989.

Sbardella, et al., New 6-Nitroquinolones: Synthesis and Antimicrobial Activities, IL Farmaco 59:463-71, 2004.

Sefton, Implantable Pumps, CRC Crit. Rev. Biomed. Eng. 14(3):201-40, 1987.

Shibamori, et al., Regioselective Displacement Reactions of 1-Cyclopropyl-5,6,7,8-tetrafluoro-4(1H)-oxoquinoline-3-carboxylic Acid with Amine Nucleophiles, Chem. Pharm. Bull. 38(9):2390-96, 1990.

Singh, R., et al., Synthesis and Antibacterial Activity of 7-hydrazinoquinolones, Eur. J. Med. Chem., 33:697-03, 1998.

English abstract of CN 1491944A to Guo, H., et al., 2004.

Atarashi, et al., J. Heterocyclic Chem., 28, 329, 1991.

Egawa, et al., Chem. Pharm. Bull., 34, 4098,, 1986.

Kaiiio, et al., J. Med. Chem., 32, 351, 1989.

Kawatsura, et al., Tetrahedron, 63, 4172, 2007.

Kobayashi, et al., Org. Lett., 7, 1319, 2005.

Kobayashi, et al., Org. Lett., 7, 183, 2005.

Koga, et al., J. Med. Chem., 23, 1358, 1980.

Mitscher, et al., J. Med. Chem., 30, 2283, 1987.

Wentland, et al., J. Med. Chem. 31, 1694, 1988.

Remuzon, et al., J. Med. Chem.,, 34, 29, 1991.

Santus and Baker, J. Controlled Release, 35, 1-21, 1995.

Verma, et al., Drug Development and Industrial Pharmacy, 26, 695-708, 2000.

Verma, et al., J. Controlled Release, 79, 7-27, 2002.

U.S.P.T.O. non-Final Office Action dated Nov. 2, 2010 for U.S. Appl. No. 12/721,454, filed on Mar. 10, 2010.

U.S.P.T.O. Notice of Allowance Apr. 8, 2011 for U.S. Appl. No. 12/721,454, filed on Mar. 10, 2010.

* cited by examiner

AMINOQUINOLONES AS GSK-3 INHIBITORS

This application claims priority to U.S. provisional application Ser. No. 60/781,628, filed Mar. 13, 2006, entitled "AMINOQUINOLONES AS GSK-3 INHIBITORS" to Cociorva et al. The disclosure of the above referenced application is incorporated by reference herein.

FIELD

Compounds, compositions and methods for treating GSK-3 mediated diseases are provided. The compounds provided herein are aminoquinolones that are GSK-3 inhibitors.

BACKGROUND

Glycogen synthase kinase-3 (GSK-3) is a serine/threonine protein kinase having α and β isoforms that are each encoded by distinct genes [Coghlan et al., *Chemistry & Biology*, 7, 793-803 (2000); and Kim and Kimmel, *Curr. Opinion Genetics Dev.*, 10, 508-514 (2000)]. GSK-3 has been implicated in various diseases including diabetes, Alzheimer's disease, CNS disorders such as manic depressive disorder and neurodegenerative diseases, and cardiomyocete hypertrophy [see, e.g., WO 99/65897; WO 00/38675; and Haq et al., *J. Cell Biol.* (2000) 151, 117]. These diseases may be caused by, or may result in, the abnormal operation of certain cell signaling pathways in which GSK-3 plays a role.

GSK-3 has been found to phosphorylate and modulate the activity of a number of regulatory proteins. These include glycogen synthase, which is the rate-limiting enzyme required for glycogen synthesis, the microtubule-associated protein Tau, the gene transcription factor β-catenin, the translation initiation factor e1F-2B, as well as ATP citrate lyase, axin, heat shock factor-1, c-Jun, c-myc, c-myb, CREB, and CEPB α. These diverse targets implicate GSK-3 in many aspects of cellular metabolism, proliferation, differentiation and development.

Small molecule inhibitors of GSK-3 have recently been reported [WO 99/65897 (Chiron) and WO 00/38675 (SmithKline Beecham)], however, there is a continued need to find more effective therapeutic agents to treat GSK-3 mediated diseases.

SUMMARY

Provided herein are compounds that are GSK-3 inhibitors, pharmaceutical compositions containing the compounds and methods of use thereof. The compounds are aminoquinolones and pharmaceutically acceptable derivatives thereof. In certain embodiments, the compounds for use in the compositions and methods provided herein have Formula Ia:

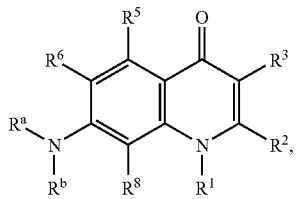

or a pharmaceutically acceptable derivative thereof, wherein the variables are chosen such that the resulting compounds show activity as GSK-3 inhibitors.

Pharmaceutical compositions containing a compound of Formula I and a pharmaceutically acceptable carrier are provided herein. Also provided are methods for treating, preventing, or ameliorating one or more symptoms of GSK-3 mediated diseases by administering the compounds and compositions provided herein.

In certain embodiments, provided herein are methods for inhibiting an action of GSK-3 by administering compounds and compositions provided herein. In other embodiments, provided herein are methods for treatment, prevention, or amelioration of one or more symptoms of diseases or conditions including, but not limited to conditions associated with diabetes, chronic neurodegenerative conditions including dementias such as Alzheimer's disease, Parkinson's disease, progressive supranuclear palsy, subacute sclerosing panencephalitic parkinsonism, postencephalitic parkinsonism, pugilistic encephalitis, guam parkinsonism-dementia complex, Pick's disease, corticobasal degeneration, frontotemporal dementia, Huntington's Disease, AIDS associated dementia, amyotrophic lateral sclerosis, multiple sclerosis, neurotraumatic diseases such as acute stroke, epilepsy, mood disorders such as depression, schizophrenia and bipolar disorders, rheumatoid arthritis, inflammatory bowel disease, ulceractive colitis, Crohn's disease, sepsis, pancreatic cancer, ovarian cancer and osteoporosis by administering compounds and compositions provided herein.

DETAILED DESCRIPTION OF EMBODIMENTS

A. Definitions

Figure 1:
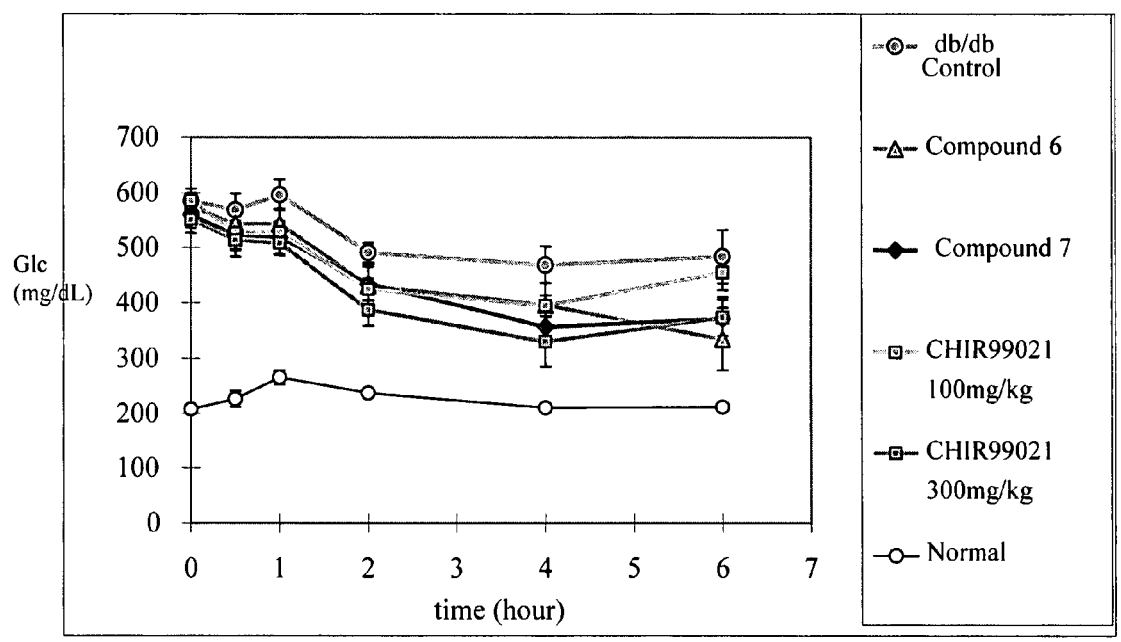
FIG. 1 shows the drop in blood glucose levels for db/db mice for exemplary compounds as compared to a reference compound CHIR99021.

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

The singular forms "a," "an," and "the" include plural references, unless the context clearly dictates otherwise.

As used herein "subject" is an animal, typically a mammal, including human, such as a patient.

The terms "GSK-3 mediated disease, or "GSK-3 mediated condition", as used herein, mean any disease or other deleterious condition or state in which GSK-3 is known to play a role. Such diseases or conditions include, without limitation, diabetes, conditions associated with diabetes, chronic neurodegenerative conditions including dementias such as Alzheimer's disease, Parkinson's disease, progressive supranuclear palsy, subacute sclerosing panencephalitic parkinsonism, postencephalitic parkinsonism, pugilistic encephalitis, guam parkinsonism-dementia complex, Pick's disease, corticobasal degeneration, frontotemporal dementia, Huntington's Disease, AIDS associated dementia, amyotrophic lateral sclerosis, multiple sclerosis, neurotraumatic diseases such as acute stroke, epilepsy, mood disorders such as depression, schizophrenia and bipolar disorders, rheumatoid arthritis, inflammatory bowel disease, ulceractive colitis, Crohn's disease, sepsis, pancreatic cancer, ovarian cancer and osteoporosis.

As used herein, biological activity refers to the in vivo activities of a compound or physiological responses that result upon in vivo administration of a compound, composition or other mixture. Biological activity, thus, encompasses therapeutic effects and pharmacokinetic behaviour of such compounds, compositions and mixtures. Biological activities can be observed in in vitro systems designed to test for such activities.

As used herein, pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and inorganic salts, such as but not limited to, sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates, mesylates, and fumarates. Pharmaceutically acceptable esters include, but are not limited to, alkyl, alkenyl, alkynyl, aryl, aralkyl, and cycloalkyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C (OR) where R is hydrogen, alkyl, alkenyl, alkynyl, aryl, aralkyl and cycloalkyl. Pharmaceutically acceptable enol esters include, but are not limited to, derivatives of formula C=C(OC(O)R) where R is hydrogen, alkyl, alkenyl, alkynyl, aryl, aralkyl and cycloalkyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, treatment means any manner in which one or more of the symptoms of a disease or disorder are ameliorated or otherwise beneficially altered. Treatment also encompasses any pharmaceutical use of the compositions herein, such as use for treating diabetes.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, and unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

As used herein, the $IC_{50}$ refers to an amount, concentration or dosage of a particular test compound that achieves a 50% inhibition of a maximal response in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, the term GSK3 inhibitor refers to a compound that exhibits an $IC_{50}$ with respect to GSK3 of no more than about 100 µM, and in one embodiment, no more than about 50 µM, as measured in the cell-free assay for GSK3 inhibitory activity described generally hereinbelow. In certain embodiments, compounds provided herein exhibit an $IC_{50}$ with respect to GSK3 of no more than about 10 µM, in one embodiment, no more than about 5 µM, or no more than 1 µM, as measured in the cell-free GSK3 kinase assay.

As used herein, the term selective refers to a relatively greater potency for inhibition against GSK3, as compared to at least one other type of kinase, such as CDK5 kinase. In certain embodiments, GSK3 inhibitor compounds provided herein are selective with respect to GSK3, as compared to at least two other types of kinases, such as CDK5 and CDK2 kinase. Kinase activity assays for kinases other than GSK3 are described herein and are generally known. See e.g., Havlicek et. al., *J. Med. Chem.*, 40: 408-12 (1997), incorporated herein by reference. An inhibitor that is selective for GSK3 exhibits a GSK3 selectivity of greater than about 1-fold, 2-fold, 5-fold, 10 fold, 20-fold, 50-fold or greater than about 100-fold with respect to inhibition of a kinase other than GSK3. As used herein, the term "other kinase" refers to a kinase other than GSK3. Such selectivities are generally measured in cell-free assays.

As used herein, substantially free of antibacterial activity or having very low antibacterial activity means the antibacterial activity measured, as a minimum inhibitory concentration (MIC), for a test compound is greater than about 0.5 µM, 1 µM, 5 µM, 10 µM, 50 µM, 75 µM, 100 µM, 150 µM, 200 µM or 250 µM. In some embodiments, MIC is with respect to inhibition of growth of *E. Coli* and/or *S. aureus*.

As used herein, a minimum inhibitory concentration (MIC) for bacterial growth assay is the lowest level of a compound needed to cause an inhibition to bacterial growth in culture medium. In certain embodiments, the antibacterial activity of compounds herein, measured as MIC.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. As such, one of skill in the art will recognize that administration of a compound in its (R) form is equivalent, for compounds that undergo epimerization in vivo, to administration of the compound in its (S) form.

As used herein, substantially pure means sufficiently homogeneous to appear free of readily detectable impurities as determined by standard methods of analysis, such as thin layer chromatography (TLC), gel electrophoresis, high performance liquid chromatography (HPLC), nuclear magnetic resonance (NMR), and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound. The instant disclosure is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

As used herein, the nomenclature alkyl, alkoxy, carbonyl, etc. is used as is generally understood by those of skill in this art.

As used herein, alkyl, alkenyl and alkynyl carbon chains, if not specified, contain from 1 to 20 carbons, 1 to 16 carbons or 1 to 6 carbons and are straight or branched. In certain embodiments, alkyl, alkenyl and alkynyl carbon chains contain from 1 to 6 carbons. Alkenyl carbon chains of from 2 to 20 carbons, in certain embodiments, contain 1 to 8 double bonds, and the alkenyl carbon chains of 2 to 16 carbons, in certain embodiments, contain 1 to 5 double bonds. The alkenyl carbon chains of 2 to 6 carbons, in certain embodiments, contain 1 to 2 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds. Alkynyl carbon chains of from 2 to 6 carbons, in certain embodiments, contain 1 to 2 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-pentyl, isohexyl, vinyl, 1-propenyl, 2-propenyl, isopropenyl, 1-butenyl, 2-butenyl, 3-butenyl, 1,3-butadienyl, ethynyl, 1-propynyl and 2-propynyl. As used herein, lower alkyl, lower alkenyl, and lower alkynyl refer to carbon chains having from about 1 or about 2 carbons up to about 6 carbons.

As used herein, "cycloalkyl" refers to a saturated mono- or multicyclic ring system, in certain embodiments of 3 to 10 carbon atoms, in other embodiments of 3 to 6 carbon atoms; cycloalkenyl and cycloalkynyl refer to mono- or multicyclic ring systems that respectively include at least one double bond and at least one triple bond. Cycloalkenyl and cycloalkynyl groups may, in certain embodiments, contain 3 to 10 carbon atoms, with cycloalkenyl groups, in further embodiments, containing 4 to 7 carbon atoms and cycloalkynyl groups, in further embodiments, containing 8 to 10 carbon atoms. The ring systems of the cycloalkyl, cycloalkenyl and cycloalkynyl groups may be composed of one ring or two or more rings which may be joined together in a fused, bridged or spiro-connected fashion.

As used herein, "substituted alkyl," "substituted alkenyl," "substituted alkynyl," "substituted cycloalkyl," "substituted cycloalkenyl," and "substitued cycloalkynyl" refer to alkyl, alkenyl, alkynyl, cycloalkyl, cycloalkenyl and cycloalkynyl groups, respectively, that are substituted with one or more substituents, in certain embodiments one to three or four substituents, where the substituents are as defined herein, generally selected from $Q^0$ or $Q^1$.

As used herein, "aryl" refers to aromatic monocyclic or multicyclic groups containing from 6 to 19 carbon atoms. Aryl groups include, but are not limited to groups such as fluorenyl, substituted fluorenyl, phenyl, substituted phenyl, naphthyl and substituted naphthyl.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrrolidinyl, pyrimidinyl, tetrazolyl, thienyl, pyridyl, pyrrolyl, N-methylpyrrolyl, quinolinyl and isoquinolinyl.

As used herein, a "heteroarylium" group is a heteroaryl group that is positively charged on one or more of the heteroatoms.

As used herein, "heterocyclyl" refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, aminocarbonyl, alkoxycarbonyl, guanidino, or the nitrogen may be quaternized to form an ammonium group where the substituents are selected as above.

As used herein, "substituted aryl," "substituted heteroaryl" and "substituted heterocyclyl" refer to aryl, heteroaryl and heterocyclyl groups, respectively, that are substituted with one or more substituents, in certain embodiments one to three or four substituents, where the substituents are as defined herein, generally selected from $Q^0$ or $Q^1$.

As used herein, "aralkyl" refers to an alkyl group in which one of the hydrogen atoms of the alkyl is replaced by an aryl.

As used herein, "heteroaralkyl" refers to an alkyl group in which one of the hydrogen atoms of the alkyl is replaced by a heteroaryl group.

As used herein, "halo", "halogen" or "halide" refers to F, Cl, Br or I.

As used herein, pseudohalides or pseudohalo groups are groups that behave substantially similar to halides. Such compounds can be used in the same manner and treated in the same manner as halides. Pseudohalides include, but are not limited to, cyano, thiocyanate, selenocyanate, trifluoromethoxy, and azide.

As used herein, "haloalkyl" refers to an alkyl group in which one or more of the hydrogen atoms are replaced by halogen. "Lower haroalkyl" refers to a lower alkyl group in which one or more of the hydrogen atoms are replaced by halogen. Such groups include, but are not limited to, chloromethyl, trifluoromethyl and 1-chloro-2-fluoroethyl.

As used herein, "fused heterocyclylaryl" refers to fused heterocyclyl and aryl. In one embodiment, fused heterocyclylalyls are those wherein heterocyclyl contains about 5 to about 6 ring atoms and the aryl thereof is phenyl. A fused heterocyclylaryl may be bonded through any atom of the ring system. Representative fused heterocyclylaryl groups include 1,3-benzodioxolan-4-yl, 1,3-benzodioxolan-5-yl, 1,3-benzodioxolan-6-yl, 1,3-benzodioxolan-7-yl, 4-indolinyl, 5-indolinyl, 6-indolinyl and 7-indolinyl.

As used herein, "fused arylheterocyclyl" refers to fused aryl and heterocyclyl. In one embodiment, fused arylheterocyclyls are those wherein the aryl thereof is phenyl and the heterocyclyl contains about 5 to about 6 ring atoms. A fused arylheterocyclyl may be bonded through any atom of the ring system. Representative fused arylheterocyclyl groups include 1-indolinyl, 2-indolinyl, 3-indolinyl, 1,2,3,4-tetrahydroqunolin-1-yl, 1,2,3,4-tetrahydroqunolin-2-yl, 1,2,3,4-tetrahydroqunolin-3-yl and 1,2,3,4-tetrahydroqunolin-4-yl.

As used herein, "haloalkoxy" refers to RO— in which R is a haloalkyl group.

As used herein, "carboxy" refers to a divalent radical, —C(O)O—.

As used herein, "aminocarbonyl" refers to —C(O)NH$_2$.

As used herein, "alkylaminocarbonyl" refers to —C(O)NHR in which R is alkyl, including lower alkyl. As used herein, "dialkylaminocarbonyl" refers to —C(O)NR'R in which R' and R are independently alkyl, including lower alkyl; "carboxamide" refers to groups of formula —NR'COR in which R' and R are independently alkyl, including lower alkyl.

As used herein, "arylalkylaminocarbonyl" refers to —C(O)NRR' in which one of R and R' is aryl, such as phenyl, and the other of R and R' is alkyl, including lower alkyl.

As used herein, "arylaminocarbonyl" refers to —C(O)NHR in which R is aryl, such as phenyl.

As used herein, "hydroxycarbonyl" refers to —COOH.

As used herein, "alkoxycarbonyl" refers to —C(O)OR in which R is alkyl, including lower alkyl.

As used herein, "aryloxycarbonyl" refers to —C(O)OR in which R is aryl, such as phenyl.

As used herein, "alkoxy" and "alkylthio" refer to RO— and RS—, in which R is alkyl, including lower alkyl.

As used herein, "aryloxy" and "arylthio" refer to RO— and RS—, in which R is aryl, such as phenyl.

Where the number of any given substituent is not specified (e.g., "haloalkyl"), there may be one or more substituents present. For example, "haloalkyl" may include one or more of the same or different halogens. As another example, "C$_{1-3}$alkoxyphenyl" may include one or more of the same or different alkoxy groups containing one, two or three carbons.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942-944).

B. Compounds

Provided herein are GSK3 inhibitor compounds, compositions containing the compounds and methods of use thereof. In certain embodiments, compounds provided herein exhibit an IC$_{50}$ with respect to GSK3 of no more than about 20 µM, in one embodiment, no more than about 10 µM, no more than about 5 µM, or more than 1 µM, as measured in the cell-free GSK3 kinase assay. In certain embodiments, compounds provided herein exhibit inhibitory activity that is selective with respect to GSK3, as compared to at least one other type of kinase. In certain embodiments, GSK3 inhibitors provided herein exhibit a selectivity for GSK3, as compared to at least one other kinase, of at least about 1 fold, 2-fold, 5-fold, 10-fold, or at least about 100-fold, or at least about 1000-fold.

In certain embodiments, GSK3 inhibitors provided herein are substantially free of antibacterial activity or having very low antibacterial activity. The antibacterial activity can be measured by methods known in the art by estimating a minimum inhibitory concentration (MIC) for test compounds. A MIC is the lowest level of a compound needed to cause an inhibition to bacterial growth in a culture medium. In certain embodiments, the antibacterial activity of compounds herein, measured as a minimum inhibitory concentration with respect to inhibition of growth of *E. Coli* and/or *S. aureus* is greater than about 0.5 µM, 1 µM, 5 µM, 10 µM, 50 µM, 75 µM, 100 µM, 150 µM, 200 µM or 250 µM. (Clinical and Laboratory Standards Institute. Methods for Dilution Antimicrobial Susceptibility Tests for Bacteria That Grow Aerobically; Approved Standard-Sixth Edition: CLSI document M7-A4. CLSI, Wayne, Pa. (2003))

In certain embodiments, the compounds for use in the compositions and methods provided herein are of Formula Ia:

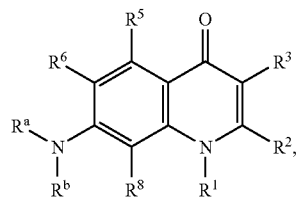

or pharmaceutically acceptable derivatives thereof, wherein R$^1$ and R$^8$ are as follows:

i) R$^1$ is hydrogen, lower alkyl, cycloalkyl, heterocyclyl, aryl, aralkyl, heterocycloalkyl or heteroaralkyl; and R$^8$ is hydrogen, halo or alkoxy; or ii) R$^1$ and R$^8$ together with the atoms on which they are substituted form a 5-8 membered substituted or unsubstituted heterocyclic or heteroaryl ring containing 1-4 heteroatoms; wherein the substituents when present are selected from one or more Q$^0$;

Q$^0$ is halo, hydroxyl, alkoxy, cycloalkyl, aryl, heteroaryl, aralkyl, pseudohalo, amino, nitro, alkyl, haloalkyl, alkenyl or alkynyl;

R$^2$ is hydrogen, lower alkyl, COOR$^{2a}$ or optionally substituted aryl, wherein the substituents when present are selected from one to four Q$^1$ groups;

R$^{2a}$ is hydrogen, or lower alkyl;

R$^3$ is H, CN or C(O)R$^{3a}$;

R$^{3a}$ is OH, NR$^{3b}$R$^{3c}$, alkoxy, alkyl, alkenyl or alkynyl;

R$^{3b}$ is hydrogen, alkyl, alkenyl or alkynyl;

R$^{3c}$ is hydrogen, alkyl, alkenyl, alkynyl;

R$^5$ is NR$^{5a}$R$^{5b}$ or SR$^{5a}$;

R$^{5a}$ and R$^{5b}$ are each independently hydrogen, lower alkyl or COR$^{5C}$;

R$^{5C}$ is lower alkyl or lower haloalkyl;

R$^6$ is halo;

R$^a$ and R$^b$ are selected as follows:

i) R$^a$ is selected from hydrogen and lower alkyl, and R$^b$ is
—(CH$_2$)$_n$(NR$^c$)$_m$R,
—(CH$_2$)$_n$OR$^d$,
—(CH$_2$)$_n$S(O)$_i$R$^d$,
—CH(R$^j$)(CH$_2$)$_n$(NR$^c$)$_m$R,
—CH(R$^j$)(CH$_2$)$_n$OR$^d$, or
CH(R$^j$)(CH$_2$)$_n$S(O)IR$^d$ ii) R$^a$ and R$^b$ together with the nitrogen atom on which they are substituted form a 5-7 membered substituted or unsubstituted heterocyclic or heteroaryl ring containing 1-4 heteroatoms; wherein the substituents when present are selected from one to four Q$^1$ groups;

R$^c$ is hydrogen or lower alkyl;

R is alkyl, aryl, heteroaryl, cycloalkyl, heterocyclyl, fused heterocyclylaryl, fused arylheterocyclyl, —C(O)OR$^d$, —C(O)R$^d$, —C(O)NR$^e$R$^e$ or —CHR$^d$R$^d$;

Each R$^d$ is selected from alkyl, aryl, heterocyclyl, heteroaryl, cycloalkyl, fused heterocyclylaryl and fused arylheterocyclyl;

Each $R^e$ is selected from hydrogen, alkyl, aryl, heterocyclyl, heteroaryl, cycloalkyl, fused heterocyclylaryl and fused arylheterocyclyl;

$R^j$ is lower alkyl or lower haloalkyl;

n is 0 to 6;

m is 0 or 1; and l is 0 to 2, where R and $R^d$ are optionally substituted with 1 to 4 substituents, each independently selected from $Q^1$, where $Q^1$ is as defined elsewhere herein.

In certain embodiments, the compounds for use in the compositions and methods provided herein have Formula Ia, wherein $R^1$ and $R^8$ are selected as follows:

i) $R^1$ is cycloalkyl, aryl or aralkyl; and $R^8$ is halo or alkoxy; or ii) $R^1$ and $R^8$ together with the atoms on which they are substituted form a 5-7 membered substituted or unsubstitued heterocyclic or heteroaryl ring containing 1-4 heteroatoms; wherein the substituents when present are selected from one or more $Q^1$;

$R^2$ is hydrogen or lower alkyl;

$R^3$ is H, CN, or $C(O)R^{3a}$;

$R^{3a}$ is OH, $NR^{3b}R^{3c}$, alkyl, alkenyl or alkynyl;

$R^{3b}$ is hydrogen, alkyl, alkenyl or alkynyl;

$R^{3c}$ is hydrogen, alkyl, alkenyl, alkynyl;

$R^5$ is amino, optionally substituted with one or two lower alkyl groups;

$R^6$ is halo;

$R^a$ and $R^b$ are selected as follows:

i) $R^a$ is selected from hydrogen and lower alkyl, and $R^b$ is —$(CH_2)_n(NR^c)_m R$ or —$(CH_2)_n OR^d$; or ii) $R^a$ and $R^b$ together with the nitrogen atom on which they are substituted form a 5-7 membered substituted or unsubstituted heterocyclic or heteroaryl ring containing 1-4 heteroatoms; wherein the substituents when present are selected from one or more $Q^1$;

$R^c$ is hydrogen or lower alkyl;

R is aryl, heteroaryl, —$C(O)OR^d$, —$C(O)R^d$ or —$C(O)NR^eR^e$;

$R^d$ is alkyl, aryl, heterocyclyl, heteroaryl or cycloalkyl;

Each $R^e$ is selected from $R^d$ and hydrogen;

n is 0 to 6;

m is 0 or 1.

In certain embodiments, $R^1$, $R^2$, $R^b$, R and $R^d$ are optionally substituted with one or more, in certain embodiments, 1, 2, 3 or 4 substituents, each independently selected from $Q^1$, where $Q^1$ is halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, —$N^+R^{51}R^{52}R^{53}$, $P(R^{50})_2$, $P(=O)(R^{50})_2$, $OP(=O)(R^{50})_2$, —$NR^{60}C(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^1$ groups, which substitute atoms in a 1,2 or 1,3 arrangement, together form alkylenedioxy (i.e., —O—$(CH_2)_y$—O—), thioalkylenoxy (i.e., —S—$(CH_2)_y$—O—) or alkylenedithioxy (i.e., —S—$(CH_2)_y$—S—) where y is 1 or 2; or two $Q^1$ groups, which substitute the same atom, together form alkylene; and each $Q^1$ is independently unsubstituted or substituted with one, two or three substituents, each independently selected from $Q^2$;

each $Q^2$ is independently halo, pseudohalo, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, —N⁺R⁵¹R⁵²R⁵³, P(R⁵⁰)₂, P(=O)(R⁵⁰)₂, OP(=O)(R⁵⁰)₂, —NR⁶⁰C(=O)R⁶³, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two Q² groups, which substitute atoms in a 1,2 or 1,3 arrangement, together form alkylenedioxy (i.e., —O—(CH₂)ᵧ—O—), thioalkylenoxy (i.e., —S—(CH₂)ᵧ—O—) or alkylenedithioxy (i.e., —S—(CH₂)ᵧ—S—) where y is 1 or 2; or two Q² groups, which substitute the same atom, together form alkylene;

R⁵⁰ is hydroxy, alkoxy, aralkoxy, alkyl, heteroaryl, heterocyclyl, aryl or —NR⁷⁰R⁷¹, where R⁷⁰ and R⁷¹ are each independently hydrogen, alkyl, aralkyl, aryl, heteroaryl, heteroaralkyl or heterocyclyl, or R⁷⁰ and R⁷¹ together form alkylene, azaalkylene, oxaalkylene or thiaalkylene;

R⁵¹, R⁵² and R⁵³ are each independently hydrogen, alkyl, aryl, aralkyl, heteroaryl, heteroaralkyl, heterocyclyl or heterocyclylalkyl;

R⁶⁰ is hydrogen, alkyl, aryl, aralkyl, heteroaryl, heteroaralkyl, heterocyclyl or heterocyclylalkyl; and R⁶³ is alkoxy, aralkoxy, alkyl, heteroaryl, heterocyclyl, aryl or —NR⁷⁰R⁷¹.

In certain embodiments, R and R$^d$ are optionally substituted with one or more, in certain embodiments, 1, 2, 3 or 4 substituents, each independently selected from Q¹, where Q¹ is alkyl, alkenyl, alkynyl, halo, hydroxyl, pseudohalo, amino, nitro, cycloalkyl, heterocyclyl, aryl or heteroaryl. In one embodiment, Q¹ is halo, hydroxy, alkoxy, pseudohalo, amino, nitro, alkyl, haloalkyl, alkenyl, alkynyl, aryl, cycloalkyl, carboxy, alkyloxycarbonyl or oxo. In certain embodiments, Q¹ is alkyl, alkenyl, alkynyl, halo, hydroxyl, pseudohalo, amino, nitro, cycloalkyl or aryl. In certain embodiments, Q¹ is lower alkyl, hydroxyl, amino, halo or pseudohalo. In certain embodiments, Q¹ is amino, hydroxyl, fluoro, chloro, cyano or methyl.

In certain embodiments, the compounds of Formula Ia are selected such that R¹ is cycloalkyl, aryl or aralkyl;
R² is hydrogen or lower alkyl;
R³ is H or COOH,
R⁵ is amino, optionally substituted with one or two lower alkyl groups;
R⁶ is halo,
R⁸ is halo or alkoxy,
R$^a$ is selected from hydrogen and lower alkyl,
R$^b$ is aralkyl, heteroaralkyl, heteroarylaminoalkyl, arylcarbonylaminoalkyl, heteroarylcarbonyl-aminoalkyl, alkyloxycarbonylaminoalkyl or alkoxyalkyl, where R$^b$ can be optionally substituted with lower alkyl, amino or halo.

In certain embodiments, the compounds of Formula Ia are selected such that R¹ is cycloalkyl, aryl or aralkyl,
R² is hydrogen or lower alkyl,
R³ is H or COOH,
R⁵ is amino,
R⁶ and R⁸ are halo,
R$^a$ is selected from hydrogen and lower alkyl,
R$^b$ is heteroaralkyl, heteroarylaminoalkyl, arylcarbonylaminoalkyl, heteroarylcarbonyl-aminoalkyl, alkyloxycarbonylaminoalkyl or alkoxyalkyl, where R$^b$ is optionally substituted with lower alkyl, amino, halo or pseudohalo.

In one embodiment, R$^b$ is heteroaralkyl, where R$^b$ is optionally substituted with lower alkyl, amino, halo or cyano.

In one embodiment, R¹ is cycloalkyl, aryl or aralkyl. In one embodiment, R¹ is cycloalkyl or aralkyl. In one embodiment, R¹ is cycloalkyl. In another embodiment, R¹ is cyclopropyl or cyclopentyl. In one embodiment, R¹ is aralkyl. In one embodiment, R¹ is benzyl or phenethyl.

In one embodiment, R² is hydrogen or lower alkyl. In one embodiment, R² is hydrogen or methyl. In one embodiment, R² is hydrogen.

In one embodiment, R³ is H or COOH. In one embodiment, R³ is H. In one embodiment, R³ is COOH.

In one embodiment, R⁵ is amino, optionally substituted with one or two lower alkyl groups. In one embodiment, R⁵ is unsubstituted amino. In one embodiment, R⁵ is SR⁵$^a$. In one embodiment, R⁵ is mercapto.

In one embodiment, R⁶ is halo. In one embodiment, R⁶ is Cl, Br or F. In one embodiment, R⁶ is F.

In one embodiment, R⁸ is halo or alkoxy. In one embodiment, R⁸ is methoxy, Cl, Br or F. In one embodiment, R⁸ is F or methoxy.

In one embodiment, R$^a$ is selected from hydrogen and lower alkyl. In one embodiment, R$^a$ is hydrogen.

In one embodiment, n is 0 to 4. In one embodiment, n is 2 or 3. In one embodiment, n is 1 or 2. In one embodiment, m is 1. In one embodiment, m is 0. In one embodiment, when m=1 then n=2. In one embodiment, when m=0 then n=3.

In one embodiment, R$^b$ is —(CH₂)$_n$(NR$^c$)$_m$R. In one embodiment, R is aryl, heteroaryl, —C(O)OR$^d$, —C(O)R$^d$. In one embodiment, R$^b$ is —OR$^d$.

In one embodiment, R$^d$ is alkyl, aryl, heterocyclyl or heteroaryl. In one embodiment, R$^c$ is alkyl, aryl, heterocyclyl or heteroaryl.

In one embodiment, R$^e$ is hydrogen or alkyl.

In one embodiment, R$^b$ is heterocyclylalkyl, aralkyl, heteroaralkyl, heteroarylaminoalkyl, arylcarbonylaminoalkyl, heteroarylcarbonylaminoalkyl, alkyloxycarbonylaminoalkyl, alkoxyalkyl, where R$^b$ can be optionally substituted with lower alkyl, amino, halo or pseudohalo. In one embodiment, R$^b$ is heteroaralkyl, heterocyclylalkyl, alkoxyalkyl, aralkyl, heteroarylaminoalkyl, cycloalkylcarboxyaminoalkyl, aryloxyalkyl, cycloalkylalkyl, arylcarbonylaminoalkyl, heteroarylcarbonylaminoalkyl, alkyloxycarbonylaminoalkyl, where R$^b$ can be optionally substituted with 1-4 groups selected from lower alkyl, haloalkyl, amino, halo, oxo, alkoxy, carboxy and cyano.

In one embodiment, R$^b$ is selected from phenethyl, 4-aminophenethyl, 4-pyridinyl, 4-chlorophenethyl, 4-fluorophenethyl, phenylpropyl, pyridin-2-ylaminoethyl, 4-chlorobenzyl, 4-aminophenethyl, indol-3-ylethyl, pyrimidin-2-ylamino, 4-hydroxyphenethyl, isopropyloxypropyl, 2,4-dichlorophenethyl, 2,4-difluorophenethyl, phenylbutyl, tert-butyloxycarbonylamino, imidazolyl, isopropyloxypropyl, 4-fluorophenylcarbonylaminoethyl, pyridin-2-ylaminoethyl, 5-cyanopyridin-2-ylaminoethyl, pyridin-2-ylaminocarbonylethyl, pyridin-4-ylaminocarbonylethyl, naphthylaminoethyl, phenoxyethyl, 1-H-imidazol-1-ylethyl, 1,2,4-triazol-1-ylethyl, imidazol-1-ylpropyl and benzimidazol-1-ylethyl.

In certain embodiments, $R^8$ is hydrogen. In certain embodiments, $R^1$ and $R^8$ together with the atoms on which they are substituted form a 5 or 6 membered substituted or unsubstituted heterocyclic or heteroaryl ring containing 2 heteroatoms. In certain embodiments, $R^1$ and $R^8$ together with the atoms on which they are substituted form a 6 membered heterocyclic ring containing 2 heteroatoms, optionally substituted with an alkyl group.

In certain embodiments, the compound has Formula II:

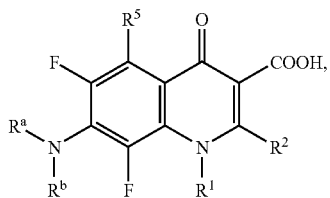

or a pharmaceutically acceptable derivative thereof, wherein the variables are as described elsewhere herein.

In certain embodiments, the compound has Formula III:

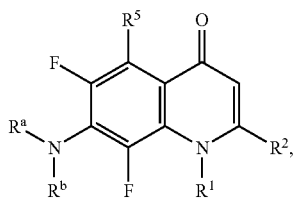

or a pharmaceutically acceptable derivative thereof, wherein the variables are as described elsewhere herein.

In certain embodiments, the compound has Formula IIIA:

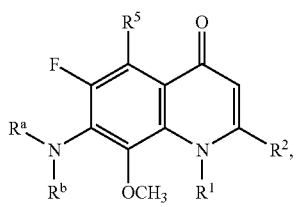

or a pharmaceutically acceptable derivative thereof, wherein the variables are as described elsewhere herein.

In certain embodiments, the compound has Formula IV:

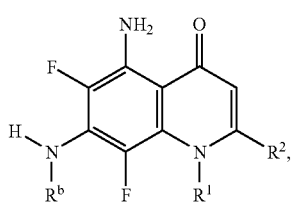

or a pharmaceutically acceptable derivative thereof, wherein the variables are as described elsewhere herein.

In certain embodiments, the compound has Formula V:

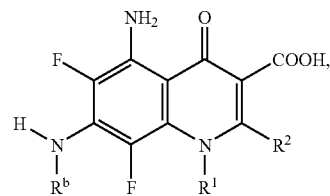

or a pharmaceutically acceptable derivative thereof, wherein the variables are as described elsewhere herein.

In certain embodiments, the compound has Formula:

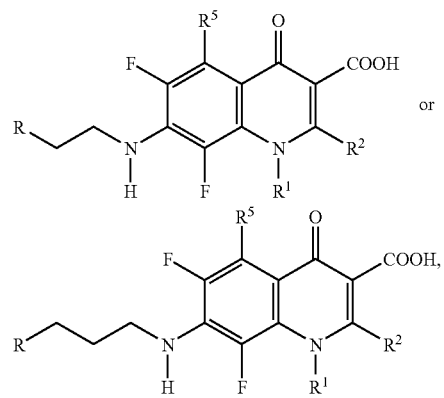

or a pharmaceutically acceptable derivative thereof, wherein the variables are as described elsewhere herein.

In certain embodiments, the compound has Formula:

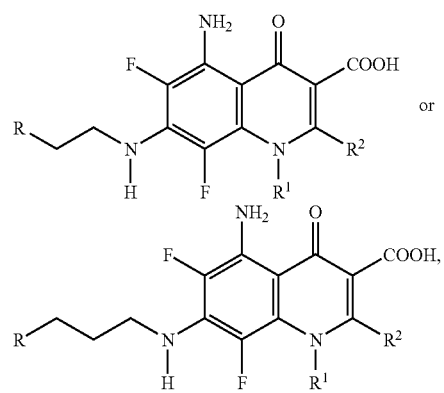

or a pharmaceutically acceptable derivative thereof, wherein the variables are as described elsewhere herein.

In certain embodiments, the compound has Formula:

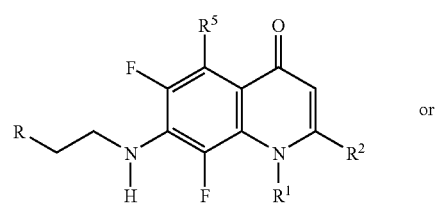

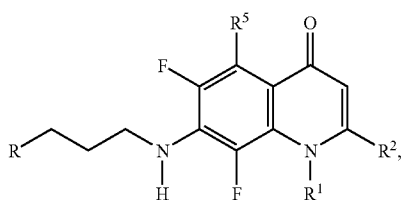

or a pharmaceutically acceptable derivative thereof, wherein the variables are as described elsewhere herein.

In certain embodiments, the compoun has Formula:

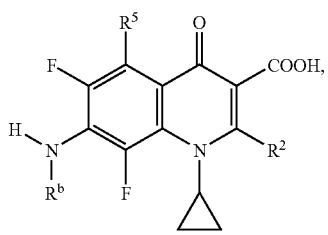

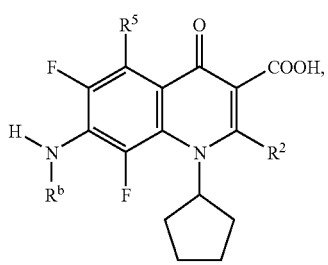

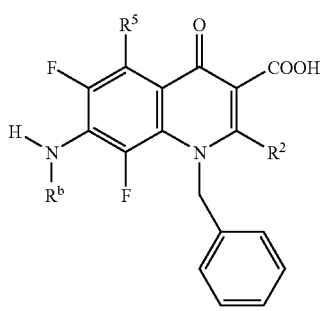 or

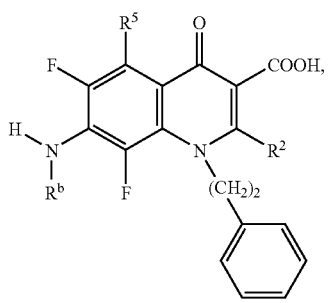

or a pharmaceutically acceptable derivative thereof, wherein the variables are as described elsewhere herein.

In certain embodiments, the compound has Formula:

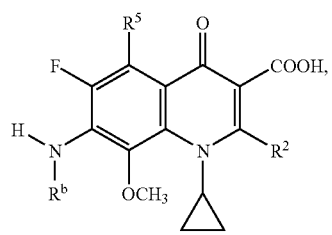

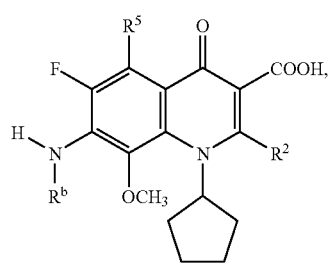

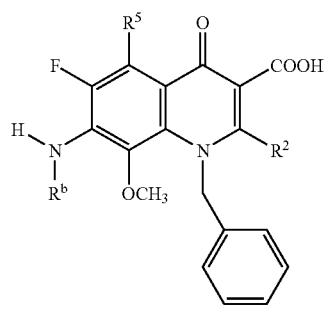 or

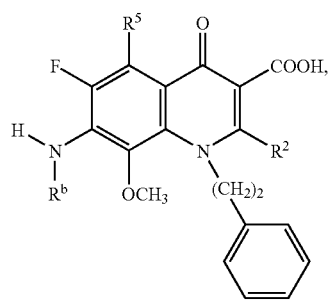

or a pharmaceutically acceptable derivative thereof, wherein the variables are as described elsewhere herein.

In certain embodiments, the compound has Formula:

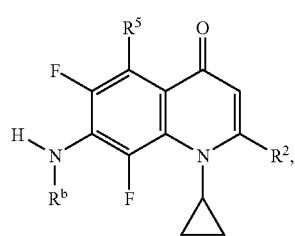

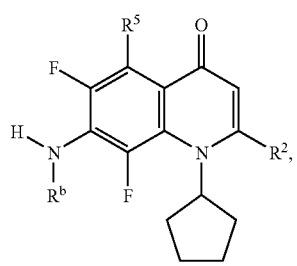

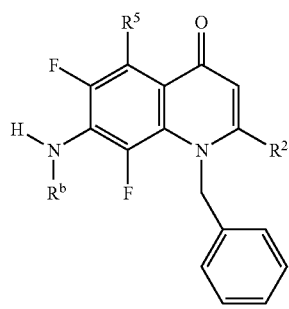

or

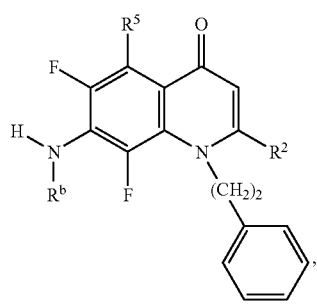

or a pharmaceutically acceptable derivative thereof, wherein the variables are as described elsewhere herein.

In certain embodiments, the compound has Formula:

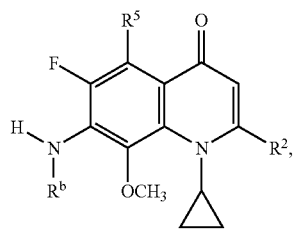

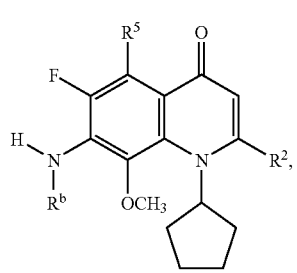

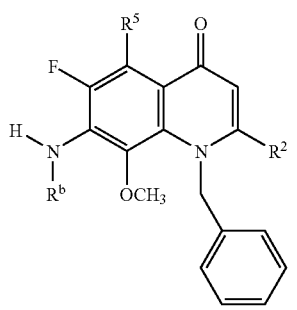

or

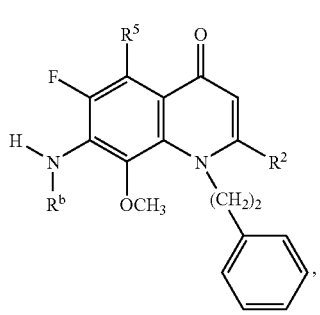

or a pharmaceutically acceptable derivative thereof, wherein the variables are as described elsewhere herein.

In certain embodiments, the compound has Formula:

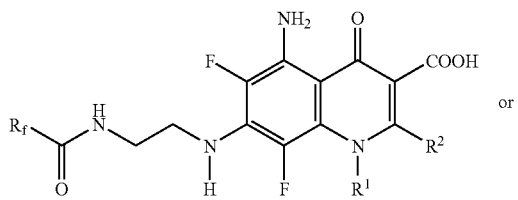

or

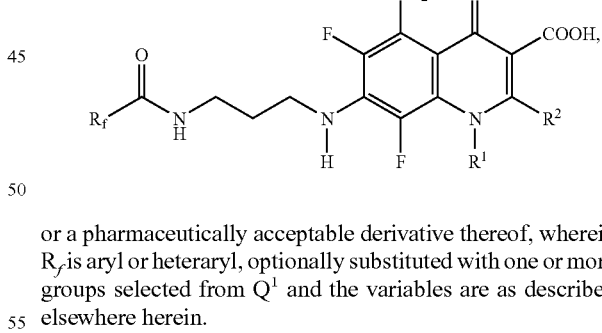

or a pharmaceutically acceptable derivative thereof, wherein $R_f$ is aryl or heteraryl, optionally substituted with one or more groups selected from $Q^1$ and the variables are as described elsewhere herein.

In certain embodiments, the compound has Formula:

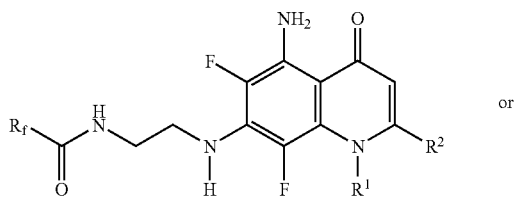

or

-continued

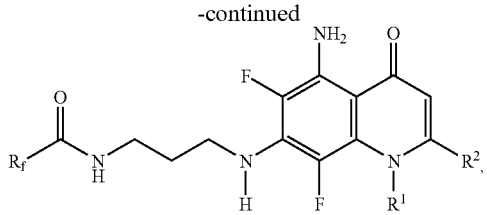

or a pharmaceutically acceptable derivative thereof, wherein the variables are as described elsewhere herein.

In certain embodiments, the compound has Formula:

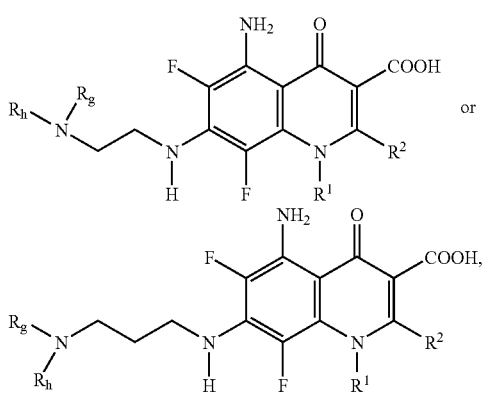

or a pharmaceutically acceptable derivative thereof, wherein $R_g$ is hydrogen or lower alkyl;

$R_h$ is aryl or heteroaryl; or $R_g$ and $R_h$ together with the nitrogen atom on which they are substituted form an optionally substituted 4-6 membered aromatic ring, wherein the substituents when present are selected from alkyl and halo; and the other variables are as described elsewhere herein. In certain embodiment, $R_g$ and $R_h$ together with the nitrogen atom on which they are substituted form an optionally substituted 4-6 membered heteroaromatic or heterocyclic ring, wherein the substituents when present are selected from alkyl and halo; and the other variables are as described elsewhere herein.

In certain embodiments, the compound has Formula:

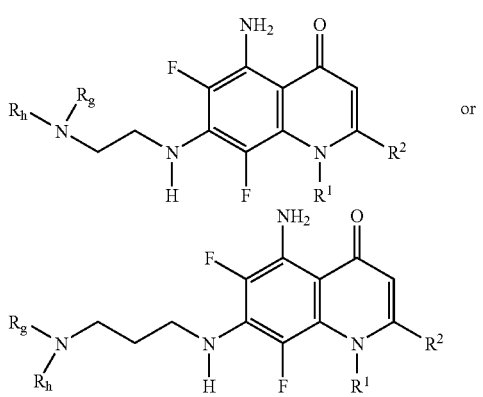

or a pharmaceutically acceptable derivative thereof, wherein the variables are as described elsewhere herein.

In certain embodiments, the compound has Formula:

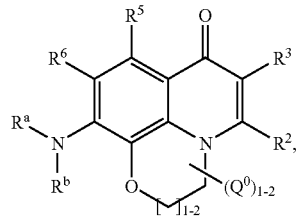

or a pharmaceutically acceptable derivative thereof, wherein the variables are as described elsewhere herein.

In certain embodiments, the compound has Formula:

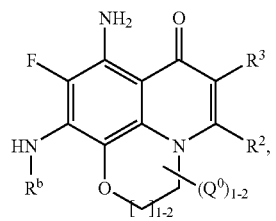

or a pharmaceutically acceptable derivative thereof, wherein the variables are as described elsewhere herein.

In certain embodiments, the compound has Formula:

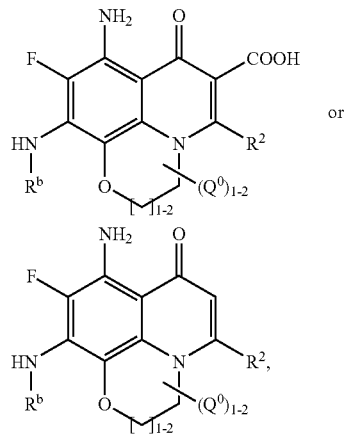

or a pharmaceutically acceptable derivative thereof, wherein the variables are as described elsewhere herein.

In certain embodiments, the compound has Formula:

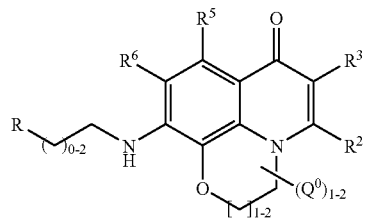

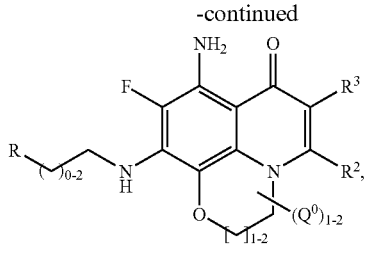

or a pharmaceutically acceptable derivative thereof, wherein the variables are as described elsewhere herein.

In certain embodiments, the compound has Formula:

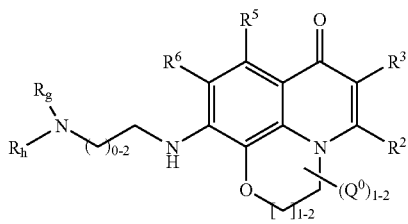

or

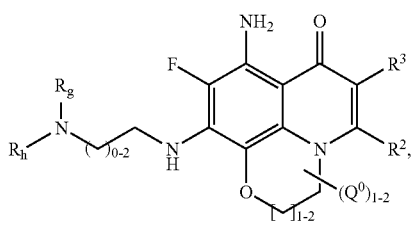

or a pharmaceutically acceptable derivative thereof, wherein $R_g$ and $R_h$ are selected as follows:

i) $R_g$ is hydrogen or lower alkyl and $R_h$ is aryl or heteroaryl; or ii) $R_g$ and $R_h$ together with the nitrogen atom on which they are substituted form an optionally substituted 4-6 membered heteroaromatic or heterocyclic ring, wherein the substituents when present are 1-4 groups selected from alkyl, aryl, alkoxy, oxo, haloalkyl and halo; and the other variables are as described elsewhere herein.

In certain embodiments, the compound has Formula:

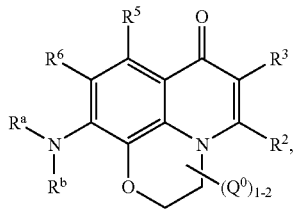

or a pharmaceutically acceptable derivative thereof, wherein the variables are as described elsewhere herein.

In certain embodiments, the compound has Formula:

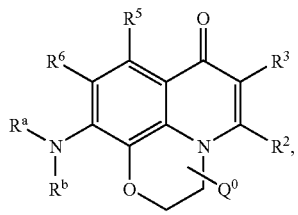

or a pharmaceutically acceptable derivative thereof, wherein the variables are as described elsewhere herein.

In certain embodiments, the compound has Formula:

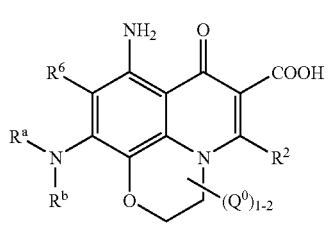

or

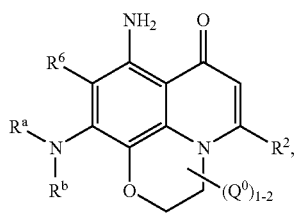

or a pharmaceutically acceptable derivative thereof, wherein the variables are as described elsewhere herein.

In certain embodiments, the compound has Formula:

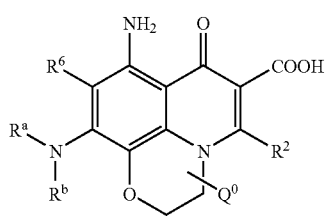

or

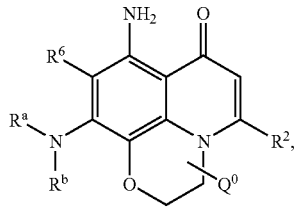

or a pharmaceutically acceptable derivative thereof, wherein the variables are as described elsewhere herein.

In certain embodiments, the compound has Formula:

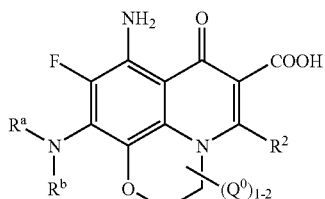

or

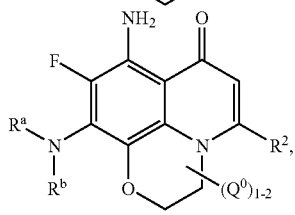

or a pharmaceutically acceptable derivative thereof, wherein the variables are as described elsewhere herein.

In certain embodiments, the compound has Formula:

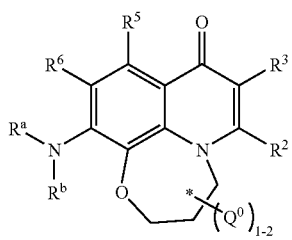

or a pharmaceutically acceptable derivative thereof, wherein the variables are as described elsewhere herein.

In certain embodiments, the compound has Formula:

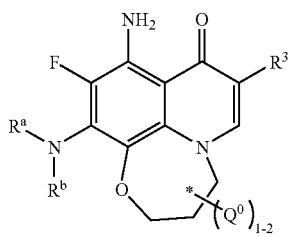

or a pharmaceutically acceptable derivative thereof, wherein the variables are as described elsewhere herein.

In certain embodiments, the compound is selected from:

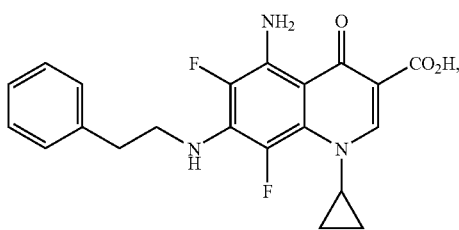

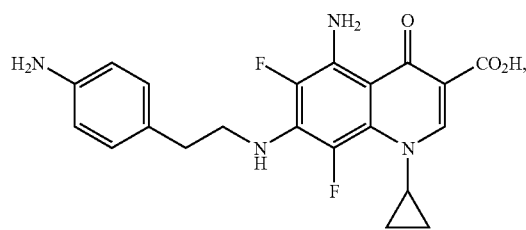

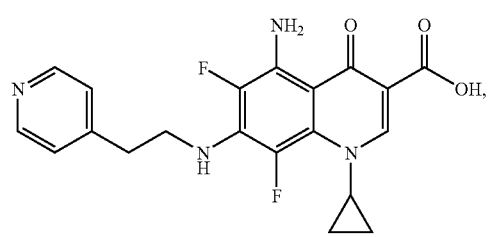

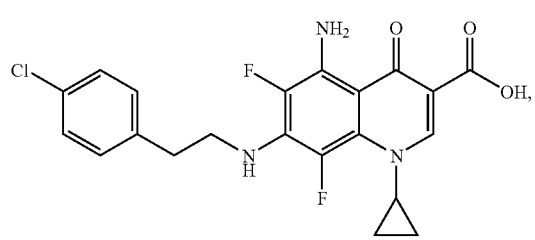

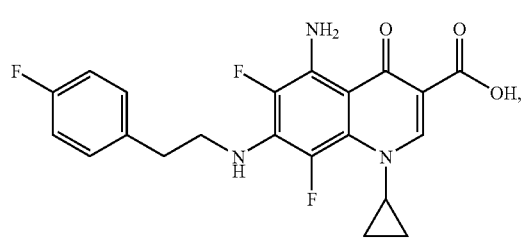

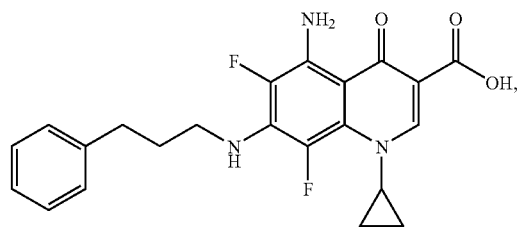

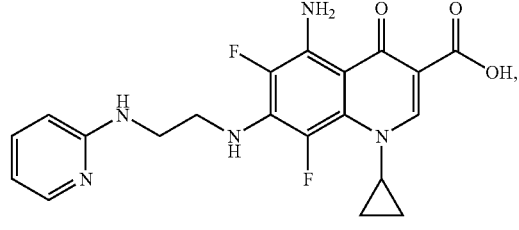

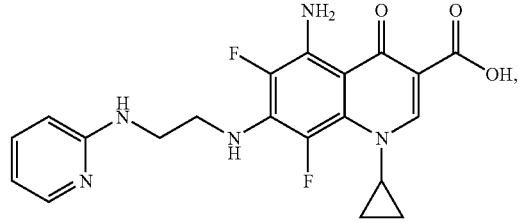

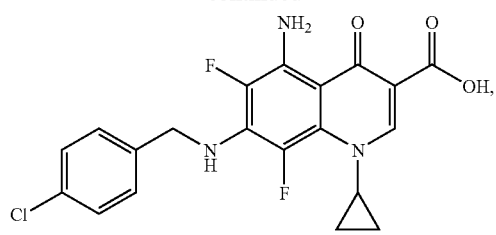
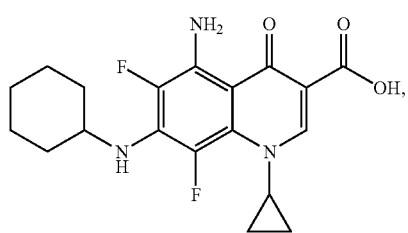
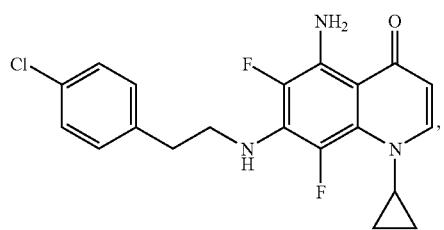
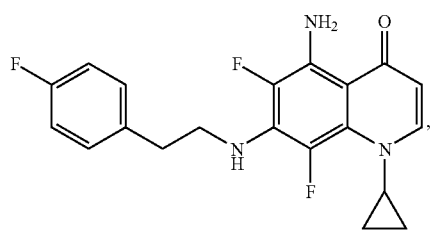
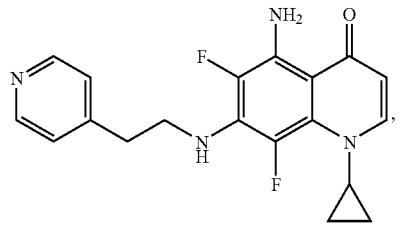
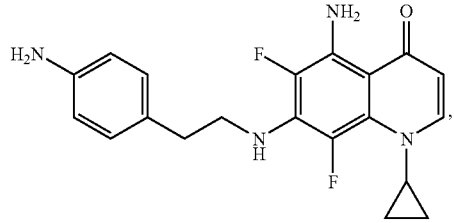
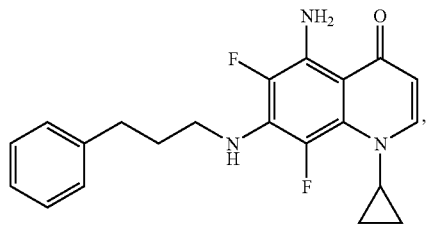
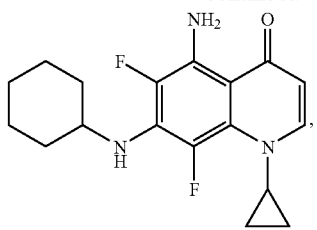
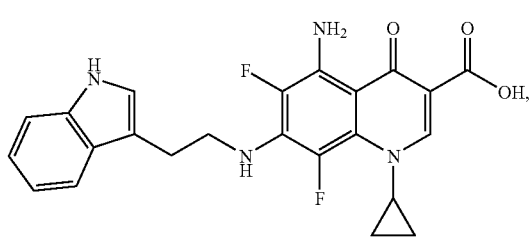
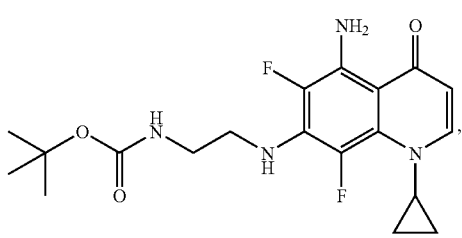
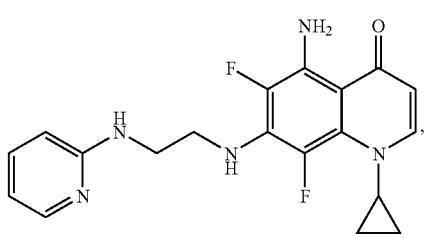
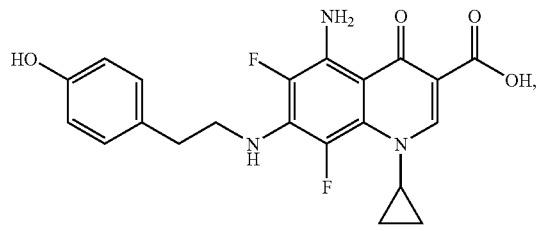
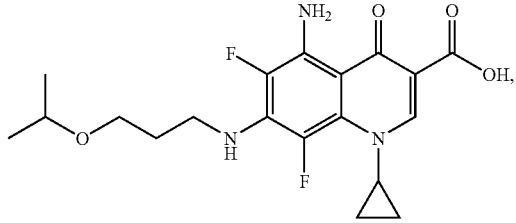
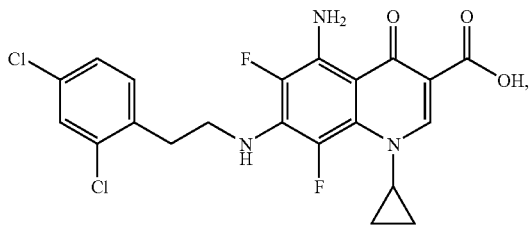

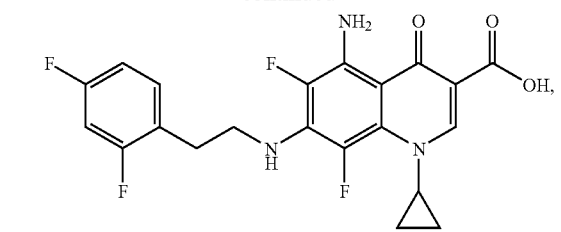
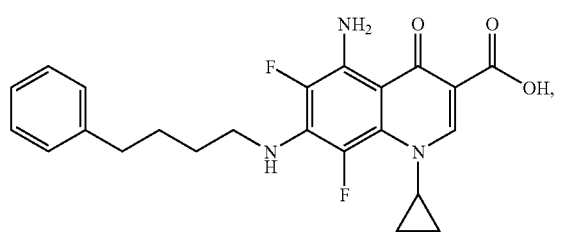
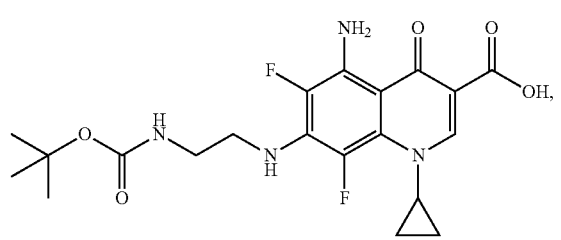
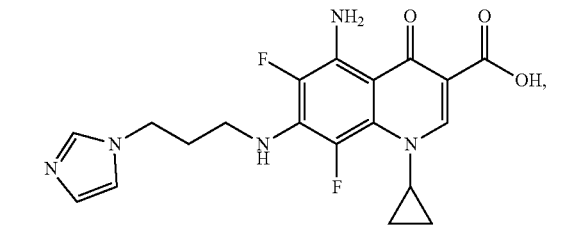
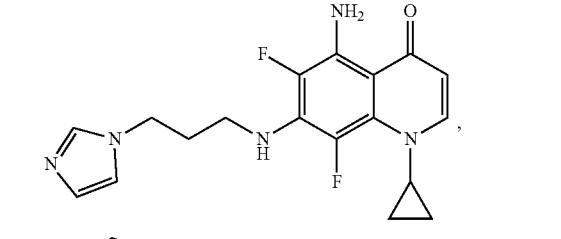
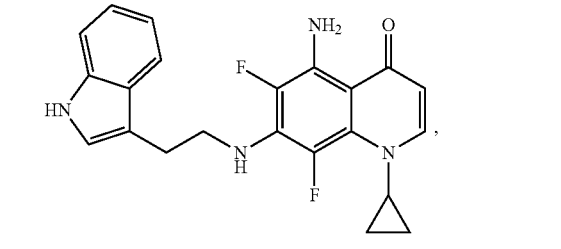
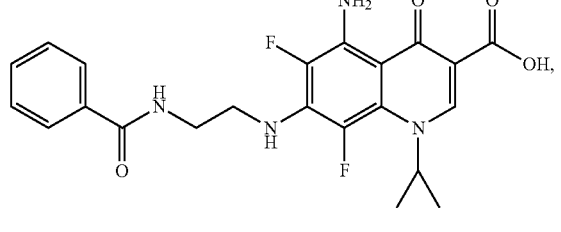
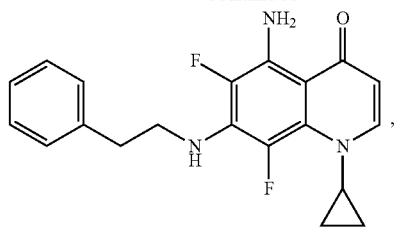
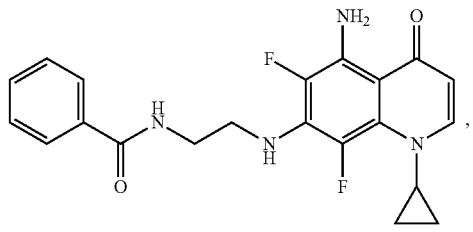
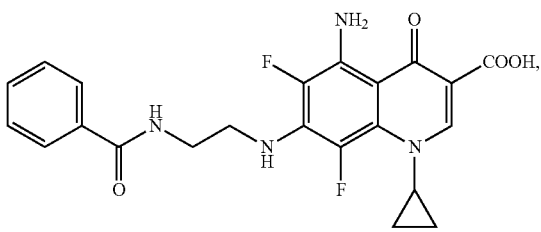
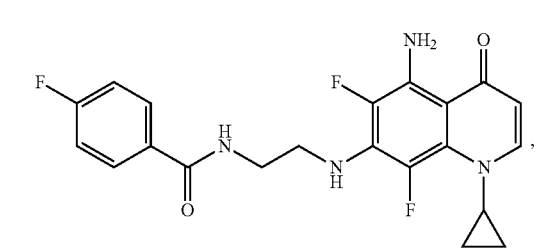
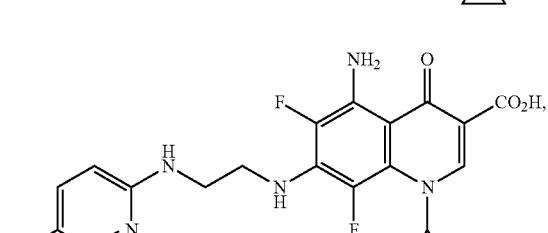
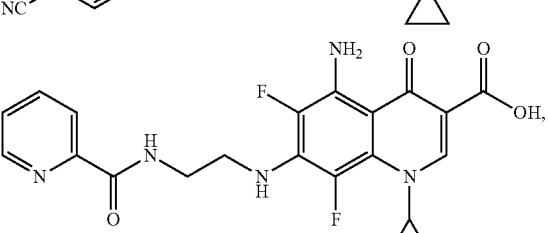
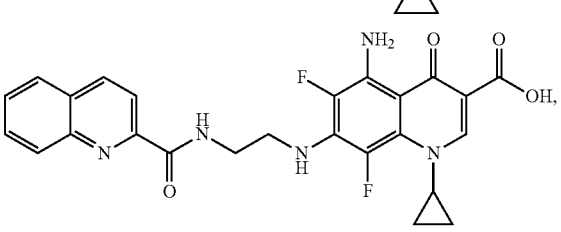

-continued
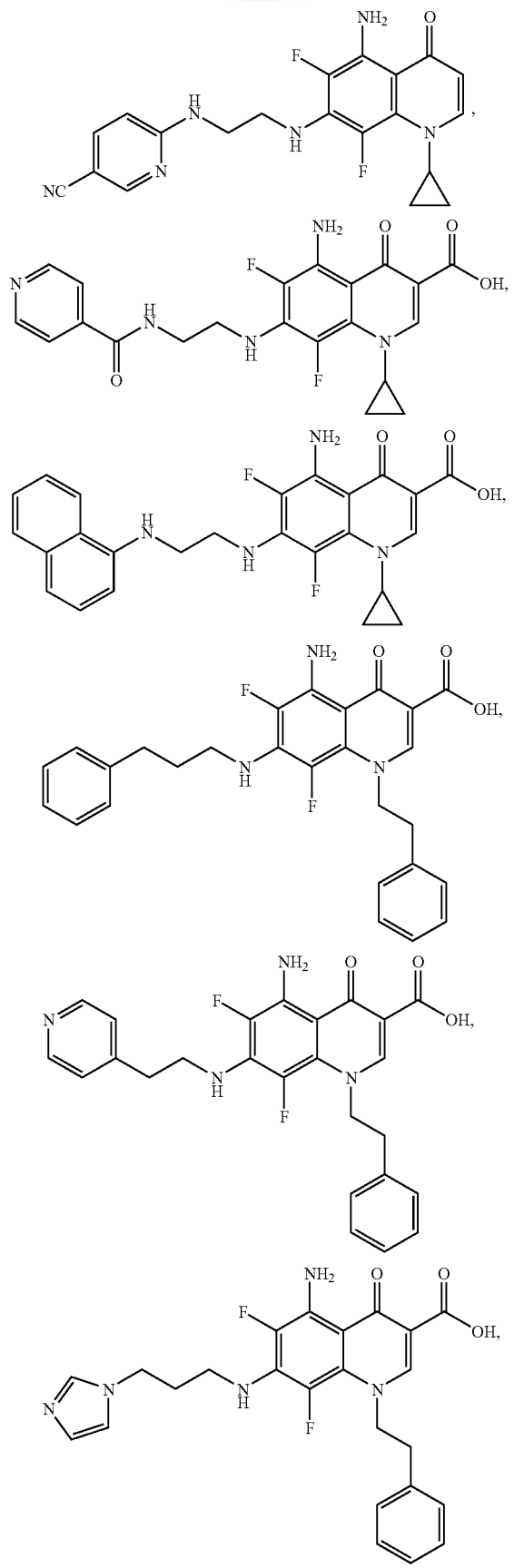
-continued
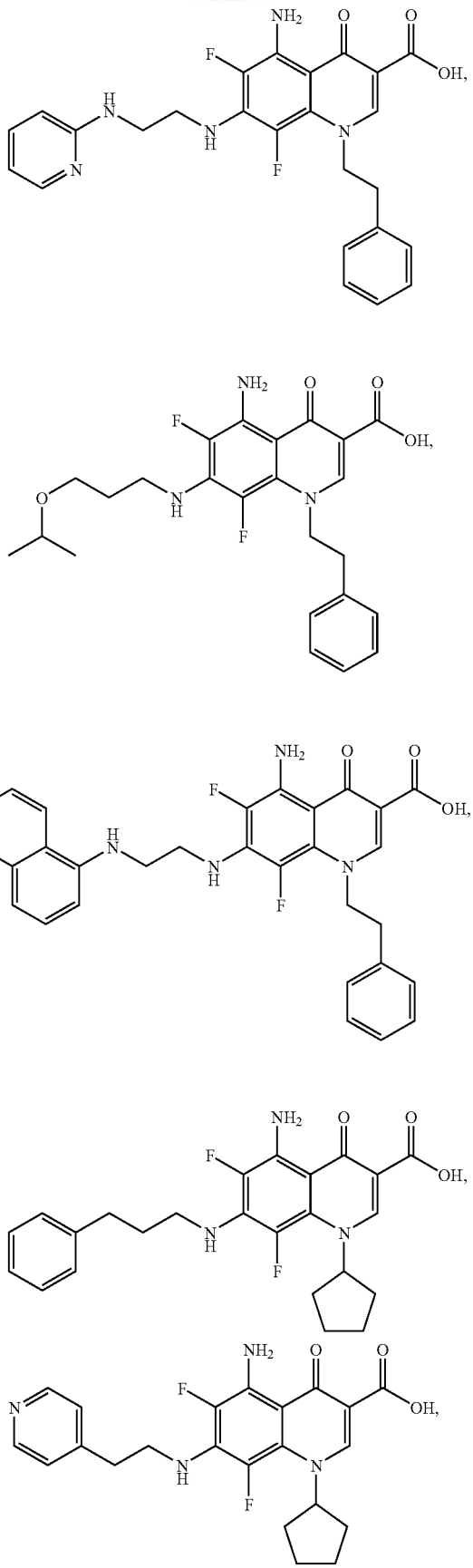

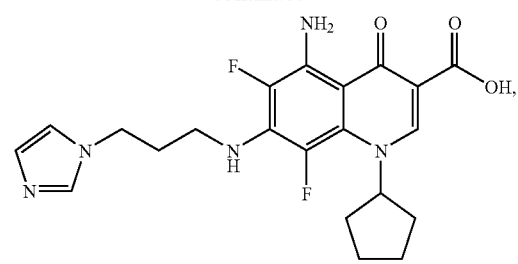
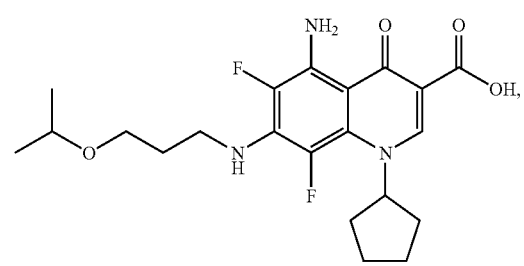
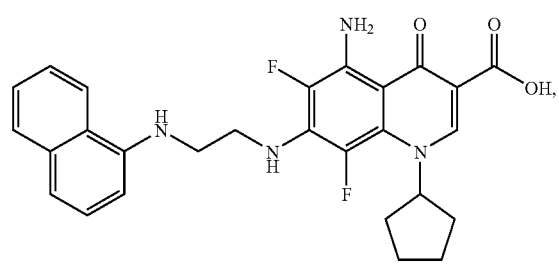
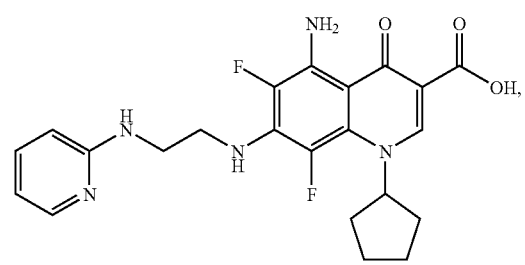
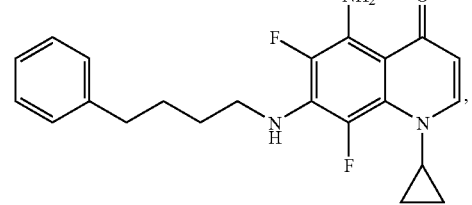
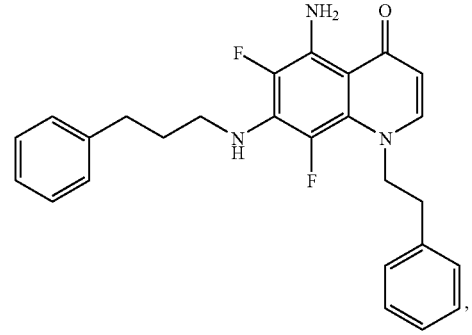
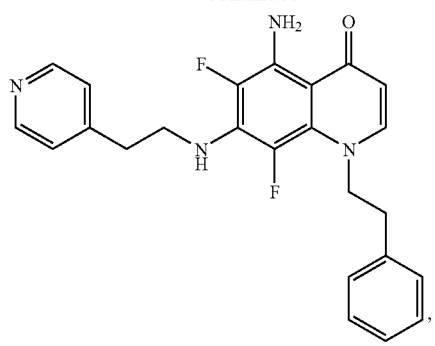
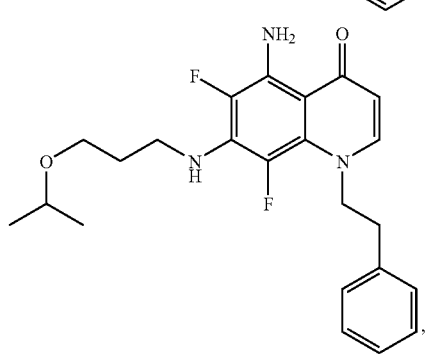
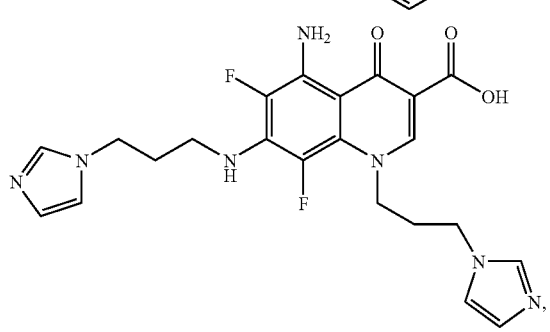
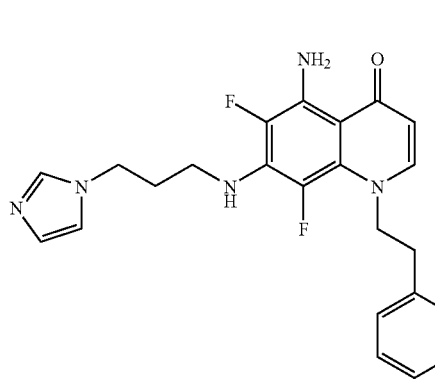
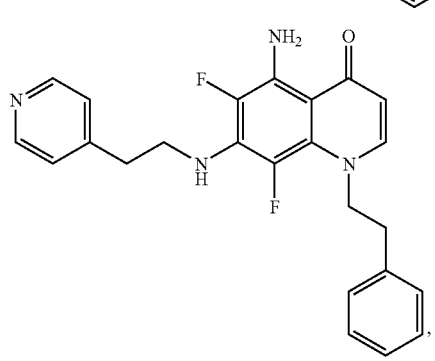

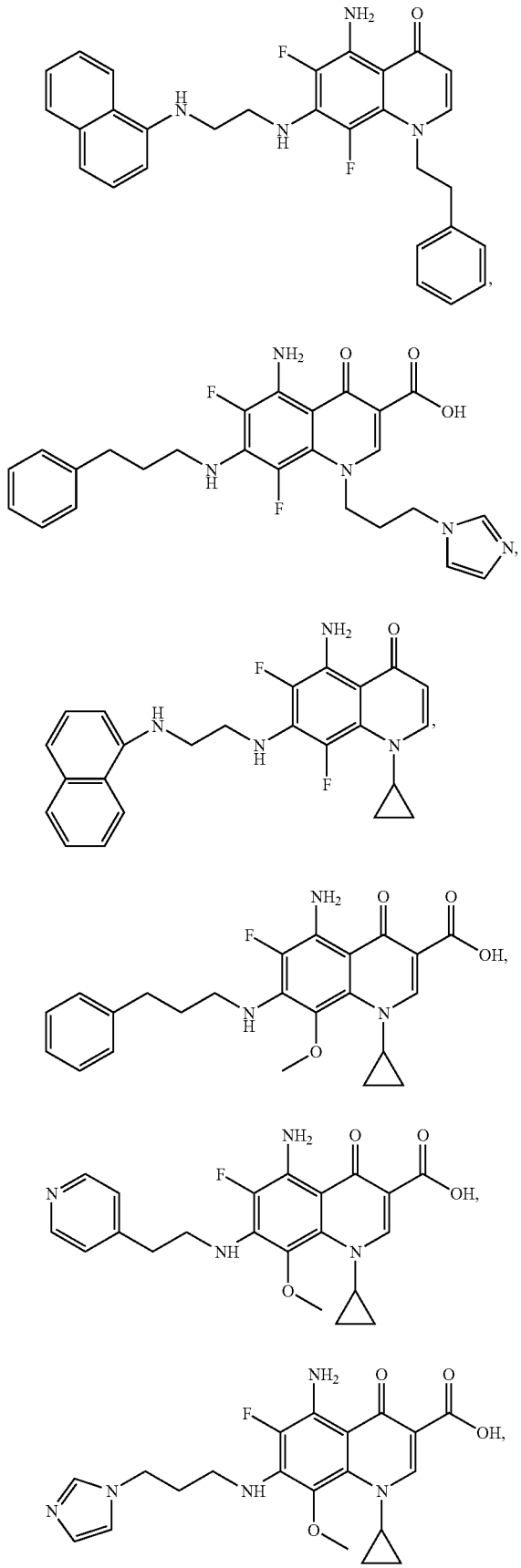
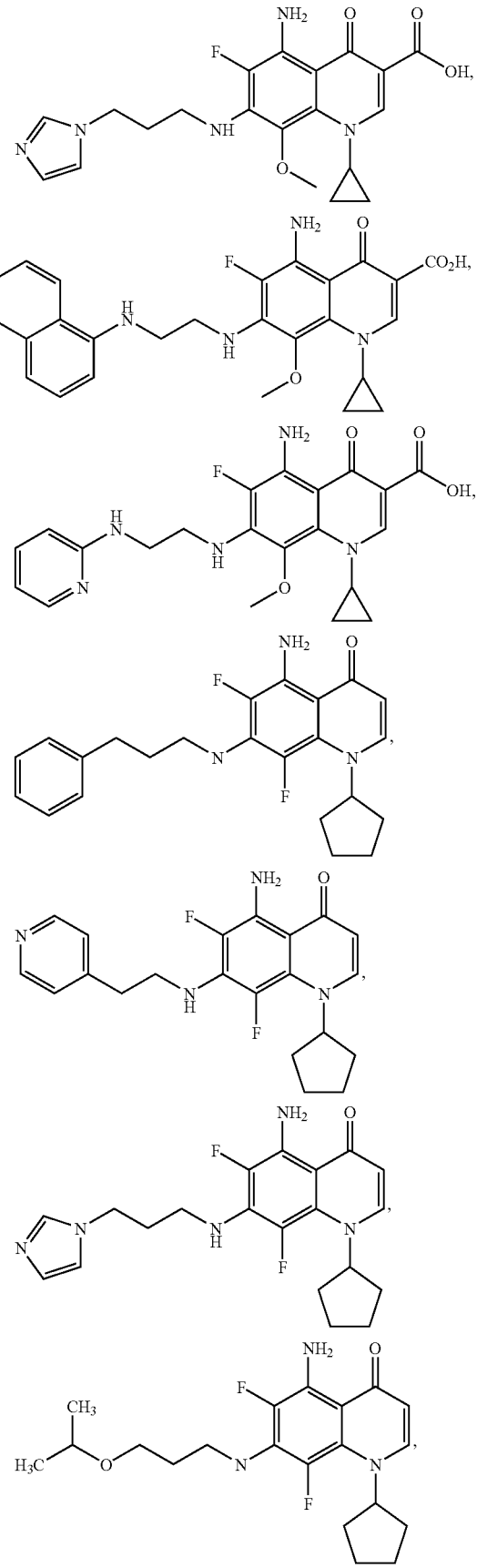

-continued
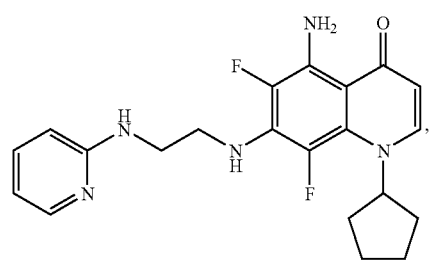
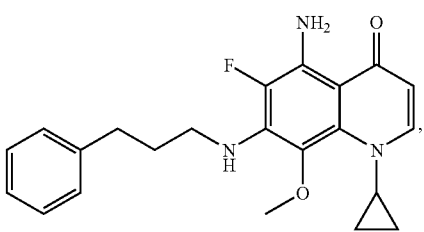
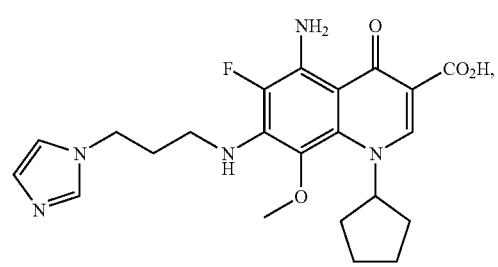
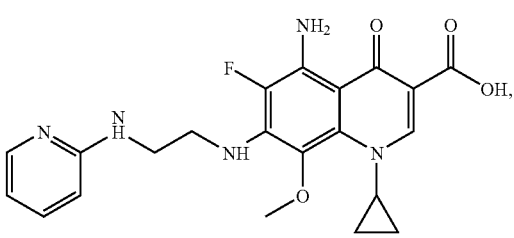
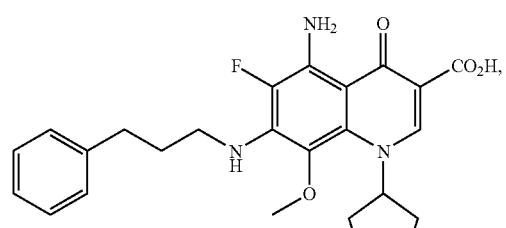
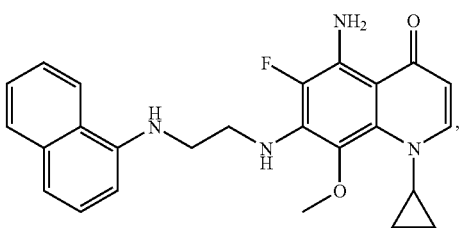
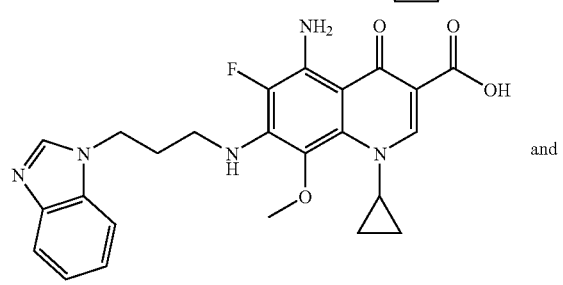
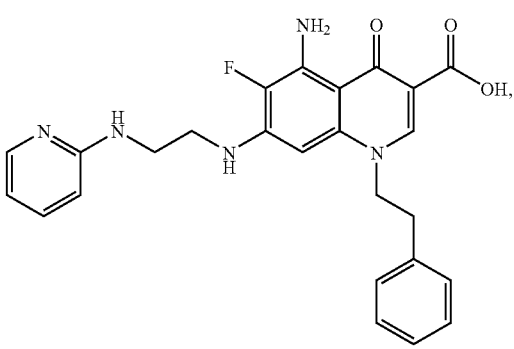
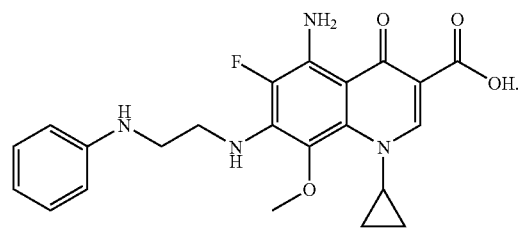
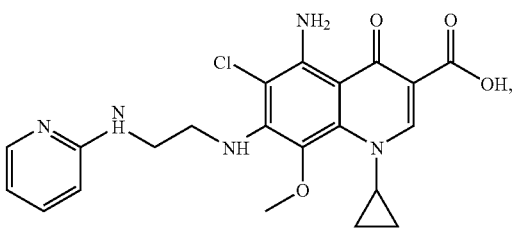
and
In certain embodiments, the compound is selected from:
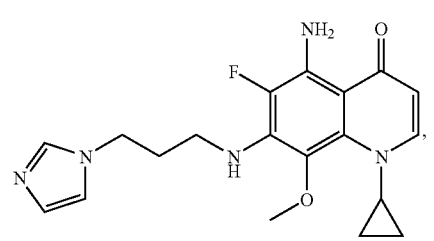

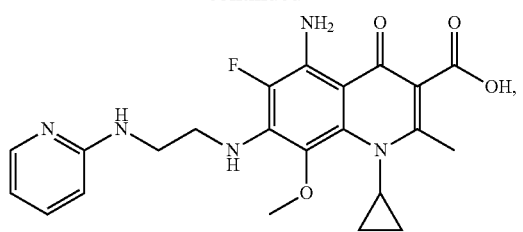
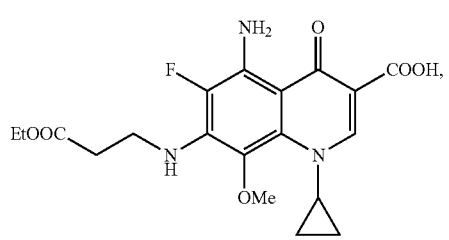
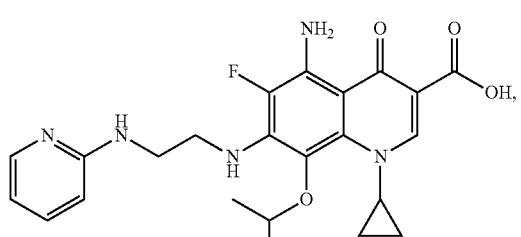
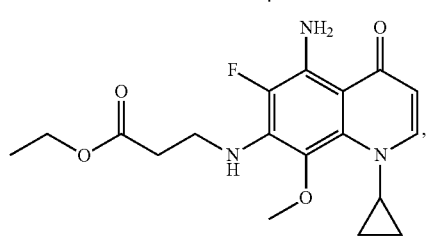
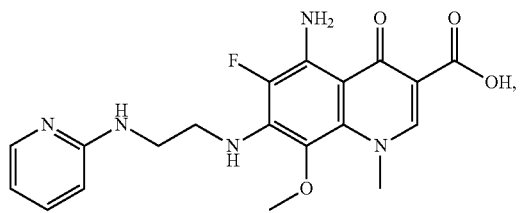
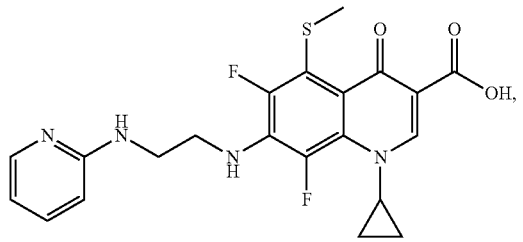
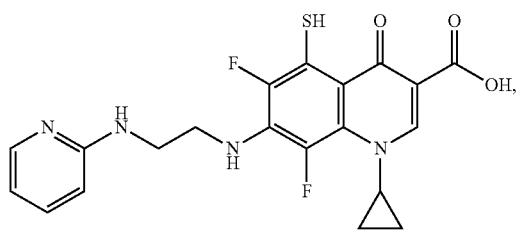
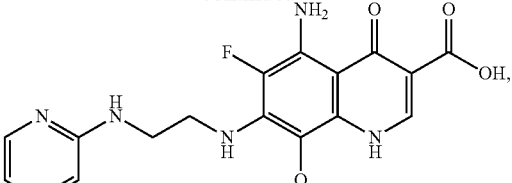
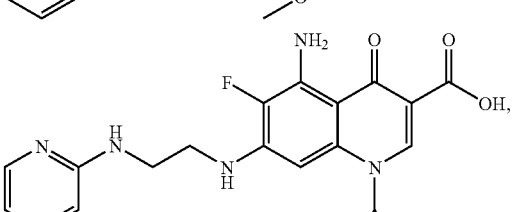
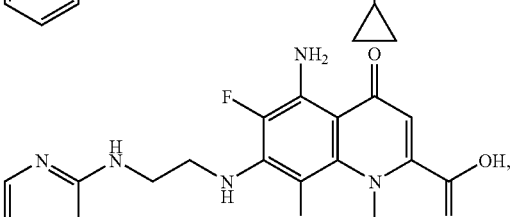
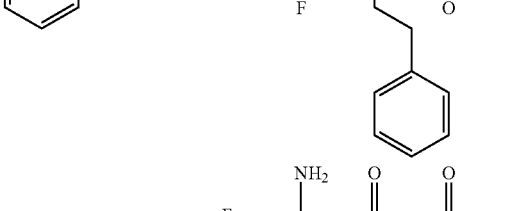
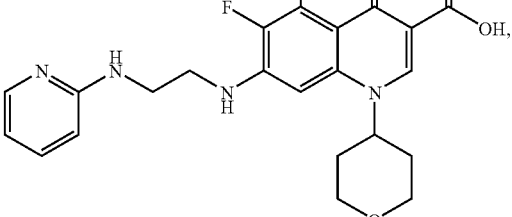
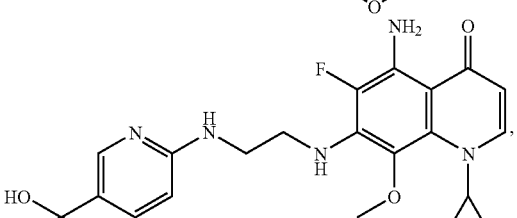
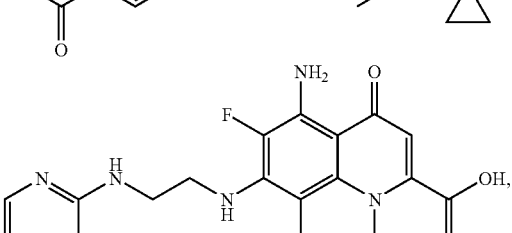
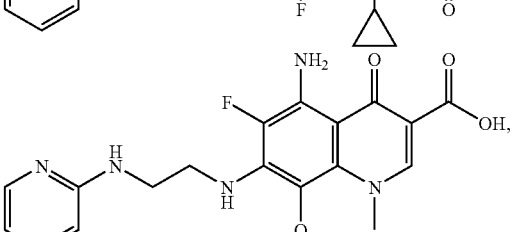

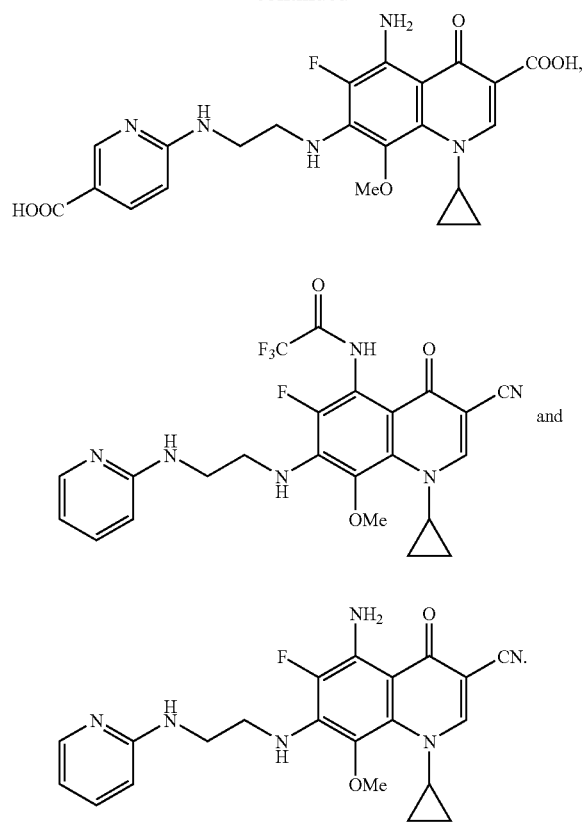
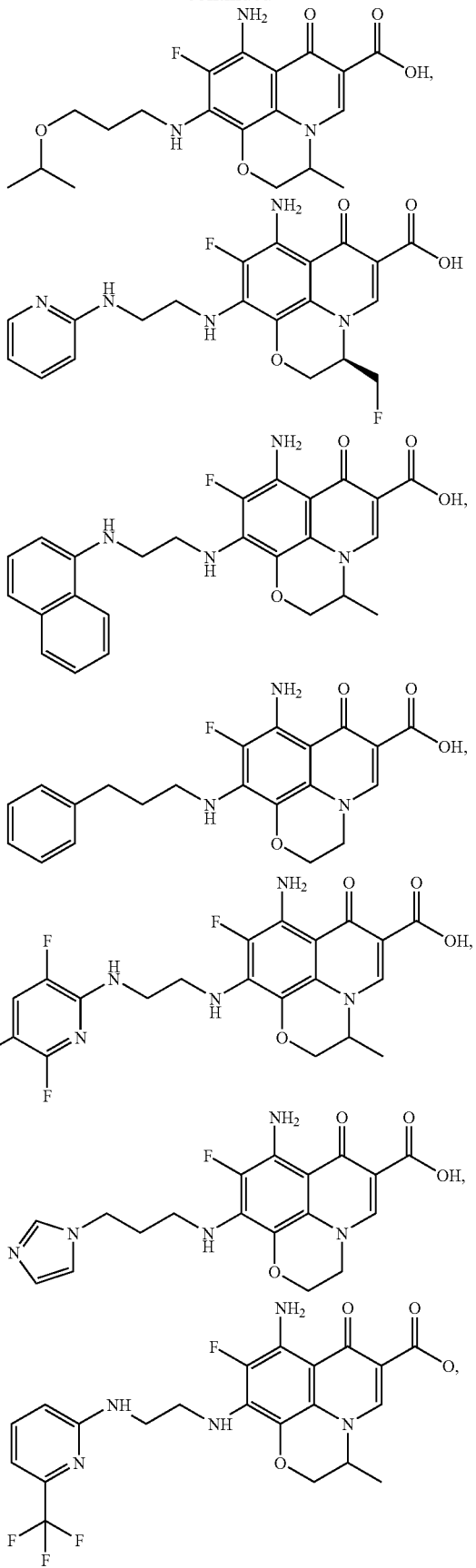
In certain embodiments, the compound is selected from:
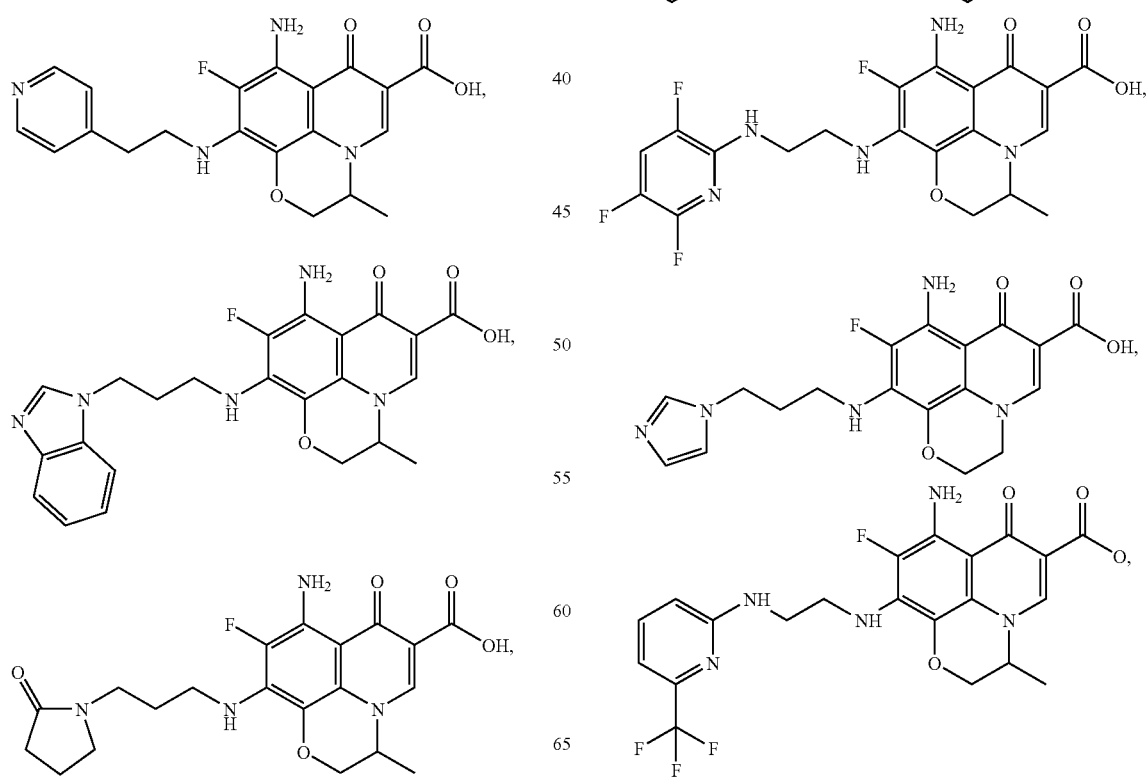

41
-continued
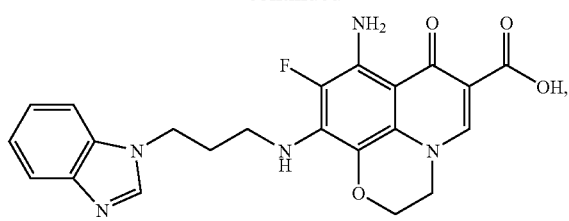
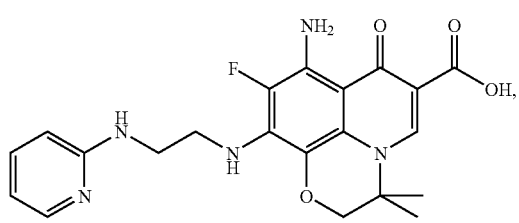
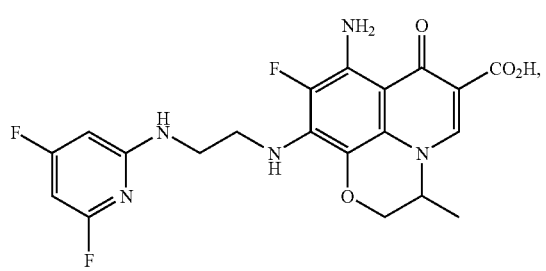
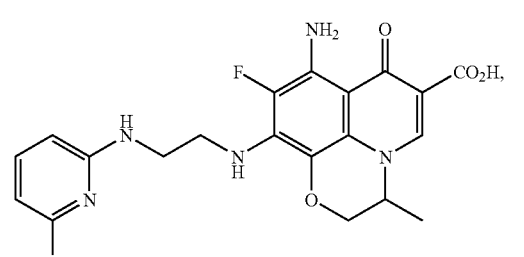
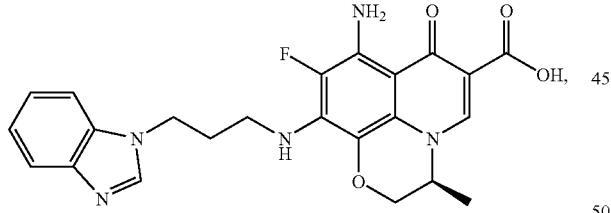
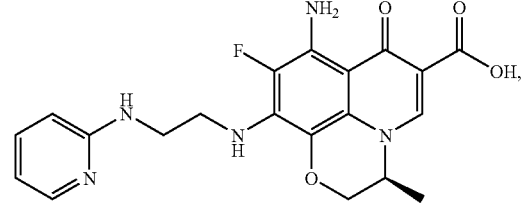
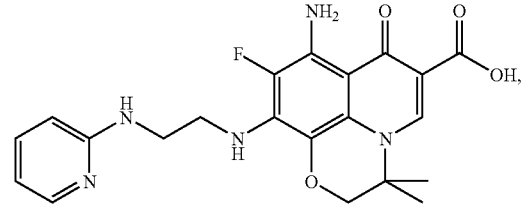
42
-continued
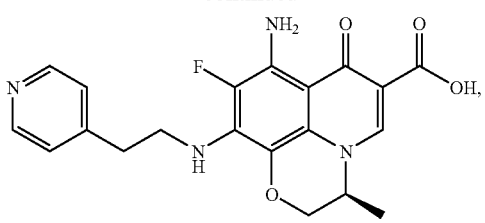
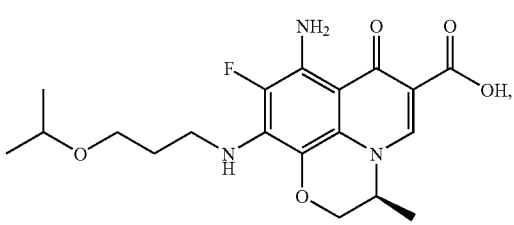
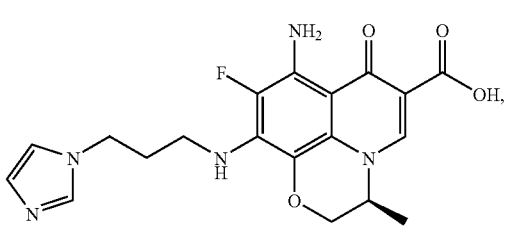
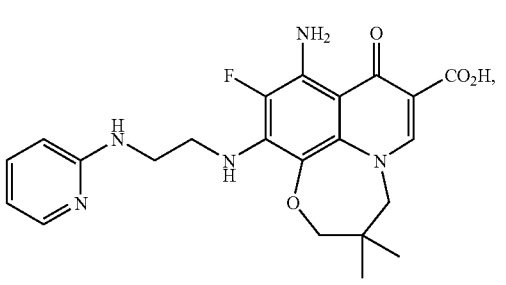
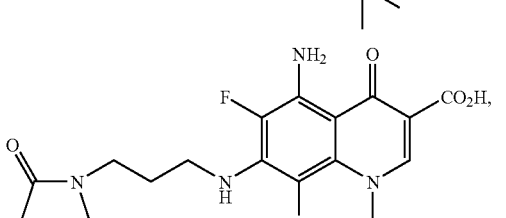
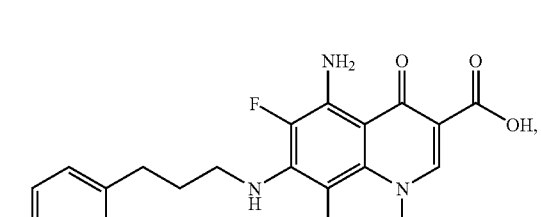
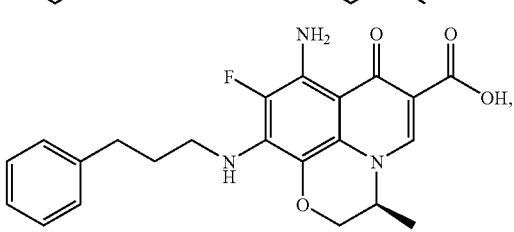

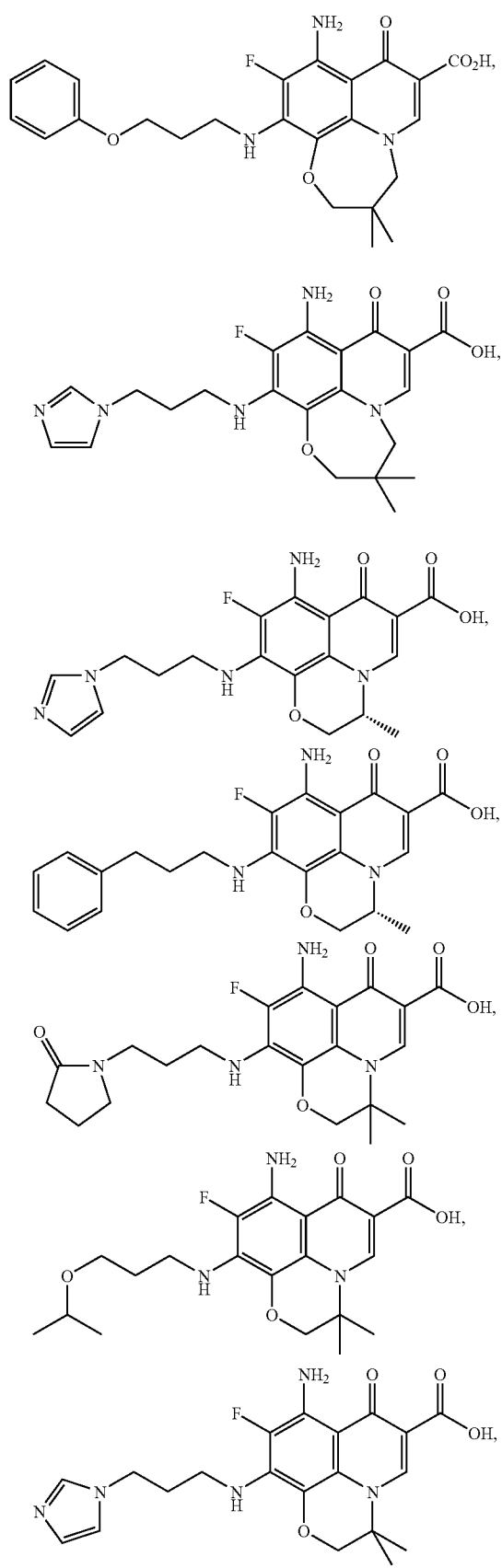
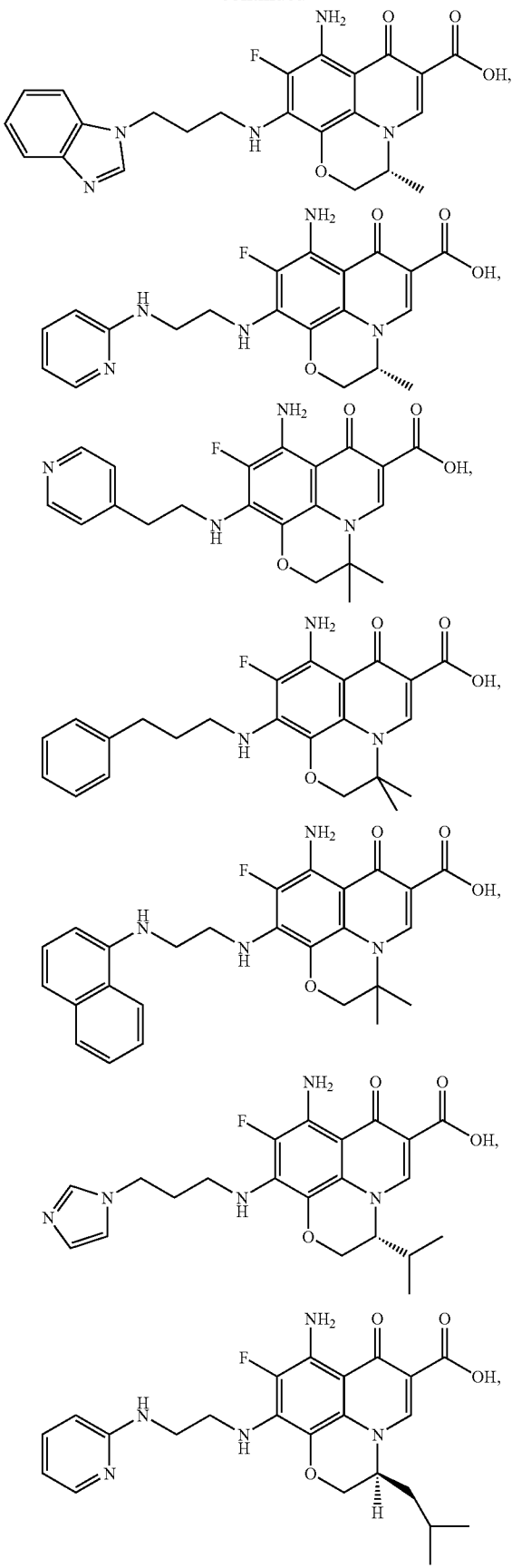

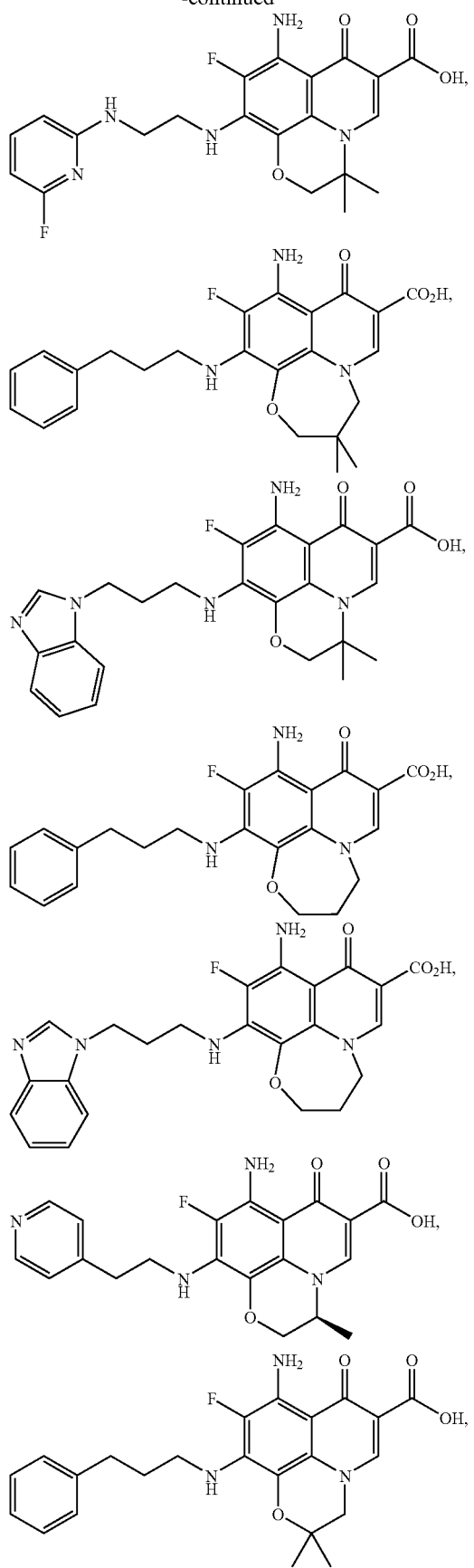
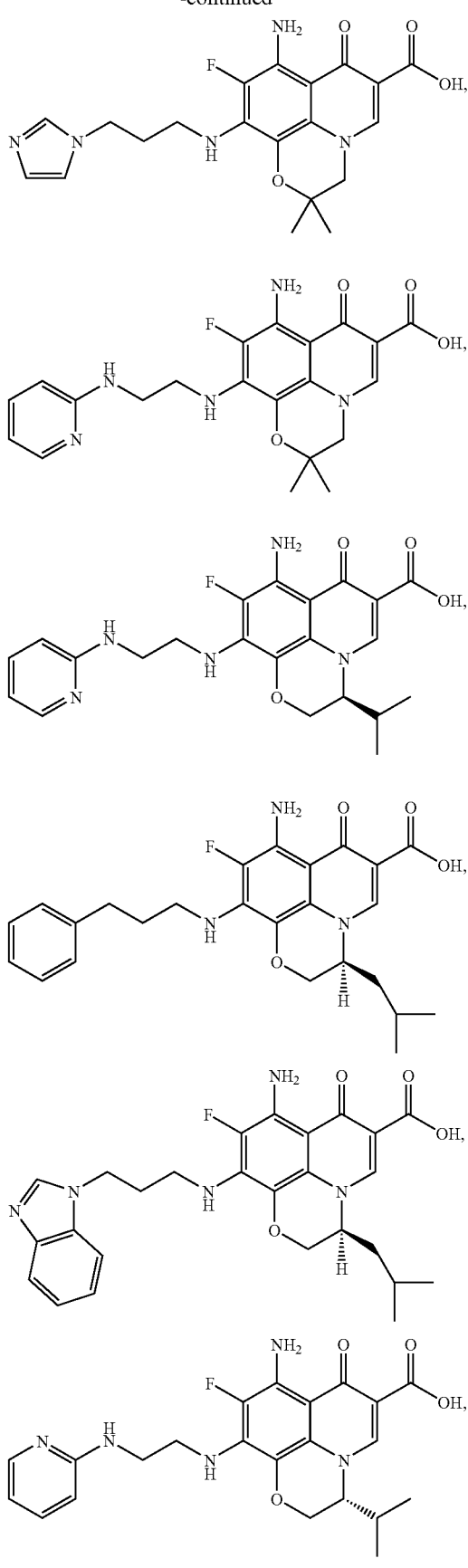

47
-continued
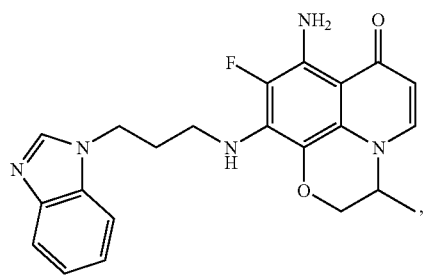
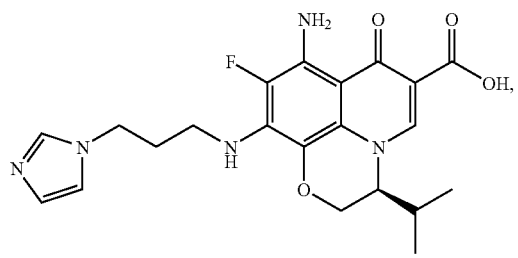
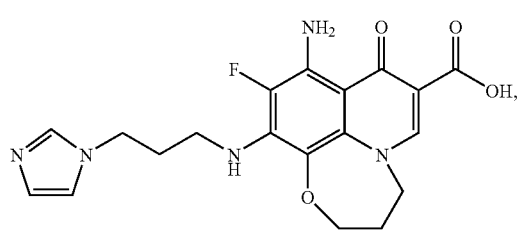
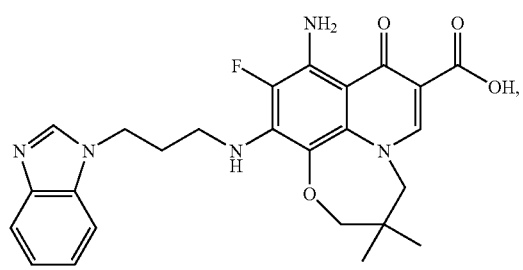
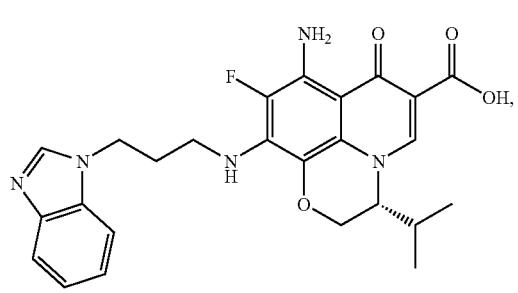
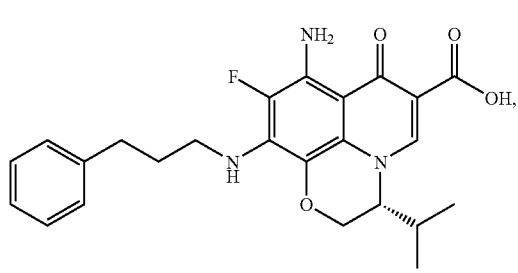
48
-continued
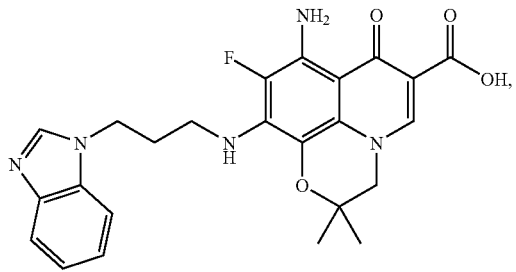
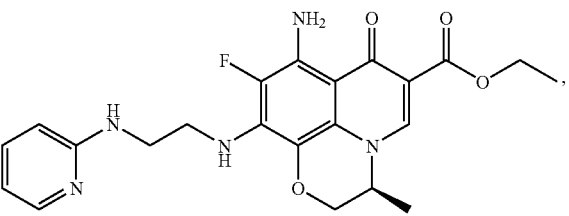
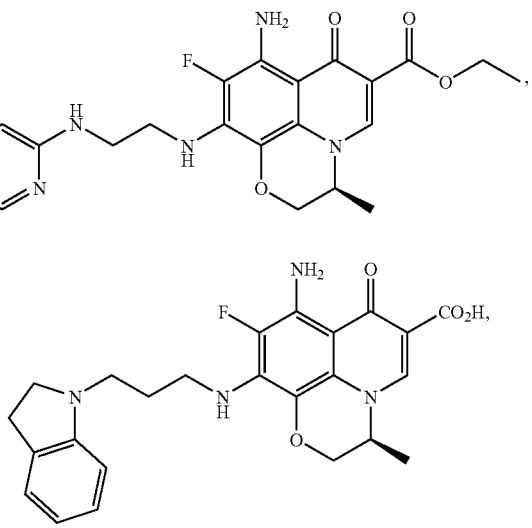
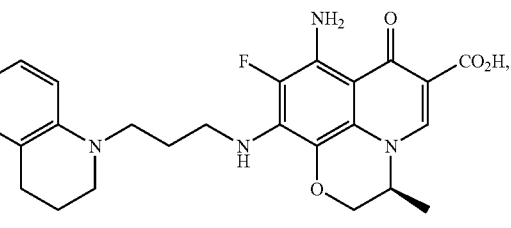
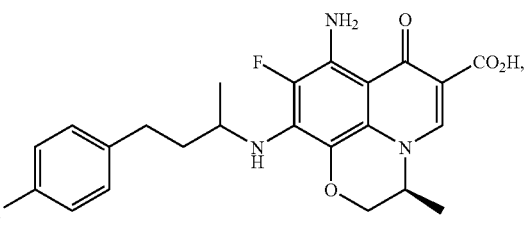
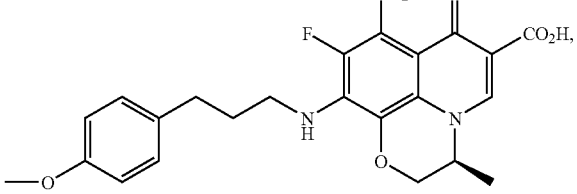
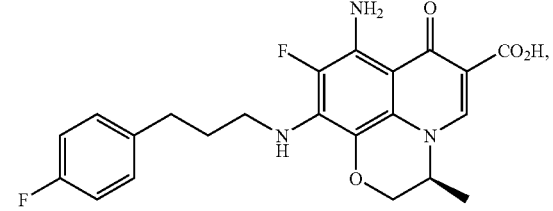

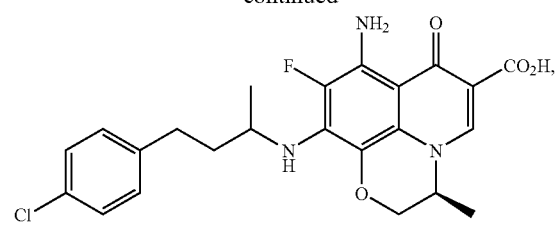
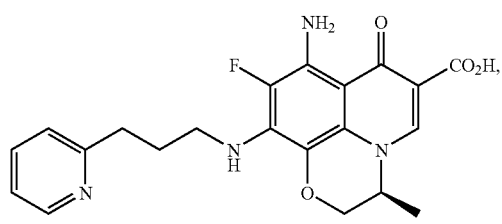
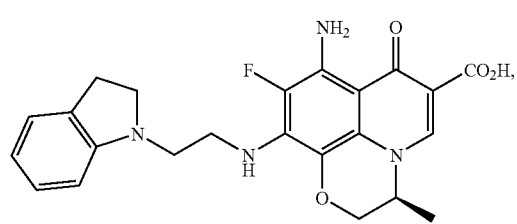
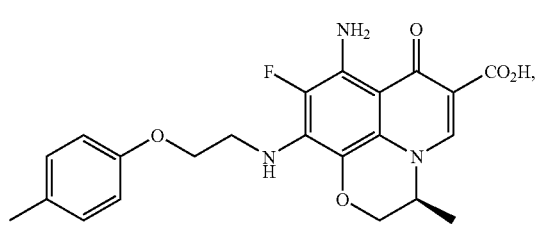
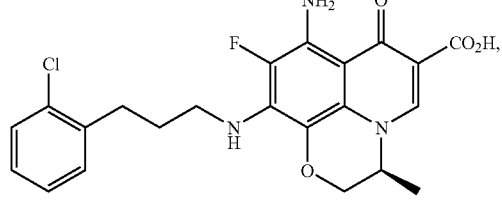
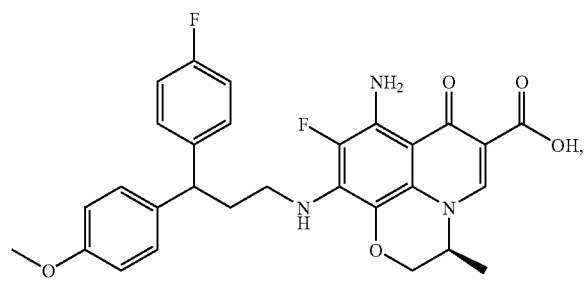
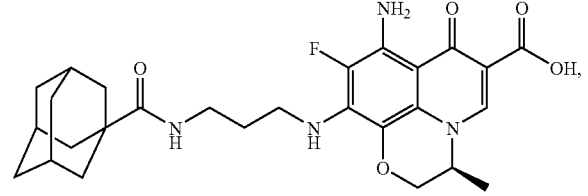
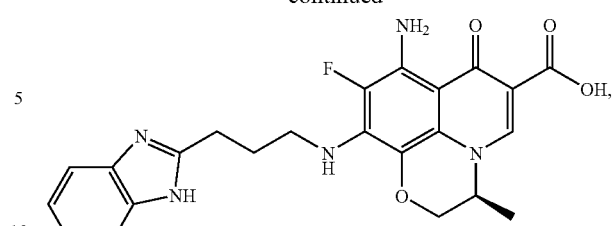
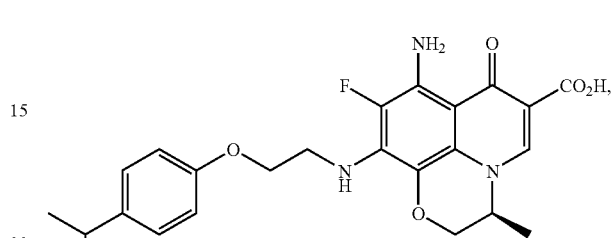

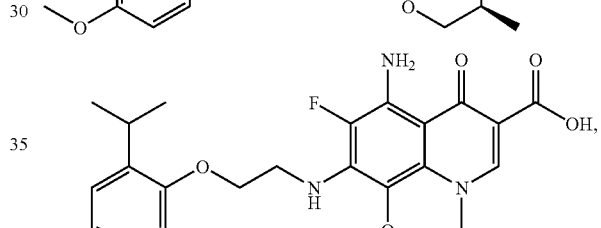
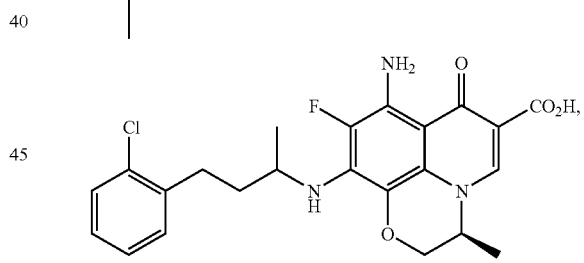
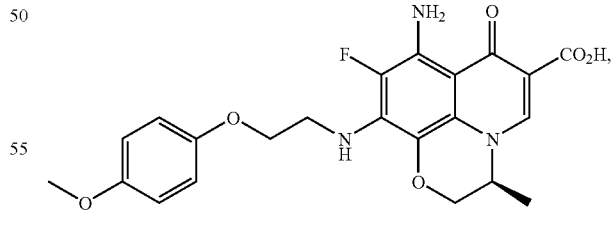
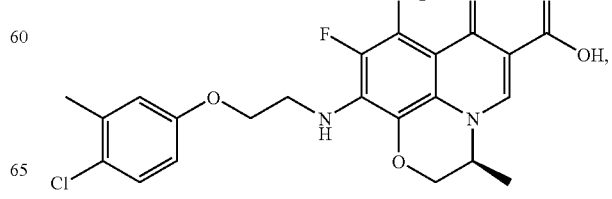

51
-continued
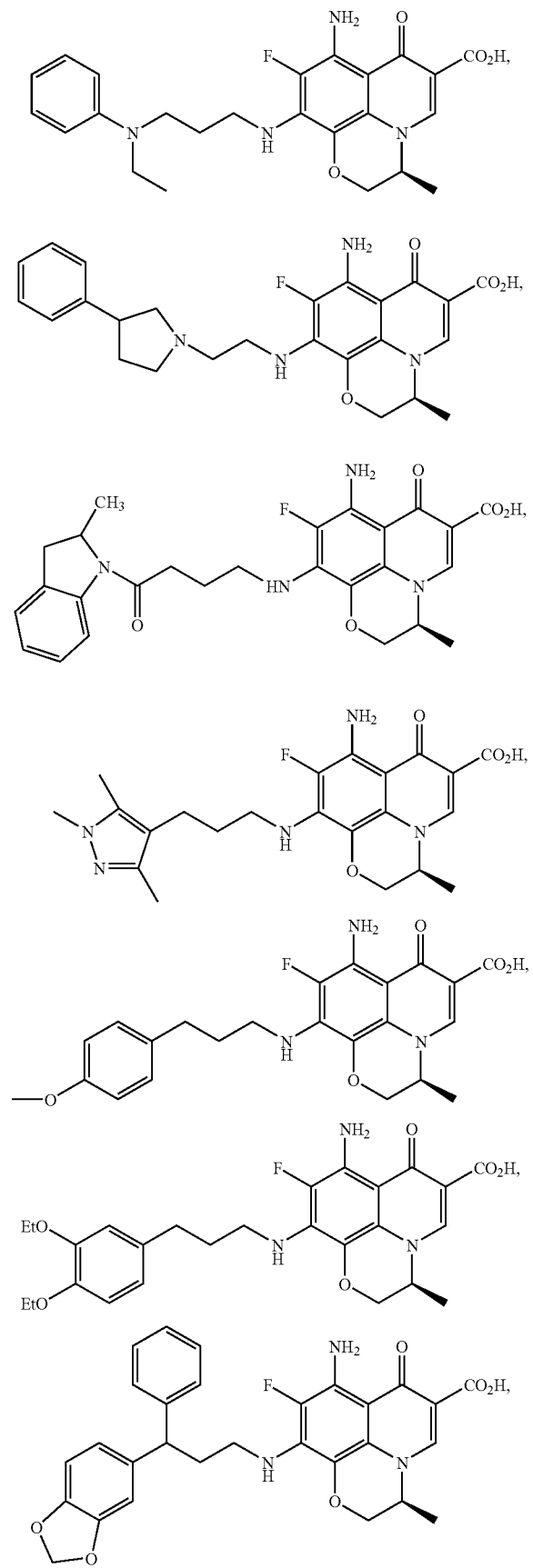
52
-continued
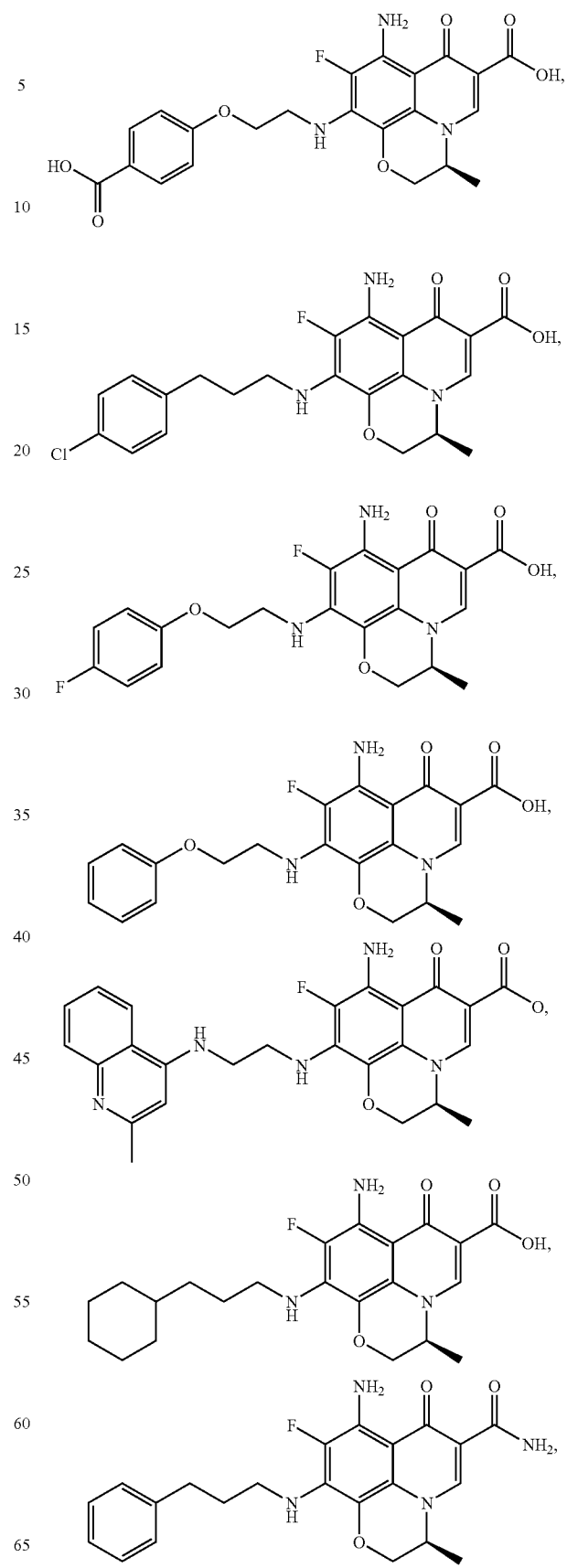

53
-continued
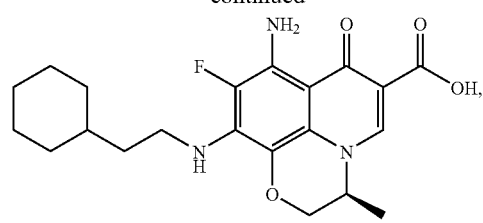
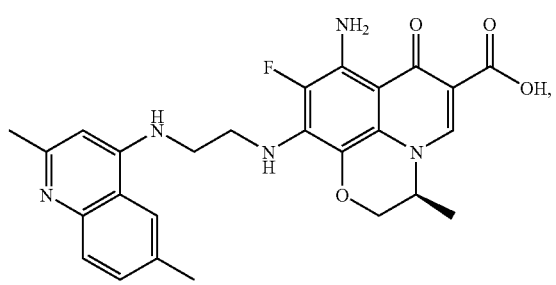
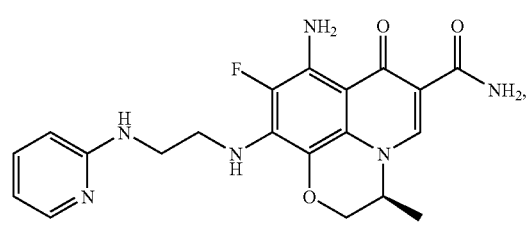
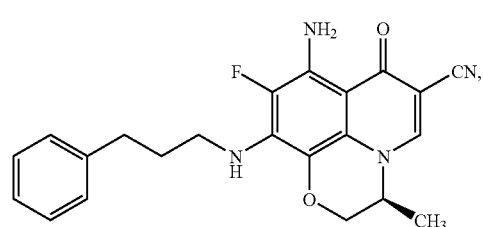
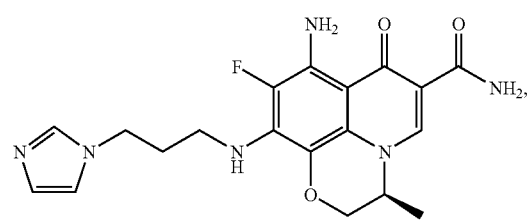
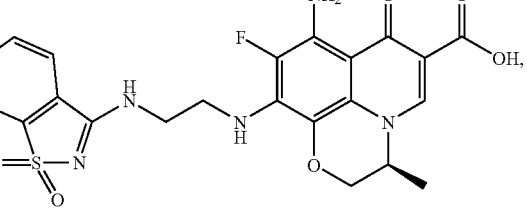
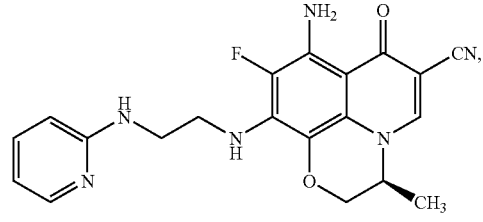
54
-continued
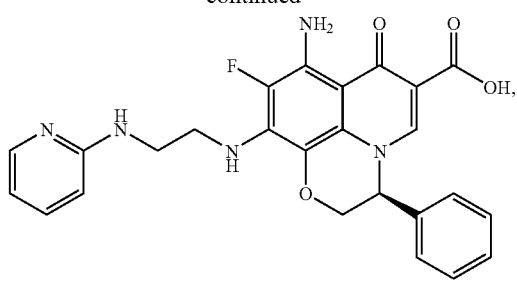
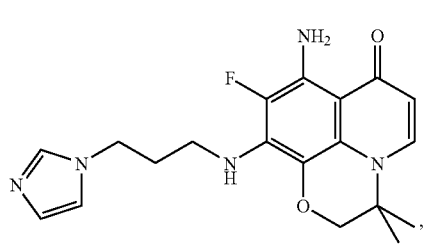
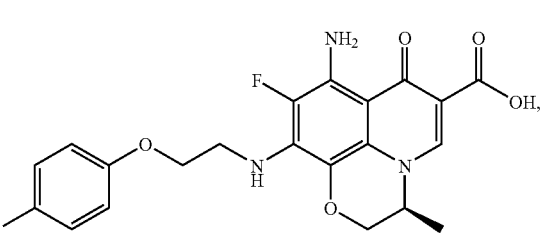
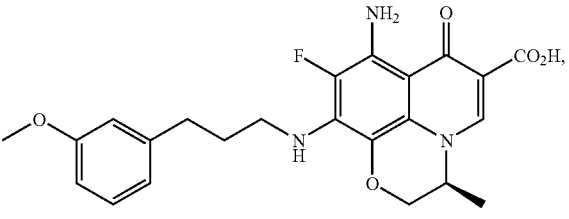
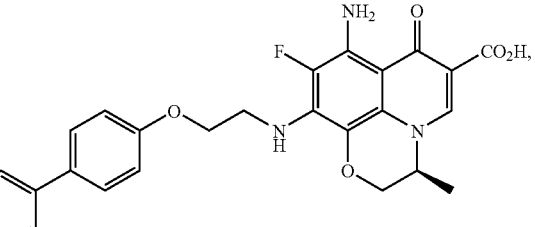
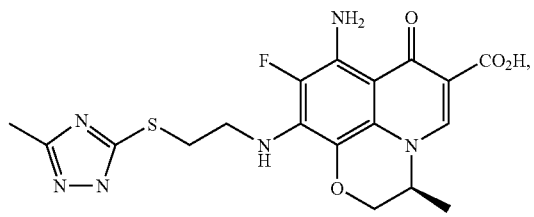
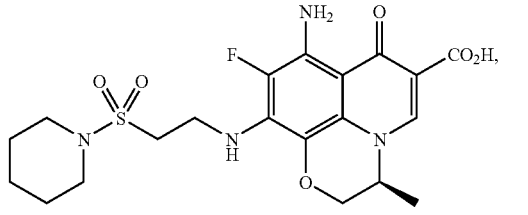

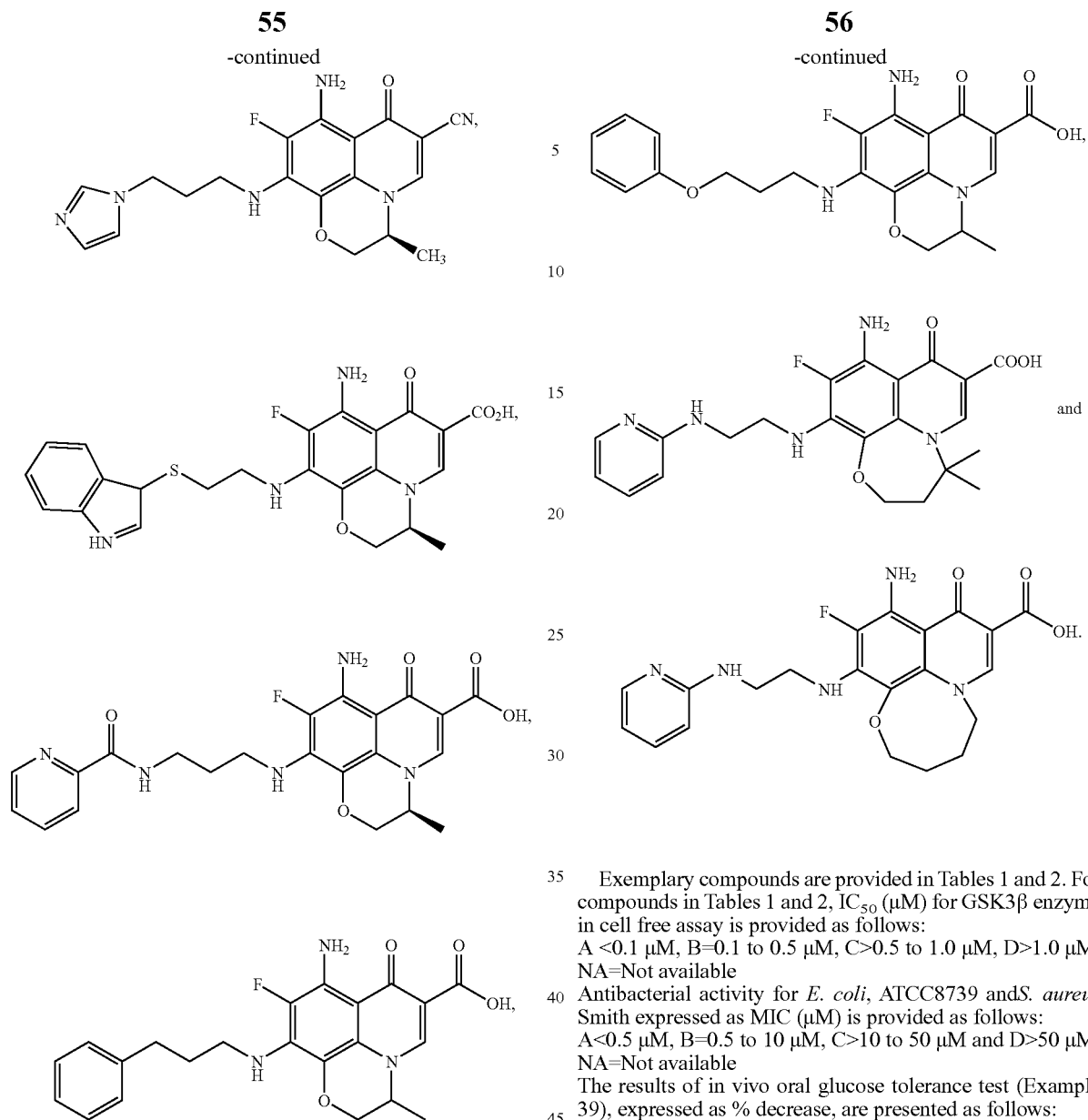

Exemplary compounds are provided in Tables 1 and 2. For compounds in Tables 1 and 2, IC$_{50}$ (μM) for GSK3β enzyme in cell free assay is provided as follows:
A <0.1 μM, B=0.1 to 0.5 μM, C>0.5 to 1.0 μM, D>1.0 μM, NA=Not available
Antibacterial activity for *E. coli*, ATCC8739 and *S. aureus* Smith expressed as MIC (μM) is provided as follows:
A<0.5 μM, B=0.5 to 10 μM, C>10 to 50 μM and D>50 μM, NA=Not available
The results of in vivo oral glucose tolerance test (Example 39), expressed as % decrease, are presented as follows:
A<5%, B=5 to 10%, C>10-20%, D>20% and NA=Not available

TABLE 1

| Comp.No | Structure | GSK3β IC50 [μM] | Antibacterial MIC (μM) | | In vivo studies 300 mg/kg |
| --- | --- | --- | --- | --- | --- |
| | | | *E.Coli* | *S. aureus* Smith | |
| 1 | 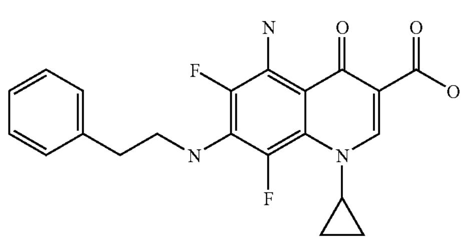 | B | B | A | NA |

TABLE 1-continued
| Comp.No | Structure | GSK3β IC50 [μM] | Antibacterial MIC (μM) | | In vivo studies 300 mg/kg |
|---|---|---|---|---|---|
| | | | E.Coli | S. aureus Smith | |
| 2 | 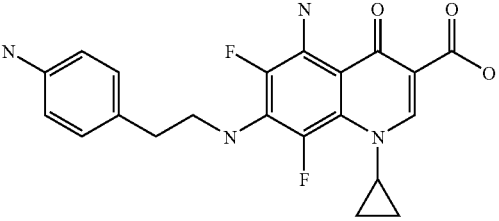 | C | NA | NA | NA |
| 3 | 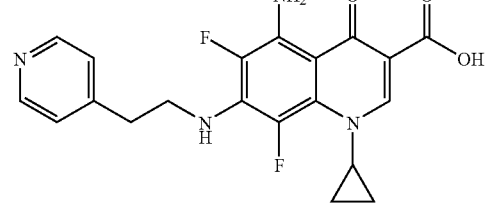 | B | B | A | NA |
| 4 | 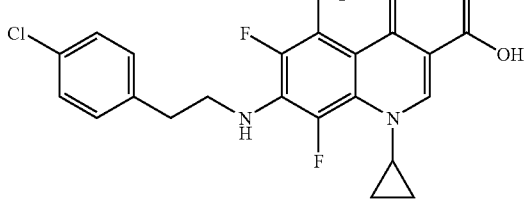 | B | NA | NA | NA |
| 5 | 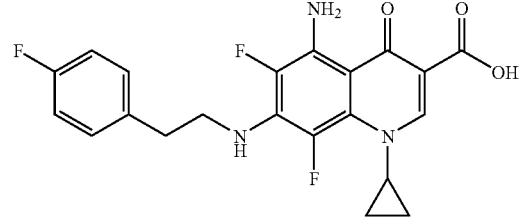 | B | B | A | NA |
| 6 | 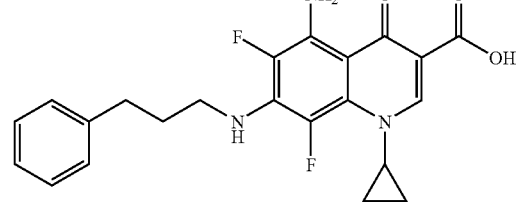 | A | C | B | NA |
| 7 | 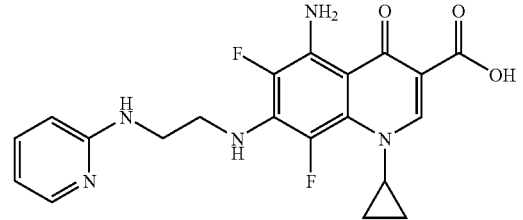 | B | B | B | NA |

TABLE 1-continued

| Comp.No | Structure | GSK3β IC50 [μM] | Antibacterial MIC (μM) | | In vivo studies 300 mg/kg |
|---|---|---|---|---|---|
| | | | E.Coli | S. aureus Smith | |
| 8 | 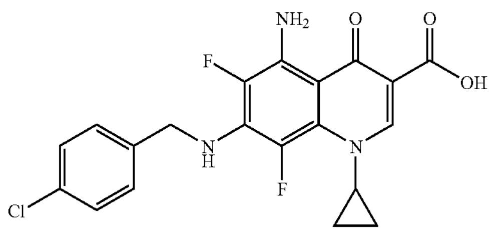 | C | NA | NA | NA |
| 9 | 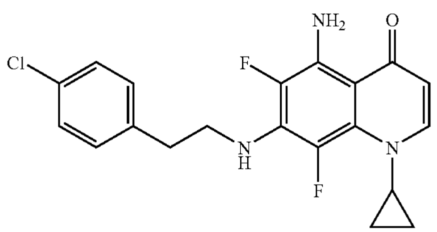 | C | NA | NA | NA |
| 10 | 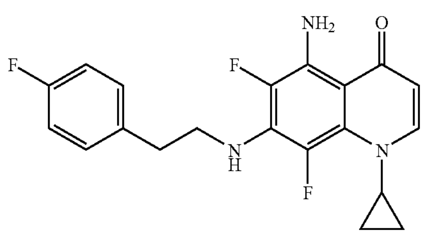 | C | C | C | NA |
| 11 | 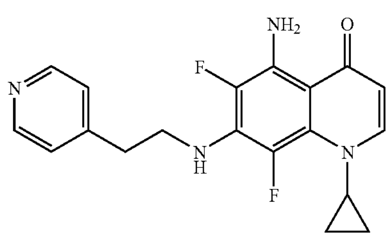 | B | D | D | NA |
| 12 | 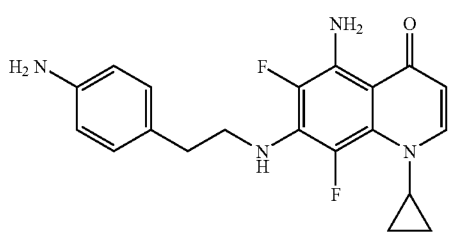 | C | D | C | NA |
| 13 | 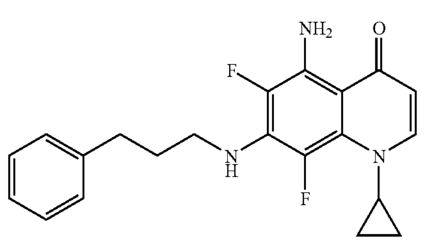 | B | C | C | NA |

TABLE 1-continued

| Comp.No | Structure | GSK3β IC50 [μM] | Antibacterial MIC (μM) | | In vivo studies 300 mg/kg |
|---|---|---|---|---|---|
| | | | E.Coli | S. aureus Smith | |
| 14 | 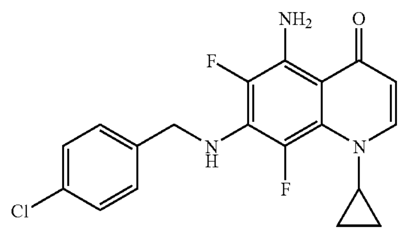 | D | NA | NA | NA |
| 15 | 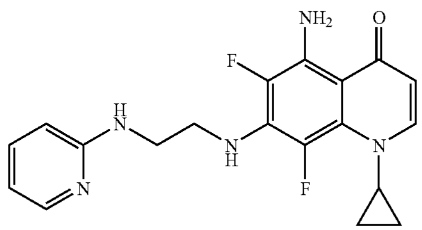 | B | D | D | NA |
| 16 | 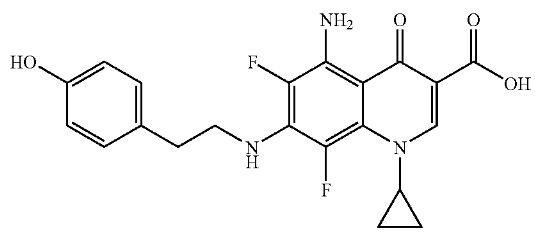 | C | B | A | NA |
| 17 | 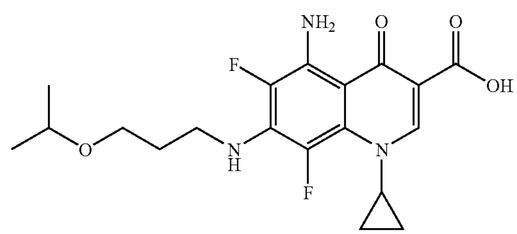 | B | B | B | NA |
| 18 | 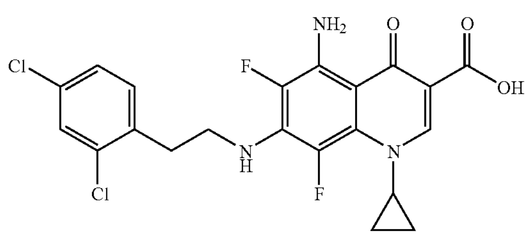 | C | NA | NA | NA |
| 19 | 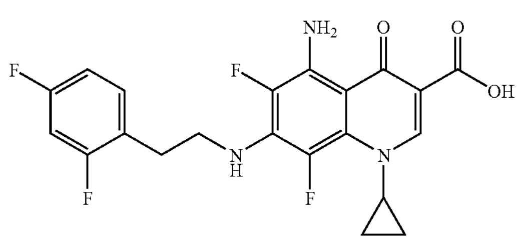 | B | B | B | NA |

TABLE 1-continued

| Comp.No | Structure | GSK3β IC50 [μM] | Antibacterial MIC (μM) | | In vivo studies 300 mg/kg |
|---|---|---|---|---|---|
| | | | E.Coli | S. aureus Smith | |
| 20 | 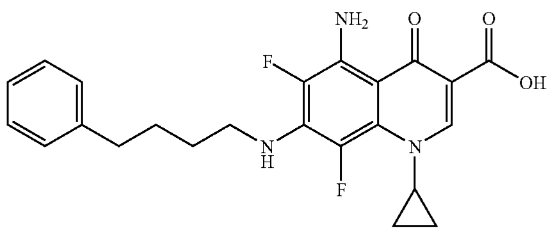 | B | C | B | NA |
| 21 | 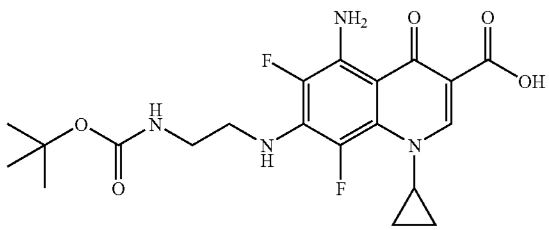 | C | B | B | NA |
| 22 | 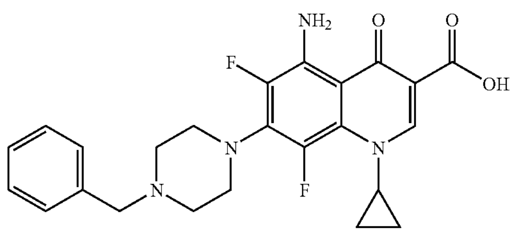 | D | NA | NA | NA |
| 23 | 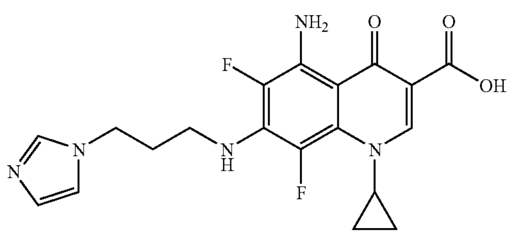 | A | B | B | NA |
| 24 | 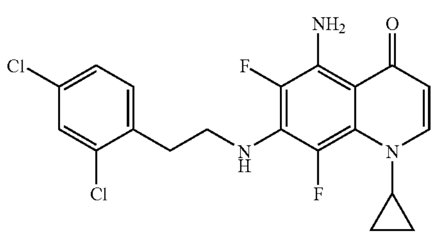 | D | NA | NA | NA |
| 25 | 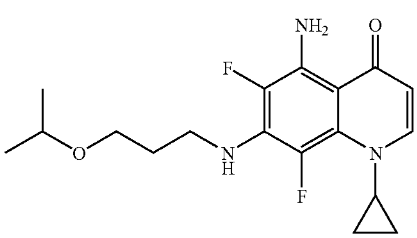 | D | NA | NA | NA |

TABLE 1-continued

| Comp.No | Structure | GSK3β IC50 [μM] | Antibacterial MIC (μM) | | In vivo studies 300 mg/kg |
|---|---|---|---|---|---|
| | | | E.Coli | S. aureus Smith | |
| 26 | 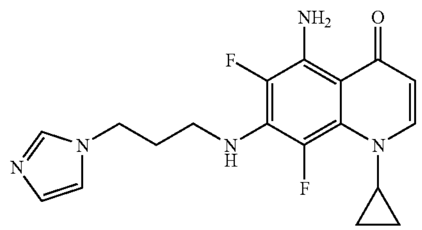 | B | D | D | NA |
| 27 | 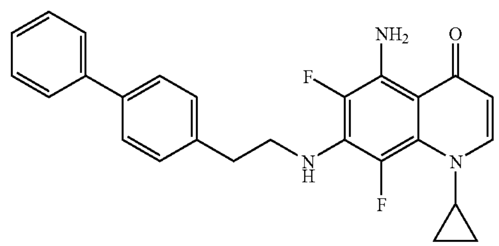 | D | NA | NA | NA |
| 28 | 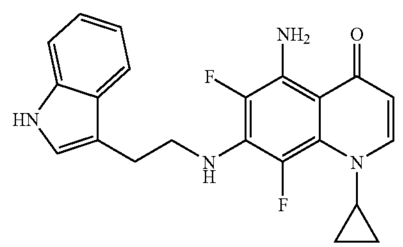 | B | D | D | NA |
| 29 | 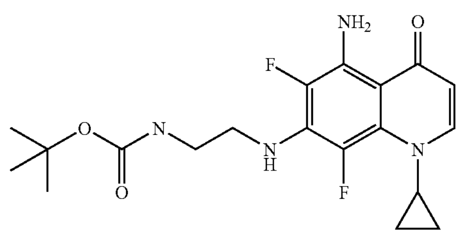 | B | D | D | NA |
| 30 | 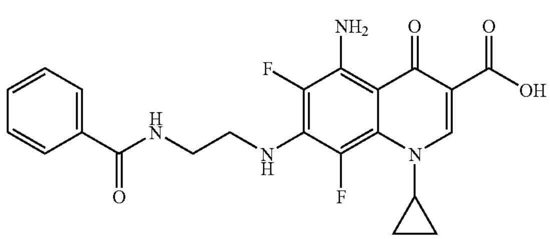 | C | NA | NA | NA |
| 31 | 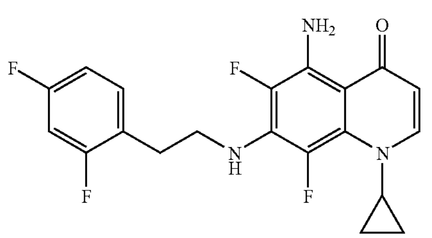 | D | NA | NA | NA |

TABLE 1-continued

| Comp.No | Structure | GSK3β IC50 [μM] | Antibacterial MIC (μM) E.Coli | S. aureus Smith | In vivo studies 300 mg/kg |
|---|---|---|---|---|---|
| 32 | 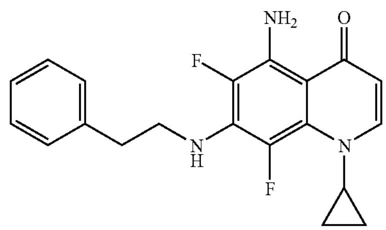 | C | NA | NA | NA |
| 33 | 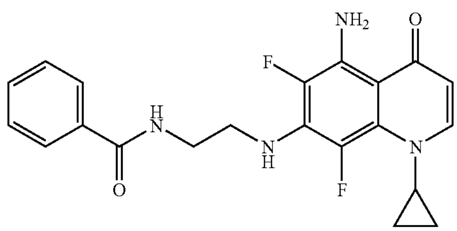 | C | NA | NA | NA |
| 34 | 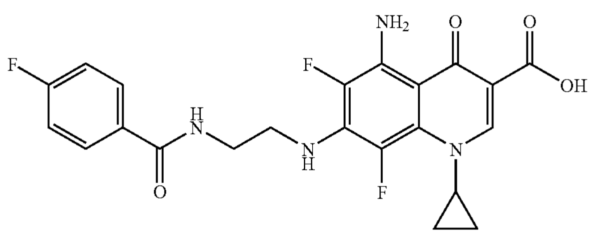 | B | NA | NA | NA |
| 35 | 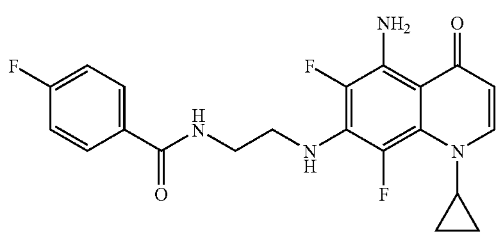 | B | NA | NA | NA |
| 36 | 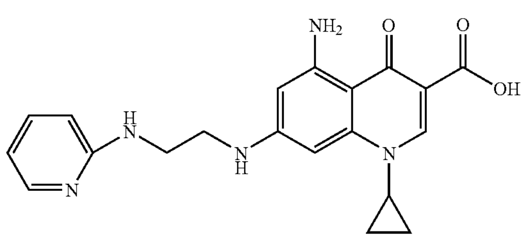 | D | NA | NA | NA |
| 37 | 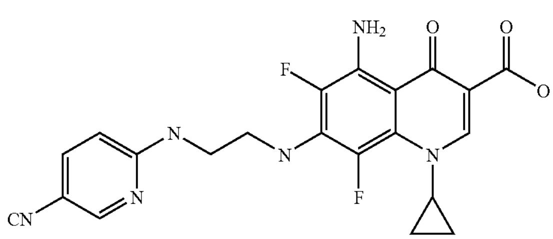 | B | NA | NA | NA |

TABLE 1-continued

| Comp.No | Structure | GSK3β IC50 [μM] | Antibacterial MIC (μM) | | In vivo studies 300 mg/kg |
|---|---|---|---|---|---|
| | | | E.Coli | S. aureus Smith | |
| 38 | 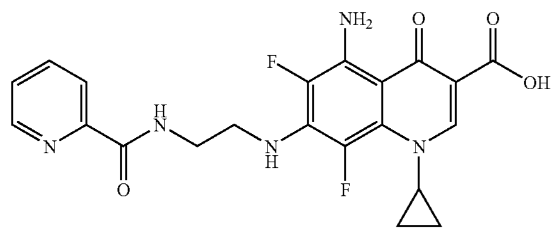 | C | NA | NA | NA |
| 39 | 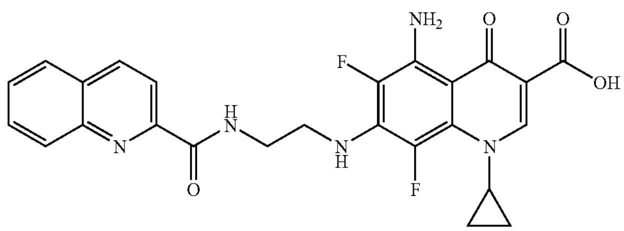 | C | NA | NA | NA |
| 40 | 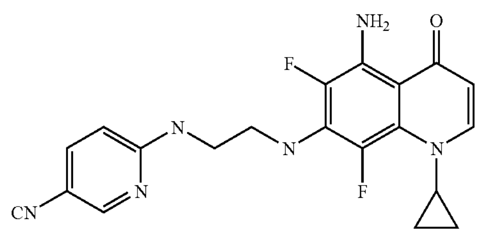 | B | NA | NA | NA |
| 41 | 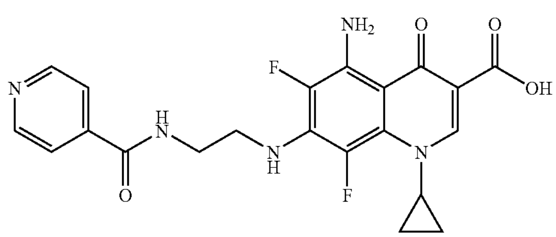 | C | NA | NA | NA |
| 42 | 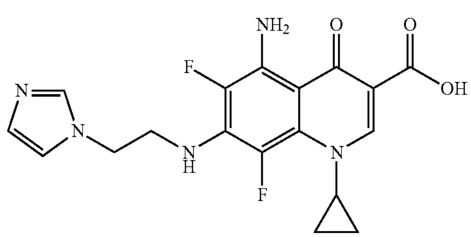 | D | NA | NA | NA |
| 43 | 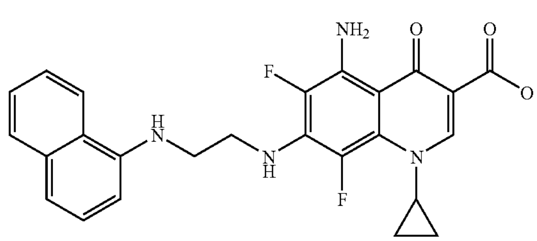 | A | B | B | NA |

TABLE 1-continued

| Comp.No | Structure | GSK3β IC50 [μM] | Antibacterial MIC (μM) E.Coli | S. aureus Smith | In vivo studies 300 mg/kg |
|---|---|---|---|---|---|
| 44 | 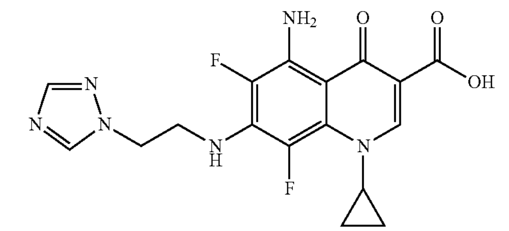 | D | NA | NA | NA |
| 45 | 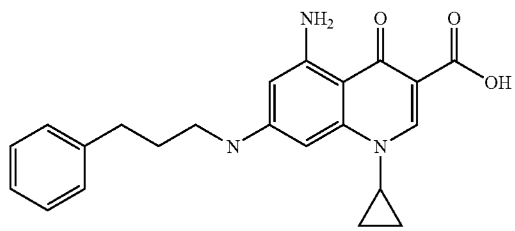 | D | NA | NA | NA |
| 46 | 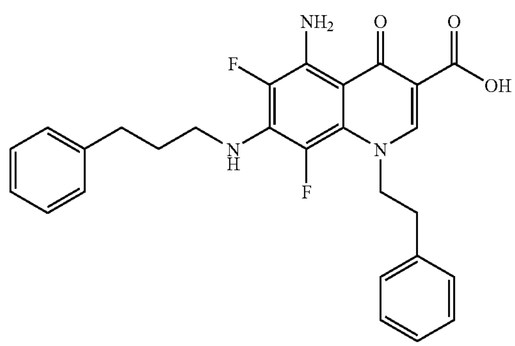 | A | C | C | NA |
| 47 | 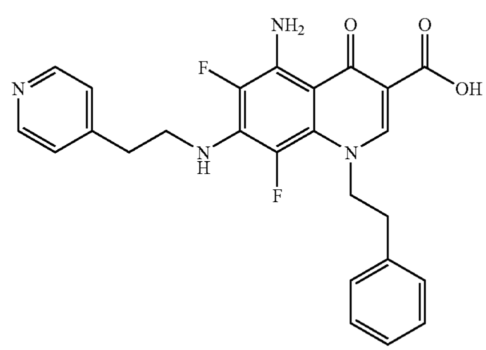 | A | C | C | NA |
| 48 | 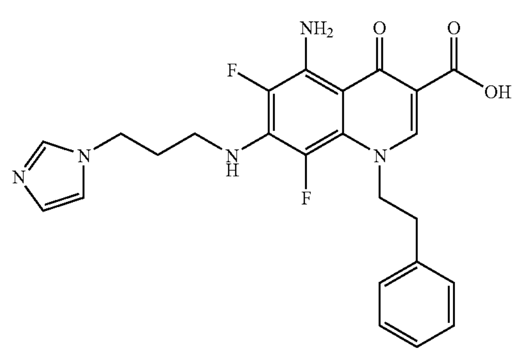 | A | D | D | NA |

TABLE 1-continued
| Comp.No | Structure | GSK3β IC50 [μM] | Antibacterial MIC (μM) E.Coli | S. aureus Smith | In vivo studies 300 mg/kg |
|---|---|---|---|---|---|
| 49 | 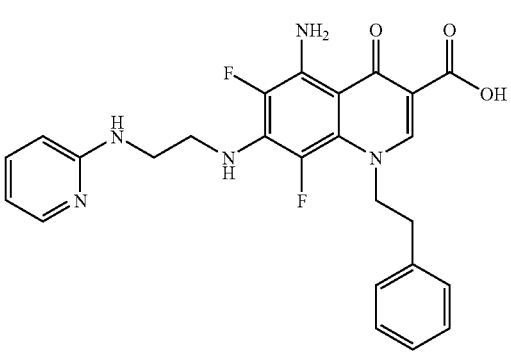 | B | C | C | NA |
| 50 | 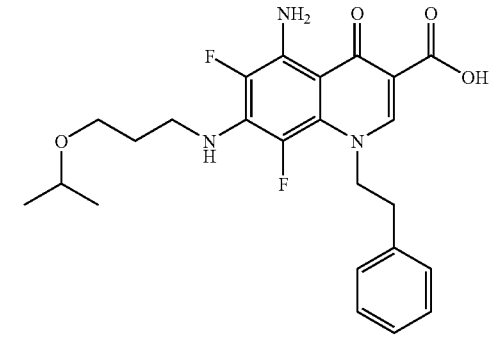 | C | B | B | NA |
| 51 | 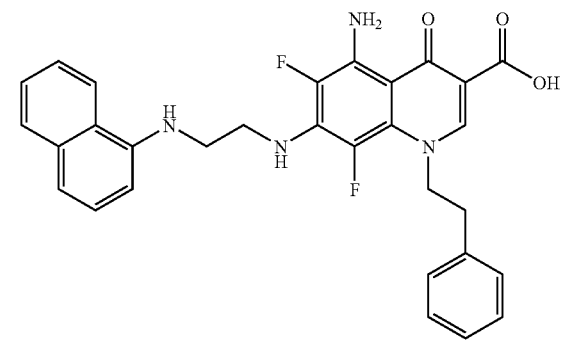 | B | C | C | NA |
| 52 | 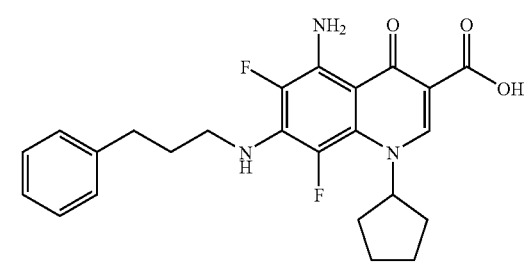 | A | C | C | NA |

TABLE 1-continued

| Comp.No | Structure | GSK3β IC50 [μM] | Antibacterial MIC (μM) | | In vivo studies 300 mg/kg |
|---|---|---|---|---|---|
| | | | E.Coli | S. aureus Smith | |
| 53 | 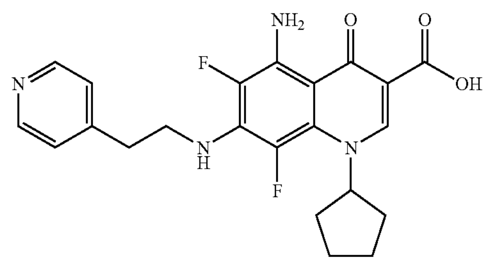 | B | C | C | NA |
| 54 | 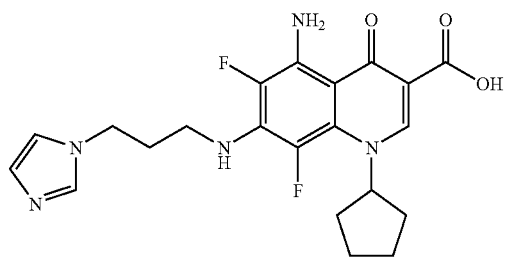 | A | D | D | NA |
| 55 | 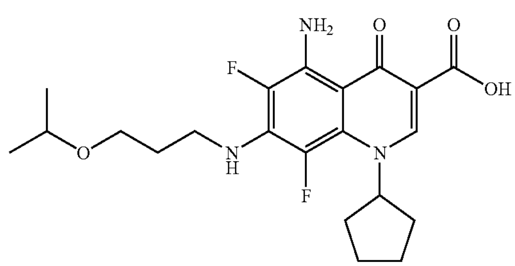 | A | C | C | NA |
| 56 | 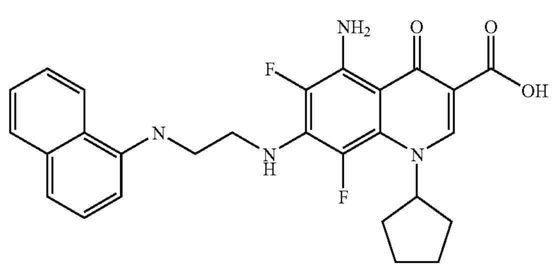 | A | C | C | NA |
| 57 | 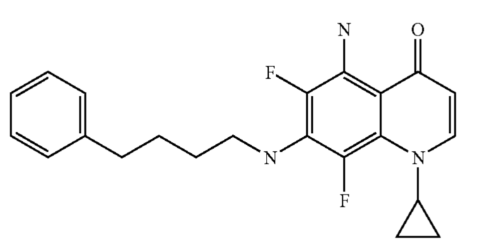 | C | C | C | NA |

TABLE 1-continued

| Comp.No | Structure | GSK3β IC50 [μM] | Antibacterial MIC (μM) | | In vivo studies 300 mg/kg |
| --- | --- | --- | --- | --- | --- |
| | | | E.Coli | S. aureus Smith | |
| 58 | 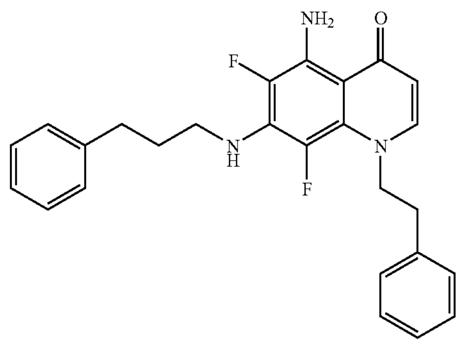 | B | C | C | NA |
| 59 | 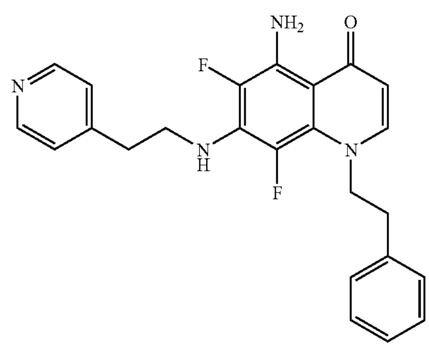 | B | D | D | NA |
| 60 | 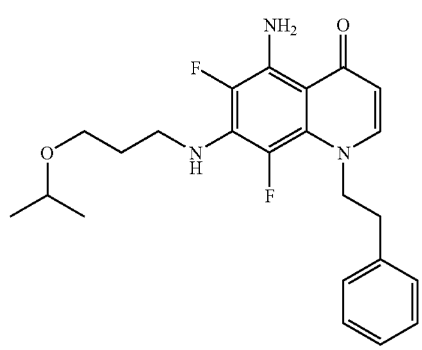 | C | C | C | NA |
| 61 | 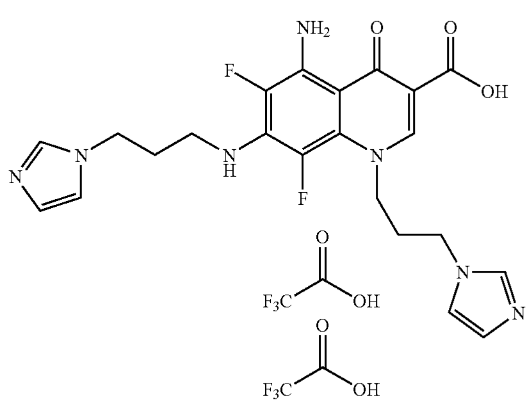 | B | D | D | NA |

TABLE 1-continued

| Comp.No | Structure | GSK3β IC50 [μM] | Antibacterial MIC (μM) E.Coli | S. aureus Smith | In vivo studies 300 mg/kg |
|---|---|---|---|---|---|
| 62 | 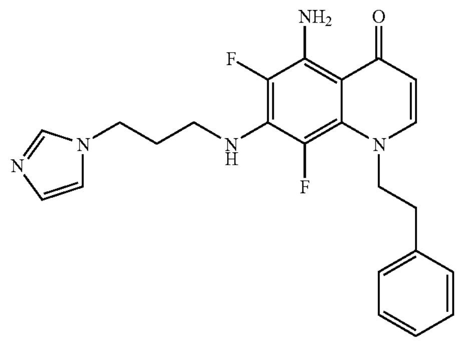 | B | D | D | B |
| 63 | 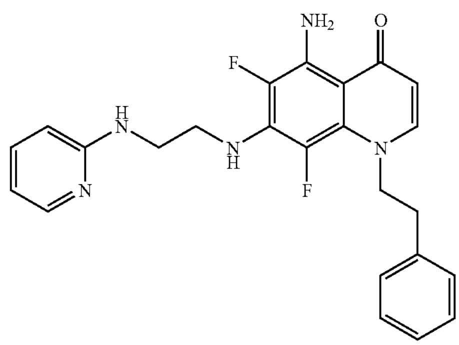 | B | C | C | NA |
| 64 | 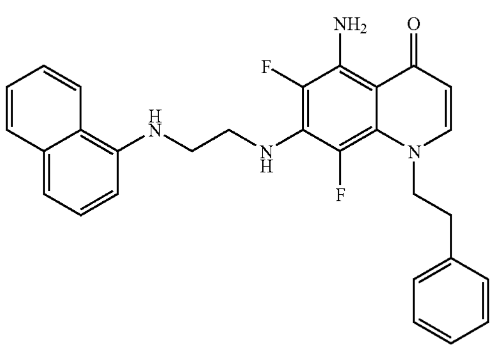 | B | C | C | NA |
| 65 | 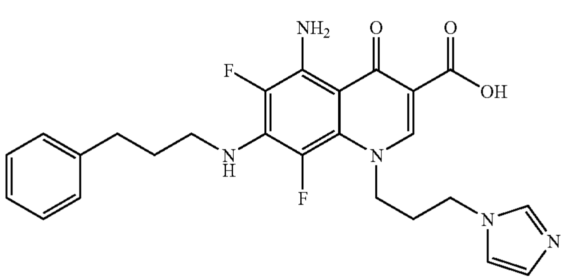 | B | C | C | NA |

TABLE 1-continued

| Comp.No | Structure | GSK3β IC50 [μM] | Antibacterial MIC (μM) | | In vivo studies 300 mg/kg |
|---|---|---|---|---|---|
| | | | E.Coli | S. aureus Smith | |
| 66 | 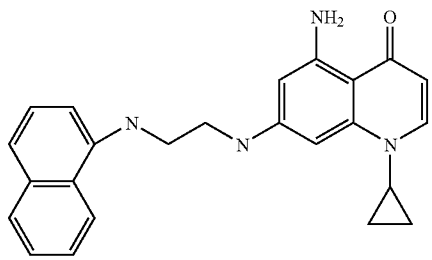 | A | C | C | NA |
| 67 | 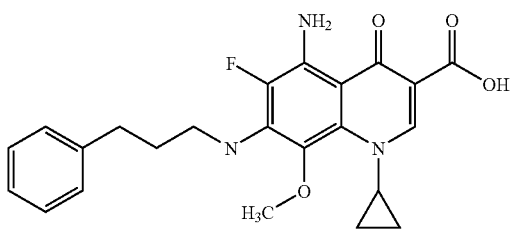 | A | C | B | NA |
| 68 | 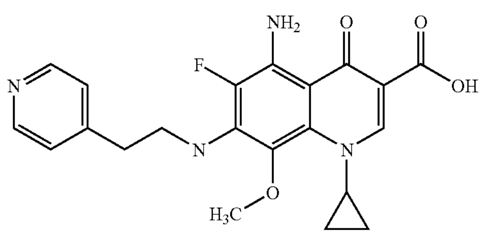 | C | C | B | NA |
| 69 | 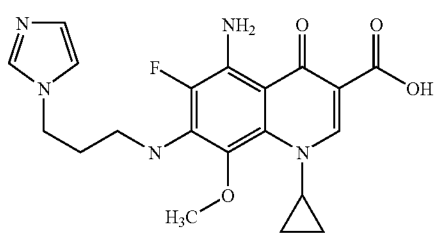 | A | C | B | NA |
| 70 | 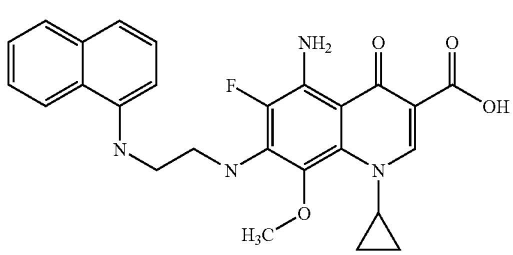 | A | D | B | A |
| 71 | 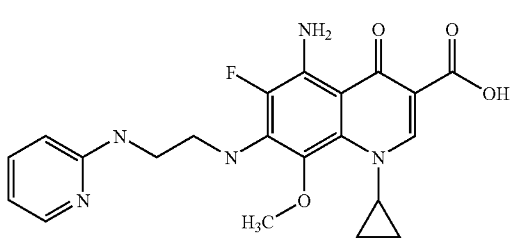 | B | B | B | C |

TABLE 1-continued

| Comp.No | Structure | GSK3β IC50 [μM] | Antibacterial MIC (μM) | | In vivo studies 300 mg/kg |
|---|---|---|---|---|---|
| | | | E.Coli | S. aureus Smith | |
| 72 | 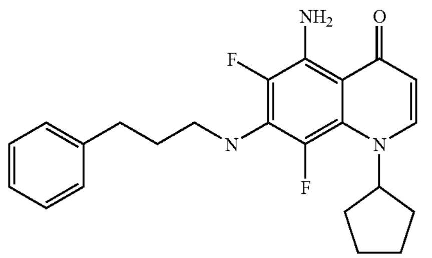 | A | C | C | NA |
| 73 | 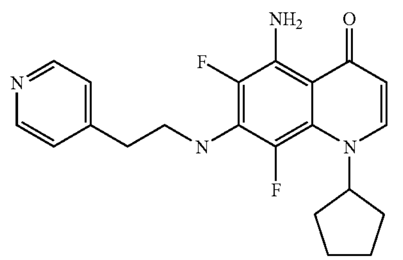 | A | D | D | NA |
| 74 | 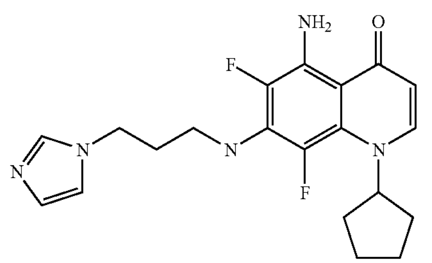 | A | D | D | NA |
| 75 | 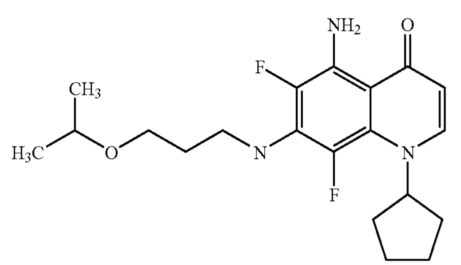 | B | D | D | NA |
| 76 | 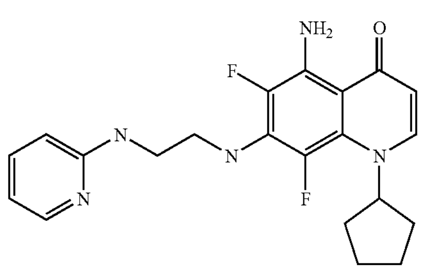 | A | D | D | NA |

TABLE 1-continued

| Comp.No | Structure | GSK3β IC50 [μM] | Antibacterial MIC (μM) E.Coli | S. aureus Smith | In vivo studies 300 mg/kg |
|---|---|---|---|---|---|
| 77 | 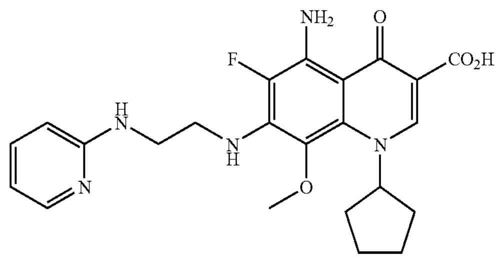 | D | C | B | NA |
| 78 | 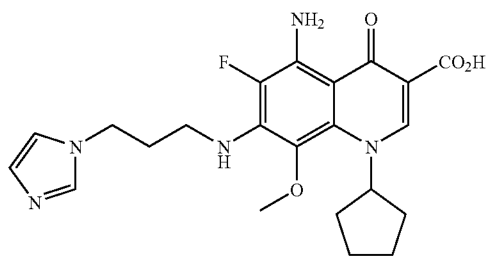 | C | D | D | NA |
| 79 | 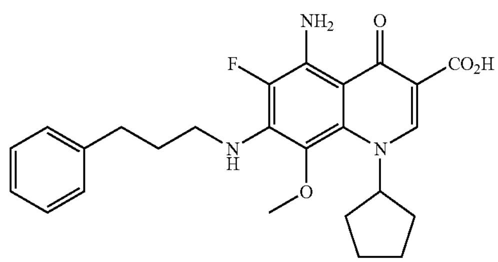 | B | C | C | NA |
| 80 | 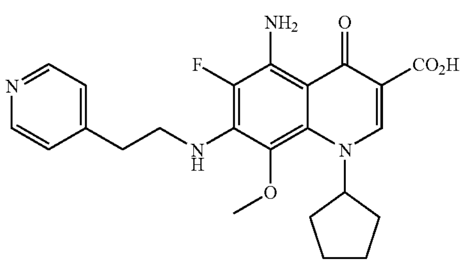 | D | D | C | NA |
| 81 | 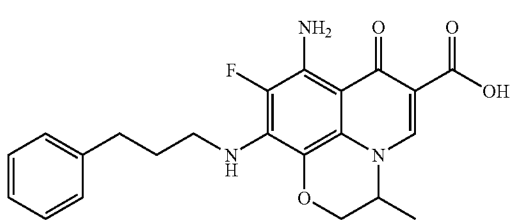 | A | C | B | NA |
| 82 | 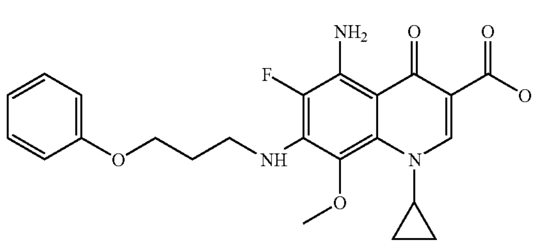 | D | C | C | NA |

TABLE 1-continued

| Comp.No | Structure | GSK3β IC50 [μM] | Antibacterial MIC (μM) | | In vivo studies 300 mg/kg |
| --- | --- | --- | --- | --- | --- |
| | | | E.Coli | S. aureus Smith | |
| 83 | 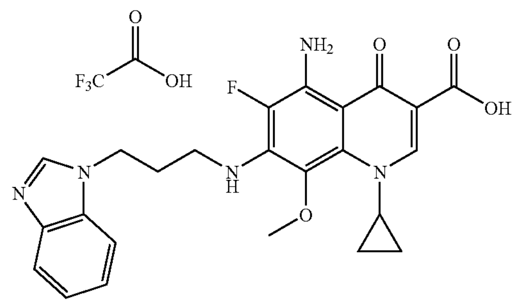 | A | C | B | NA |
| 84 | 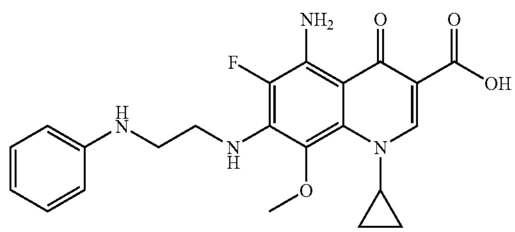 | B | C | B | NA |
| 85 | 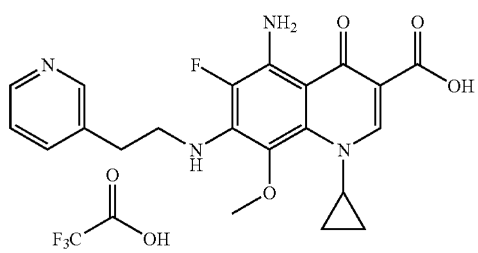 | D | B | A | NA |
| 86 | 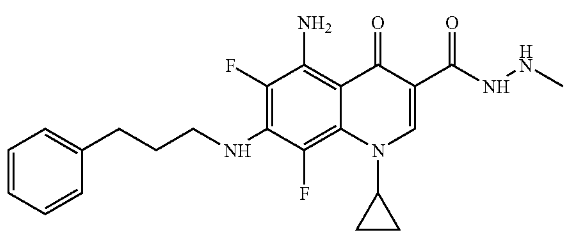 | D | NA | NA | NA |
| 87 | 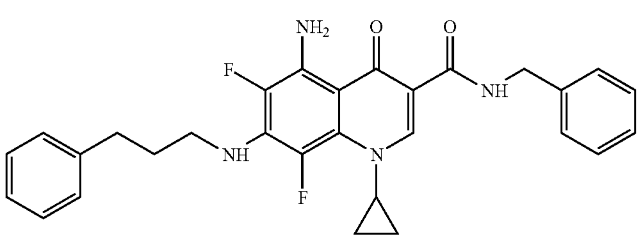 | NA | NA | NA | NA |
| 88 | 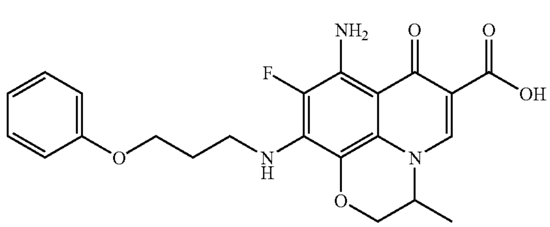 | B | NA | NA | NA |

TABLE 1-continued
| Comp.No | Structure | GSK3β IC50 [μM] | Antibacterial MIC (μM) E.Coli | S. aureus Smith | In vivo studies 300 mg/kg |
|---|---|---|---|---|---|
| 89 | 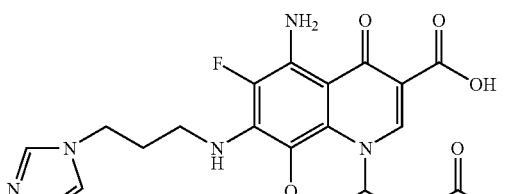 | A | NA | NA | NA |
| 90 | 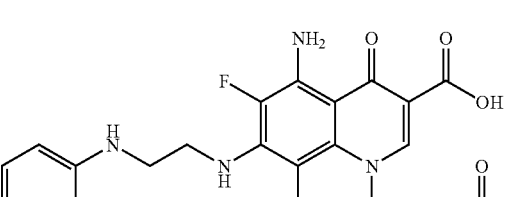 | A | B | B | NA |
TABLE 2
| Compound Number | Structure | GSK3β IC$_{50}$ [μM] | In vivo studies 300 mg/kg | Antimicrobial MIC [μM] E. Coli | S. aureus |
|---|---|---|---|---|---|
| 1 | 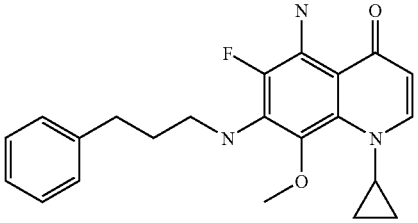 | B | NA | C | C |
| 2 | 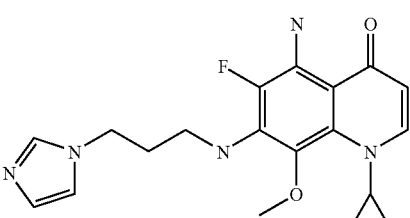 | B | NA | D | D |
| 3 | 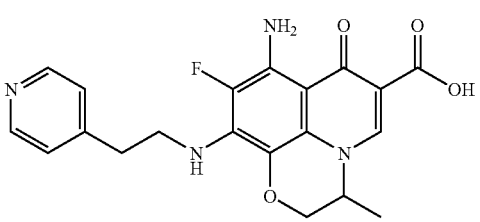 | B | NA | B | B |

TABLE 2-continued

| Compound Number | Structure | GSK3β IC$_{50}$ [μM] | In vivo studies 300 mg/kg | Antimicrobial MIC [μM] | |
| --- | --- | --- | --- | --- | --- |
| | | | | E. Coli | S. aureus |
| 4 | 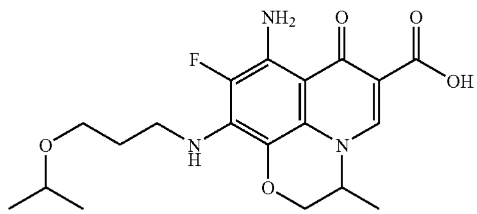 | B | NA | D | B |
| 5 | 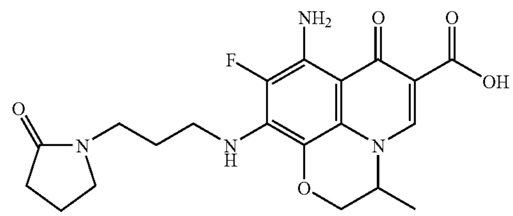 | A | NA | D | B |
| 6 | 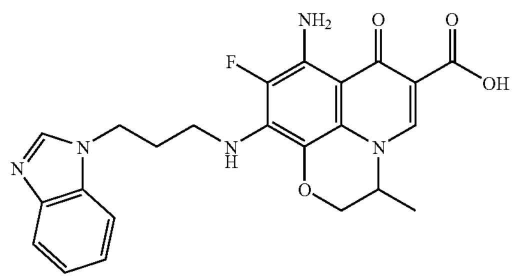 | A | NA | C | B |
| 7 | 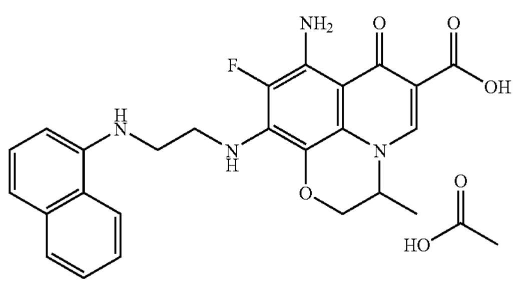 | A | NA | NA | NA |
| 8 | 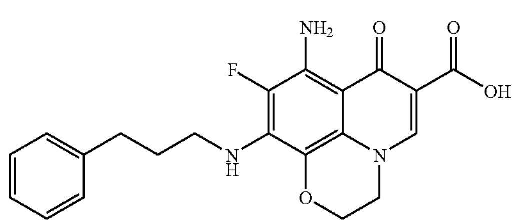 | D | NA | C | C |
| 9 | 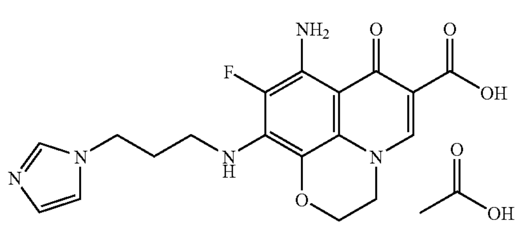 | C | NA | C | D |

TABLE 2-continued

| Compound Number | Structure | GSK3β IC$_{50}$ [μM] | In vivo studies 300 mg/kg | Antimicrobial MIC [μM] E. Coli | S. aureus |
|---|---|---|---|---|---|
| 10 | 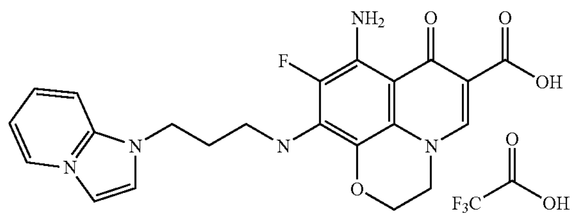 | C | NA | NA | NA |
| 11 | 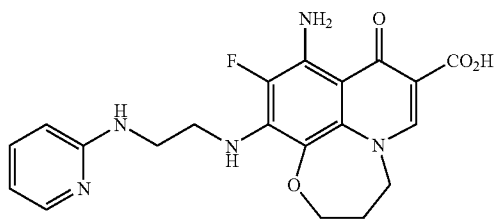 | D | NA | NA | NA |
| 12 | 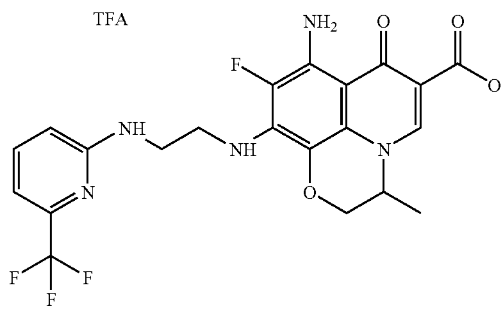 | A | NA | C | B |
| 13 | 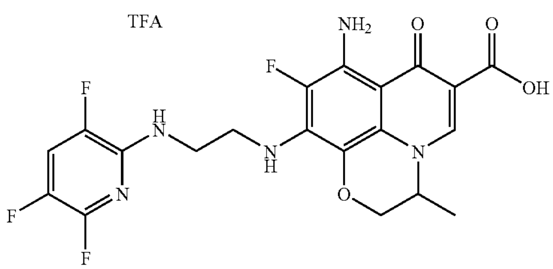 | A | NA | C | B |
| 14 | 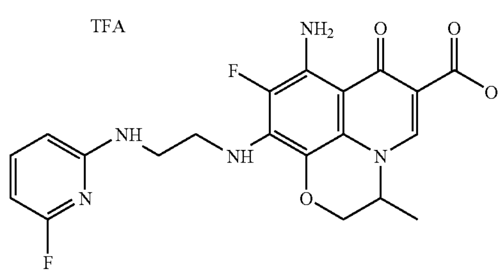 | A | NA | C | B |

TABLE 2-continued

| Compound Number | Structure | GSK3β IC$_{50}$ [μM] | In vivo studies 300 mg/kg | Antimicrobial MIC [μM] | |
| --- | --- | --- | --- | --- | --- |
| | | | | E. Coli | S. aureus |
| 15 | TFA (structure) | A | NA | B | B |
| 16 | TFA (structure) | A | NA | D | D |
| 17 | HCl (structure) | NA | C | NA | NA |
| 18 | TFA (structure) | A | C | B | B |
| 19 | TFA (structure) | A | NA | C | B |
| 20 | TFA (structure) | B | NA | C | B |

TABLE 2-continued

| Compound Number | Structure | GSK3β IC$_{50}$ [µM] | In vivo studies 300 mg/kg | Antimicrobial MIC [µM] | |
| --- | --- | --- | --- | --- | --- |
| | | | | E. Coli | S. aureus |
| 21 | 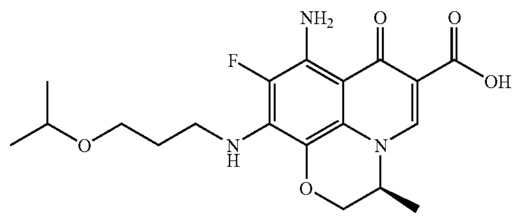 | B | NA | D | B |
| 22 | TFA | B | NA | B | B |
| 23 | 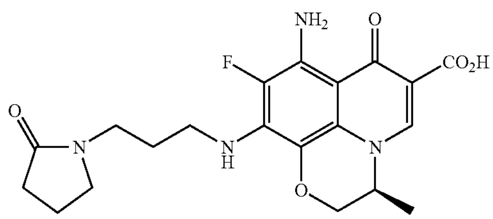 | B | NA | B | B |
| 24 | TFA | B | NA | B | B |
| 25 | 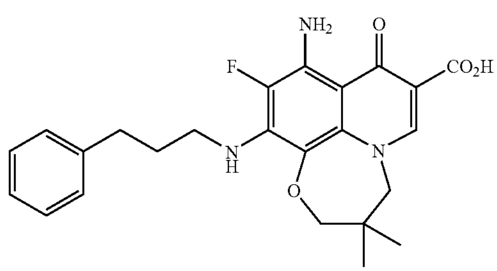 | A | NA | B | B |
| 26 | TFA | A | NA | C | C |

TABLE 2-continued

| Compound Number | | Structure | GSK3β IC$_{50}$ [μM] | In vivo studies 300 mg/kg | Antimicrobial MIC [μM] | |
|---|---|---|---|---|---|---|
| | | | | | E. Coli | S. aureus |
| 27 | | 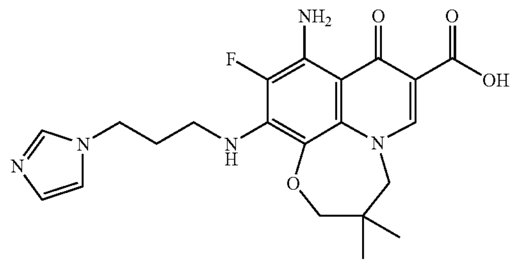 | A | NA | NA | NA |
| 28 | | 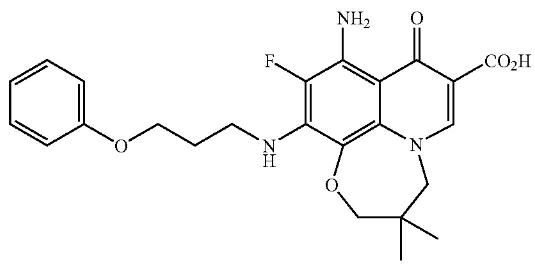 | B | NA | NA | NA |
| 29 | | 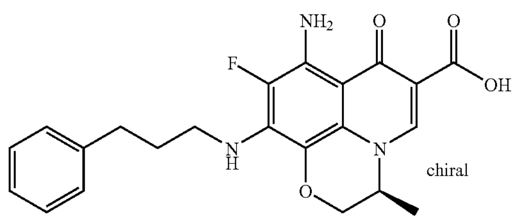 | A | NA | C | B |
| 30 | TFA | 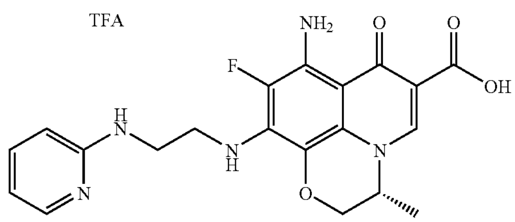 | C | NA | D | D |
| 31 | HCl | 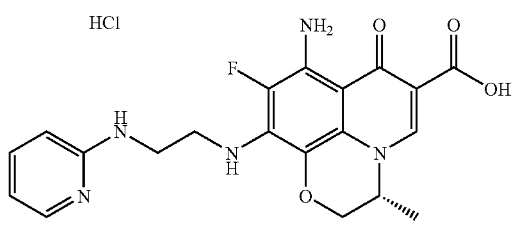 | B | D | C | C |
| 32 | TFA | 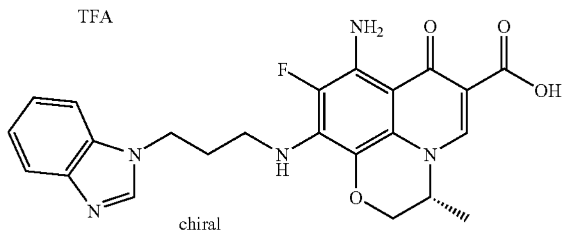 | B | NA | C | C |

TABLE 2-continued

| Compound Number | Structure | | GSK3β IC$_{50}$ [μM] | In vivo studies 300 mg/kg | Antimicrobial MIC [μM] | |
| --- | --- | --- | --- | --- | --- | --- |
| | | | | | E. Coli | S. aureus |
| 33 | TFA | (structure) | B | D | D | D |
| 34 | HCl | (structure) | B | D | NA | NA |
| 35 | 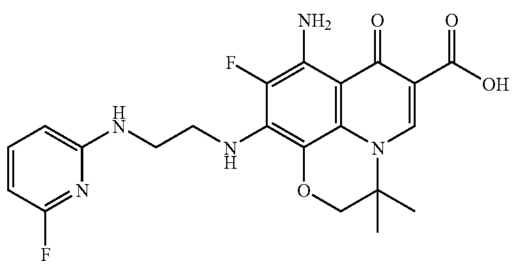 | (structure) | A | NA | NA | NA |
| 36 | 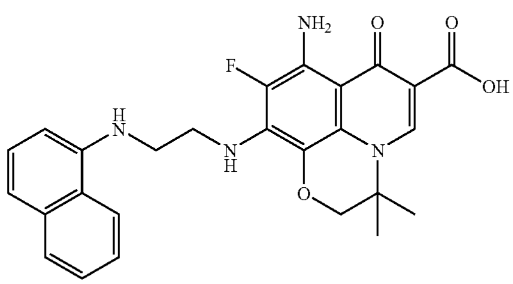 | (structure) | A | NA | C | C |
| 37 | 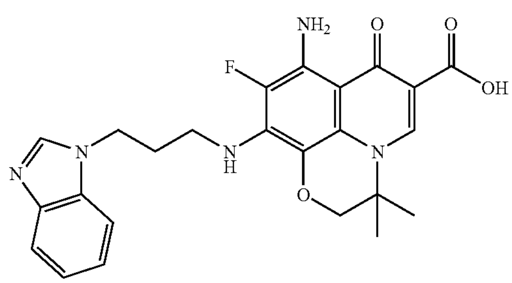 | (structure) | A | NA | B | B |

TABLE 2-continued

| Compound Number | Structure | GSK3β IC$_{50}$ [μM] | In vivo studies 300 mg/kg | Antimicrobial MIC [μM] E. Coli | Antimicrobial MIC [μM] S. aureus |
|---|---|---|---|---|---|
| 38 | 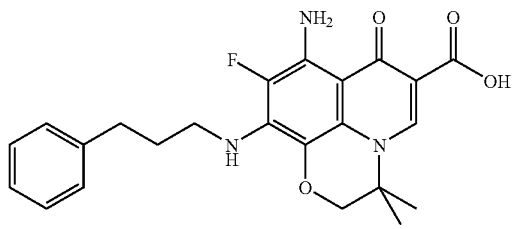 | A | NA | C | C |
| 39 | 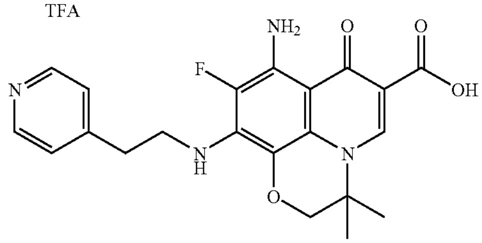 | B | NA | D | C |
| 40 | 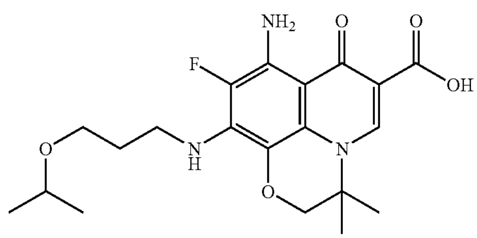 | B | NA | D | D |
| 41 | 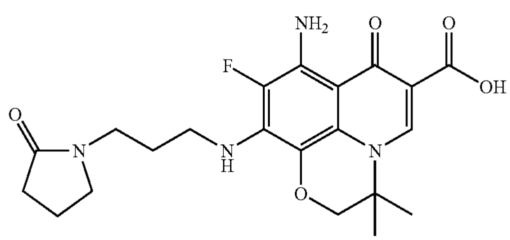 | A | NA | D | D |
| 42 | 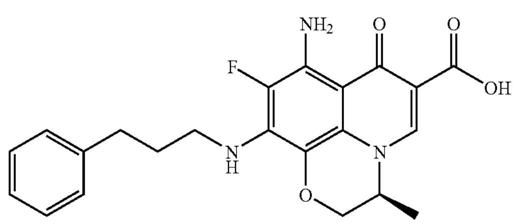 | A | NA | C | C |
| 43 | 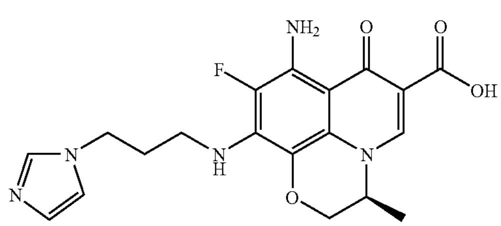 | B | NA | NA | NA |

TABLE 2-continued

| Compound Number | Structure | GSK3β IC$_{50}$ [μM] | In vivo studies 300 mg/kg | Antimicrobial MIC [μM] | |
|---|---|---|---|---|---|
| | | | | E. Coli | S. aureus |
| 44 | 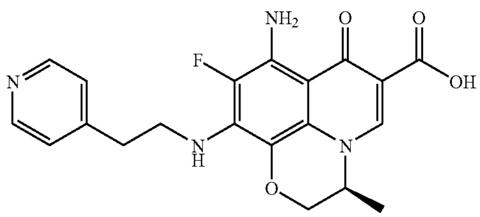 | B | NA | D | D |
| 45 | 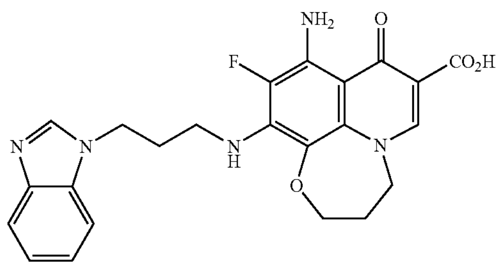 | B | NA | NA | NA |
| 46 | 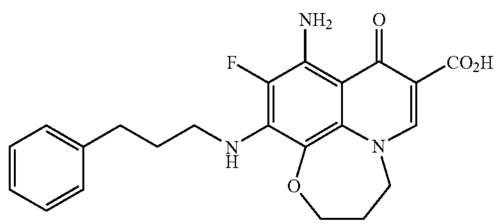 | B | NA | NA | NA |
| 47 | 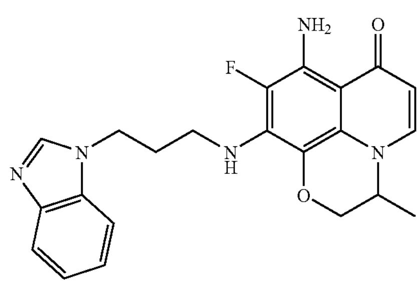 | B | NA | NA | NA |
| 48 | 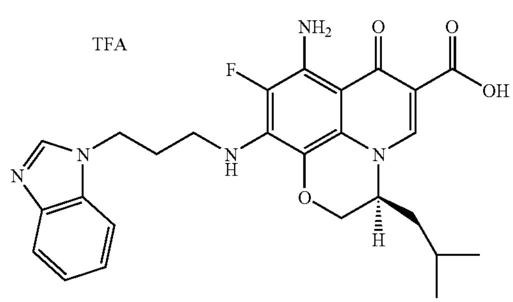 | A | NA | C | C |

TABLE 2-continued
| Compound Number | Structure | GSK3β IC$_{50}$ [μM] | In vivo studies 300 mg/kg | Antimicrobial MIC [μM] | |
| --- | --- | --- | --- | --- | --- |
| | | | | E. Coli | S. aureus |
| 49 | 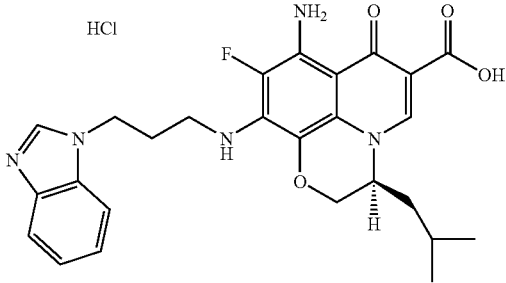 | NA | C | NA | NA |
| 50 | 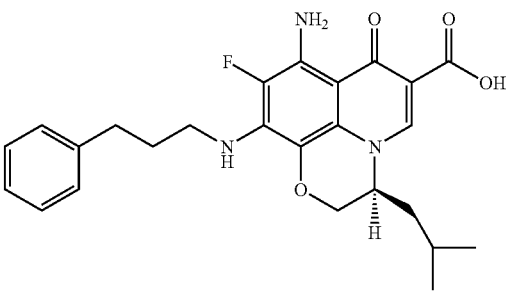 | A | NA | C | C |
| 51 | 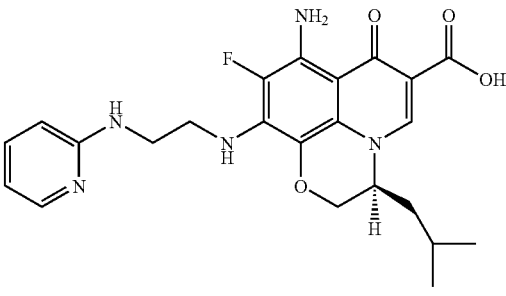 | A | NA | C | C |
| 52 | 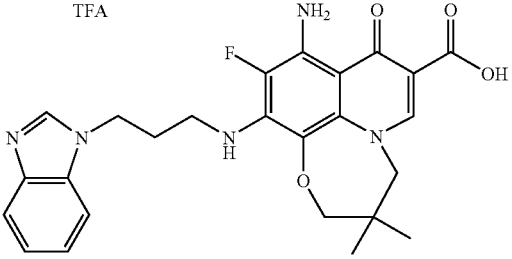 | B | NA | B | B |
| 53 | 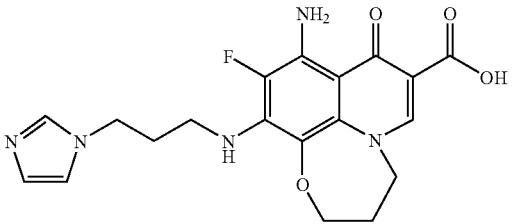 | B | NA | NA | NA |

TABLE 2-continued

| Compound Number | Structure | GSK3β IC₅₀ [μM] | In vivo studies 300 mg/kg | Antimicrobial MIC [μM] E. Coli | S. aureus |
|---|---|---|---|---|---|
| 54 | (TFA salt; 8-amino-9-fluoro-10-{[3-(1H-imidazol-1-yl)propyl]amino}-3-isopropyl-7-oxo-2,3-dihydro-7H-[1,4]oxazino[2,3,4-ij]quinoline-6-carboxylic acid) | A | NA | D | C |
| 55 | (HCl salt; (S)-8-amino-9-fluoro-10-{[3-(1H-imidazol-1-yl)propyl]amino}-3-isopropyl-7-oxo-2,3-dihydro-7H-[1,4]oxazino[2,3,4-ij]quinoline-6-carboxylic acid, chiral) | NA | C | NA | NA |
| 56 | (8-amino-10-{[3-(1H-benzimidazol-1-yl)propyl]amino}-9-fluoro-3,3-dimethyl-7-oxo-2,3-dihydro-7H-[1,4]oxazino[2,3,4-ij]quinoline-6-carboxylic acid) | B | NA | C | C |
| 57 | (8-amino-9-fluoro-3,3-dimethyl-7-oxo-10-{[2-(pyridin-2-ylamino)ethyl]amino}-2,3-dihydro-7H-[1,4]oxazino[2,3,4-ij]quinoline-6-carboxylic acid) | B | D | C | C |
| 58 | (TFA salt; 8-amino-9-fluoro-10-{[3-(1H-imidazol-1-yl)propyl]amino}-3,3-dimethyl-7-oxo-2,3-dihydro-7H-[1,4]oxazino[2,3,4-ij]quinoline-6-carboxylic acid) | B | NA | D | D |

TABLE 2-continued
| Compound Number | Structure | GSK3β IC$_{50}$ [μM] | In vivo studies 300 mg/kg | Antimicrobial MIC [μM] | |
| --- | --- | --- | --- | --- | --- |
| | | | | E. Coli | S. aureus |
| 59 | 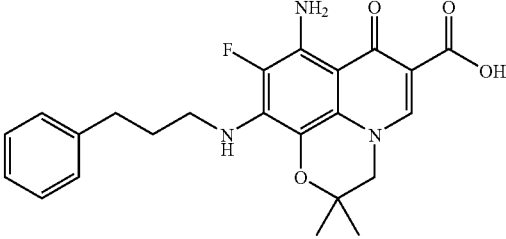 | B | NA | C | C |
| 60 | 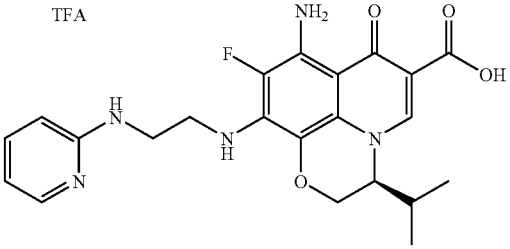 | A | NA | C | C |
| 61 | 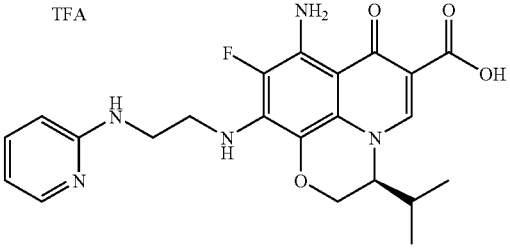 | NA | C | NA | NA |
| 62 | 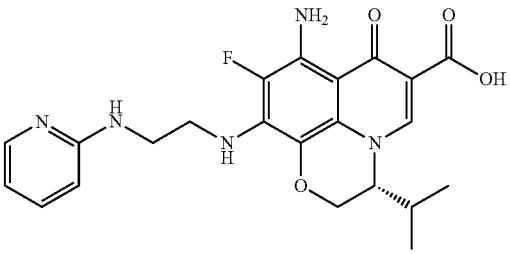 | A | NA | B | B |
| 63 | 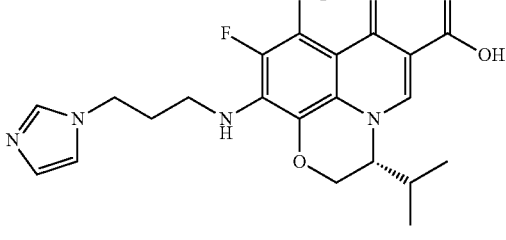 | A | NA | D | C |

TABLE 2-continued

| Compound Number | Structure | GSK3β IC$_{50}$ [μM] | In vivo studies 300 mg/kg | Antimicrobial MIC [μM] | |
| --- | --- | --- | --- | --- | --- |
| | | | | E. Coli | S. aureus |
| 64 | 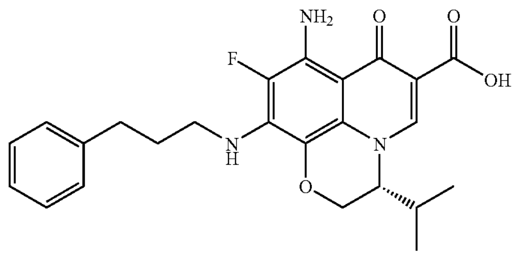 | A | NA | B | B |
| 65 | 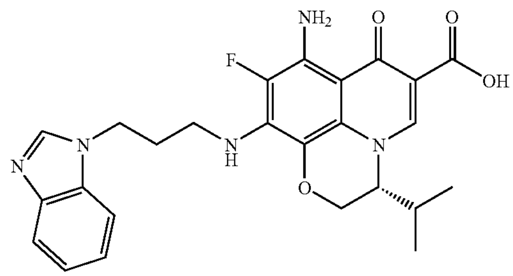 | A | NA | B | B |
| 66 | 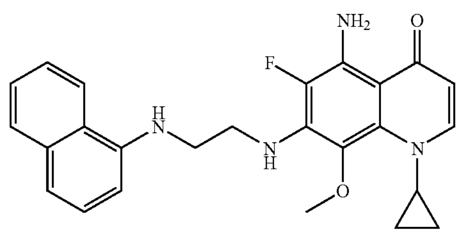 | A | NA | NA | NA |
| 67 | 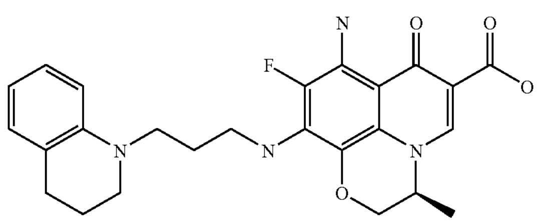 | A | C | NA | NA |
| 68 | 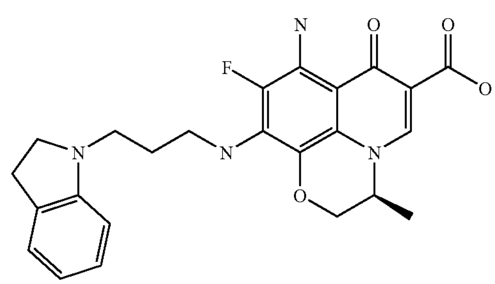 | B | NA | NA | NA |
| 69 | 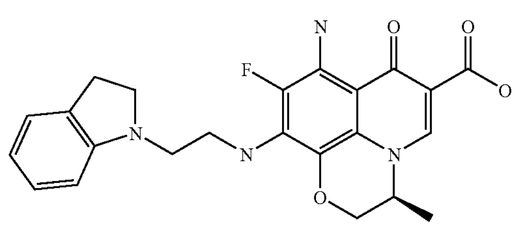 | A | NA | NA | NA |

TABLE 2-continued

| Compound Number | Structure | GSK3β IC$_{50}$ [μM] | In vivo studies 300 mg/kg | Antimicrobial MIC [μM] | |
| --- | --- | --- | --- | --- | --- |
| | | | | E. Coli | S. aureus |
| 70 | 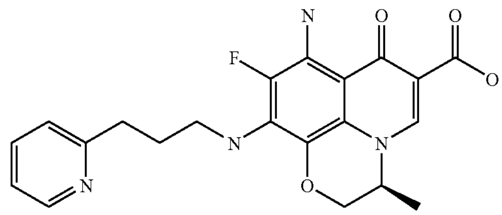 | A | D | NA | NA |
| 71 | 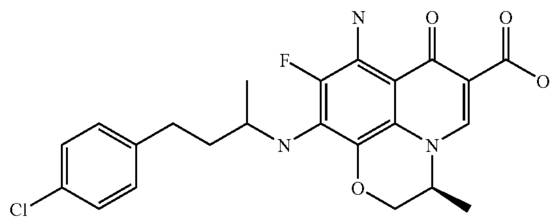 | A | NA | NA | NA |
| 72 | 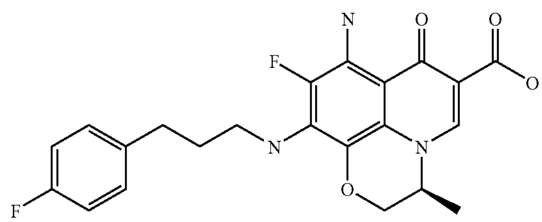 | A | D | NA | NA |
| 73 | 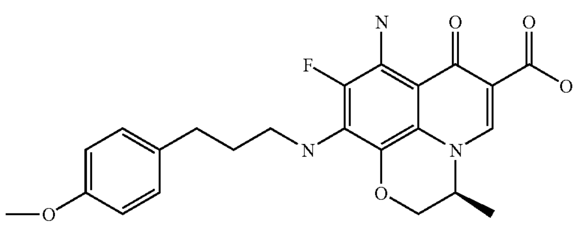 | A | NA | NA | NA |
| 74 | 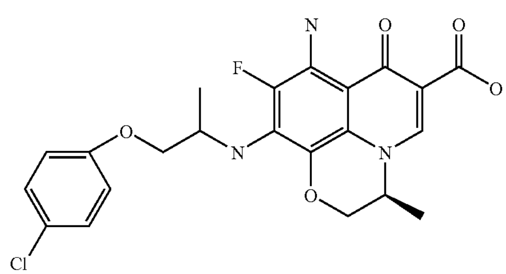 | C | NA | NA | NA |
| 75 | 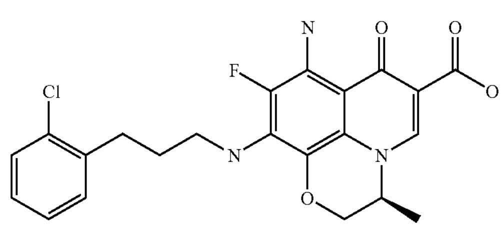 | A | NA | NA | NA |

TABLE 2-continued

| Compound Number | Structure | GSK3β IC$_{50}$ [μM] | In vivo studies 300 mg/kg | Antimicrobial MIC [μM] | |
| --- | --- | --- | --- | --- | --- |
| | | | | E. Coli | S. aureus |
| 76 | 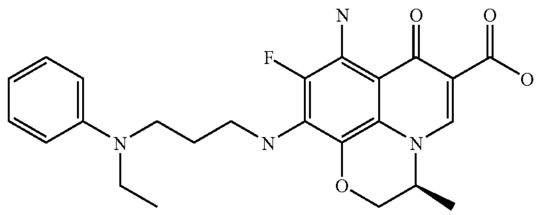 | A | D | NA | NA |
| 77 | 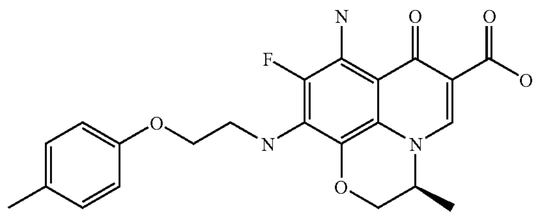 | B | NA | NA | NA |
| 78 | 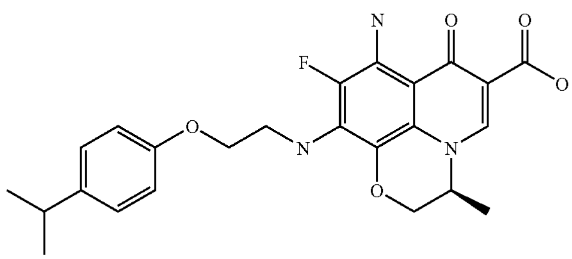 | B | NA | NA | NA |
| 79 | 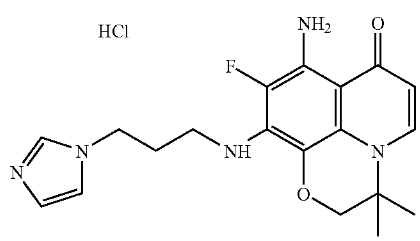 | A | NA | D | D |
| 80 | 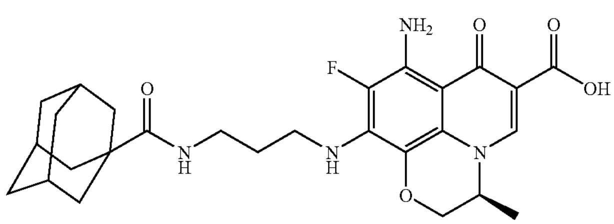 | A | B | NA | NA |
| 81 | 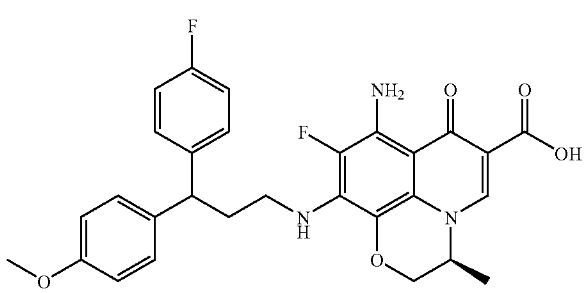 | A | NA | NA | NA |

TABLE 2-continued

| Compound Number | Structure | GSK3β IC$_{50}$ [μM] | In vivo studies 300 mg/kg | Antimicrobial MIC [μM] | |
| --- | --- | --- | --- | --- | --- |
| | | | | E. Coli | S. aureus |
| 82 | 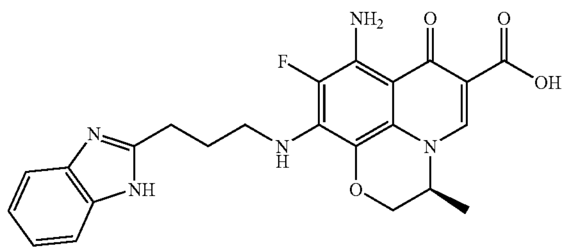 | A | NA | NA | NA |
| 83 | 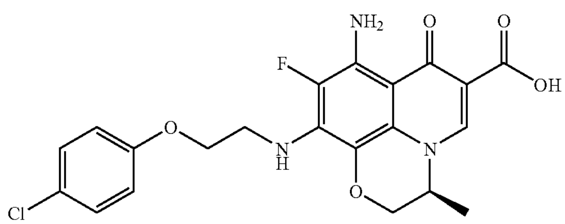 | A | NA | NA | NA |
| 84 | 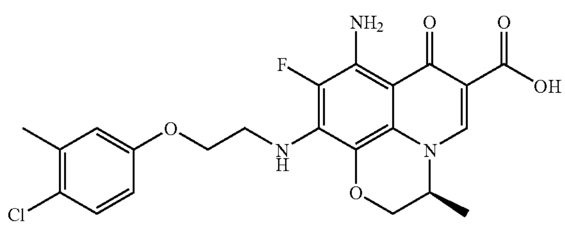 | A | NA | NA | NA |
| 85 | 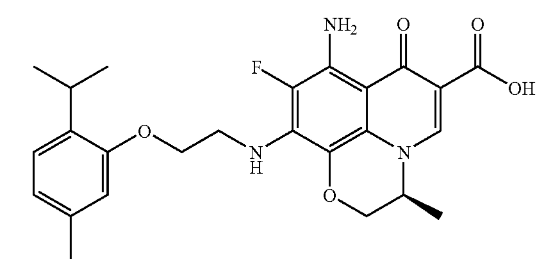 | B | NA | NA | NA |
| 86 | 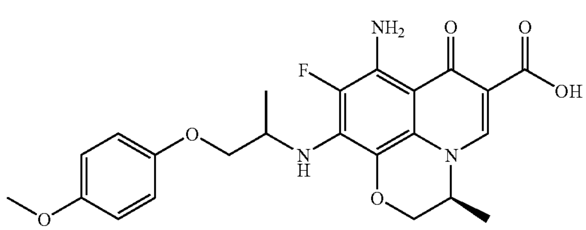 | C | NA | NA | NA |
| 87 | 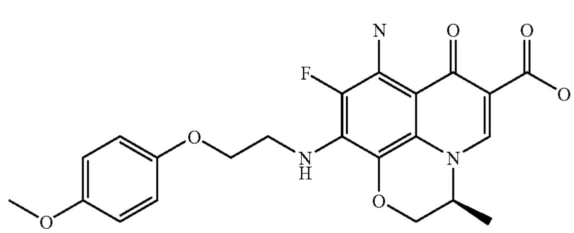 | B | NA | NA | NA |

TABLE 2-continued

| Compound Number | Structure | GSK3β IC$_{50}$ [μM] | In vivo studies 300 mg/kg | Antimicrobial MIC [μM] E. Coli | S. aureus |
|---|---|---|---|---|---|
| 88 | 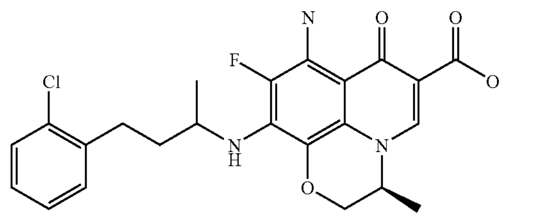 | B | NA | NA | NA |
| 89 | 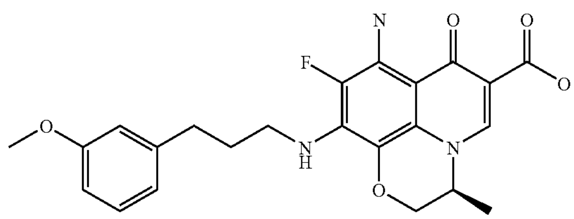 | A | NA | NA | NA |
| 90 | 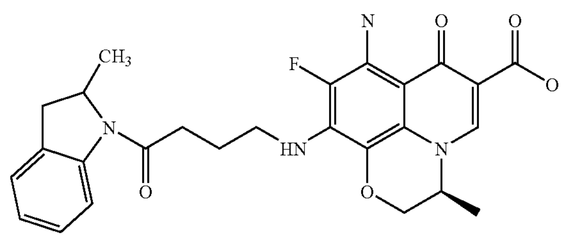 | C | NA | NA | NA |
| 91 | 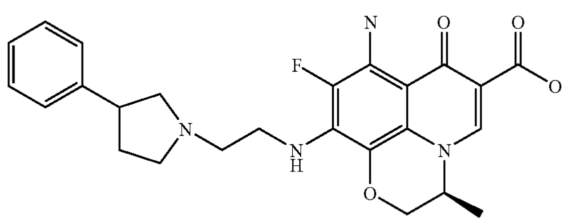 | D | NA | NA | NA |
| 92 | TFA | A | NA | NA | NA |
| 93 | 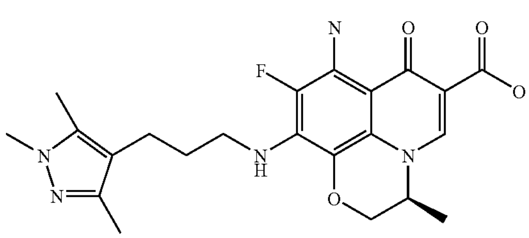 | NA | D | NA | NA |

TABLE 2-continued

| Compound Number | Structure | GSK3β IC$_{50}$ [μM] | In vivo studies 300 mg/kg | Antimicrobial MIC [μM] E. Coli | S. aureus |
|---|---|---|---|---|---|
| 94 | 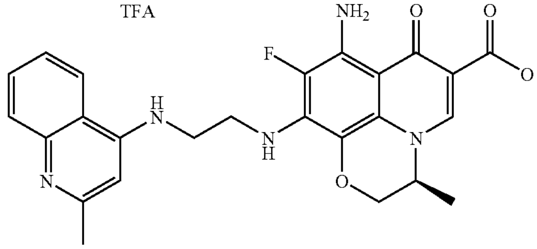 | A | NA | NA | NA |
| 95 | 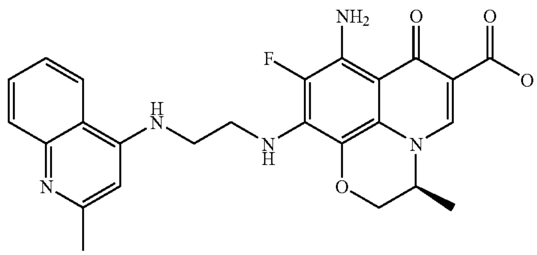 | A | NA | NA | NA |
| 96 | 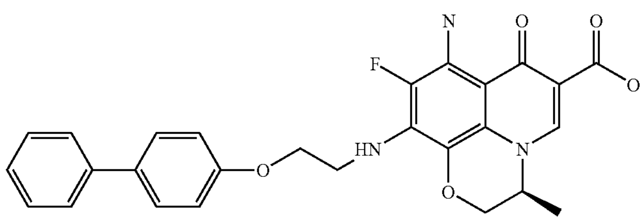 | C | NA | NA | NA |
| 97 | 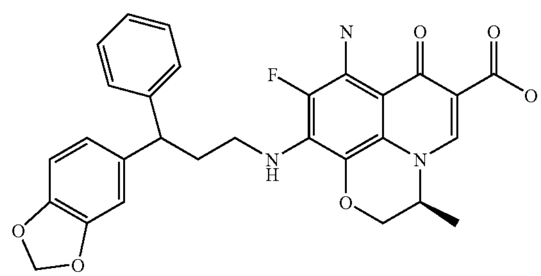 | B | NA | NA | NA |
| 98 | 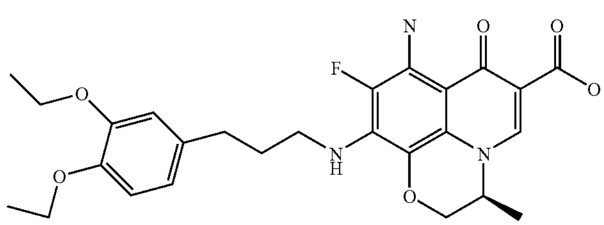 | A | NA | NA | NA |
| 99 | 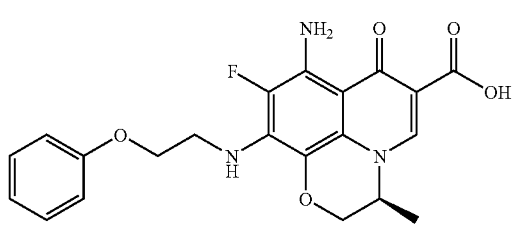 | A | NA | NA | NA |

TABLE 2-continued

| Compound Number | Structure | GSK3β IC$_{50}$ [μM] | In vivo studies 300 mg/kg | Antimicrobial MIC [μM] | |
| --- | --- | --- | --- | --- | --- |
| | | | | E. Coli | S. aureus |
| 100 | 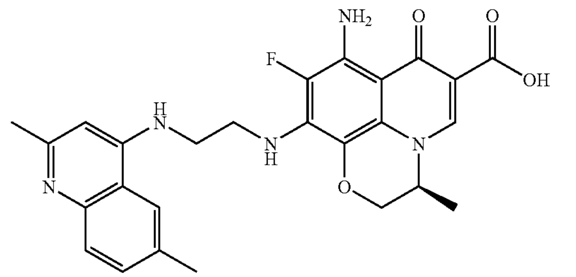 | A | NA | NA | NA |
| 101 | 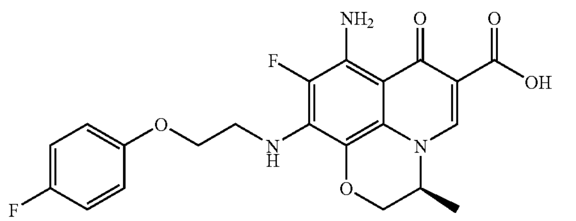 | A | C | NA | NA |
| 102 | 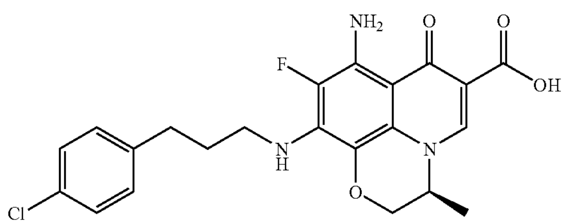 | A | NA | NA | NA |
| 103 | 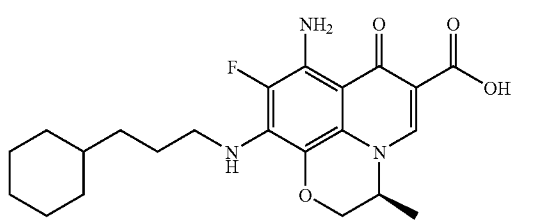 | A | NA | C | C |
| 104 | 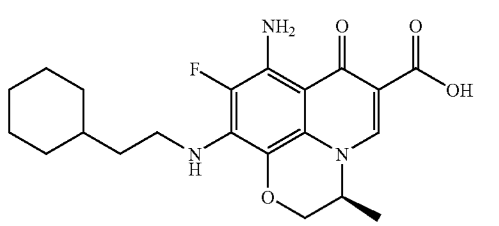 | A | NA | NA | NA |
| 105 | 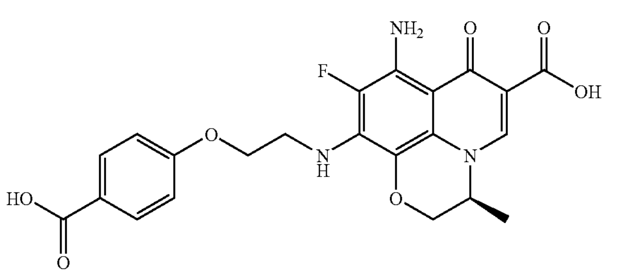 | A | NA | NA | NA |

TABLE 2-continued

| Compound Number | Structure | GSK3β IC$_{50}$ [μM] | In vivo studies 300 mg/kg | Antimicrobial MIC [μM] | |
| --- | --- | --- | --- | --- | --- |
| | | | | E. Coli | S. aureus |
| 106 | 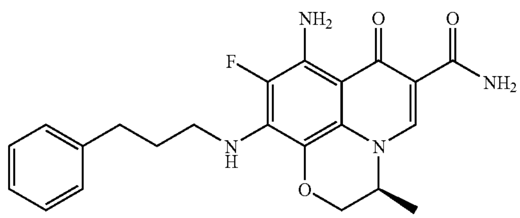 | A | NA | NA | NA |
| 107 | (TFA) | B | C | NA | NA |
| 108 | 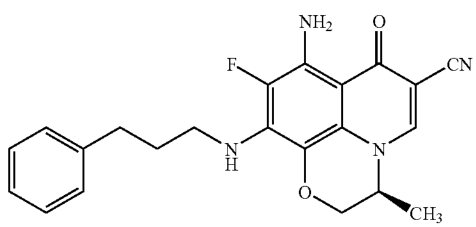 | A | NA | NA | NA |
| 109 | (HCl) | A | C | NA | NA |
| 110 | (TFA) | A | NA | NA | NA |
| 111 | 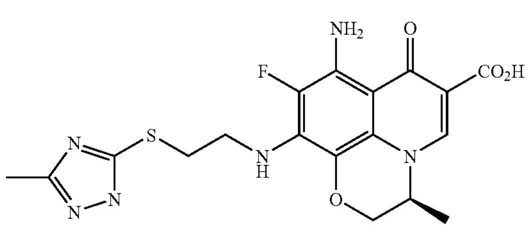 | A | NA | NA | NA |

TABLE 2-continued

| Compound Number | Structure | GSK3β IC₅₀ [μM] | In vivo studies 300 mg/kg | Antimicrobial MIC [μM] E. Coli | S. aureus |
|---|---|---|---|---|---|
| 112 | 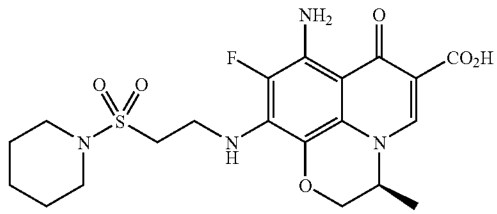 | A | A | NA | NA |
| 113 | 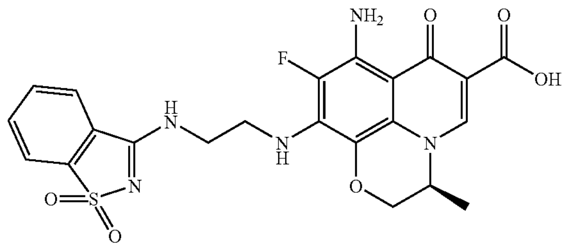 | A | A | NA | NA |
| 114 | 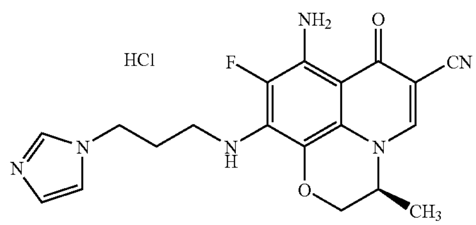 | A | D | NA | NA |
| 115 | 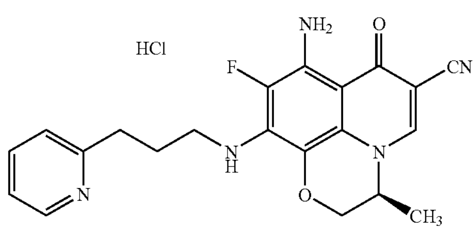 | A | A | NA | NA |
| 116 | 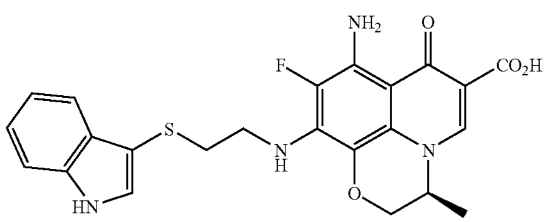 | A | NA | NA | NA |
| 117 | 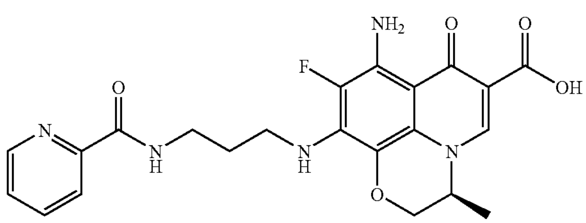 | A | NA | NA | NA |

TABLE 2-continued

| Compound Number | Structure | GSK3β IC$_{50}$ [μM] | In vivo studies 300 mg/kg | Antimicrobial MIC [μM] | |
|---|---|---|---|---|---|
| | | | | E. Coli | S. aureus |
| 118 | 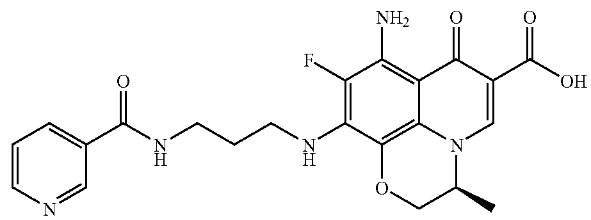 | A | NA | NA | NA |
| 119 | 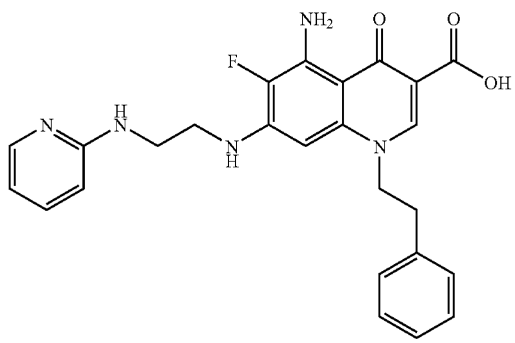 | A | A | C | C |
| 120 | 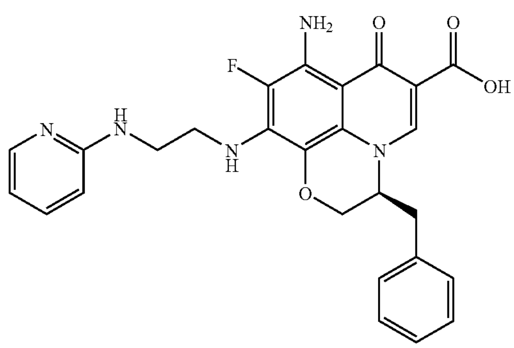 | B | NA | C | C |
| 121 | 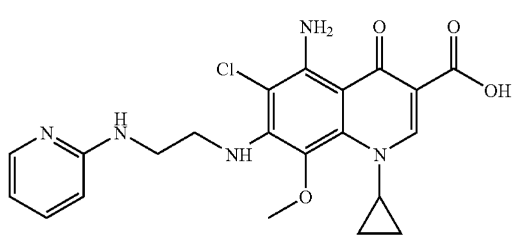 | A | NA | C | B |
| 122 | 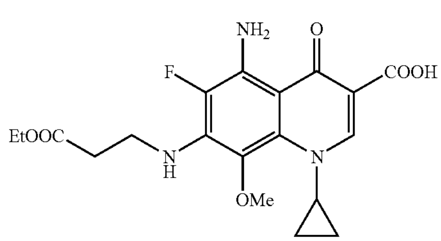 | C | NA | C | B |

TABLE 2-continued

| Compound Number | Structure | GSK3β IC$_{50}$ [μM] | In vivo studies 300 mg/kg | Antimicrobial MIC [μM] | |
| --- | --- | --- | --- | --- | --- |
| | | | | E. Coli | S. aureus |
| 123 | 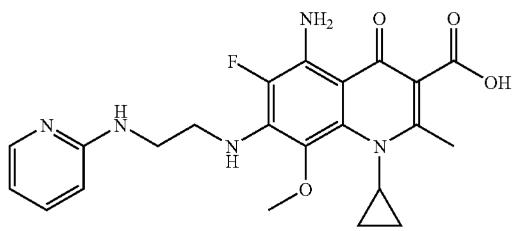 | A | NA | D | D |
| 124 | 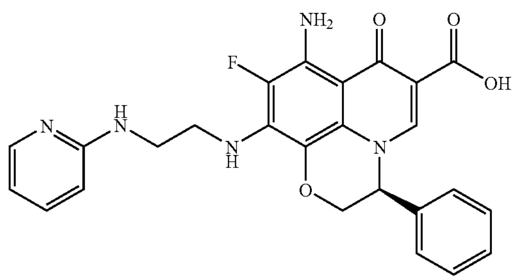 | B | NA | C | C |
| 125 | 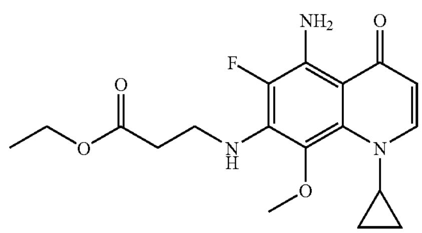 | B | NA | D | D |
| 126 | 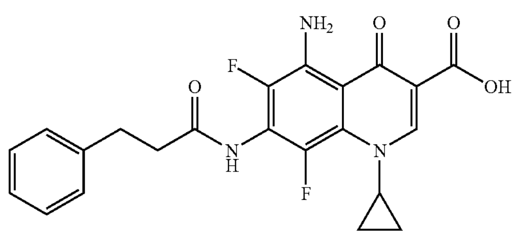 | D | NA | B | B |
| 127 | 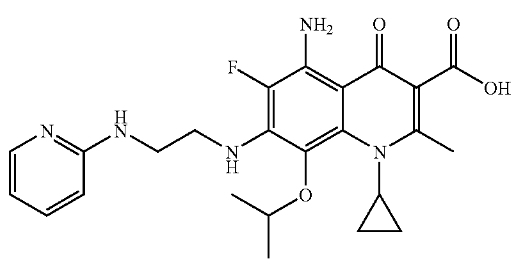 | B | NA | C | B |
| 128 | 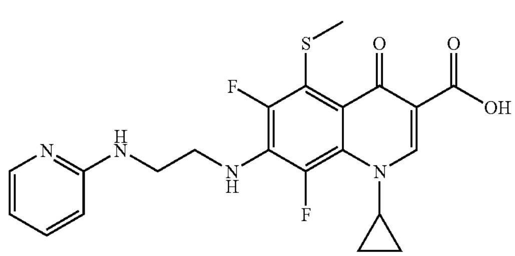 | NA | NA | B | B |

TABLE 2-continued

| Compound Number | Structure | GSK3β IC$_{50}$ [μM] | In vivo studies 300 mg/kg | Antimicrobial MIC [μM] E. Coli | S. aureus |
|---|---|---|---|---|---|
| 129 | 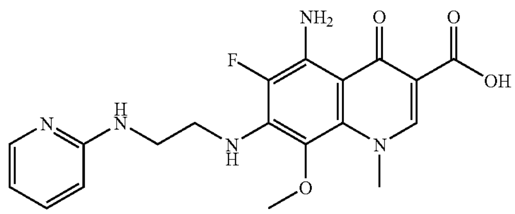 | B | NA | C | C |
| 130 | 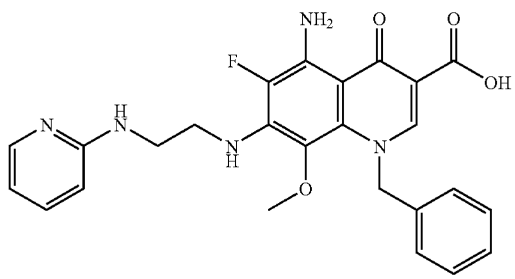 | D | NA | B | B |
| 131 | 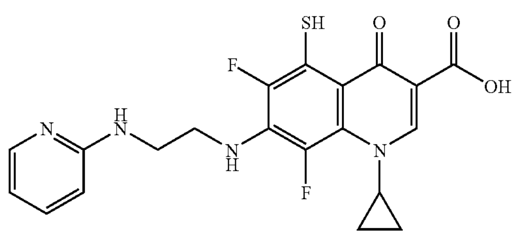 | A | NA | B | B |
| 132 | 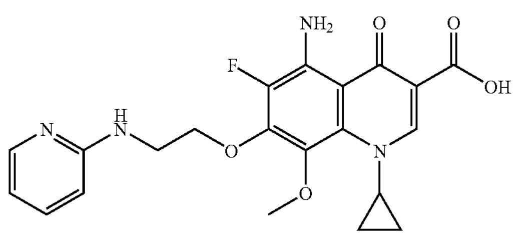 | D | NA | B | A |
| 133 | 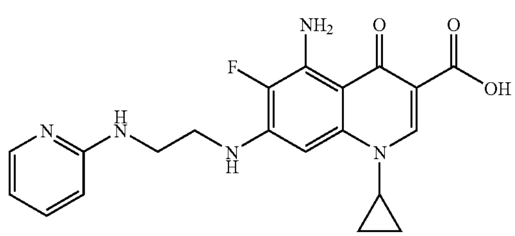 | A | NA | B | A |
| 134 | 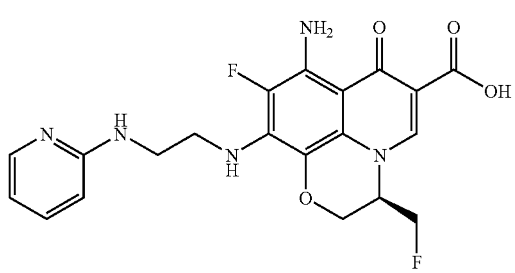 | A | NA | A | A |

TABLE 2-continued

| Compound Number | Structure | GSK3β IC$_{50}$ [μM] | In vivo studies 300 mg/kg | Antimicrobial MIC [μM] | |
|---|---|---|---|---|---|
| | | | | E. Coli | S. aureus |
| 135 | 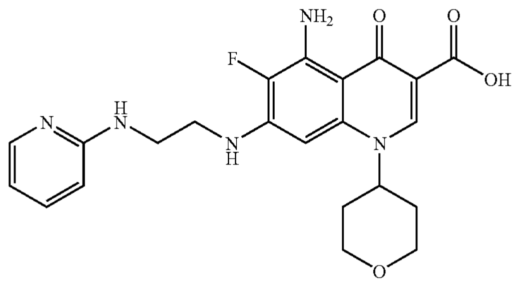 | A | NA | C | C |
| 136 | 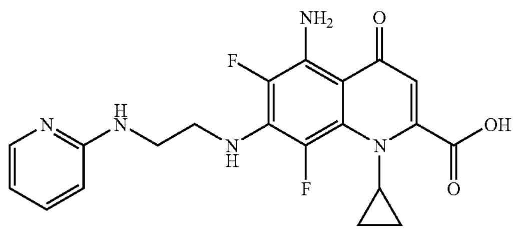 | D | NA | D | D |
| 137 | 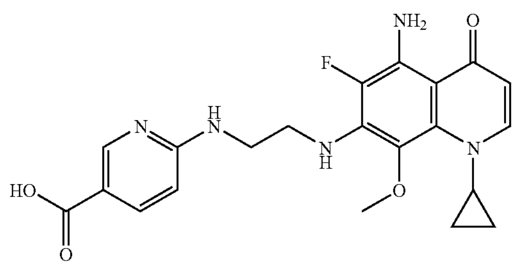 | A | NA | D | D |
| 138 | 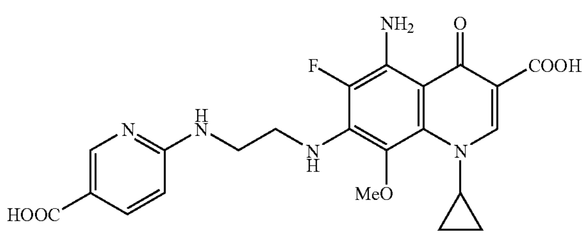 | A | NA | D | D |
| 139 | 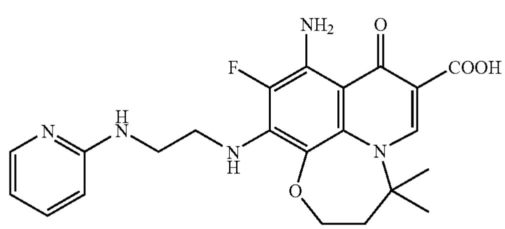 | B | D | D | D |
| 140 | 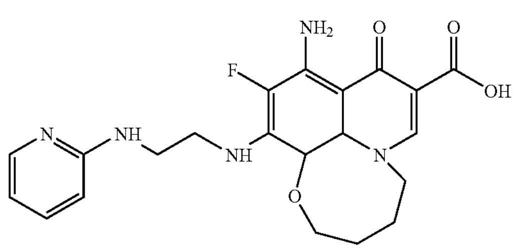 | C | NA | D | D |

TABLE 2-continued

| Compound Number | Structure | GSK3β IC$_{50}$ [μM] | In vivo studies 300 mg/kg | Antimicrobial MIC [μM] | |
|---|---|---|---|---|---|
| | | | | E. Coli | S. aureus |
| 141 | 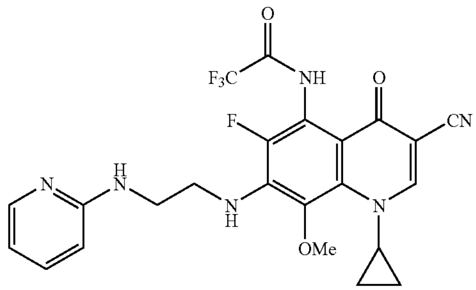 | A | NA | B | B |
| 142 | 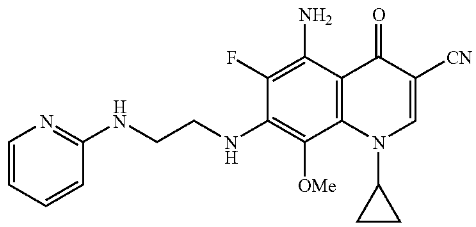 | A | NA | D | D |

C. Preparation of the Compounds

The compounds provided herein can be prepared by methods known to one of skill in the art and following procedures similar to those described in the Examples section herein and routine modifications thereof. Exemplary procedures are described below:

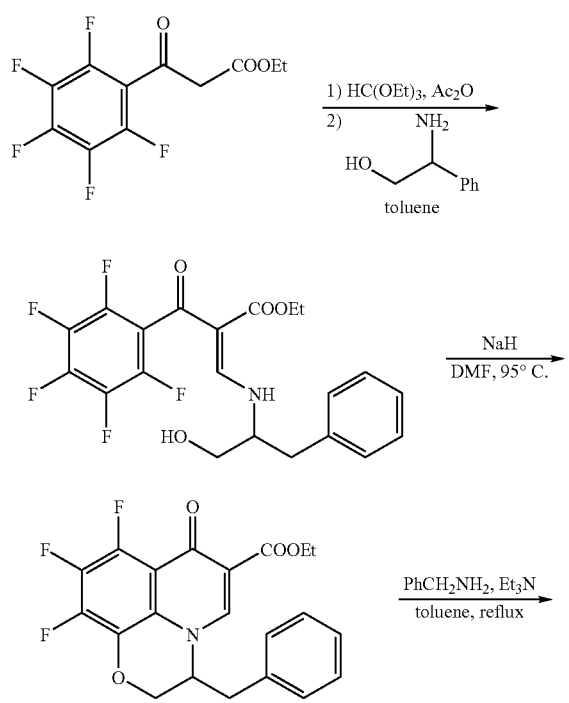

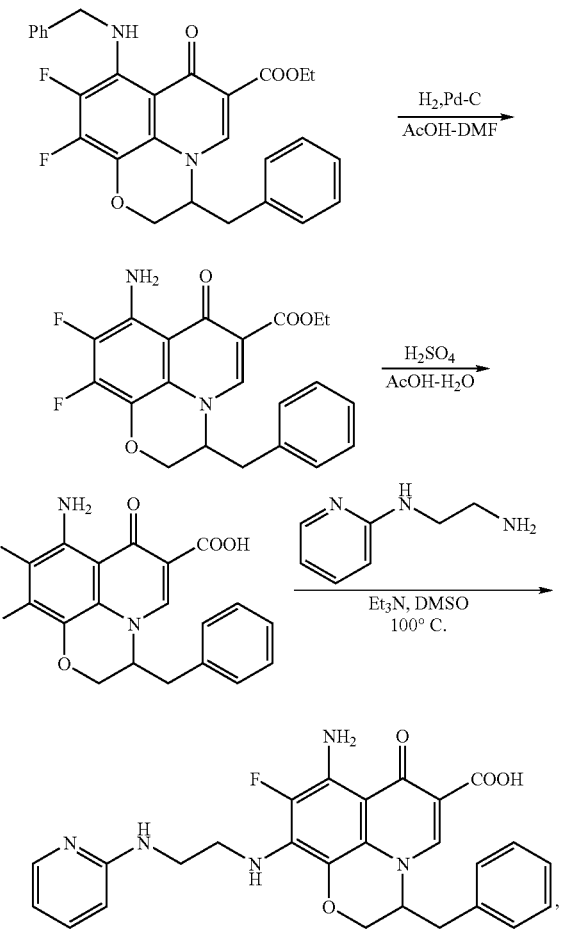

See, *Chem Parm. Bull.,* 38(9), 2390 (1990).
Scheme 2: Regioselective displacement reaction of quinolone with amine
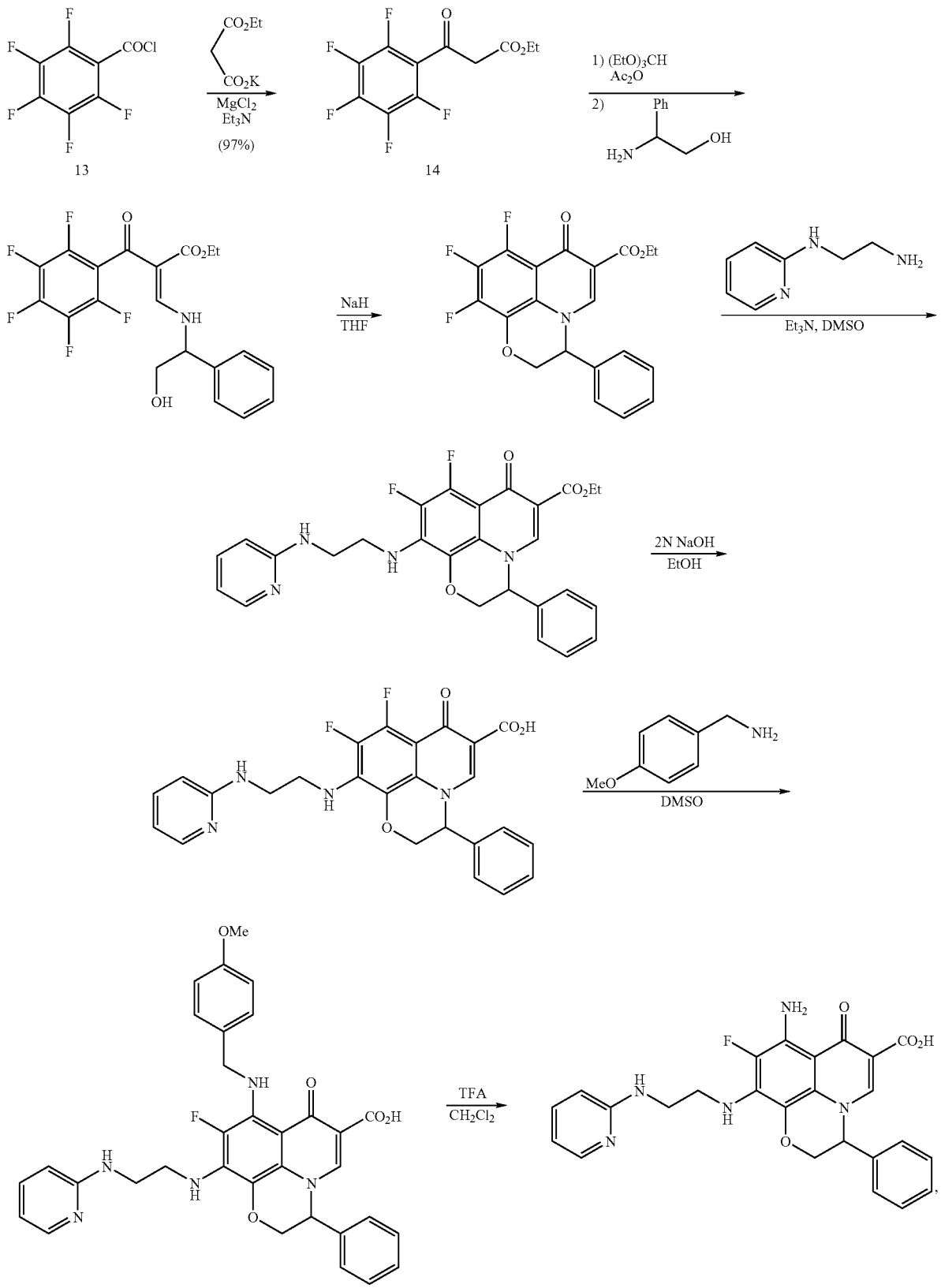

See, *Chem Parm. Bull.*, 38(9), 2390 (1990).
A: *Chem. Pharm. Bull.* 1985, 35, 1896-1902.
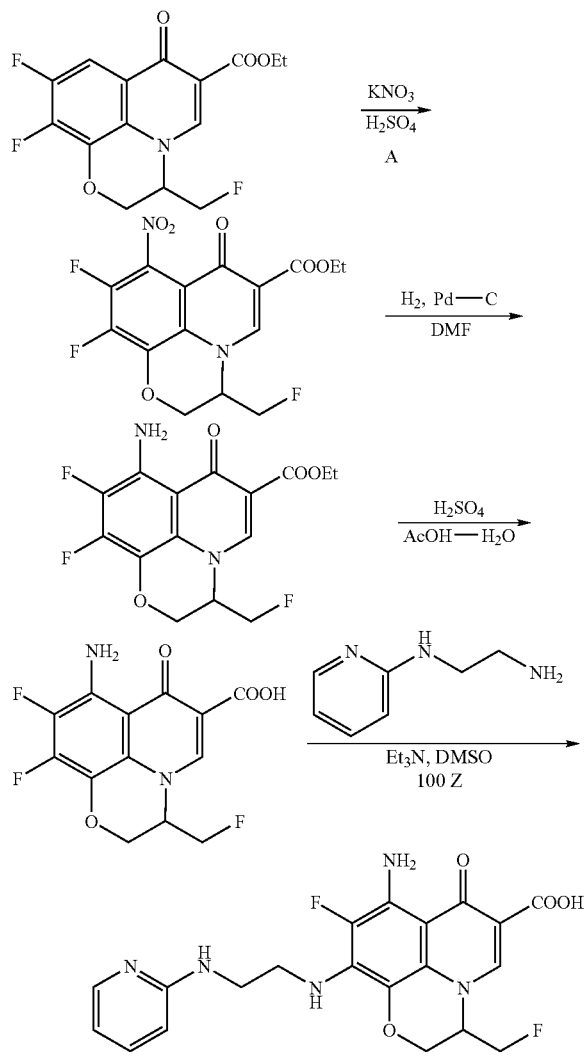
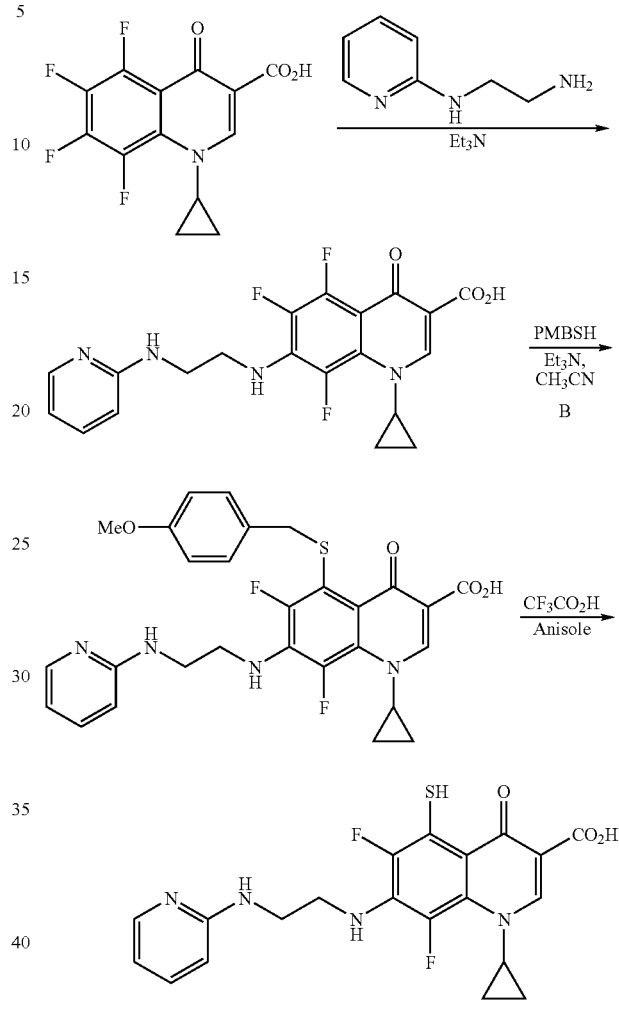
B: *J. Med. Chem.*, 1990, 33, 1645 (Synthesis of 7-amino-5-mercaptquinolone)
Scheme 5: Conversion of 1-substituent of quinolone
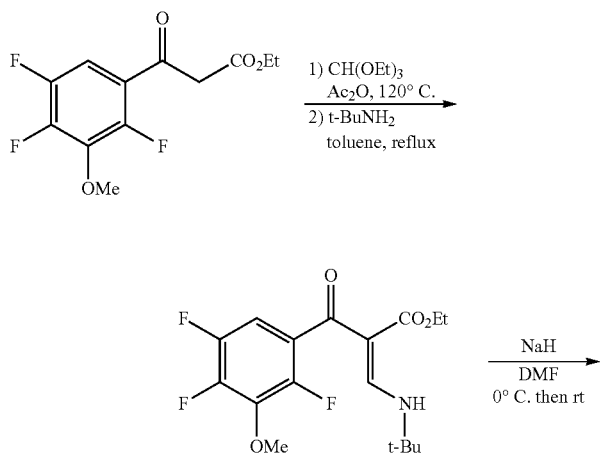

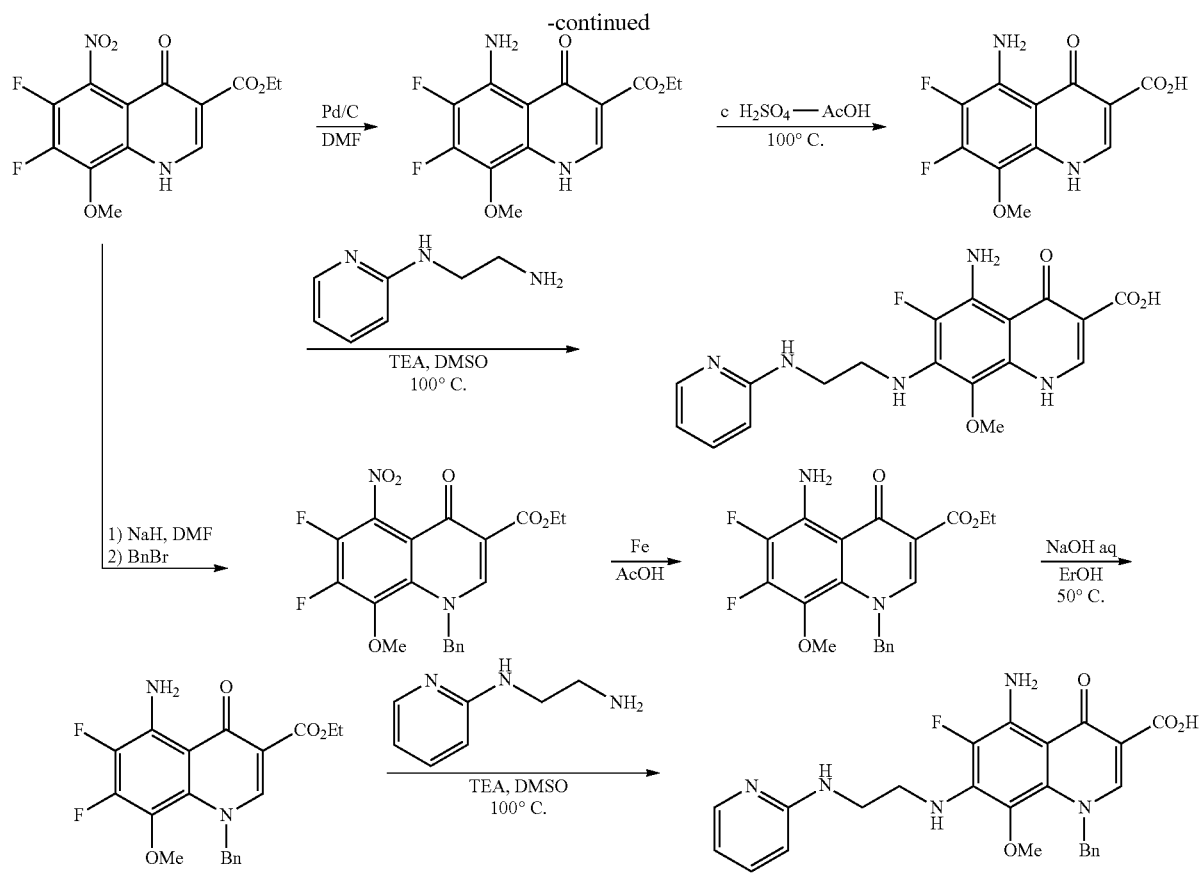
C: *Farmaco,* 2004, 59, 463.
Scheme 6: Conversion of 1-substituent of quinolone
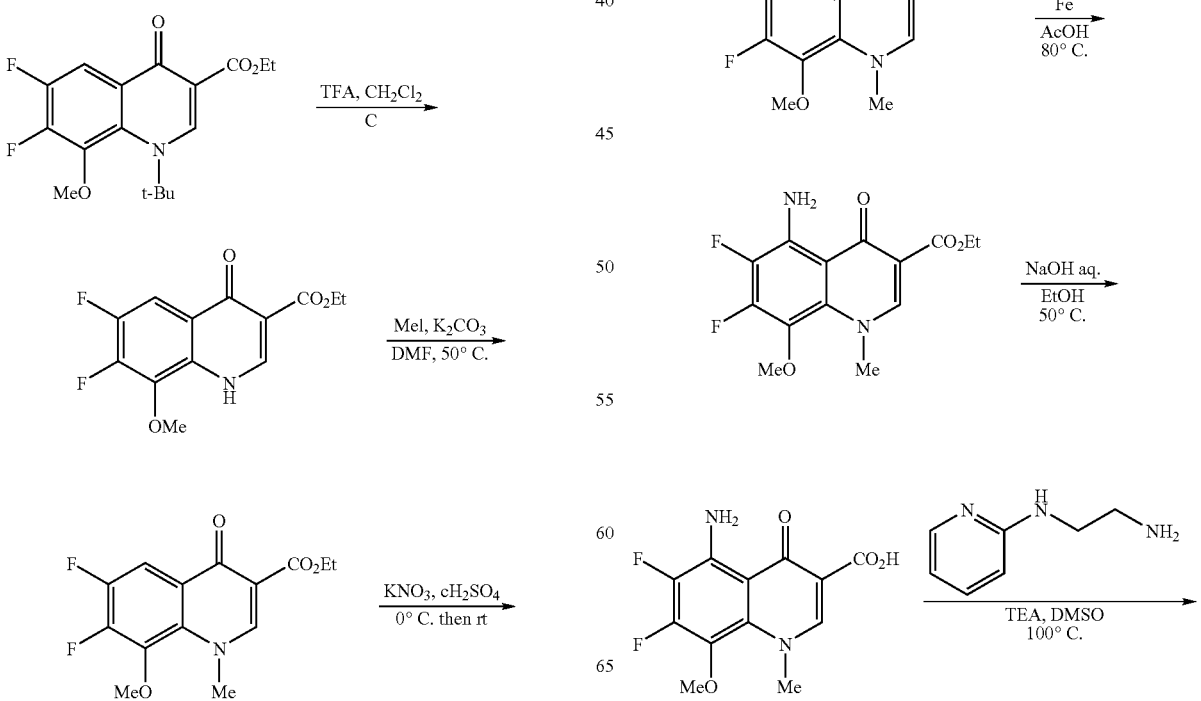

147
-continued
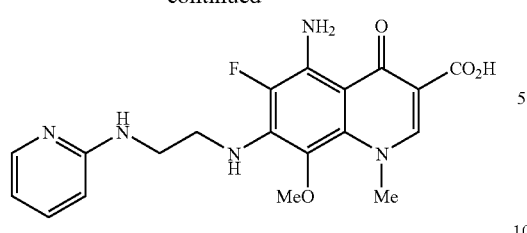
148
-continued
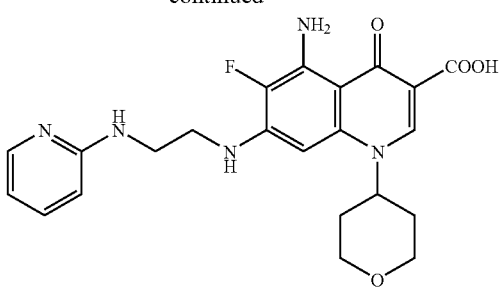
Scheme 7: Conversion of 1-substituent of quinolone
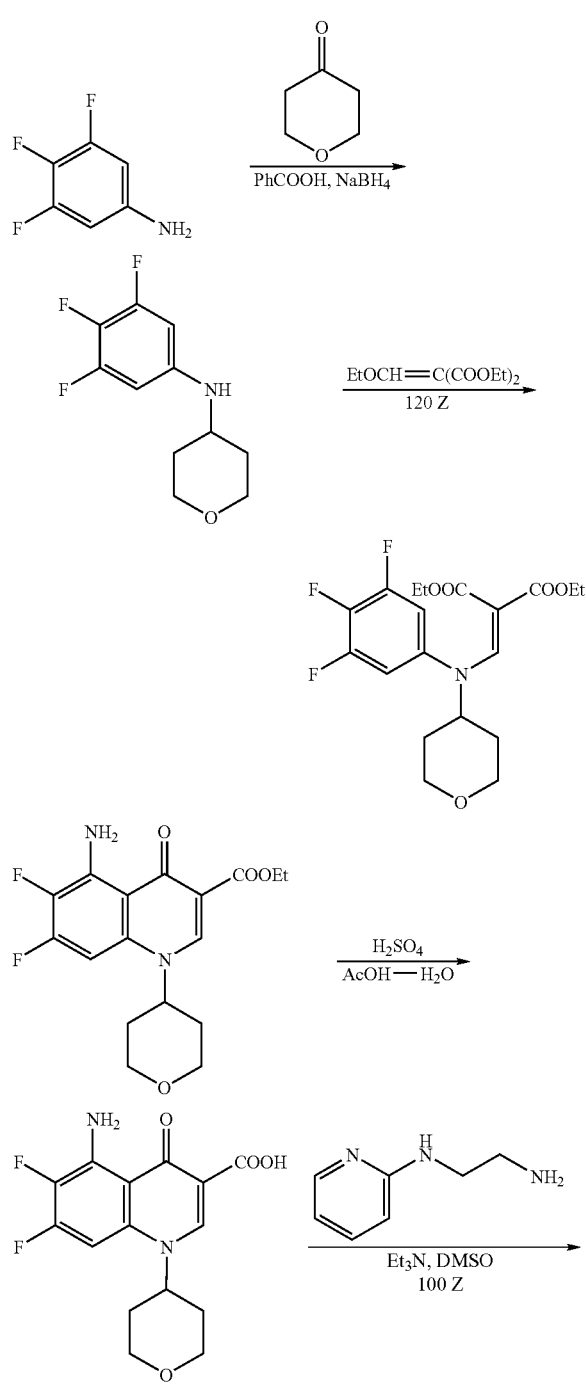
Scheme 8: 2-COOH analog
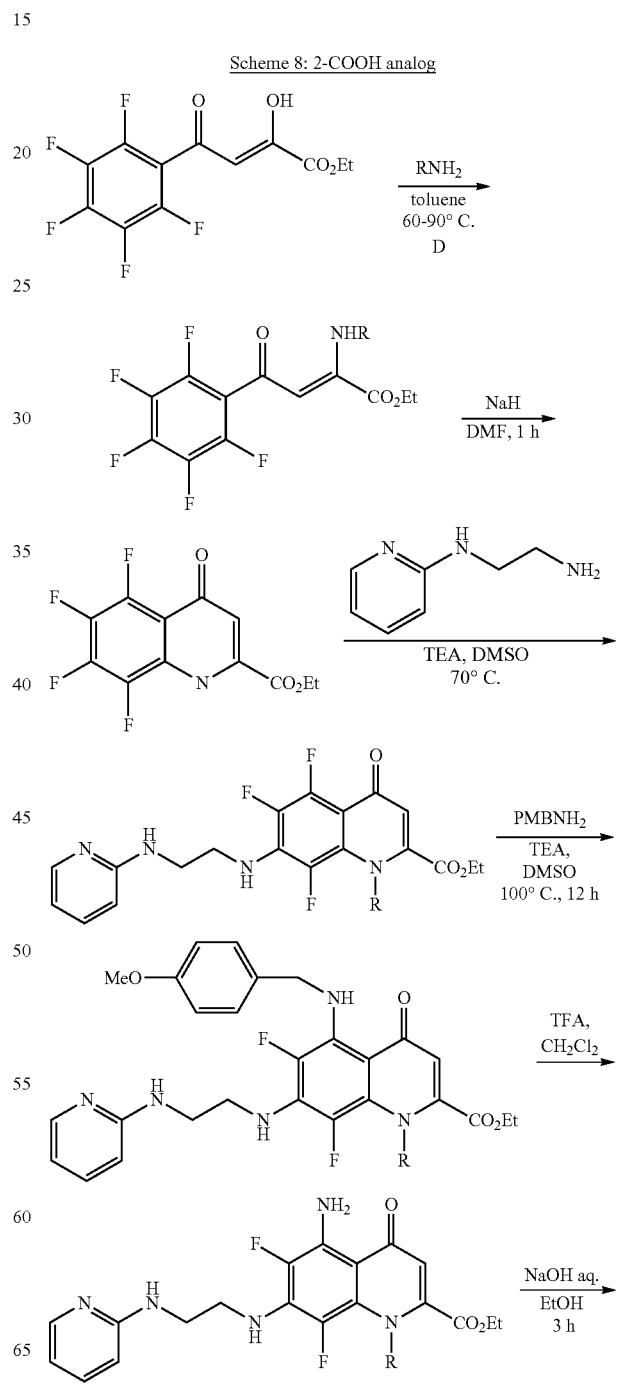

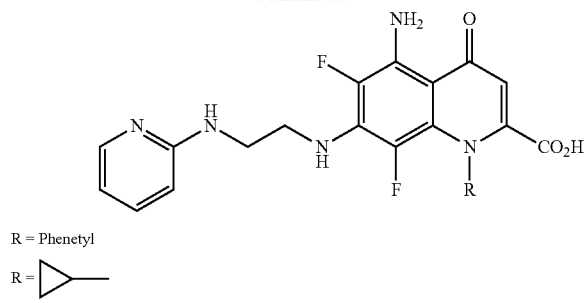
R = Phenetyl
R = ▷
D: *J. Fluoerine Chem.*, 1993, 65, 37
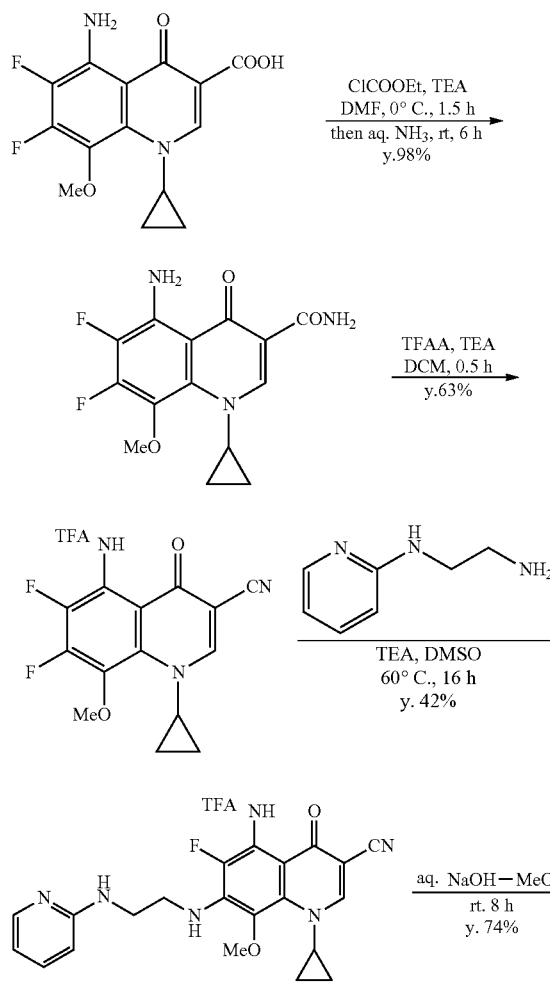
Scheme 10: Conversion of 5-NH₂ into 5-MeNH
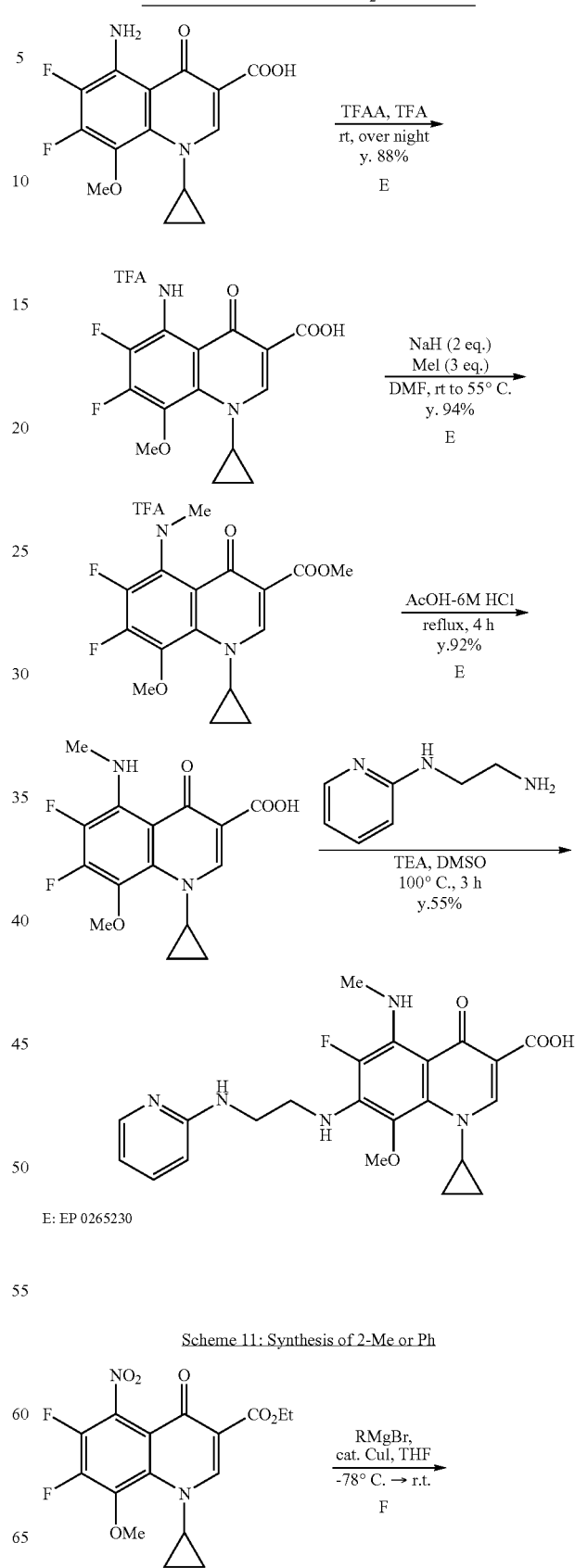
E: EP 0265230
Scheme 11: Synthesis of 2-Me or Ph
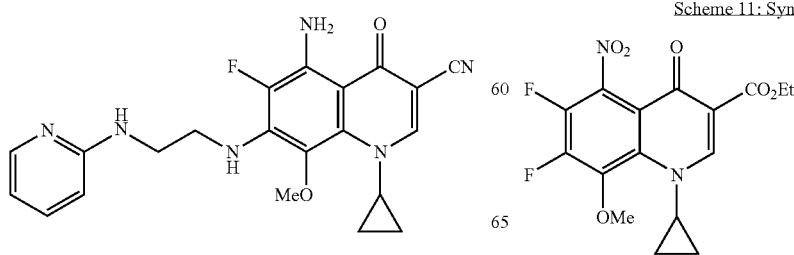

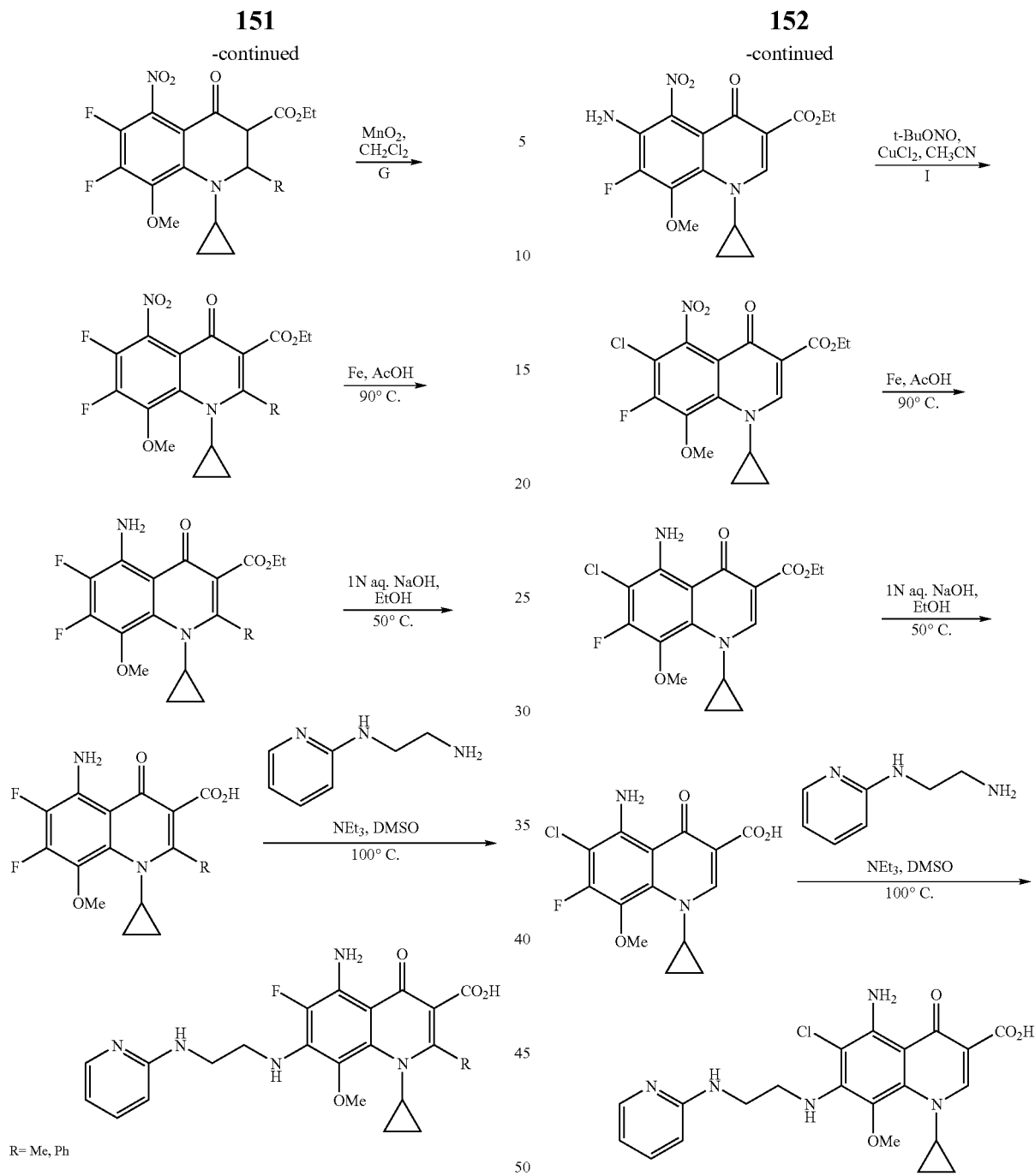
F: *Heterocyclic Chem.*, 1989, 26, 1675-1681
G: *J. Med. Chem.*, 1988, 31, 221-225
H: *Chem. Pharm. Bull.*, 1996, 44, 987-990
I: *J. Org. Chem.*, 1977, 42, 2426-2431
Scheme 12: Conversion of 6-F into 6-Cl
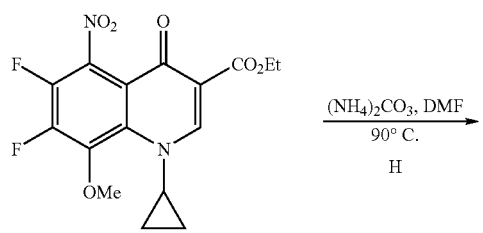
Scheme 13: Synthesis of 8-i-PrO analog
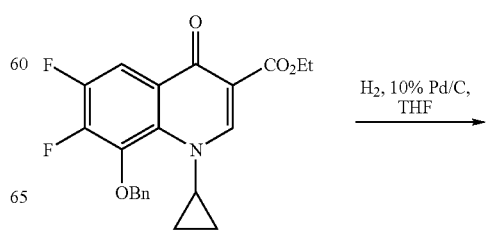

-continued

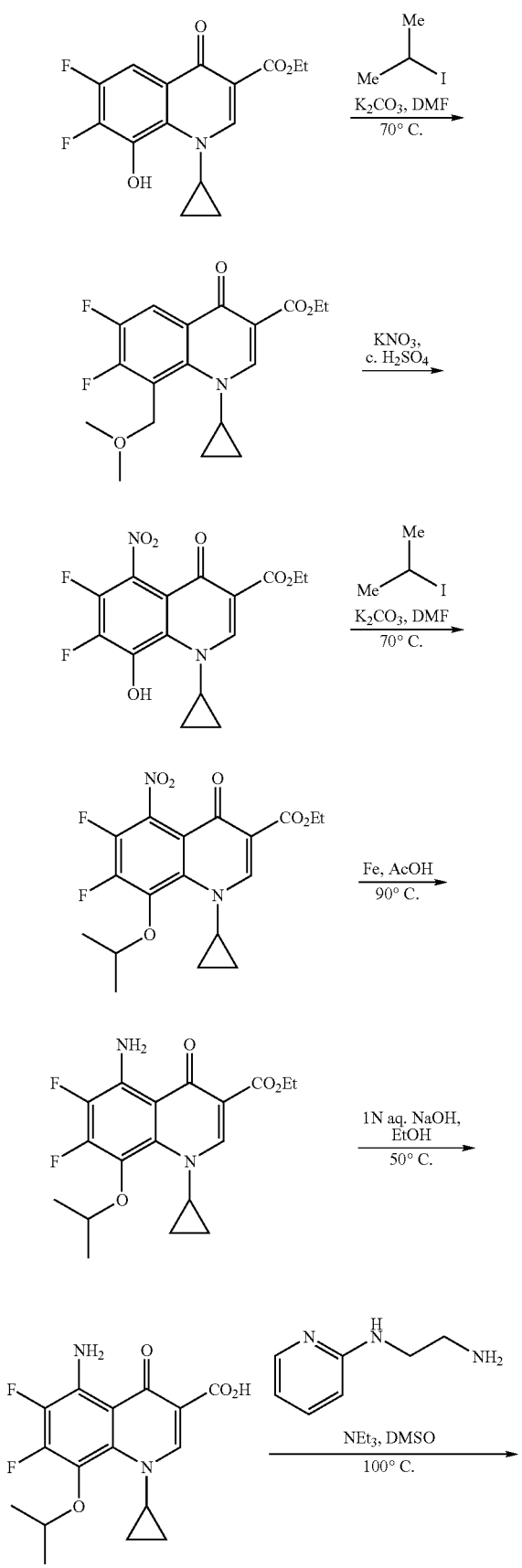

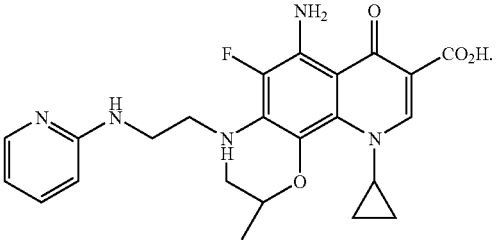

Scheme 14: Reduction of the 5-NO$_2$ group to 5-NH$_2$

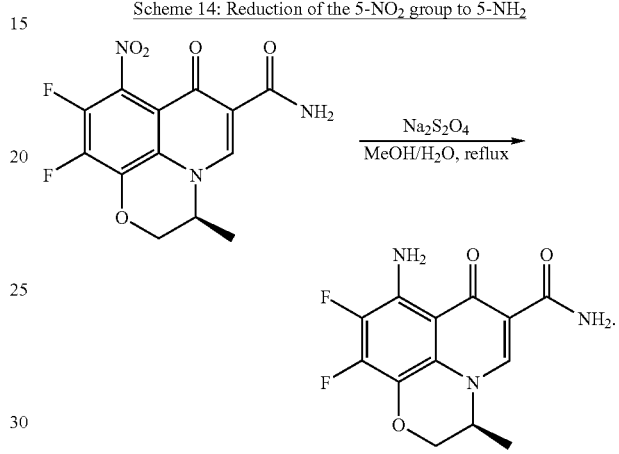

D. Formulation of Pharmaceutical Compositions

The pharmaceutical compositions provided herein contain therapeutically effective amounts of one or more of compounds provided herein that are useful in the prevention, treatment, or amelioration of one or more of the symptoms of GSK-3 mediated diseases.

The compositions contain one or more compounds provided herein. The compounds can be formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically the compounds described above are formulated into pharmaceutical compositions using techniques and procedures well known in the art (see, e.g., Ansel Introduction to Pharmaceutical Dosage Forms, Seventh Edition 1999).

In the compositions, effective concentrations of one or more compounds or pharmaceutically acceptable derivatives is (are) mixed with a suitable pharmaceutical carrier or vehicle. The compounds may be derivatized as the corresponding salts, esters, enol ethers or esters, acids, bases, solvates, hydrates or prodrugs prior to formulation, as described above. The concentrations of the compounds in the compositions are effective for delivery of an amount, upon administration, that treats, prevents, or ameliorates one or more of the symptoms of GSK-3 mediated diseases.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as known in the art. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of GSK-3 mediated diseases.

Typically a therapeutically effective dosage should produce a serum concentration of active ingredient of from about 0.1 ng/ml to about 50-100 µg/ml. The pharmaceutical compositions typically should provide a dosage of from about 0.001 mg to about 2000 mg of compound per kilogram of body weight per day. Pharmaceutical dosage unit forms are prepared to provide from about 1 mg to about 1000 mg and in certain embodiments, from about 10 mg to about 500 mg of the essential active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Pharmaceutically acceptable derivatives include acids, bases, enol ethers and esters, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives thereof are mixed with a suitable pharmaceutical carrier or vehicle for systemic, topical or local administration to form pharmaceutical compositions. Compounds are included in an amount effective for ameliorating one or more symptoms of, or for treating or preventing GSK-3 mediated diseases. The concentration of active compound in the composition will depend on absorption, inactivation, excretion rates of the active compound, the dosage schedule, amount administered, particular formulation as well as other factors known to those of skill in the art.

The compositions are intended to be administered by a suitable route, including, but not limited to, orally, parenterally, rectally, topically and locally. For oral administration, capsules and tablets can be formulated. The compositions are in liquid, semi-liquid or solid form and are formulated in a manner suitable for each route of administration.

Solutions or suspensions used for parenteral, intradermal, subcutaneous, or topical application can include any of the following components: a sterile diluent, such as water for injection, saline solution, fixed oil, polyethylene glycol, glycerine, propylene glycol, dimethyl acetamide or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. In one embodiment, the effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are typically formulated and administered in unit-dosage forms or multiple-dosage forms. Unit-dose forms as used herein refer to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Sustained-release preparations can also be prepared. Suitable examples of sustained-release preparations include semipermeable matrices of solid hydrophobic polymers containing the compound provided herein, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides, copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated compound remain in the body for a long time, they may denature or aggregate as a result of exposure to moisture at 37° C., resulting in a loss of biological activity and possible changes in their structure. Rational strategies can be devised for stabilization depending on the mechanism of action involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions Dosage forms or compositions containing active ingredient in the range of 0.005% to 100% with the balance made up from non-toxic carrier may be prepared. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain about 0.001%-100% active ingredient, in certain embodiments, about 0.1-85%, typically about 75-95%.

The active compounds or pharmaceutically acceptable derivatives may be prepared with carriers that protect the compound against rapid elimination from the body, such as time release formulations or coatings.

The compositions may include other active compounds to obtain desired combinations of properties. The compounds provided herein, or pharmaceutically acceptable derivatives thereof as described herein, may also be advantageously administered for therapeutic or prophylactic purposes together with another pharmacological agent known in the general art to be of value in treating one or more of the diseases or medical conditions referred to hereinabove, such as GSK-3 mediated diseases. It is to be understood that such combination therapy constitutes a further aspect of the compositions and methods of treatment provided herein.

1. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, such as capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl)acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

2. Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, such as more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

3. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (10-1000 mg or 100-500 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, about 5-35 mg, or about 9-30 mg of lyophilized powder, is added per mL of sterile water or other suitable carrier. The precise amount depends upon the selected compound. Such amount can be empirically determined.

4. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns or less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

5. Compositions for Other Routes of Administration

Other routes of administration, such as topical application, transdermal patches, and rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

6. Sustained Release Compositions

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, 5,639,480, 5,733,566, 5,739,108, 5,891,474, 5,922,356, 5,972,891, 5,980,945, 5,993,855, 6,045,830, 6,087,324, 6,113,943, 6,197,350, 6,248,363, 6,264,970, 6,267,981, 6,376,461, 6,419,961, 6,589,548, 6,613,358, 6,699,500 and 6,740,634, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In one embodiment, a pump may be used (see, Sefton, *CRC Crit. Ref. Biomed. Eng.* 14:201 (1987); Buchwald et al., *Surgery* 88:507 (1980); Saudek et al., *N. Engl. J. Med.* 321: 574 (1989). In another embodiment, polymeric materials can be used. In yet another embodiment, a controlled release system can be placed in proximity of the therapeutic target, i.e., thus requiring only a fraction of the systemic dose (see, e.g., Goodson, *Medical Applications of Controlled Release*, vol. 2, pp. 115-138 (1984). In some embodiments, a controlled release device is introduced into a subject in proximity of the site of inappropriate immune activation or a tumor. Other controlled release systems are discussed in the review by Langer (*Science* 249:1527-1533 (1990). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

7. Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

8. Articles of Manufacture

The compounds or pharmaceutically acceptable derivatives can be packaged as articles of manufacture containing packaging material, a compound or pharmaceutically acceptable derivative thereof provided herein, which is used for treatment, prevention or amelioration of one or more symptoms associated with GSK-3 activity, and a label that indicates that the compound or pharmaceutically acceptable derivative thereof is used for treatment, prevention or amelioration of one or more symptoms of GSK-3 mediated diseases.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated.

E. Evaluation of the Activity of the Compounds

Standard physiological, pharmacological and biochemical procedures are available for testing the compounds to identify those that possess a desired biological activity. GSK3 inhibitory activity of the compounds provided herein can be readily detected using the assays described herein, as well as assays generally known to those of ordinary skill in the art.

Exemplary methods for identifying specific inhibitors of GSK3 include both cell-free and cell-based GSK3 kinase assays. A cell-free GSK3 kinase assay detects inhibitors that act by direct interaction with the polypeptide GSK3, while a cell-based GSK3 kinase assay may identify inhibitors that function either by direct interaction with GSK3 itself, or by interference with GSK3 expression or with post-translational processing required to produce mature active GSK3. U.S. Application No. 20050054663 describes exemplary cell-free and cell-based GSK3 kinase assays. Exemplary assays used herein are discussed briefly below:

Luciferase-Coupled Protein Kinase Assays

All coupled-luciferase assays are performed by using a brief incubation with firefly luciferase (Promega) after completion of the kinase assay. KinaseGlo Plus is used for reading kinase reactions with ATP>10 μM, KinaseGlo for ATP <10 μM. The assay volume in a 384-well plate for the kinase reaction is 30 microliters.

GSK3β

10-25 ng of recombinant full-length human GSK3β (Upstate) is incubated in the presence or absence of compound at varying concentrations for 1 hour at 30 degrees Celsius in 20 mM MOPS, pH 7.0, 10 mM magnesium acetate, 0.2 mM EDTA, 2 mM EGTA, 30 mM magnesium chloride, 62.5 μM phospho-glycogen synthase peptide-2, 5 μM ATP, 10 mM β-glycerol phosphate, 1 mM sodium orthovanadate and 1 mM dithiothreitol. Proceed to KinaseGlo luciferase reaction (see below).

CDK2

20-50 ng of recombinant full-length human CDK2 (Upstate) complexed with recombinant, human full length Cyclin A (Upstate) is incubated in the presence or absence of compound at varying concentrations for 1 hour at 30 degrees Celsius in 20 mM MOPS, pH 7.0, 0.2 mM EDTA, 2 mM EGTA, 30 mM magnesium chloride, 1 mg/mL Histone HI (Roche), 10 μM ATP, 10 mM β-glycerol phosphate, 1 mM sodium orthovanadate and 1 mM dithiothreitol. Proceed to KinaseGlo Plus luciferase reaction (see below).

CDK5

10-25 ng of recombinant full-length human CDK5 complexed with recombinant, human full length p35 (Upstate), is incubated in the presence or absence of compound at varying concentrations for 1 hour at 30 degrees Celsius in 20 mM MOPS, pH 7.0, 0.2 mM EDTA, 2 mM EGTA, 30 mM magnesium chloride, 1 mg/mL Histone HI (Roche), 10 μM ATP, 10 mM β-glycerol phosphate, 1 mM sodium orthovanadate and 1 mM dithiothreitol. Proceed to KinaseGlo Plus luciferase reaction (see below).

IKKβ

100-200 ng of recombinant full-length human IKKβ (Upstate) is incubated in the presence or absence of compound at varying concentrations for 1 hour at 30 degrees Celsius in 20 mM MOPS, pH 7.0, 0.2 mM EDTA, 2 mM EGTA, 30 mM magnesium chloride, 100 μM IKKtide (IKK substrate peptide), 1 μM ATP, 10 mM β-glycerol phosphate, 1 mM sodium orthovanadate and 1 mM dithiothreitol. Proceed to KinaseGlo luciferase reaction (see below).

Luciferase Reaction:

Following the completion of the kinase reaction an equal volume of KinaseGlo or KinaseGlo Plus luciferase reagent (Promega) is added and the luminescence read using a luminescence plate reader within 5-10 minutes. Compound activity is expressed as % inhibition relative to maximal inhibition observed at the maximal dose and IC50 values then calculated using curve fitting software (GraphPad Prizm).

F. Methods of Use of the Compounds and Compositions

Methods of use of the compounds and compositions are also provided. The methods involve both in vitro and in vivo uses of the compounds and compositions.

In certain embodiments, provided herein are methods for inhibiting an action of GSK-3 by administering a compound provided herein or a pharmaceutically acceptable derivative thereof. In certain embodiments, provided herein are methods for treatment, prevention or amelioration of a GSK-3 mediated disease, including but not limited to diabetes, conditions associated with diabetes, Alzheimer's disease, Parkinson's disease, progressive supranuclear palsy, subacute sclerosing panencephalitic parkinsonism, postencephalitic parkinsonism, pugilistic encephalitis, guam parkinsonism-dementia complex, Pick's disease, corticobasal degeneration, frontotemporal dementia, Huntington's Disease, AIDS associated dementia, amyotrophic lateral sclerosis, multiple sclerosis, neurotraumatic diseases, depression, bipolar mood disorders, rheumatoid arthritis, inflammatory bowel disease, ulceractive colitis, Crohn's disease, sepsis, pancreatic cancer, ovarian cancer and osteoporosis. In certain embodiments, provided herein are methods for treatment, prevention or amelioration of a GSK-3 mediated disease, including but not limited to diabetes, conditions associated with diabetes, Alzheimer's disease, Parkinson's disease, progressive supranuclear palsy, subacute sclerosing panencephalitic parkinsonism, postencephalitic parkinsonism, pugilistic encephalitis, guam parkinsonism-dementia complex, Pick's disease, corticobasal degeneration, frontotemporal dementia, Huntington's Disease, AIDS associated dementia, amyotrophic lateral sclerosis, multiple sclerosis and neurotraumatic diseases. In one embodiment, the GSK-3 mediated disease is diabetes.

G. Combination Therapy

The compounds provided herein may be administered as the sole active ingredient or in combination with other active ingredients. Other active ingredients that may be used in combination with the compounds provided herein include but are not limited to, compounds known to treat GSK-3 mediated diseases such as conditions associated with diabetes, chronic neurodegenerative conditions including dementias such as Alzheimer's disease, Parkinson's disease, progressive supranuclear palsy, subacute sclerosing panencephalitic parkinsonism, postencephalitic parkinsonism, pugilistic encephalitis, guam parkinsonism-dementia complex, Pick's disease, corticobasal degeneration, frontotemporal dementia, Huntington's Disease, AIDS associated dementia, amyotrophic lateral sclerosis, multiple sclerosis and neurotraumatic diseases such as acute stroke, epilepsy, mood disorders such as depression, schizophrenia and bipolar disorders. Administration of the active ingredient combination may take place either by separate administration of the active ingredients to the patient or in the form of combination products in which a plurality of active ingredients are present in one pharmaceutical preparation.

In certain embodiments, the compound provided herein can be administered in combination with one or more antidiabetics known in the art. The antidiabetics include insulin and insulin derivatives such as, for example, Lantus® (see www-.lantus.com) or HMR 1964, fast-acting insulins (see U.S. Pat. No. 6,221,633), GLP-1 derivatives such as, for example, those disclosed in WO 98/08871 and orally effective hypoglycemic active ingredients.

The orally effective hypoglycemic active ingredients include, but are not limited to, sulfonylureas (e.g. tolbutamide, glibenclamide, glipizide or glimepiride), biguanidines (e.g. metformin), meglitinides (for example, repaglinide), oxadiazolidinediones, thiazolidinediones (for example, troglitazone, ciglitazone, pioglitazone, rosiglitazone or the compounds disclosed in WO 97/41097), glucosidase inhibitors (for example, miglitol or acarbose), glucagon antagonists, GLP-1 agonists, potassium channel openers such as, for example, those disclosed in WO 97/26265 and WO 99/03861, insulin sensitizers, inhibitors of liver enzymes involved in the stimulation of gluconeogenesis and/or glycogenolysis, modulators of glucose uptake, compounds which alter lipid metabolism, such as antihyperlipidemic active ingredients and antilipidemic active ingredients, compounds which reduce food intake, PPAR and PXR agonists and active ingredients which act on the ATP-dependent potassium channel of the beta cells.

In one embodiment, the compounds provided herein can be administered in combination with an HMGCoA reductase inhibitor such as simvastatin, fluvastatin, pravastatin, lovastatin, atorvastatin, cerivastatin, rosuvastatin. In one embodiment, the compounds provided herein can be administered in combination with a cholesterol absorption inhibitor such as, for example, ezetimibe, tiqueside, pamaqueside. In one embodiment, the compounds provided herein can be administered in combination with a PPAR gamma agonist, such as, for example, rosiglitazone, pioglitazone, JTT-501, GI 262570. In one embodiment, the compounds provided herein can be administered in combination with PPAR alpha agonist, such as, for example, GW 9578, GW 7647. In one embodiment, the compounds provided herein can be administered in combination with a mixed PPAR alpha/gamma agonist. In one embodiment, the compounds of the Formula Ia are administered in combination with a fibrate such as, for example, fenofibrate, clofibrate, bezafibrate. In one embodiment, the compounds provided herein can be administered in combination with an MTP inhibitor such as, for example, implitapide, BMS-201038, R-103757. In another embodiment, the compounds provided herein can be administered in combination with bile acid absorption inhibitor (see, for example, U.S. Pat. No. 6,245,744 or U.S. Pat. No. 6,221,897), such as, for example, HMR 1741; a CETP inhibitor, such as, for example, JTF-705; a polymeric bile acid adsorbent such as, for example, cholestyramine, colesevelam; an LDL receptor inducer (see U.S. Pat. No. 6,342,512), such as, for example, HMR1171, HMR1586; an ACAT inhibitor, such as, for example, avasimibe; an antioxidant, such as, for example, OPC-14117; a lipoprotein lipase inhibitor, such as, for example, NO-1886; an ATP-citrate lyase inhibitor, such as, for example, SB-204990; a squalene synthetase inhibitor, such as, for example, BMS-188494; a lipoprotein(a) antagonist, such as, for example, CI-1027 or nicotinic acid; a lipase inhibitor, such as, for example, orlistat. In one embodiment, the compounds provided herein, such as compounds of the formula Ia are administered in combination with insulin.

In a further embodiment, the compounds provided herein, such as compounds of the formula Ia can be administered in combination with CART modulators (see "Cocaine-amphetamine-regulated transcript influences energy metabolism, anxiety and gastric emptying in mice" Asakawa, A, et al., M.: *Hormone and Metabolic Research* (2001), 33(9), 554-558), NPY antagonists, e.g. naphthalene-1-sulfonic acid {4-[(4-aminoquinazolin-2-ylamino)methyl]cyclo-hexylmethyl} amide; hydrochloride (CGP 71683A)), $MC_4$ agonists (e.g. 1-amino-1,2,3,4-tetrahydronaphthalene-2-carboxylic acid

[2-(3a-benzyl-2-methyl-3-oxo-2,3,3a,4,6,7-hexahydropyrazolo[4,3-c]pyridin-5-yl)-1-(4-chlorophenyl)-2-oxoethyl]-amide; (WO 01/91752)), orexin antagonists (e.g. 1-(2-methylbenzoxazol-6-yl)-3-[1,5]naphthyridin-4-ylurea; hydrochloride (SB-334867-A)), H3 agonists (3-cyclohexyl-1-(4,4-dimethyl-1-1,4,6,7-tetrahydroimidazo[4,5-c]-pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl]dipropyla-mine (WO 00/66585)), CRF BP antagonists (e.g. urocortin), urocortin agonists, β3 agonists (e.g. 1-(4-chloro-3-methanesulfonylmethylpheny-1)-2-[2-(2,3-dimethyl-1H-indol-6-yloxy)-ethylamino]-ethanol hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexyl-ethyl-)thiazol-2-ylcarbamoyl]-5,7-dimethylindol-1-yl}acetic acid trifluoroacetic acid salt (WO 99/15525)), serotonin reuptake inhibitors (e.g. dexfenfluramine), mixed sertoninergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1-H-isoquinoline-2-carboxylic acid tert-butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. *Drugs of the Future* (2001), 26(9), 873-881), DA agonists (bromocriptine, Doprexin), lipase/amylase inhibitors (e.g. WO 00/40569), PPAR modulators (e.g. WO 00/78312), RXR modulators or TR-β agonists.

In one embodiment, the other active ingredient is leptin; see, for example, "Perspectives in the therapeutic use of leptin", Salvador, Javier; Gomez-Ambrosi, Javier; Fruhbeck, Gema, *Expert Opinion on Pharmacotherapy* (2001), 2(10), 1615-1622. In one embodiment, the other active ingredient is dexamphatamine or amphetamine. In one embodiment, the other active ingredient is fenfluramine or dexfenfluramine. In another embodiment, the other active ingredient is sibutramine.

In one embodiment, the other active ingredient is orlistat. In one embodiment, the other active ingredient is mazindol or phentermine.

It will be appreciated that every suitable combination of the compounds provided herein with one or more of the aforementioned compounds and optionally one or more further pharmacologically active substances is contemplated herein.

It is understood that the foregoing detailed description and accompanying examples are merely illustrative, and are not to be taken as limitations upon the scope of the subject matter. Various changes and modifications to the disclosed embodiments will be apparent to those skilled in the art. Such changes and modifications, including without limitation those relating to the chemical structures, substituents, derivatives, intermediates, syntheses, formulations and/or methods of use provided herein, may be made without departing from the spirit and scope thereof. U.S. patents and publications referenced herein are incorporated by reference.

EXAMPLES

Example 1

5-Amino-1-cyclopropyl-6,8-difluoro-7-[2-(2-pyridylamino)ethylamino]-1,4-dihydro-4-oxoquinoline-3-carboxylic acid (8)

Ethyl 2-(2,3,4,5,6-pentafluorobenzoyl)-3-cyclopropylaminoacrylate (3)

A stirred solution of ethyl (pentafluorobenzoyl)acetate 1 (5.77 g, 20 mmol), Ac2O (8.02 mL, 8.34 g, 80 mmol) and triethyl orthoformate (5.1 mL, 4.54 g, 30 mmol) was heated at 130° C. for 1.5 h. The mixture was concentrated in vacuo and dried under high vacuum for 3 hours. The crude product 2 was dissolved in anhydrous $CH_2Cl_2$ (10 mL) and cyclopropyl amine (2.15 mL, 1.75 g, 30 mmol) was added very slowly at room temperature. After 1.5 h, the solvent was removed by evaporation to yield 3 as a dark yellow solid (7.55 g crude, quantitative) that was used in the next step without further purification.

Ethyl 1-cyclopropyl-5,6,7,8-tetrafluoro-1,4-dihydro-4-oxoquinoline-3-carboxylate (4)

Method A.
A solution of crude 3 (7.55 g, 21 mmol) and $K_2CO_3$ (11.95 g, 86 mmol) in THF (57 mL) was heated at 50° C. for 2 h. During this time, the reaction mixture turned cloudy and yellow. The solvent was removed by evaporation. The crude product was taken up in 80 mL of ice water. The precipitate was collected by vacuum filtration and washed several times with EtOH (3×10 mL) and MeOH (3×10 mL) to yield 4 as a white solid (5.18 g, 77%)
Method B.
To a solution of 3 (0.1 g, 0.28 mmol) in THF (5 mL), 1M $^t$BuOK in THF (0.28 mL, 0.28 mmol) was added drop wise under ice-cooling. After 1.5 h, the reaction mixture was poured into ice-water (20 mL) and the product extracted with $CH_2Cl_2$ (3×20 mL). After drying and evaporation of solvent, 4 was obtained as a dark yellow solid (65 mg, 70%)

Ethyl 5-benzylamino-1-cyclopropyl-6,7,8-trifluoro-1,4-dihydro-4-oxoquinoline-3-carboxylate (5)

A solution of 4 (5.0 g, 15 mmol) and benzylamine (8.02 g, 8.1 mL, 75 mmol) in toluene (50 mL) was stirred at 90° C. for 2 h. The solvent was removed by evaporation. The crude product was dissolved in ethanol (30 mL) and stirred at room temperature for several minutes. The precipitate that formed was collected by filtration and washed with cold ethanol (3×10 mL) to yield 5 as a light yellow solid (5.12 g, 82%).

Ethyl 5-amino-1-cyclopropyl-6,7,8-trifluoro-1,4-dihydro-4-oxoquinoline-3-carboxylate (6)

A solution of 5 (5.12 g, 12.3 mmol) in AcOH (200 mL) was hydrogenated under atmospheric pressure over 10% Pd/C (3.0 g) at 50° C. for 2 h. The catalyst was removed by filtration over Celite and the filtrate was concentrated in vacuo to dryness to yield 6 (3.58 g, 89%) which was used crude in the next step.

5-Amino-1-cyclopropyl-6,7,8-trifluoro-1,4-dihydro-4-oxoquinoline-3-carboxylic acid (7)

A solution of 6 (1.85 g, 5.7 mmol) in a mixture of AcOH—$H_2O$—$H_2SO_4$ (8:6:1 v/v, 75 mL) was heated at reflux for 2 h.

The reaction mixture was poured into ice water and adjusted to pH 4 with 1M NaOH solution. A precipitate formed and was collected by filtration, washed successively with water and ethanol and then dried to give 7 (1.3 g, 77%) as a light yellow solid.

5-Amino-1-cyclopropyl-6,8-difluoro-7-[2-(2-pyridylamino)ethylamino]-1,4-dihydro-4-oxoquinoline-3-carboxylic acid (8)

A solution of 7 (270 mg, 0.91 mmol) and N-2-pyridinyl-1,2-ethanediamine (250 mg, 1.82 mmol) in DMSO (7 mL) was stirred at 80° C. for 1 h. The reaction mixture was cooled and freeze-dried overnight. The crude product was taken up in methanol (75 mL) and the resulting precipitate was removed by filtration, washed with cold methanol and dried to yield 8 (285 mg, 75%) as a yellow solid.

5-Amino-1-cyclopropyl-6,8-difluoro-7-[2-(2-pyridylamino)ethylamino]-1,4 dihydro-4-oxoquinoline (9)

A mixture of 8 (100 mg, 0.24 mmol) and NaCN (117 mg, 2.4 mmol) in DMSO (2 mL) was stirred at 120° C. for 2 h. The reaction mixture was cooled and freeze-dried overnight. The crude product was purified by column chromatography (CH$_2$Cl$_2$: EtOAc 10:1) to yield 9 (71 mg, 80%) as a yellow solid.

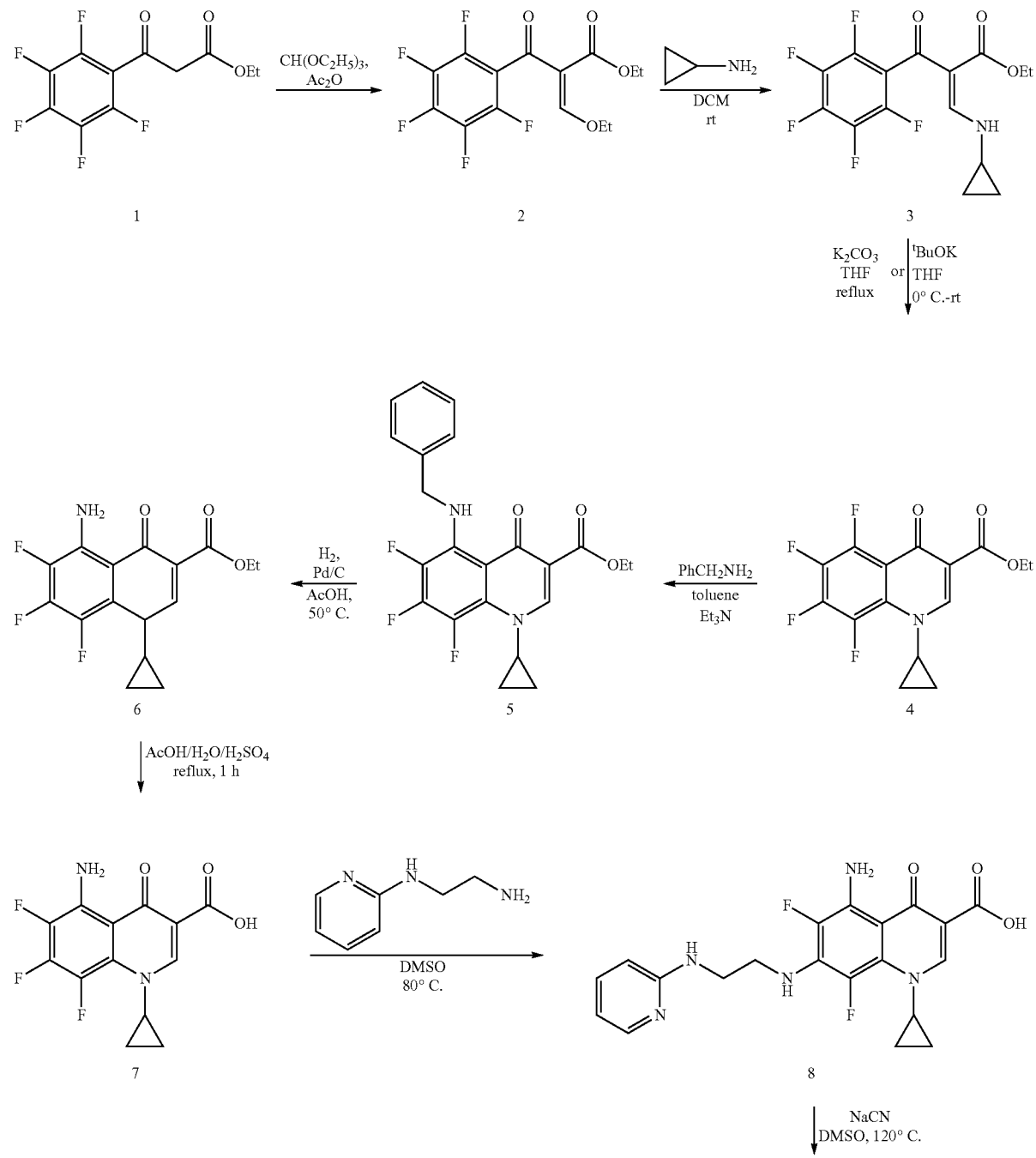

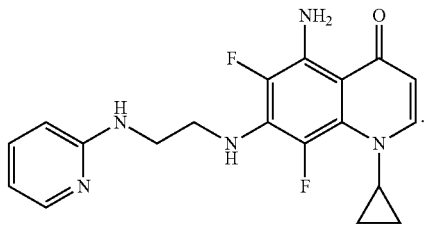

9

Example 2

5-Amino-1-cyclopentyl-6,8-difluoro-7-(3-phenylpropylamino)-1,4-dihydro-4-oxoquinoline-3-carboxylic acid (11)

Intermediate 10 was prepared using procedures similar to those described in Example 1. A mixture of 10 (75 mg, 0.23 mmol) and 3-phenyl-propylamine (67 mg, 70 µL, 0.5 mmol) in DMSO (3 mL) was stirred at 80° C. for 1 h. The reaction mixture was cooled down and freeze-dried overnight. The crude product was purified by column chromatography ($CH_2Cl_2$: EtOAc 10:1) to yield 11 (72 mg, 71%) as a yellow solid.

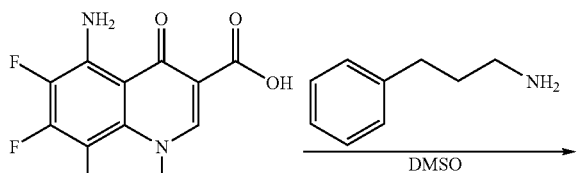

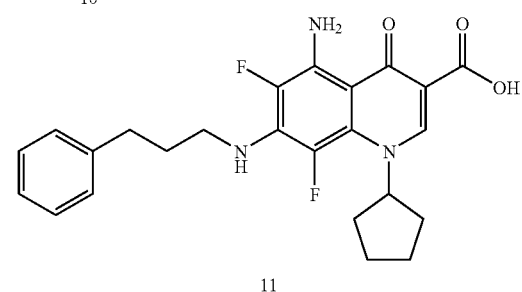

Example 3

5-Amino-1-cyclopentyl-6-fluoro-8-methoxy-7-[2-(2-pyridylamino)ethylamino]-1,4 dihydro-4-oxoquinoline-3-carboxylic acid and 5-Amino-1-cyclopentyl-6-fluoro-8-methoxy-7-[2-(2-pyridylamino) ethylamino]-1,4 dihydro-4-oxoquinoline

Ethyl 2-(3-methoxy-2,4,5-trifluorobenzoyl)-3-cyclopentylaminoacrylate (14)

A solution of ethyl (3-methoxy-2,4,5-trifluorobenzoyl)acetate (12, 7.6 g, 27.5 mmol), $Ac_2O$ (6.5 mL, 69 mmol) and triethyl orthoformate (6.9 mL, 41 mmol) was heated at 150° C. for 1.5 h. The mixture was concentrated in vacuo and dried under high vacuum for 3 hours. The crude product 13 was dissolved in ethanol (50 mL) and cyclopentyl amine (2.8 mL, 27 mmol) was added very slowly at 0° C. After 1.5 h, the solvent was removed by evaporation to yield 14 as a dark yellow solid (9.55 g crude, quantitative).

Ethyl 1-cyclopentyl-6,7-difluoro-8-methoxy-1,4-dihydro-4-oxoquinoline-3-carboxylate (15)

To a solution of 14 (9.5 g, 25 mmol) in THF (100 mL), 1M $^t$BuOK in THF (25 mL, 25 mmol) was added dropwise under ice-cooling. After 1.5 h, the reaction mixture was poured into ice-water (20 mL) and the product extracted with $CH_2Cl_2$ (3×20 mL). After evaporation of the solvent, 15 was obtained as an orange solid (6.1 g, 69%)

Ethyl 1-cyclopentyl-6,7-difluoro-8-methoxy-5-nitro-1,4-dihydro-4-oxoquinoline-3-carboxylate (16)

A solution of 15 (6.1 g, 17.4 mmol) in concentrated $H_2SO_4$ (60 mL) was treated portionwise at 0° C. with solid $KNO_3$ (2.64 g, 26 mmol). After stirring at 0° C. for 1 h, the reaction mixture was poured into 500 mL of ice-water and the resulting precipitate was removed by filtration, washed with water and dissolved in $CH_2Cl_2$. The resulting solution washed with 5% $NaHCO_3$, dried and evaporated to yield 16 as a yellow solid (6.0 g, 87%).

Ethyl 1-cyclopentyl-6,7-difluoro-8-methoxy-5-amino-1,4-dihydro-4-oxoquinoline-3-carboxylate (17)

A solution of 16 (6.0 g, 15 mmol) in EtOH-DMF (4:1, v/v, 250 mL) was hydrogenated under atmospheric pressure over 10% Pd/C (600 mg) at room temperature overnight. The catalyst was removed by filtration over Celite and the filtrate was concentrated in vacuo to dryness to yield 17 (5.0 g, 90%) which was used crude in the next step.

5-Amino-1-cyclopentyl-6,7-trifluoro-8-methoxy-1,4-dihydro-4-oxoquinoline-3-carboxylic acid (18)

A solution of 17 (5.0 g, 13.6 mmol) in a mixture of AcOH—$H_2O$—$H_2SO_4$ (8:6:1 v/v, 120 mL) was heated at reflux for 2 h. The reaction mixture was poured into 500 mL ice water and extracted with $CH_2Cl_2$ (3×100 mL). The organic layer was washed with brine (3×50 mL), dried and evaporated. The crude product was purified by column chromatography ($CH_2Cl_2$: EtOAc 90:10, v/v) to yield pure 18 (2.0 g, 44%) as a brown solid.

5-Amino-1-cyclopentyl-6-fluoro-8-methoxy-7-[2-(2-pyridylamino)ethylamino]-1,4 dihydro-4-oxoquinoline-3-carboxylic acid (19) and 5-Amino-1-cyclopentyl-6-fluoro-8-methoxy-7-[2-(2-pyridylamino)ethylamino]-1,4-dihydro-4-oxoquinoline (20) were prepared from intermediate 18 following similar procedures as described in Examples 1 and 2.

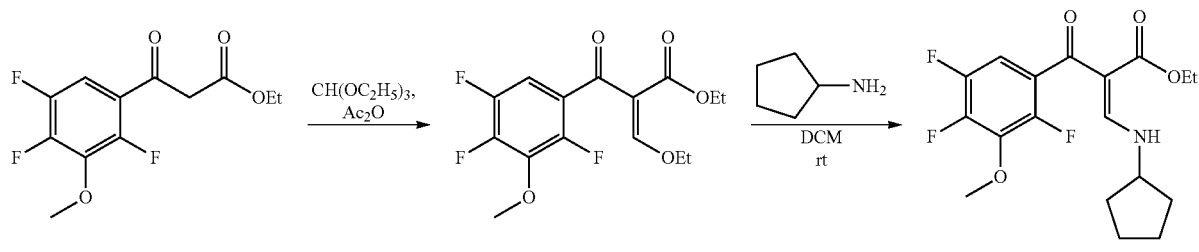
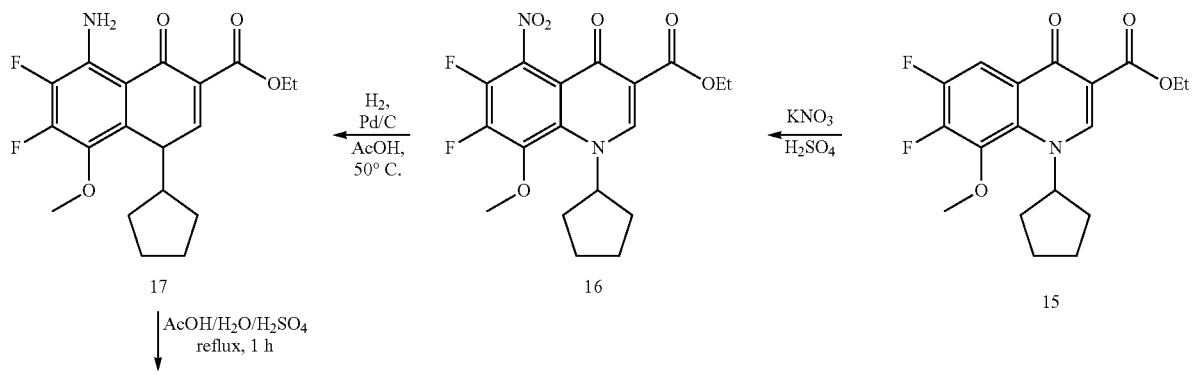
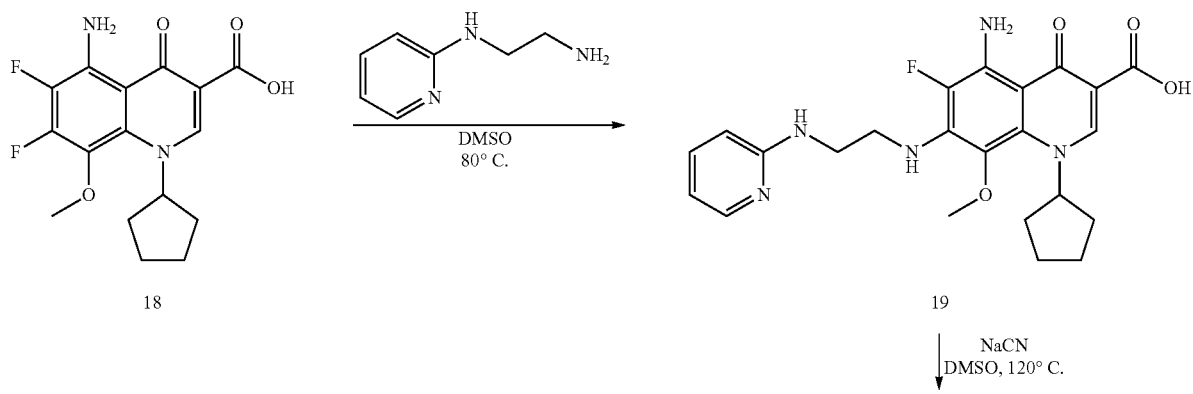

Example 4

5-Amino-1-cyclopropyl-6-fluoro-1,4-dihydro-8-methoxy-7-[2-[methyl(2-pyridyl)amino]ethylamino]-4-oxoquinoline-3-carboxylic acid

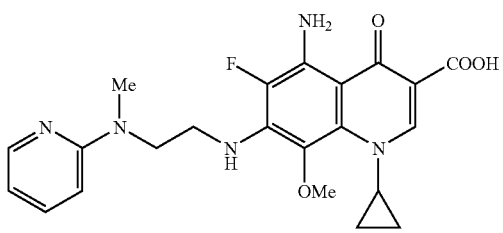

A mixture of 5-amino-1-cyclopropyl-6,7-difluoro-1,4-dihydro-8-methoxy-4-oxoquinoline-3-carboxylic acid (400 mg, 1.44 mmol), N-methyl-N-(2-pyridyl)-1,2-ethanediamine (326 mg, 2.16 mmol) and triethylamine (0.300 mL, 2.15 mmol) in anhydrous DMSO (6 mL) was stirred at 100° C. for 3 h. After cooling, the reaction mixture was poured into ice-water (50 mL), the resulting precipitate was collected by filtration and washed with water. The obtained solid was recrystallized from EtOH to give 5-amino-1-cyclopropyl-6-fluoro-1,4-dihydro-8-methoxy-7-[2-[methyl(2-pyridyl)amino]ethylamino]-4-oxoquinoline-3-carboxylic acid (303 mg, 48%) as yellow needles.

$^1$H-NMR (400 MHz, DMSO-d6) δ 0.78-0.90 (2H, m), 0.93-1.03 (2H, m), 3.01 (3H, s), 3.41 (3H, s), 3.60-3.70 (2H, m), 3.77 (2H, t, J=6.1 Hz), 3.94-4.00 (2H, m), 3.94-4.00 (1H, m), 6.38-6.46 (1H, m), 6.54 (1H, dd, J=6.7, 4.9 Hz), 6.63 (1H, d, J=8.6 Hz), 7.13 (2H, brs), 7.45-7.50 (1H, m), 8.04 (1H, dd, J=4.9, 1.2 Hz), 8.42 (1H, s), 15.08 (1H, s).

HRESIMS (+): 442.19010 (calcd for $C_{22}H_{25}FN_5O_4$, 442.18906).

Example 5

5-Amino-1-cyclopropyl-6-fluoro-1,4-dihydro-8-methoxy-7-[methyl[2-(2-pyridylamino)ethyl]amino]-4-oxoquinoline-3-carboxylic acid

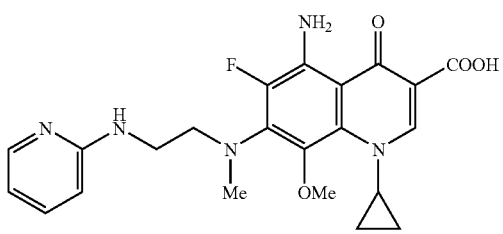

A mixture of 5-amino-1-cyclopropyl-6,7-difluoro-1,4-dihydro-8-methoxy-4-oxoquinoline-3-carboxylic acid (400 mg, 1.44 mmol), N-methyl-N'-(2-pyridyl)-1,2-ethanediamine (326 mg, 2.16 mmol) and triethylamine (0.300 mL, 2.15 mmol) in anhydrous DMSO (6 mL) was stirred at 100° C. for 3 h. Triethylamine (0.300 mL, 2.15 mmol) was added and the mixture was stirred at 100° C. for 3 h. After cooling, the reaction mixture was poured into ice-water (50 mL), the resulting precipitate was collected by filtration, washed with water and dried to give 5-amino-1-cyclopropyl-6-fluoro-1,4-dihydro-8-methoxy-7-[methyl[2-(2-pyridylamino)ethyl]amino]-4-oxoquinoline-3-carboxylic acid (392 mg, 62%) as a yellow solid.

$^1$H-NMR (400 MHz, DMSO-d$_6$) δ 0.78-0.87 (2H, m), 0.96-1.03 (2H, m), 3.06 (3H, d, J=3.1 Hz), 3.45-3.51 (7H, m), 3.94-4.05 (1H, m), 6.36-6.49 (3H, m), 7.13 (2H, brs), 7.28-7.32 (1H, m), 7.91 (1H, dd, J=4.9, 1.2 Hz), 8.52 (1H, s), 14.91 (1H, s).

HRESIMS (+): 442.18910 (calcd for $C_{22}H_{25}FN_5O_4$, 442.18906).

Example 6

5-Amino-1-cyclopropyl-6-fluoro-1,4-dihydro-8-methoxy-7-[methyl[2-[methyl(2-pyridyl)amino]ethyl]amino]-4-oxoquinoline-3-carboxylic acid

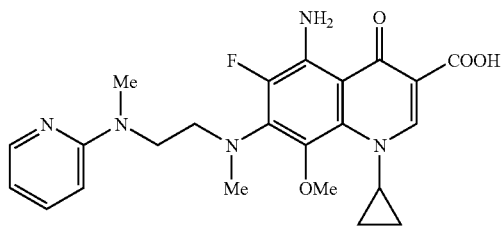

A mixture of 5-amino-1-cyclopropyl-6,7-difluoro-1,4-dihydro-8-methoxy-4-oxoquinoline-3-carboxylic acid (400 mg, 1.44 mmol), N,N'-dimethyl-N-(2-pyridyl)-1,2-ethanediamine (355 mg, 2.15 mmol) and triethylamine (0.300 mL, 2.15 mmol) in anhydrous DMSO (6 mL) was stirred at 100° C. for 3 h. Triethylamine (0.300 mL, 2.15 mmol) was added and the mixture was stirred at 100° C. for 3 h. After cooling, the reaction mixture was poured into ice-water (50 mL). The resulting precipitate was collected by filtration, washed with water and dried to give 5-Amino-1-cyclopropyl-6-fluoro-1,4-dihydro-8-methoxy-7-[methyl[2-[methyl(2-pyridyl)amino]ethyl]amino]-4-oxoquinoline-3-carboxylic acid (480 mg, 73%) as a brown solid.

$^1$H-NMR (400 MHz, DMSO-d$_6$) δ 0.73-0.81 (2H, m), 0.91-0.99 (2H, m), 2.93 (3H, s), 3.09 (3H, d, J=4.3 Hz), 3.47 (3H, s), 3.54 (2H, t, J=6.7 Hz), 3.76 (2H, t, J=6.7 Hz), 3.98-4.04 (1H, m), 6.48-6.54 (2H, m), 7.11 (2H, brs), 7.41-7.45 (1H, m), 8.01 (1H, dd, J=4.9, 1.8 Hz), 8.51 (1H, s), 14.91 (1H, s).

HRESIMS (+): 456.20597 (calcd for $C_{23}H_{27}FN_5O_4$, 456.20471).

Example 7

5-Amino-1-cyclopropyl-7-[2-(ethoxycarbonyl)ethylamino]-6-fluoro-1,4-dihydro-8-methoxy-4-oxoquinoline-3-carboxylic acid

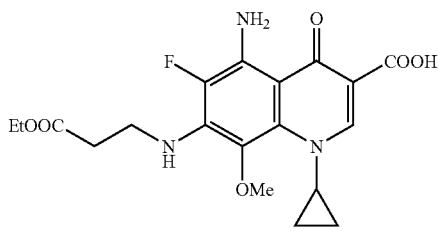

A mixture of 5-amino-1-cyclopropyl-6,7-difluoro-1,4-dihydro-8-methoxy-4-oxoquinoline-3-carboxylic acid (1.50 g, 5.39 mmol), β-alanine ethyl ester hydrochloride (2.48 g, 16.1 mmol) and triethylamine (4.50 mL, 32.3 mmol) in anhydrous DMSO (30 mL) was stirred at 100° C. for 10 h. After cooling, the reaction mixture was poured into ice-water (50 mL) and acidified with 1M HCl. The product was extracted with EtOAc, washed with water and brine, dried over $Na_2SO_4$ and concentrated in vacuo. Trituration of the residue with MeOH (30 mL) gave 5-amino-1-cyclopropyl-7-[2-(ethoxycarbonyl)ethylamino]-6-fluoro-1,4-dihydro-8-methoxy-4-oxoquinoline-3-carboxylic acid (1.54 g, 70%) as a yellow solid.

$^1$H-NMR (400 MHz, DMSO-$d_6$) δ 0.82-0.91 (2H, m), 0.98-1.06 (2H, m), 1.16 (3H, t, J=7.3 Hz), 2.63 (2H, t, J=6.7 Hz), 3.53 (3H, s), 3.65-3.74 (2H, m), 3.97-4.10 (3H, m), 6.08-6.17 (1H, m), 7.18 (2H, brs), 8.45 (1H, s), 15.12 (1H, s).

Example 8

Ethyl 3-[(5-amino-1-cyclopropyl-6-fluoro-1,4-dihydro-8-methoxy-4-oxoquinolin-7-yl)amino]propionate

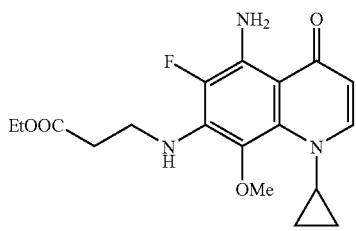

A mixture of 5-amino-1-cyclopropyl-7-[2-(ethoxycarbonyl)ethyl amino]-6-fluoro-1,4-dihydro-8-methoxy-4-oxoquinoline-3-carboxylic acid (1.30 g, 3.19 mmol) and NaCN (1.57 g, 32.0 mmol) in DSMO (25 mL) was stirred at 120° C. for 2 h. After cooling, the reaction mixture was poured in to ice-water (300 mL) and extracted with EtOAc (3×100 mL). The organic layers were combined, washed with water (3×100 mL) and brine (100 mL), dried over $Na_2SO_4$ and concentrated in vacuo. The residue was purified by column chromatography (Chromatorex NH-DM2035 (Fuji Sylysia Chemical Co., Ltd.), hexane:EtOAc 1:1) to give ethyl 3-[(5-amino-1-cyclopropyl-6-fluoro-1,4-dihydro-8-methoxy-4-oxoquinolin-7-yl)amino]propionate (723 mg, 63%) as a pale yellow solid.

$^1$H-NMR (400 MHz, DMSO-$d_6$) δ 0.72-0.79 (2H, m), 0.93-1.02 (2H, m), 1.27 (3H, t, J=7.3 Hz), 2.64 (2H, t, J=6.1 Hz), 3.55 (3H, s), 3.65-3.70 (1H, m), 3.73-3.80 (2H, m), 4.17 (2H, q, J=7.3 Hz), 4.76-4.85 (1H, m), 5.88 (1H, d, J=7.9 Hz), 6.64 (2H, brs), 7.40 (1H, d, J=7.3 Hz).

HRESIMS (+): 364.16624 (calcd for $C_{18}H_{23}FN_3O_4$, 364.16726).

Example 9

5-Amino-1-cyclopropyl-7-[2-[(5-ethoxycarbonyl-2-pyridyl)amino]ethylamino]-6-fluoro-1,4-dihydro-8-methoxy-4-oxoquinoline-3-carboxylic acid

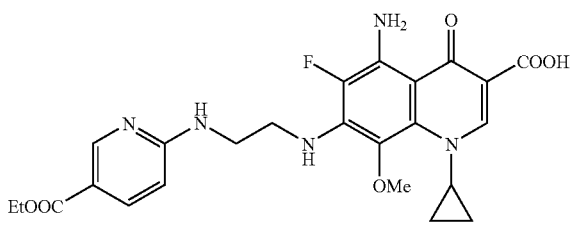

A mixture of 5-amino-1-cyclopropyl-6,7-difluoro-1,4-dihydro-8-methoxy-4-oxoquinoline-3-carboxylic acid (740 mg, 2.39 mmol), ethyl 2-(2-aminoethylamino)pyridine-5-carboxylate (1.00 g, 4.78 mmol) and triethylamine (0.670 mL, 4.81 mmol) in anhydrous DMSO (7 mL) was stirred at 100° C. for 8 h. After cooling, the reaction mixture was poured into water (300 mL) and extracted with $CH_2Cl_2$ (2×100 mL). The organic layers were combined, washed with water, dried over $Na_2SO_4$, and concentrated in vacuo. The residue was purified by column chromatography (EtOAc) to give 5-amino-1-cyclopropyl-7-[2-[(5-ethoxycarbonyl-2-pyridyl)amino]ethylamino]-6-fluoro-1,4-dihydro-8-methoxy-4-oxoquinoline-3-carboxylic acid (600 mg, 50%) as a yellow solid.

$^1$H-NMR (400 MHz, DMSO-$d_6$) δ 0.80-0.89 (2H, m), 0.95-1.04 (2H, m), 1.26 (3H, t, J=7.3 Hz), 3.48 (3H, s), 3.52-3.68 (4H, m), 3.95-4.02 (1H, m), 4.21 (2H, q, J=7.3 Hz), 6.31 (1H, brs), 6.51 (1H, d, J=8.6 Hz), 7.14 (2H, brs), 7.58 (1H, t, J=5.5 Hz), 7.80 (1H, dd, J=8.6, 1.8 Hz), 8.43 (1H, s), 8.54 (1H, d, J=1.8 Hz), 15.13 (1H, s).

HRESIMS (+): 500.19448 (calcd for $C_{24}H_{27}FN_5O_6$, 500.19454).

Example 10

Ethyl 2-[2-[(5-Amino-1-cyclopropyl-6-fluoro-1,4-dihydro-8-methoxy-4-oxoquinolin-7-yl)amino]ethylamino]pyridine-5-carboxylate

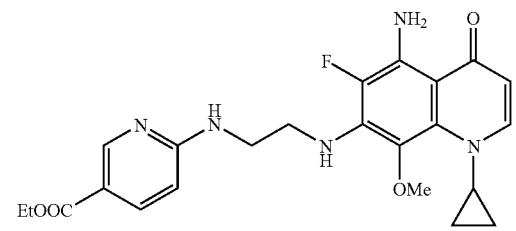

A mixture of 5-amino-1-cyclopropyl-7-[2-[(5-ethoxycarbonyl-2-pyridyl)amino]ethylamino]-6-fluoro-1,4-dihydro-8-methoxy-4-oxoquinoline-3-carboxylic acid (540 mg, 1.08 mmol) and NaCN (540 mg, 11.0 mmol) in DMSO (10 mL) was stirred at 120° C. for 2 h. After cooling, the reaction mixture was poured into water (100 mL) and extracted with EtOAc (2×50 mL). The organic layer washed with water (2×50 mL) and brine (50 mL), dried over $Na_2SO_4$, and concentrated in vacuo. The residue was purified by column chromatography (hexane: EtOAc 1:3) of the residue gave crude product as a brown oil (600 mg). The obtained oil was further purified by column chromatography (Chromatorex NH-DM2035 (Fuji Sylysia Chemical Co., Ltd.), hexane: EtOAc 1:3) to give ethyl 2-[2-[(5-amino-1-cyclopropyl-6-fluoro-1,4-dihydro-8-methoxy-4-oxoquinolin-7-yl)amino]ethylamino]pyridine-5-carboxylate (397 mg, 81%) as a yellow amorphous solid.

$^1$H-NMR (400 MHz, DMSO-$d_6$) δ 0.64-0.71 (2H, m), 0.887 (2H, q, J=6.7 Hz), 1.26 (3H, t, J=7.3 Hz), 3.42 (3H, s), 3.48-3.63 (4H, m), 3.68-3.75 (1H, m), 4.22 (2H, q, J=7.3 Hz), 5.61 (1H, d, J=7.9 Hz), 5.68-5.75 (1H, m), 6.51 (1H, d, J=8.6 Hz), 7.17 (2H, brs), 7.52-7.60 (2H, m), 7.80 (1H, dd, J=8.6, 2.4 Hz), 8.55 (1H, d, J=2.4 Hz).

HRESIMS (+): 456.20421 (calcd for $C_{23}H_{27}FN_5O_4$, 456.20471).

Example 11

2-[2-[[(5-Amino-1-cyclopropyl-6-fluoro-1,4-dihydro-8-methoxy-4-oxoquinolin-7-yl)amino]ethylamino]pyridine-5-carboxylic acid

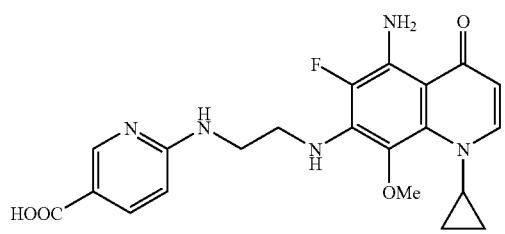

To a solution of ethyl 2-[2-[(5-amino-1-cyclopropyl-6-fluoro-1,4-dihydro-8-methoxy-4-oxoquinolin-7-yl)amino]ethylamino]pyridine-5-carboxylate (320 mg, 0.703 mmol) in EtOH (8 mL), 1M aq. NaOH was added. The mixture was stirred at room temperature for 5 h and then stirred at 50° C. for 3 h. After cooling, the reaction mixture was diluted with water (30 mL) and neutralized with 1M HCl. The product was extracted with $CH_2Cl_2$-MeOH (5:1, 2×50 mL). The extaction mixture was dried over $Na_2SO_4$ and concentrated in vacuo. The residue was dissolved in a mixture of MeOH (50 mL) and water (50 mL), and the solution was concentrated in vacuo until ca. 30 mL. The resulting precipitate was collected by filtration, washed with water and dried to give 2-[2-[(5-amino-1-cyclopropyl-6-fluoro-1,4-dihydro-8-methoxy-4-oxoquinolin-7-yl)amino]ethylamino]pyridine-5-carboxylic acid (115 mg, 38%) as a yellow solid.

$^1$H-NMR (400 MHz, DMSO-$d_6$) δ 0.64-0.72 (2H, m), 0.84-0.94 (2H, m), 3.42 (3H, s), 3.48-3.62 (4H, m), 3.68-3.76 (1H, m), 5.61 (1H, d, J=7.9 Hz), 5.69-5.78 (1H, m), 6.50 (1H, d, J=8.6 Hz), 7.14 (2H, brs), 7.46-7.52 (1H, m), 7.57 (1H, d, J=7.9 Hz), 7.79 (1H, dd, J=8.6, 2.4 Hz), 8.53 (1H, d, J=2.4 Hz), 12.35 (1H, brs).

HRESIMS (+): 428.17312 (calcd for $C_{21}H_{23}FN_5O_4$, 428.17341).

Example 12

5-Amino-1-cyclopropyl-6-fluoro-1,4-dihydro-7-[2-[(5-hydroxycarbonyl-2-pyridyl)amino]ethylamino]-8-methoxy-4-oxoquinoline-3-carboxylic acid

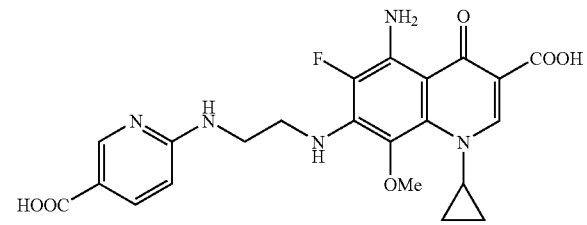

To a suspension of 5-amino-1-cyclopropyl-7-[2-[(5-ethoxycarbonyl-2-pyridyl)amino]ethylamino]-6-fluoro-1,4-dihydro-8-methoxy-4-oxoquinoline-3-carboxylic acid (390 mg, 0.781 mmol) in MeOH (5 mL), 1M aq. NaOH (5 mL) was added. The mixture was stirred at room temperature for 8 h. The reaction mixture was diluted with water (30 mL) and saturated aq $NH_4Cl$ (20 mL). The solution was saturated with NaCl and the crude product was extracted with EtOAc (2×100 mL). The organic layers were combined, washed with brine, dried over $Na_2SO_4$, and evaporated. The residue was dissolved in a mixture of MeOH (100 mL) and water (30 mL). The solution was concentrated in vacuo until ca. 50 mL and the resulting precipitate was collected by filtration, washed with water and dried to give 5-amino-1-cyclopropyl-6-fluoro 1,4-dihydro-7-[2-[(5-hydroxycarbonyl-2-pyridyl)amino]ethylamino]-8-methoxy-4-oxoquinoline-3-carboxylic acid (86.6 mg, 24%) as a yellow solid.

$^1$H-NMR (400 MHz, DMSO-$d_6$) δ 0.79-0.89 (2H, m), 0.95-1.04 (2H, m), 3.48 (3H, s), 3.52-3.68 (4H, m), 3.95-4.03 (1H, m), 6.29-6.36 (1H, m), 6.50 (1H, d, J=8.6 Hz), 7.14 (2H, brs), 7.46-7.54 (1H, m), 7.79 (1H, dd, J=8.6, 2.4 Hz), 8.43 (1H, s), 8.53 (1H, d, J=2.4 Hz), 12.36 (1H, s), 15.13 (1H, s).

HRESIMS (+): 472.16313 (calcd for $C_{22}H_{23}FN_5O_6$, 472.16324).

Example 13

1-Cyclopropyl-6-fluoro-8-methoxy-5-methylamino-7-[2-(2-pyridylamino)ethylamino]-1,4-dihydro-4-oxoquinoline-3-carboxylic acid Step 1: 1-Cyclopropyl-6,7-difluoro-1,4-dihydro-8-methoxy-4-oxo-5-(trifluoroacetamido)quinoline-3-carboxylic acid

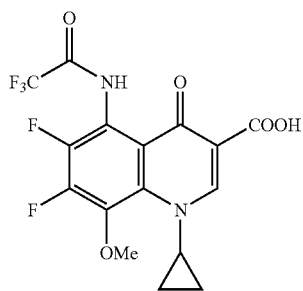

Trifluoroacetic anhydride (4 mL) was added to a suspension of 5-amino-1-cyclopropyl-6,7-difluoro-1,4-dihydro-8-methoxy-4-oxoquinoline-3-carboxylic acid (1.00 g, 3.22 mmol) in trifluoroacetic acid (20 mL) at room temperature. The mixture was stirred for 3 h and stood overnight. After removal of solvent, water (50 ml) was added. The resulting precipitate was collected by filtration, washed with water and MeOH and dried to give 1-cyclopropyl-6,7-difluoro-1,4-dihydro-8-methoxy-4-oxo-5-(trifluoroacetamido)quinoline-3-carboxylic acid as a pale brown solid (1.15 g, 88%).

$^1$H-NMR (400 MHz, DMSO-$d_6$) δ 1.06-1.21 (4H, m), 4.11 (3H, d, J=1.8 Hz), 4.21-4.29 (1H, m), 8.75 (1H, s), 11.69 (1H, s), 14.42 (1H, brs).

Step 2 Methyl 1-cyclopropyl-6,7-difluoro-1,4-dihydro-8-methoxy-5-(N-methyltrifluoroacetamido)-4-oxoquinoline-3-carboxylate

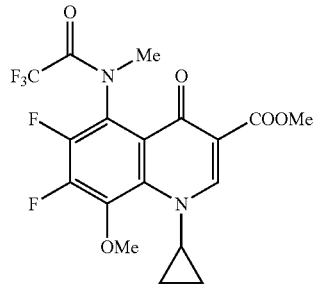

To a solution of 1-cyclopropyl-6,7-difluoro-1,4-dihydro-8-methoxy-4-oxo-5-trifluoroacetamidoquinoline-3-carboxylic acid (1.00 g, 2.46 mmol) in DMF (10 mL), 60% NaH in mineral oil (220 mg, 5.51 mmol) was added at 0° C. After stirring at 0° C. for 15 minutes, the mixture was stirred at room temperature for 0.5 h and then stirred at 50-55° C. for 0.5 h. Iodomethane (0.490 mL, 7.87 mmol) was added at 0° C. and the mixture was stirred at room temperature for 6 h. The reaction mixture was poured into ice-water (100 mL) and extracted with EtOAc (3×100 mL). The organic layers were combined, washed with water and brine, dried over Na$_2$SO$_4$ and evaporated. The residue was purified by column chromatography (Chromatorex NH-DM2035 (Fuji Sylysia Chemical Co., Ltd.), hexane: EtOAc 3:2→1:3) to give methyl 1-cyclopropyl-6,7-difluoro-1,4-dihydro-8-methoxy-5-(N-methyltrifluoroacetamido)-4-oxoquinoline-3-carboxylate (1.01 g, 94%) as a colorless solid.

$^1$H-NMR (400 MHz, CDCl$_3$) δ 0.89-1.06 (2H, m), 1.13-1.27 (2H, m), 3.33 (3H×⅔, s), 3.47-3.50 (3H×⅓, m), 3.88 (3H×⅓, s), 3.89 (3H×⅔, s), 4.00-4.08 (1H, m), 4.12 (3H×⅓, d, J=2.4 Hz), 4.16 (3H×⅔, d, J=3.1 Hz), 8.56 (1H×⅓, s), 8.58 (1H×⅔, s).

Step 3: 1-Cyclopropyl-6,7-difluoro-1,4-dihydro-5-methylamino-8-methoxy-4-oxoquinoline-3-carboxylic acid

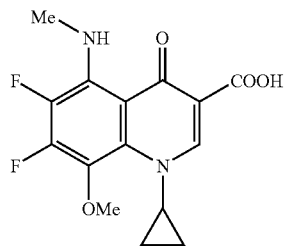

To a solution of methyl 1-cyclopropyl-6,7-difluoro-1,4-dihydro-8-methoxy-5-(N-methyltrifluoroacetamido)-4-oxoquinoline-3-carboxylate (880 mg, 2.03 mmol) in AcOH (10 mL), 6M HCl (5 mL) was added. The mixture was stirred at 100° C. for 4 h. After cooling, the solvent was removed by evaporation. 50 mL water was added, and the resulting precipitate was collected by filtration, washed with water and dried to give 1-cyclopropyl-6,7-difluoro-1,4-dihydro-8-methoxy-5-methylamino-4-oxoquinoline-3-carboxylic acid (605 mg, 92%) as a yellow solid.

$^1$H-NMR (400 MHz, CDCl$_3$) δ 0.95-1.01 (2H, m), 1.15-1.26 (2H, m), 3.19 (3H, dd, J=7.3, 4.9 Hz), 3.88 (3H, s), 3.99-4.06 (1H, m), 8.71 (1H, s), 9.47 (1H, s), 14.43 (1H, s).

Step 4: 1-Cyclopropyl-6-fluoro-1,4-dihydro-8-methoxy-5-methylamino-7-[2-(2-pyridylamino)ethylamino]-4-oxoquinoline-3-carboxylic acid

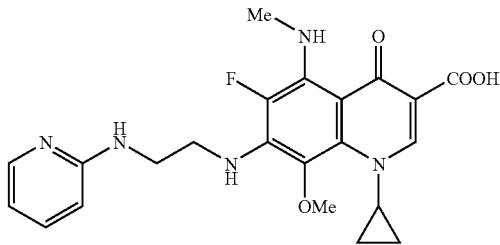

A mixture of 1-cyclopropyl-6,7-difluoro-1,4-dihydro-8-methoxy-5-methylamino-4-oxoquinoline-3-carboxylic acid (500 mg, 1.54 mmol), N-2-pyridyl-1,2-ethanediamine (423 mg, 3.03 mmol) and triethylamine (0.430 mL, 3.09 mmol) in anhydrous DMSO (8 mL) was stirred at 100° C. for 3 h. After cooling, the reaction mixture was poured into ice-water (50 mL) and extracted with EtOAc (2×100 mL). The organic layers were combined, washed with water, dried over Na$_2$SO$_4$, and evaporated. The residue was purified by column chromatography (hexane: EtOAc 1:1→EtOAc) to give 1-cyclopropyl-6-fluoro-1,4-dihydro-8-methoxy-5-methylamino-7-[2-(2-pyridylamino)ethylamino]-4-oxoquinoline-3-carboxylic acid (373 mg, 55%) as a yellow solid.

$^1$H-NMR (400 MHz, CDCl$_3$) δ 0.80-0.86 (2H, m), 1.06 (2H, q, J=7.3 Hz), 3.12 (3H, dd, J=7.3, 5.5 Hz), 3.45 (3H, s), 3.70 (2H, q, J=5.5 Hz), 3.74-3.80 (2H, m), 3.80-3.87 (1H, m), 4.67 (1H, t, J=6.1 Hz), 5.71-5.77 (1H, m), 6.44 (1H, d, J=8.6 Hz), 6.60-6.64 (1H, m), 7.38-7.44 (1H, m), 8.12 (1H, dd, J=4.9, 1.2 Hz), 8.58 (1H, s), 9.12 (1H, s), 15.08 (1H, s).

HRESIMS (+): 442.18868 (calcd for C$_{22}$H$_{25}$FN$_5$O$_4$, 442.18906).

Example 14

5-Amino-1-cyclopropyl-6-fluoro-1,4-dihydro-8-methoxy-4-oxo-7-[2-(2-pyridylamino)ethylamino]quinoline-3-carbonitrile Step 1: 5-Amino-1-cyclopropyl-6,7-difluoro-8-methoxy-1,4-dihydro-4-oxoquinoline-3-carboxamide

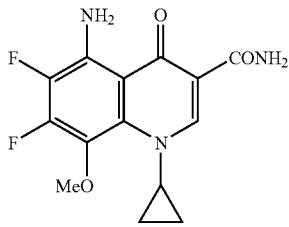

To a suspension of 5-Amino-1-cyclopropyl-6,7-difluoro-1,4-dihydro-8-methoxy-4-oxoquinoline-3-carboxylic acid (4.97 g, 16.0 mmol) in DMF (200 mL), triethylamine (3.35 mL, 24.0 mmol) and ethyl chloroformate (1.84 mL, 19.2 mmol) were added. After stirring at 0° C. for 2 h., 25% aq. NH₃ (5 mL) was added and the mixture was stirred at room temperature for 3 h. The reaction mixture was poured into water (1.5 L) and the resulting precipitate was collected by filtration, washed with water and dried to give 5-amino-1-cyclopropyl-6,7-difluoro-8-methoxy-1,4-dihydro-4-oxoquinoline-3-carboxamide (4.83 g, 97%) as a pale brown solid.

¹H-NMR (400 MHz, DMSO-d₆) δ 0.89-0.96 (2H, m), 1.04-1.11 (2H, m), 3.80 (3H, s), 3.99-4.06 (1H, m), 7.47 (1H, d, J=4.3 Hz), 7.69 (1H, brs), 8.55 (1H, s), 8.87 (1H, d, J=4.3 Hz).

Step 2: 1-Cyclopropyl-6,7-difluoro-1,4-dihydro-8-methoxy-4-oxo-5-(trifluoroacetamido)quinoline-3-carbonitrile

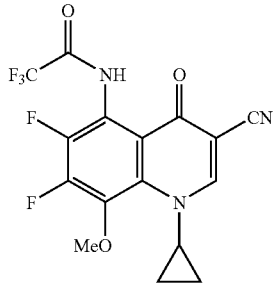

To a suspension of 5-amino-1-cyclopropyl-6,7-difluoro-8-methoxy-1,4-dihydro-4-oxoquinoline-3-carboxamide (2.00 g, 6.47 mmol) in CH₂Cl₂ (70 mL), triethylamine (5.60 mL, 40.2 mmol) and a solution of trifluoroacetic anhydride (3.42 mL, 24.6 mmol) in CH₂Cl₂ (30 mL) were added at 0° C. After stirring at 0° C. for 0.5 h, the reaction mixture washed with water and saturated aq. NaHCO₃, dried over Na₂SO₄, and concentrated in vacuo. The residue was purified by column chromatography (Hexane:EtOAc 2:1→1:1) to give 1-cyclopropyl-6,7-difluoro-1,4-dihydro-8-methoxy-4-oxo-5-(trifluoroacetamido)quinoline-3-carbonitrile (1.57 g, 63%) as a collarless solid.

¹H-NMR (400 MHz, DMSO-d₆) δ 1.04-1.11 (4H, m), 4.06 (3H, d, J=1.8 Hz), 4.07-4.11 (1H, m), 8.83 (1H, s), 11.89 (1H, s).

Step 3: 1-Cyclopropyl-6-fluoro-1,4-dihydro-8-methoxy-4-oxo-7-[2-(2-pyridylamino)ethylamino]-5-(trifluoroacetamido)quinoline-3-carbonitrile

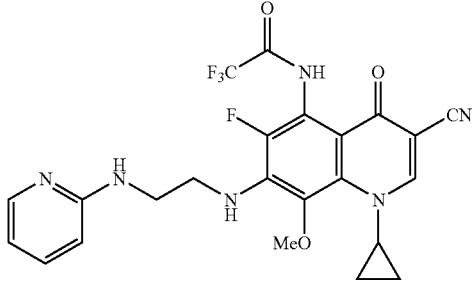

A mixture of 1-cyclopropyl-6,7-difluoro-1,4-dihydro-8-methoxy-4-oxo-5-(trifluoroacetamido) quinoline-3-carbonitrile (500 mg, 1.29 mmol), N-2-pyridyl-1,2-ethanediamine (354 mg, 2.58 mmol) and triethylamine (0.36 mL, 2.58 mmol) in anhydrous DMSO (8 mL) was stirred at 60° C. for 16 h. After cooling, the reaction mixture was poured into ice-water (50 mL). The resulting precipitate was collected by filtration, washed with water and then dried. The crude product was purified by column chromatography (Hexane:EtOAc 1:1→2:3→EtOAc→CH₂Cl₂:MeOH 8:1) to give 1-cyclopropyl-6-fluoro-1,4-dihydro-8-methoxy-4-oxo-7-[2-(2-pyridylamino)ethylamino]-5-(trifluoroacetamido)quinoline-3-carbonitrile (276 mg, 42%) as a brown solid.

¹H-NMR (400 MHz, DMSO-d₆) δ 0.88-1.02 (4H, m), 3.48 (2H, q, J=5.5 Hz), 3.56-3.64 (5H, m), 3.92-3.99 (1H, m), 6.44-6.50 (2H, m), 6.68-6.78 (2H, m), 7.32-7.38 (1H, m), 7.94 (1H, dd, J=5.5, 1.2 Hz), 8.64 (1H, s), 11.96 (1H, s).

Step 4: 5-Amino-1-cyclopropyl-6-fluoro-1,4-dihydro-8-methoxy-4-oxo-7-[2-(2-pyridylamino)ethylamino]quinoline-3-carbonitrile

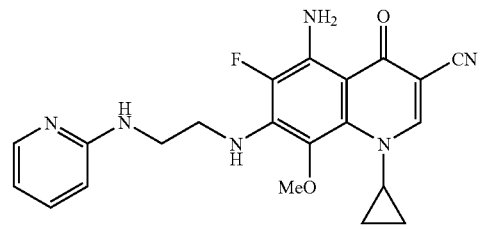

1 M aq. NaOH (1 mL) was added to a suspension of 1-cyclopropyl-6-fluoro-1,4-dihydro-8-methoxy-4-oxo-7-[2-(2-pyridylamino)ethylamino]-5-(trifluoroacetamido)quinoline-3-carbonitrile (100 mg, 0.198 mmol) in MeOH (5 mL). After stirring at room temperature for 8 h, water (10 mL) was added. The resulting precipitate was collected by filtration, washed with water and MeOH, and dried to give 5-amino-1-cyclopropyl-6-fluoro-1,4-dihydro-8-methoxy-4-oxo-7-[2-(2-pyridylamino)ethylamino]quinoline-3-carbonitrile (60.1 mg, 74%) as a pale brown solid.

¹H-NMR (400 MHz, DMSO-d₆) δ 0.80-0.95 (4H, m), 3.44-3.50 (5H, m), 3.54-3.62 (2H, m), 3.77-3.84 (1H, m), 6.12-6.19 (2H, m), 6.44-6.49 (2H, m), 6.69 (1H, t, J=5.5 Hz), 7.21 (2H, brs), 7.32-7.38 (1H, m), 7.95 (1H, dd, J=5.5, 1.2 Hz), 8.38 (1H, s).

HRESIMS (+): 409.17588 (calcd for C₂₁H₂₂FN₆O₂, 409.17883).

Example 15

Ethyl 5-amino-1-cyclopropyl-6-fluoro-1,4-dihydro-8-methoxy-4-oxo-7-[2-(2-pyridylamino)ethylamino]quinoline-3-carboxylate

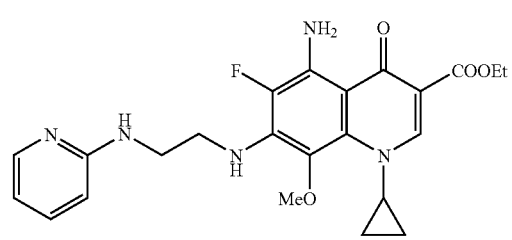

A mixture of 5-Amino-1-cyclopropyl-6-fluoro-1,4-dihydro-8-methoxy-4-oxo-7-[2-(2-pyridylamino)ethylamino]quinoline-3-carboxylic acid (428 mg, 1.00 mmol) and concentrated H$_2$SO$_4$ (1.0 mL) in EtOH (15 mL) was refluxed for 8 h. After cooling, the mixture was poured into ice water (100 mL). Saturated aq. NaHCO$_3$ (50 mL) was added and the crude product was extracted with CH$_2$Cl$_2$ (2×50 mL). The extraction mixture washed with brine, dried over Na$_2$SO$_4$ and concentrated in vacuo. The residue was purified by column chromatography (Chromatorex NH-DM2035 (Fuji Sylysia Chemical Co., Ltd.), EtOAc) to give ethyl 5-amino-1-cyclopropyl-6-fluoro-1,4-dihydro-8-methoxy-4-oxo-7-[2-(2-pyridylamino)ethylamino]quinoline-3-carboxylate (311 mg, 44%) as a pale yellow solid.

$^1$H-NMR (400 MHz, CDCl$_3$) δ 0.79-0.85 (2H, m), 1.03 (2H, q, J=7.3 Hz), 1.38 (3H, t, J=7.3 Hz), 3.47 (3H, s), 3.65 (2H, q, J=6.1 Hz), 3.70-3.78 (3H, m), 4.37 (2H, q, J=7.3 Hz), 4.65 (1H, t, J=6.1 Hz), 5.18-5.25 (1H, m), 6.43 (1H, d, J=8.6 Hz), 6.60 (1H, td, J=6.1, 1.2 Hz), 6.73 (2H, brs), 7.38-7.43 (1H, m), 8.10 (1H, dd, J=6.1, 1.8 Hz), 8.36 (1H, s).

HRESIMS (+): 456.20553 (calcd for C$_{23}$H$_{27}$FN$_5$O$_4$, 456.20471).

Example 16

1-Cyclopropyl-6,8-difluoro-1,4-dihydro-5mercapto-4-oxo-7-[2-(2-pyridylamino)ethylamino]quinoline-3-carboxylic acid Step 1: 1-cyclopropyl-5,6,8-trifluoro-1,4-dihydro-4-oxo-7-[2-(2-pyridylamino) ethylamino]quinoline-3-carboxylic acid

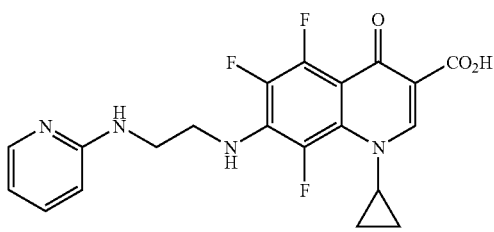

A solution of 1-cyclopropyl-5,6,7,8-tetrafluoro-1,4-dihydro-4-oxoquinoline-3-carboxylic acid (3.70 g, 12.3 mmol), N-2-pyridyl-1,2-ethanediamine (1.77 g, 12.9 mmol) and triethylamine (3.50 mL) in EtOH (50 mL) was stirred at room temperature for 3 h, and refluxed for 1 h. The reaction mixture was cooled at room temperature. The resulting precipitate was combined by filtration. The cake washed with EtOH and collected by filtration and then dried to give 1-cyclopropyl-1,4-dihydro-5,6,8-trifluoro-4-oxo-7-[2-(2-pyridylamino) ethylamino]quinoline-3-carboxylic acid (2.90 g, 56%) as a pale yellow solid.

$^1$H-NMR (400 MHz, DMSO-d$_6$) δ 1.03-1.20 (4H, m), 3.46-3.56 (2H, m), 3.60-3.70 (2H, m), 3.97-4.07 (1H, m), 6.42-6.52 (2H, m), 6.76 (1H, t, J=5.5 Hz), 7.30-7.40 (2H, m), 7.94 (1H, dd, J=5.5 and 1.2 Hz), 8.53 (1H, s), 15.03 (1H, s).

Step 2: 1-cyclopropyl-6,8-difluoro-1,4-dihydro-5-(4-methoxybenzylthio)-4-oxo-7-[2-(2-pyridylamino) ethylamino]quinoline-3-carboxylic acid

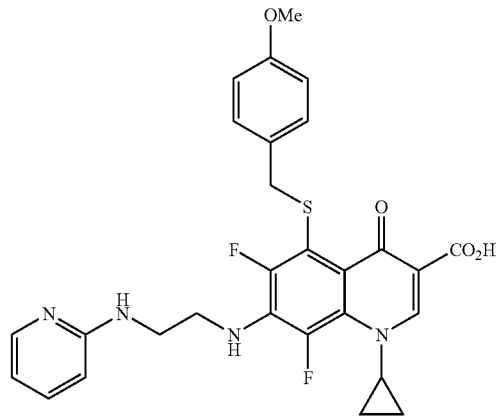

A solution of 1-cyclopropyl-5,6,8-trifluoro-1,4-dihydro-4-oxo-7-[2-(2-pyridylamino) ethylamino]quinoline-3-carboxylic acid (380 mg, 1.17 mmol), p-methoxybenzylmercaptane (170 μL, 1.22 mmol) and triethylamine (0.70 mL) in CH$_3$CN (20 mL) was refluxed for 12 h. The reaction mixture was cooled at room temperature. The resulting precipitate was combined by filtration. The cake washed with CH$_3$CN and collected by filtration and then dried to give 1-cyclopropyl-6,8-difluoro-1,4-dihydro-5-(4-methoxybenzylthio)-4-oxo-7-[2-(2-pyridylamino)ethylamino]quinoline-3-carboxylic acid (252 mg, 46%) as a yellow solid.

$^1$H-NMR (400 MHz, DMSO-d$_6$) δ 1.02-1.25 (4H, s), 3.50 (2H, q, J=5.5 Hz), 3.57-3.67 (2H, m), 3.70 (3H, s), 4.00-4.09 (1H, m), 4.12 (2H, d, J=2.4 Hz), 6.48 (2H, td, J=6.1 and 2.4 Hz), 6.75 (1H, t, J=6.1 Hz), 6.81 (2H, d, J=8.6 Hz), 6.99 (1H, brs), 7.52 (2H, d, J=8.6 Hz), 7.36 (1H, td, J=7.3 and 1.8 Hz), 7.95 (1H, dd, J=4.3 and 1.8 Hz), 8.51 (1H, s), 15.03 (1H, brs).

Step 3: 1-Cyclopropyl-6,8-difluoro-1,4-dihydro-5-mercapto-4-oxo-7-[2-(2-pyridyl amino)ethylamino] quinoline-3-carboxylic acid

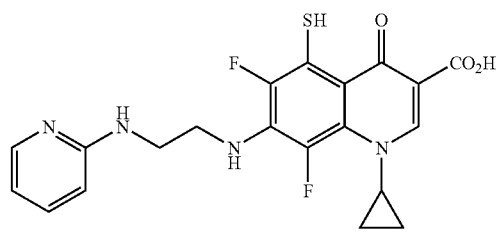

A mixture of 1-cyclopropyl-6,8-difluoro-1,4-dihydro-5-(4-methoxybenzylthio)-4-oxo-7-[2-(2-pyridylamino)ethylamino]quinoline-3-carboxylic acid (290 mg, 0.525 mmol) and trifluoroacetic acid (1.5 mL) in anisole (1.5 mL) was stirred at room temperature for 24 h. The mixture was concentrated in vacuo. The residue was dissolved in water (5 mL), then added saturated aq. NaHCO$_3$ until pH=7. The resulting precipitate was combined by filtration. Recrystallization of the cake from MeOH (30 mL) gave 1-cyclopropyl- 6,8-difluoro-1,4-dihydro-5-mercapto-4-oxo-7-[2-(2-pyridylamino)ethylamino]quinoline-3-carboxylic acid as a pale yellow solid (155 mg, 68%).

$^1$H-NMR (400 MHz, DMSO-$d_6$) δ 1.05-1.15 (4H, m), 3.50 (2H, q, J=6.1 Hz), 3.57-3.68 (2H, m), 4.00-4.10 (1H, m), 6.42-6.52 (2H, m), 6.75 (1H, t, J=5.5 Hz), 7.06 (1H, brs), 7.36 (1H, td, J=6.7 and 1.8 Hz), 7.95 (1H, dd, J=5.5 and 1.2 Hz), 8.53 (1H, s), 14.63 (1H, brs).

HRESIMS (+) 433.11553 (Calcd for $C_{20}H_{19}F_2N_4O_3S$, 433.11459).

Example 17

9-Amino-10-difluoro-2,3-dihydro-4,4-dimethyl-8-oxo-11-[2-(2-pyridylamino)ethylamino]-4H,8H-pyrido[1,2,3-ef]-1,5-benzoxazepine-7-carboxylic acid Step 1: Ethyl 3-benzylamino-3-methylbutyrate

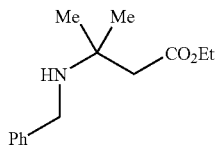

A solution of ethyl 3,3-dimethylacrylate (19.3 g, 0.151 mol) in EtOH (150 mL) was added benzylamine (16.2 g, 0.151 mol) and refluxed for 24 h. The reaction mixture was concentrated in vacuo. The distillation of the residue gave ethyl 3-benzylamino-3-methylbutyrate as a colorless oil (7.48 g, 21%).

$^1$H-NMR (400 MHz, CDCl$_3$) δ 1.24 (6H, s), 1.26 (3H, t, J=7.3 Hz), 2.51 (2H, s), 3.72 (2H, s), 4.14 (2H, q, J=7.3 Hz), 7.20-7.38 (5H, m).

Step 2: 3-Benzylamino-3-methyl-1-butanol

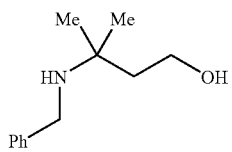

To a solution of ethyl 3-benzylamino-3-methylbutyrate (7.35 g, 31.2 mmol) in THF (150 mL) was added LiAlH$_4$ (2.40 g, 63.2 mmol) portionwise at 0° C. for 0.5 h, and the mixture was stirred at room temperature for 5 h. The mixture was cooled on iced-water bath, then dropped a little water. The mixture was diluted with ethyl acetate, then dried over anhydrous Na$_2$SO$_4$, filtered, and then concentrated in vacuo. Flash chromatography (EtOAc:MeOH=5:1) of the residue gave 3-benzylamino-3-methyl-1-butanol as a pale yellow oil (3.91 g, 65%).

$^1$H-NMR (400 MHz, CDCl$_3$) δ 1.26 (6H, s), 1.66 (2H, t, J=5.5 Hz), 3.76 (2H, s), 3.88 (2H, t, J=5.5 Hz), 7.22-7.35 (5H, m).

Step 3: 3-Amino-3-methyl-1-butanol

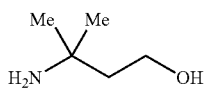

To a solution of 3-benzylamino-3-methyl-1-butanol (3.86 g, 20.0 mmol) in EtOH (80 mL) was added 10% Pd—C (400 mg) and the mixture was stirred under H$_2$ gas 5 kgf/cm$^2$ at room temperature for 6 h. The mixture was filtered, and the filtrate was concentrated in vacuo. The distillation of the residue gave 3-amino-3-methyl-1-butanol as a colorless oil (2.00 g, 97%).

$^1$H-NMR (400 MHz, CDCl$_3$) δ 1.21 (6H, s), 1.59 (2H, t, J=5.5 Hz), 2.63-2.76 (3H, br), 3.85 (2H, t, J=5.5 Hz).

Step 4: Ethyl 2-(2,3,4,5-tetrafluorobenzoyl)-3-[(1-hydroxy-3-methylbutane-3-yl)amino]acrylate

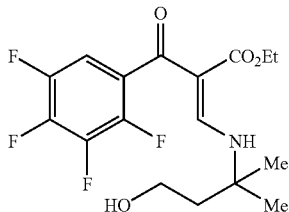

A stirred solution of ethyl (2,3,4,5-tetrafluorobenzoyl)acetate (3.73 g, 14.1 mmol), Ac$_2$O (8.50 mL, 85.7 mmol) and triethyl orthoformate (4.70 mL, 28.2 mmol) was heated at 120° C. for 3 h. The mixture was concentrated in vacuo and dried under high vacuum. To the mixture of the residue in anhydrous toluene (50 mL) was added 3-amino-3-methyl-1-butanol (1.45 g, 14.1 mmol) in anhydrous toluene (20 mL) very slowly at 0° C. and stirred at room temperature for 2 h. The solvent was removed by evaporation. Flash chromatography (EtOAc:Hexane=1:1) of the residue gave ethyl 2-(2,3,4,5-tetrafluorobenzoyl)-3-[(1-hydroxy-3-methylbutane-3-yl)amino]acrylate as a colorless solid (3.91 g, 73%).

$^1$H-NMR (400 MHz, CDCl$_3$) δ 0.95 (0.6H, t, J=7.3 Hz), 1.08 (2.4H, t, J=7.3 Hz), 1.46 (6H, d, J=3.7 Hz), 1.64 (1H, brs), 1.87-1.94 (2H, m), 3.87 (2H, t, J=6.1 Hz), 4.01 (0.4H, q, J=7.3 Hz), 4.06 (1.6H, q, J=7.3 Hz), 6.95-7.12 (1H, m), 8.23 (0.8H, d, J=14.7 Hz), 8.26 (0.2H, d, J=14.7 Hz), 10.14 (0.2H, d, J=14.1 Hz), 11.49 (0.8H, d, J=14.1 Hz).

Step 5: Ethyl 10,11-difluoro-2,3-dihydro-4,4-dimethyl-8-oxo-4H,8H-pyrido[1,2,3-ef]-1,5-benzoxazepine-7-carboxylate

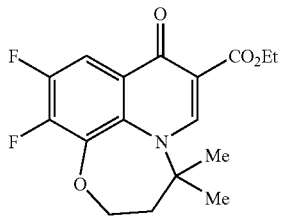

To a ice cold solution of ethyl 2-(2,3,4,5-tetrafluorobenzoyl)-3-[(1-hydroxy-3-methylbutane-3-yl)amino]acrylate (3.78 g, 10.0 mmol) in DMF (40 mL) NaH (4×200 mg) was added portion wise for 2 h. After stirring at room temperature for 1 h, it was heated at 80° C. for 1 h. The mixture was treated portion wise at 0° C. with water and the resulting precipitate was combined by filtration, washed successively with water and ethyl acetate, and then dried to give ethyl 10,11-difluoro-2,3-dihydro-4,4-dimethyl-8-oxo-4H,8H-pyrido[1,2,3-ef]-1,5-benzoxazepine-7-carboxylate (1.13 g, 33%) as a pale yellow solid.

$^1$H-NMR (400 MHz, DMSO-d$_6$) δ 1.28 (3H, t, J=7.3 Hz), 1.72 (6H, s), 2.36 (2H, t, J=6.1 Hz), 4.24 (2H, q, J=7.3 Hz), 4.44 (2H, t, J=6.1 Hz), 7.81 (1H, dd, J=10.4 and 8.6 Hz), 8.74 (1H, s).

Step 6: Ethyl 10,11-difluoro-2,3-dihydro-4,4-dimethyl-9-nitro-8-oxo-4H,8H-pyrido[1,2,3-ef]-1,5-benzoxazepine-7-carboxylate

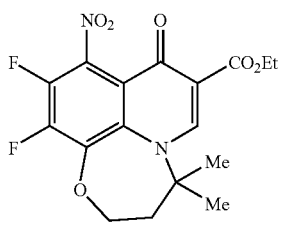

A solution of ethyl 10,11-difluoro-2,3-dihydro-4,4-dimethyl-8-oxo-4H,8H-pyrido[1,2,3-ef]-1,5-benzoxazepine-7-carboxylate (1.08 g, 3.20 mmol) in concentrated H$_2$SO$_4$ (14 mL) was treated portion wise at 0° C. with solid KNO$_3$ (438 mg, 4.33 mmol). After stirring at 0° C. for 2 h, the reaction mixture was poured into ice-water and the resulting precipitate was filtered and washed with water. Recrystallization of the cake from DMF (15 mL) gave ethyl 10,11-difluoro-2,3-dihydro-4,4-dimethyl-9-nitro-8-oxo-4H,8H-pyrido[1,2,3-ef]-1,5-benzoxazepine-7-carboxylate as a pale yellow solid (888 mg, 73%).

$^1$H-NMR (400 MHz, DMSO-d$_6$) δ 1.27 (3H, t, J=7.3 Hz), 1.72 (6H, s), 2.39 (2H, t, J=6.1 Hz), 4.24 (2H, q, J=7.3 Hz), 4.49 (2H, t, J=6.1 Hz), 8.78 (1H, s).

Step 7: Ethyl 9-amino-10,11-difluoro-2,3-dihydro-4,4-dimethyl-8-oxo-4H,8H-pyrido[1,2,3-ef]-1,5-benzoxazepine-7-carboxylate

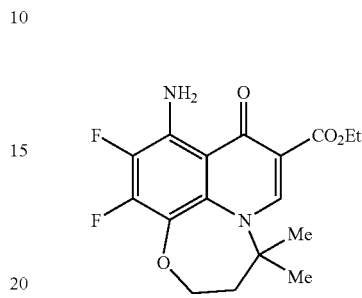

A solution of ethyl 10,11-difluoro-2,3-dihydro-4,4-dimethyl-9-nitro-8-oxo-4H,8H-pyrido[1,2,3-ef]-1,5-benzoxazepine-7-carboxylate (860 mg, 2.25 mmol) in DMF (55 mL) was hydrogenated under atmospheric pressure over 10% Pd/C (172 mg) at 50° C. for 3 h. The catalyst was removed by filtration over Celite and the filtrate was concentrated in vacuo. The residue washed with EtOH and collected by filtration and then dried to give ethyl 9-amino-10,11-difluoro-2,3-dihydro-4,4-dimethyl-8-oxo-4H,8H-pyrido[1,2,3-ef]-1,5-benzoxazepine-7-carboxylate (351 mg, 44%) as a yellow solid.

$^1$H-NMR (400 MHz, DMSO-d$_6$) δ 1.27 (3H, t, J=7.3 Hz), 1.69 (6H, s), 2.22 (2H, t, J=6.1 Hz), 4.17-4.25 (4H, m), 7.50-7.65 (2H, br), 8.56 (1H, s).

Step 8: 9-Amino-10,11-difluoro-2,3-dihydro-4,4-dimethyl-8-oxo-4H,8H-pyrido[1,2,3-ef]-1,5-benzoxazepine-7-carboxylic acid

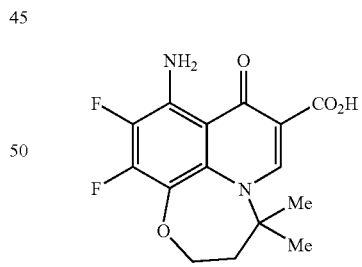

To a mixture of ethyl 9-amino-10,11-difluoro-2,3-dihydro-4,4-dimethyl-8-oxo-4H,8H-pyrido[1,2,3-ef]-1,5-benzoxazepine-7-carboxylate (599 mg, 1.70 mmol) in EtOH (17 mL) was added 2M aq. NaOH (8.5 mL) at room temperature and the mixture was heated at 50° C. for 3 h. The reaction mixture was added 2N HCl (8.5 mL) and water. The precipitate formed was collected by filtration, washed successively with water and then dried to give 9-amino-10,11-difluoro-2,3-dihydro-4,4-dimethyl-8-oxo-4H,8H-pyrido[1,2,3-ef]-1,5-benzoxazepine-7-carboxylic acid (432 mg, 78%) as a yellow solid.

$^1$H-NMR (400 MHz, DMSO-d$_6$) δ 1.76 (6H, s), 2.29 (2H, t, J=6.1 Hz), 4.25 (2H, t, J=6.1 Hz), 7.57 (2H, brs), 8.84 (1H, s), 14.52 (1H, brs).

Step 9: 9-Amino-10-fluoro-2,3-dihydro-4,4-dimethyl-8-oxo-11-[2-(2-pyridylamino)ethylamino]-4H,8H-pyrido[1,2,3-ef]-1,5-benzoxazepine-7-carboxylic acid

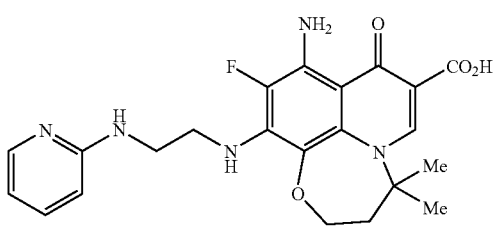

A solution of 9-amino-10,11-difluoro-2,3-dihydro-4,4-dimethyl-8-oxo-4H,8H-pyrido[1,2,3-ef]-1,5-benzoxazepine-7-carboxylic acid (380 mg, 1.17 mmol), N-2-pyridyl-1,2-ethanediamine (240 mg, 1.75 mmol) and triethylamine (0.25 mL) in DMSO (5 mL) was stirred at 120° C. for 5 h. The reaction mixture was added portionwise at 0° C. with ice-water and the mixture was extracted with CH$_2$Cl$_2$. The combined extracts were dried over anhydrous Na$_2$SO$_4$, filtered, and then concentrated in vacuo. Flash chromatography (CH$_2$Cl$_2$:MeOH=10:1) of the residue gave 9-amino-10-fluoro-2,3-dihydro-4,4-dimethyl-8-oxo-11-[2-(2-pyridylamino) ethylamino]-4H,8H-pyrido[1,2,3-ef]-1,5-benzoxazepine-7-carboxylic acid as a yellow amorphous solid (300 mg, 58%).

$^1$H-NMR (400 MHz, DMSO-d$_6$) δ 1.68 (6H, s), 2.13 (2H, t, J=6.1 Hz), 3.47 (2H, q, J=6.1 Hz), 3.55-3.64 (2H, m), 4.06 (2H, t, J=6.1 Hz), 6.32 (1H, brs), 6.42-6.50 (2H, m), 6.70 (1H, t, J=5.5 Hz), 7.10 (2H, brs), 7.32-7.40 (1H, m), 7.97 (1H, dd, J=4.9 and 1.2 Hz), 8.62 (1H, s), 15.15 (1H, brs).

HRESIMS (+) 442.18968 (Calcd for C$_{22}$H$_{25}$FN$_5$O$_4$, 442.18906).

Example 18

(R)-8-amino-9-fluoro-2,3-dihydro-7-oxo-3-phenyl-10-[2-(2-pyridylamino)ethylamino]-7H-pyrido[1,2,3-de]-1,4-benzoxazine-6-carboxylic acid Step 1: Ethyl (R)-2-(2,3,4,5,6-pentafluorobenzoyl)-3-[(2-hydroxy-1-phenylethyl)amino]acrylate

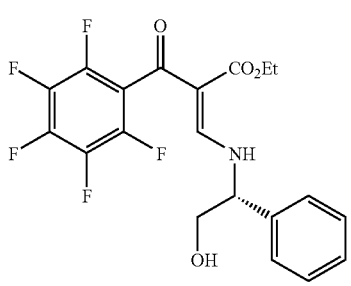

A stirred solution of ethyl (2,3,4,5,6-pentafluorobenzoyl)acetate (8.47 g, 30.0 mmol), Ac$_2$O (17.0 mL, 0.180 mol) and triethyl orthoformate (10.0 mL, 60.1 mmol) was heated at 120° C. for 3 h. The mixture was concentrated in vacuo and dried under high vacuum. To the mixture of the residue in anhydrous toluene (120 mL) was added (R)-phenylglicinol (4.12 g, 30.0 mmol) in anhydrous toluene (20 mL) very slowly at 0° C. and stirred at room temperature for 2 h. The solvent was removed by evaporation. Flash chromatography (EtOAc:Hexane=2:1) of the residue gave ethyl (R)-2-(2,3,4,5,6-pentafluorobenzoyl)-3-[(2-hydroxy-1-phenylethyl)amino]acrylate as a colorless oil (12.3 g, 95%).

$^1$H-NMR (400 MHz, CDCl$_3$) δ 0.98 (0.5H, t, J=7.3 Hz), 1.10 (2.5H, t, J=7.3 Hz), 1.97-2.05 (1H, br), 3.93-4.08 (4H, m), 4.63-4.71 (1H, m), 7.28-7.49 (5H, m), 8.27 (0.83H, d, J=14.7 Hz), 8.33 (0.17H, d, J=14.7 Hz), 10.25-10.32 (0.17H, br), 10.56-10.32 (0.83H, br).

Step 2: Ethyl (R)-5,6,7,8-tetrafluoro-1,4-dihydro-1-[(2-hydroxy-1-phenylethyl)amino]-4-oxo-3-quinolinecarboxylate

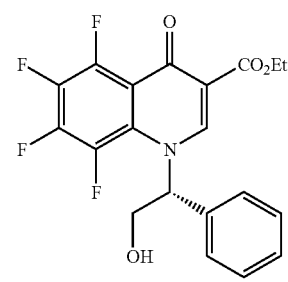

To a ice cold solution of Ethyl (R)-2-(2,3,4,5,6-pentafluorobenzoyl)-3-[(2-hydroxy-1-phenylethyl)amino]acrylate (2.15 g, 5.01 mmol) in DMF (20 mL) was added NaH (240 mg, 6.00 mmol, 60% in oil) and the mixture was stirred at 0° C. for 1 h. The mixture was treated portionwise at room temperature for 18 h with water. The resulting mixture was extracted with ethyl acetate. The combined extracts were concentrated in vacuo. Flash chromatography (EtOAc:Hexane=2:1) of the residue gave more ethyl (R)-5,6,7,8-tetrafluoro-1,4-dihydro-1-[(2-hydroxy-1-phenylethyl)amino]-4-oxo-3-quinolinecarboxylate as a solid (3.14 g, 37%).

$^1$H-NMR (400 MHz, DMSO-d$_6$) δ 1.23 (3H, t, J=7.3 Hz), 4.13-4.23 (2H, m), 4.64 (1H, dd, J=11.6 and 2.4 Hz), 4.89 (1H, dd, J=11.6 and 2.4 Hz), 5.96 (1H, t, J=2.4 Hz), 7.15 (2H, dd, J=7.9 and 2.4 Hz), 7.32-7.45 (3H, m), 8.54 (1H, s).

Step 3: Ethyl (R)-8,9,10-trifluoro-2,3-dihydro-7-oxo-3-phenyl-7H-pyrido[1,2,3-de]-1,4-benzoxazine-6-carboxylate

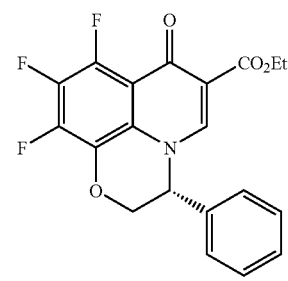

To a solution of ethyl (R)-5,6,7,8-tetrafluoro-1,4-dihydro-1-[(2-hydroxy-1-phenylethyl)amino]-4-oxo-3-quinolinecarboxylate (3.10 g, 7.57 mmol) in THF (60 mL) was added NaH (364 mg, 9.10 mmol, 60% in oil) and the mixture was stirred at room temperature for 10 h. The mixture was treated portionwise at 0° C. with water. A precipitate formed and was collected by filtration, washed successively with EtOAc and then dried to give ethyl(R)-8,9,10-trifluoro-2,3-dihydro-7-oxo-3-phenyl-7H-pyrido[1,2,3-de]-1,4-benzoxazine-6-carboxylate (329 mg, 11%) as a solid.

$^1$H-NMR (400 MHz, DMSO-d$_6$) δ 1.23 (3H, t, J=7.3 Hz), 4.13-4.24 (2H, m), 4.64 (1H, dd, J=11.6 and 2.4 Hz), 4.89 (1H, dd, J=11.6 and 2.4 Hz), 5.96 (1H, t, J=2.4 Hz), 7.15 (2H, dd, J=7.9 and 1.8 Hz), 7.33-7.43 (3H, m), 8.54 (1H, s).

Step 4: Ethyl (R)-8,9-difluoro-2,3-dihydro-7-oxo-3-phenyl-10-[2-(2-pyridyl amino)ethylamino]-7H-pyrido[1,2,3-de]-1,4-benzoxazine-6-carboxylate

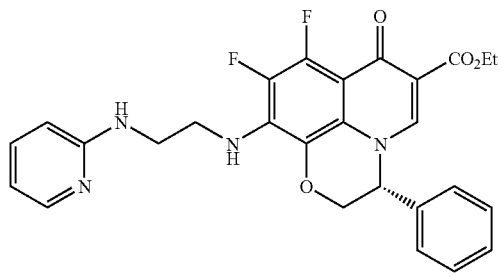

A solution of ethyl (R)-8,9,10-tetrafluoro-2,3-dihydro-7-oxo-3-phenyl-7H-pyrido[1,2,3-de]-1,4-benzoxazine-6-carboxylate (1.00 g, 2.57 mmol), N-2-pyridyl-1,2-ethanediamine (423 mg, 3.08 mmol) and Et$_3$N (0.75 mL, 5.38 mmol) in DMSO (10 mL) was stirred at 100° C. for 3 h. The reaction mixture was added portionwise at 0° C. with ice-water and the resulting precipitate was combined by filtration, washed with water. The cake washed with EtOH and collected by filtration and then dried to give ethyl (R)-8,9-difluoro-2,3-dihydro-7-oxo-3-phenyl-10-[2-(2-pyridylamino)ethylamino]-7H-pyrido[1,2,3-de]-1,4-benzoxazine-6-carboxylate (656 mg, 50%) as a pale yellow solid.

$^1$H-NMR (400 MHz, DMSO-d$_6$) δ 1.20 (3H, t, J=7.3 Hz), 3.26-3.45 (4H, m), 3.49-3.59 (2H, m), 4.08-4.19 (2H, m), 4.43 (1H, dd, J=11.6 and 2.4 Hz), 4.72 (1H, dd, J=11.6 and 2.4 Hz), 5.79 (1H, t, J=2.4 Hz), 6.34-6.40 (1H, m), 6.40 (1H, d, J=8.6 Hz), 6.44 (1H, dd, J=6.1 and 4.9 Hz), 6.65 (1H, t, J=6.1 Hz), 7.10 (2H, dd, J=7.8 and 1.8 Hz), 7.29-7.40 (4H, m), 7.89 (1H, dd, J=5.5 and 1.2 Hz), 8.32 (1H, s).

Step 5: (R)-8,9-Difluoro-2,3-dihydro-7-oxo-3-phenyl-10-[2-(2-pyridylamino) ethylamino]-7H-pyrido[1,2,3-de]-1,4-benzoxazine-6-carboxylic acid

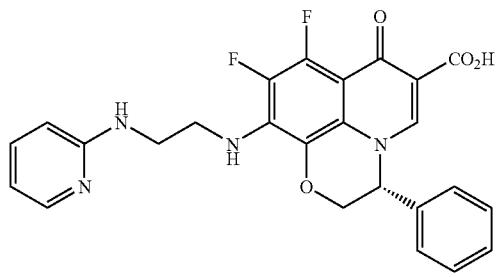

To a mixture of ethyl (R)-8,9-difluoro-2,3-dihydro-7-oxo-3-phenyl-10-[2-(2-pyridylamino)ethylamino]-7H-pyrido[1,2,3-de]-1,4-benzoxazine-6-carboxylate (627 mg, 1.24 mmol) in EtOH (8 mL) was added 2M aq. NaOH (6.20 mL, 12.4 mmol) at room temperature and the mixture was heated at 50° C. for 3 h. The reaction mixture was added 2N HCl (11.4 mL) and water. A precipitate formed and was collected by filtration, washed successively with water and then dried to give (R)-8,9-difluoro-2,3-dihydro-7-oxo-3-phenyl-10-[2-(2-pyridylamino)ethylamino]-7H-pyrido[1,2,3-de]-1,4-benzoxazine-6-carboxylic acid (452 mg, 75%) as a yellow solid.

$^1$H-NMR (400 MHz, DMSO-d$_6$) δ 3.40-3.50 (2H, m), 3.57-3.68 (2H, m), 4.51 (1H, dd, J=11.6 and 3.1 Hz), 4.81 (1H, dd, J=11.6 and 3.1 Hz), 6.00 (1H, t, J=3.1 Hz), 6.40-6.52 (2H, m), 6.70-6.84 (1H, br), 6.86-6.95 (1H, br), 7.14 (2H, dd, J=7.9 and 2.2 Hz), 7.30-7.42 (4H, m), 7.91 (1H, dd, J=4.9 and 1.2 Hz), 8.70 (1H, s), 15.32 (1H, s).

Step 6: (R)-9-Fluoro-2,3-dihydro-8-(4-methoxybenzylamino)-7-oxo-3-phenyl-10-[2-(2-pyridylamino)ethylamino]-7H-pyrido[1,2,3-de]-1,4-benzoxazine-6-carboxylic acid

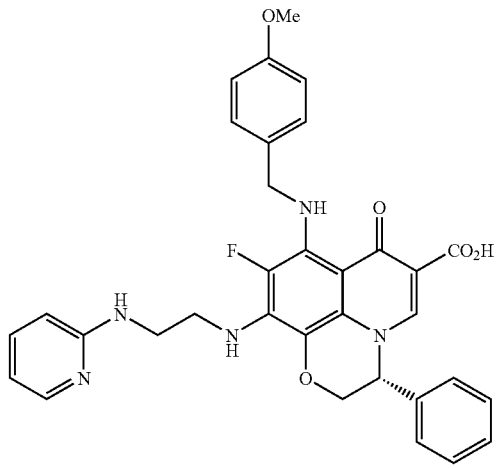

A solution of (R)-8,9-difluoro-2,3-dihydro-7-oxo-3-phenyl-10-[2-(2-pyridylamino)ethylamino]-7H-pyrido[1,2,3-de]-1,4-benzoxazine-6-carboxylic acid (432 mg, 0.903 mmol) and 4-methoxybenzylamine (400 μL, 4.51 mmol) in DMSO (4 mL) was stirred at 150° C. for 2 h. The reaction mixture was added portionwise at 0° C. with ice-water and the resulting precipitate was combined by filtration, washed with water. The cake washed with EtOH and collected by filtration and then dried to give (R)-9-fluoro-2,3-dihydro-8-(4-methoxybenzylamino)-7-oxo-3-phenyl-10-[2-(2-pyridylamino)ethylamino]-7H-pyrido[1,2,3-de]-1,4-benzoxazine-6-carboxylic acid (411 mg, 78%) as a pale yellow solid.

$^1$H-NMR (400 MHz, DMSO-d$_6$) δ 3.30-3.40 (2H, m), 3.52-3.60 (2H, m), 3.72 (3H, s), 4.37 (1H, dd, J=11.6 and 2.4 Hz), 4.45-4.52 (2H, m), 4.68 (1H, dd, J=11.6 and 2.4 Hz), 5.89 (1H, t, J=2.4 Hz), 6.41 (2H, d, J=8.6 Hz), 6.42-6.48 (1H, m), 6.65 (1H, t, J=5.5 Hz), 6.89 (2H, d, J=9.2 Hz), 7.12 (2H, dd, J=7.9 and 1.8 Hz), 7.28 (2H, d, J=8.6 Hz), 7.30-7.40 (6H, m), 7.92 (1H, dd, J=4.9 and 1.2 Hz), 8.55 (1H, s), 8.99-9.05 (1H, m).

Step 7: (R)-8-Amino-9-fluoro-2,3-dihydro-7-oxo-3-phenyl-10-[2-(2-pyridylamino) ethylamino]-7H-pyrido[1,2,3-de]-1,4-benzoxazine-6-carboxylic acid

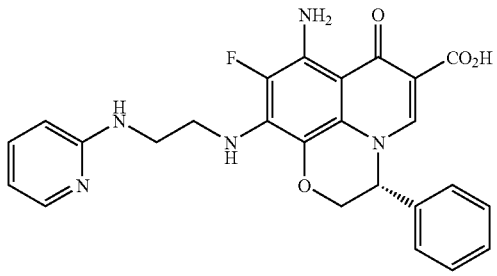

To a solution of (R)-9-fluoro-2,3-dihydro-8-(4-methoxybenzylamino)-7-oxo-3-phenyl-10-[2-(2-pyridylamino)ethylamino]-7H-pyrido[1,2,3-de]-1,4-benzoxazine-6-carboxylic acid (366 mg, 0.614 mmol) in CH$_2$Cl$_2$ (10 mL) was added TFA (2.0 mL, 26.9 mmol) at 0° C. and the mixture was stirred at room temperature for 2 h. The reaction mixture was concentrated in vacuo. The solution of the residue in DMSO (3 mL) was added water and 2M aq. NaOH to adjust pH=7. A precipitate formed and was collected by filtration. The cake was added EtOH (10 mL), and boiled on water-bath. A precipitate was collected by and then dried to give (R)-8-amino-9-fluoro-2,3-dihydro-7-oxo-3-phenyl-10-[2-(2-pyridylamino)ethylamino]-7H-pyrido[1,2,3-de]-1,4-benzoxazine-6-carboxylic acid (124 mg, 42%) as a yellow solid.

$[\alpha]_D^{24}$+130 (c 0.256, DMSO).

$^1$H-NMR (400 MHz, DMSO-d$_6$) δ 3.38-3.46 (2H, m), 3.53-3.64 (2H, m), 4.36 (1H, dd, J=11.6 and 2.4 Hz), 4.69 (1H, dd, J=11.6 and 2.4 Hz), 5.88 (1H, t, J=2.4 Hz), 6.30-6.40 (1H, br), 6.43 (1H, d, J=8.6 Hz), 6.45 (1H, dd, J=6.1 and 4.9 Hz), 6.67 (1H, t, J=5.5 Hz), 6.85-7.00 (2H, br), 7.14 (2H, dd, J=7.9 and 1.8 Hz), 7.30-7.42 (4H, m), 7.92 (1H, dd, J=4.9 and 1.2 Hz), 8.53 (1H, s), 15.27 (1H, s).

HRESIMS (+) 476.17366 (Calcd for C$_{25}$H$_{23}$FN$_5$O$_4$, 476.17341).

Example 19

(S)-8-Amino-9-fluoro-2,3-dihydro-7-oxo-3-phenyl-10-[2-(2-pyridyl amino)ethylamino]-7H-pyrido[1,2,3-de]-1,4-benzoxazine-6-carboxylic acid Step 1: Ethyl (S)-2-(2,3,4,5,6-pentafluorobenzoyl)-3-[(2-hydroxy-1-phenylethyl)amino]acrylate

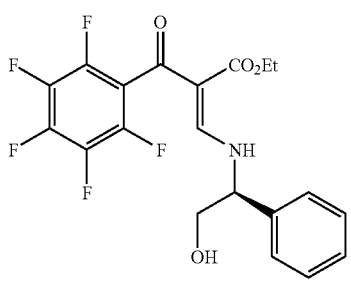

A stirred solution of ethyl (2,3,4,5,6-pentafluorobenzoyl) acetate (8.47 g, 30.0 mmol), Ac$_2$O (17.0 mL, 0.180 mol) and triethyl orthoformate (10.0 mL, 60.1 mmol) was heated at 120° C. for 3 h. The mixture was concentrated in vacuo and dried under high vacuum. To the mixture of the residue in anhydrous toluene (120 mL) was added (S)-phenylglicinol (4.12 g, 30.0 mmol) in anhydrous toluene (20 mL) very slowly at 0° C. and stirred at room temperature for 2 h. The solvent was removed by evaporation. Flash chromatography (EtOAc:Hexane=2:1) of the residue gave ethyl (S)-2-(2,3,4,5,6-pentafluorobenzoyl)-3-[(2-hydroxy-1-phenylethyl)amino]acrylate as a colorless oil (12.6 g, 98%).

$^1$H-NMR (400 MHz, CDCl$_3$) δ 0.98 (0.5H, t, J=7.3 Hz), 1.09 (2.5H, t, J=7.3 Hz), 2.00-2.10 (1H, br), 3.93-4.08 (4H, m), 4.63-4.71 (1H, m), 7.28-7.48 (5H, m), 8.27 (0.83H, d, J=14.7 Hz), 8.33 (0.17H, d, J=14.7 Hz), 10.25-10.37 (0.17H, br), 10.57-11.70 (0.83H, br).

Step 2: Ethyl (S)-8,9,10-trifluoro-2,3-dihydro-7-oxo-3-phenyl-7H-pyrido[1,2,3-de]-1,4-benzoxazine-6-carboxylate

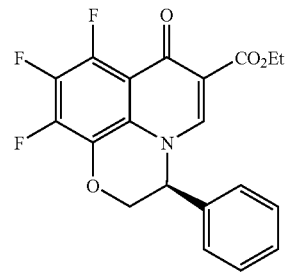

To a solution of ethyl (S)-2-(2,3,4,5,6-pentafluorobenzoyl)-3-[(2-hydroxy-1-phenylethyl)amino]acrylate (2.15 g, 5.00 mmol) in THF (20 mL) was added NaH (440 mg, 11.0 mmol, 60% in oil) at 0° C. and the mixture was stirred at 0° C. for 0.5 h, at room temperature for 1 h, and then refluxed for 2 h. The mixture was treated portionwise at 0° C. with water. A precipitate formed and was collected by filtration, washed successively with EtOAc and then dried to give ethyl (S)-8,9,10-trifluoro-2,3-dihydro-7-oxo-3-phenyl-7H-pyrido[1,2,3-de]-1,4-benzoxazine-6-carboxylate (465 mg, 24%) as a pale yellow solid.

$^1$H-NMR (400 MHz, DMSO-d$_6$) δ 1.23 (3H, t, J=7.3 Hz), 4.12-4.23 (2H, m), 4.64 (1H, dd, J=11.6 and 2.4 Hz), 4.89 (1H, dd, J=11.6 and 2.4 Hz), 5.96 (1H, t, J=2.4 Hz), 7.15 (2H, dd, J=7.3 and 1.8 Hz), 7.35-7.43 (3H, m), 8.54 (1H, s).

Step 3: Ethyl (S)-8,9-difluoro-2,3-dihydro-7-oxo-3-phenyl-10-[2-(2-pyridylamino) ethylamino]-7H-pyrido[1,2,3-de]-1,4-benzoxazine-6-carboxylate

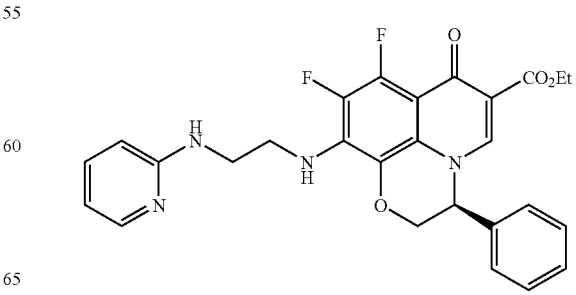

A solution of ethyl (S)-8,9,10-tetrafluoro-2,3-dihydro-7-oxo-3-phenyl-7H-pyrido[1,2,3-de]-1,4-benzoxazine-6-carboxylate (1.00 g, 2.57 mmol), N-2-pyridyl-1,2-ethanediamine (423 mg, 3.08 mmol) and Et₃N (0.75 mL, 5.38 mmol) in DMSO (10 mL) was stirred at 100° C. for 3 h. The reaction mixture was added portionwise at 0° C. with ice-water and the resulting precipitate was combined by filtration, washed with water. The cake washed with EtOH and collected by filtration and then dried to give ethyl (S)-8,9-difluoro-2,3-dihydro-7-oxo-3-phenyl-10-[2-(2-pyridylamino)ethylamino]-7H-pyrido[1,2,3-de]-1,4-benzoxazine-6-carboxylate (849 mg, 65%) as a pale yellow solid.

¹H-NMR (400 MHz, DMSO-d₆) δ 1.21 (3H, t, J=7.3 Hz), 3.32-3.45 (2H, m), 3.50-3.60 (2H, m), 4.08-4.20 (2H, t, J=2.4 Hz), 4.44 (1H, dd, J=11.6 and 2.4 Hz), 4.74 (1H, dd, J=11.6 and 2.4 Hz), 5.80 (1H, t, J=2.4 Hz), 6.35-6.48 (2H, m), 6.41 (1H, d, J=7.9 Hz), 6.66 (1H, t, J=5.5 Hz), 7.12 (2H, dd, J=7.9 and 1.2 Hz), 7.30-7.40 (4H, m), 7.90 (1H, dd, J=4.9 and 1.2 Hz), 8.33 (1H, s).

Step 4: (S)-8,9-Difluoro-2,3-dihydro-7-oxo-3-phenyl-10-[2-(2-pyridylamino)ethyl amino]-7H-pyrido[1,2,3-de]-1,4-benzoxazine-6-carboxylic acid

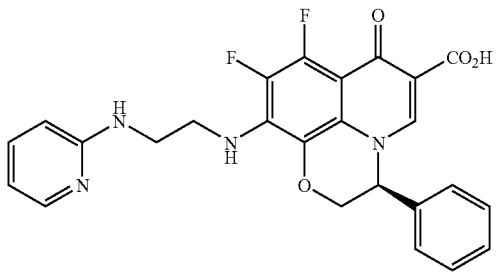

To a solution of ethyl (S)-8,9-difluoro-2,3-dihydro-7-oxo-3-phenyl-10-[2-(2-pyridylamino)ethylamino]-7H-pyrido[1,2,3-de]-1,4-benzoxazine-6-carboxylate (800 mg, 1.58 mmol) in EtOH (10 mL) was added 2M aq. NaOH (7.90 mL, 15.8 mmol) at room temperature and the mixture was heated at 50° C. for 3 h. To the reaction mixture was added 2N HCl (15.8 mL) and water. A precipitate formed and was collected by filtration, washed successively with water and then dried to give 23 (578 mg, 75%) as a yellow solid.

¹H-NMR (400 MHz, DMSO-d₆) δ 3.40-3.70 (4H, m), 4.51 (1H, dd, J=11.6 and 2.4 Hz), 4.81 (1H, dd, J=11.6 and 2.4 Hz), 6.00 (1H, t, J=2.4 Hz), 6.50 (3H, t, J=6.1 Hz), 6.82-6.92 (2H, br), 7.14 (2H, dd, J=7.3 and 1.8 Hz), 7.27-7.45 (3H, m), 7.91 (1H, dd, J=5.5 and 1.2 Hz), 8.70 (1H, s), 15.32 (1H, s).

Step 5: (S)-9-Fluoro-2,3-dihydro-8-(4-methoxybenzylamino)-7-oxo-3-phenyl-10-[2-(2-pyridylamino)ethylamino]-7H-pyrido[1,2,3-de]-1,4-benzoxazine-6-carboxylic acid

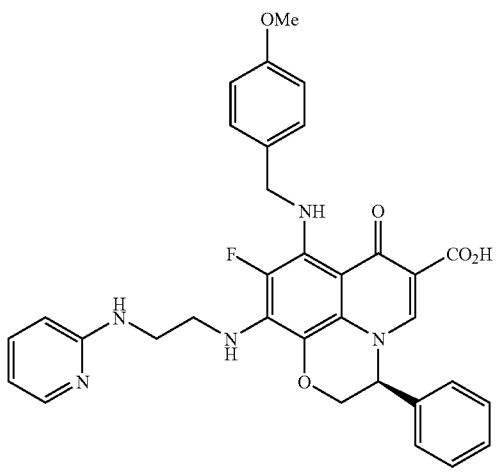

A solution of (S)-8,9-difluoro-2,3-dihydro-7-oxo-3-phenyl-10-[2-(2-pyridylamino)ethylamino]-7H-pyrido[1,2,3-de]-1,4-benzoxazine-6-carboxylic acid (560 mg, 1.15 mmol) and 4-methoxybenzylamine (520 µL, 5.86 mmol) in DMSO (5 mL) was stirred at 150° C. for 2 h. The reaction mixture was added portionwise at 0° C. to ice-water and the resulting precipitate was combined by filtration, washed with water. The cake washed with EtOH, collected by filtration and then dried to give (S)-9-fluoro-2,3-dihydro-8-(4-methoxybenzylamino)-7-oxo-3-phenyl-10-[2-(2-pyridylamino)ethylamino]-7H-pyrido[1,2,3-de]-1,4-benzoxazine-6-carboxylic acid (390 mg, 57%) as a pale yellow solid.

¹H-NMR (400 MHz, DMSO-d₆) δ 3.30-3.43 (2H, m), 3.50-3.62 (2H, m), 3.72 (3H, s), 4.37 (1H, dd, J=11.6 and 2.4 Hz), 4.47 (2H, t, J=6.1 Hz), 4.68 (1H, dd, J=11.6 and 2.4 Hz), 5.89 (1H, t, J=2.4 Hz), 6.41 (2H, d, J=8.6 Hz), 6.46 (1H, t, J=5.5 Hz), 6.65 (1H, t, J=6.1 Hz), 6.89 (2H, d, J=8.6 Hz), 7.12 (2H, dd, J=7.9 and 1.8 Hz), 7.28 (2H, d, J=8.6 Hz), 7.30-7.40 (4H, m), 7.92 (1H, dd, J=4.9 and 1.2 Hz), 8.55 (1H, s), 9.00-9.08 (1H, br), 14.90-15.20 (1H, br).

Step 6: (S)-8-Amino-9-fluoro-2,3-dihydro-7-oxo-3-phenyl-10-[2-(2-pyridylamino) ethylamino]-7H-pyrido[1,2,3-de]-1,4-benzoxazine-6-carboxylic acid

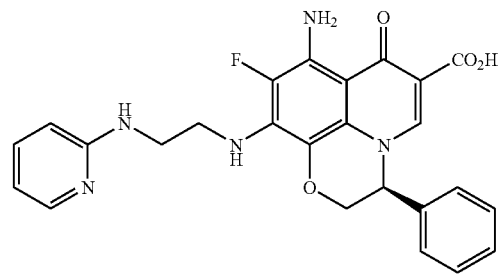

To a solution of (S)-9-fluoro-2,3-dihydro-8-(4-methoxybenzylamino)-7-oxo-3-phenyl-10-[2-(2-pyridylamino)ethylamino]-7H-pyrido[1,2,3-de]-1,4-benzoxazine-6-carboxylic acid (355 mg, 0.596 mmol) in CH₂Cl₂ (4 mL) was added TFA (2.0 mL, 26.9 mmol) at 0° C. and the mixture was stirred at room temperature for 2 h. The reaction mixture was concentrated in vacuo. The solution of the residue in DMSO (3 mL) was added water and 2M aq. NaOH was added to adjust pH=7. A precipitate formed and was collected by filtration. The cake was added to EtOH (10 mL), and boiled on waterbath. A precipitate was collected by and then dried to give (S)-8-amino-9-fluoro-2,3-dihydro-7-oxo-3-phenyl-10-[2-(2-pyridylamino)ethylamino]-7H-pyrido[1,2,3-de]-1,4-benzoxazine-6-carboxylic acid (163 mg, 58%) as a yellow solid.

$[\alpha]_D^{25}$ −120 (c 0.26, DMSO).

¹H-NMR (400 MHz, DMSO-d₆) δ 3.39-3.49 (2H, m), 3.52-3.62 (2H, m), 4.36 (1H, dd, J=11.6 and 2.4 Hz), 4.69 (1H, dd, J=11.6 and 2.4 Hz), 5.88 (1H, t, J=2.4 Hz), 6.32-6.40 (1H, br), 6.43 (1H, d, J=8.6 Hz), 6.45 (1H, dd, J=6.1 and 4.9 Hz), 6.66 (1H, t, J=5.5 Hz), 6.86-7.00 (2H, br), 7.13 (2H, dd, J=8.6 and 1.8 Hz), 7.30-7.42 (4H, m), 7.92 (1H, dd, J=4.9 and 1.8 Hz), 8.53 (1H, s), 15.27 (1H, s).

HRESIMS (+) 476.17735 (Calcd for C₂₅H₂₃FN₅O₄, 476.17341).

Example 20

5-Amino-6-fluoro-1,4-dihydro-8-methoxy-4-oxo-7-[2-(2-pyridylamino)ethylamino]quinoline-3-carboxylic acid Step 1: Ethyl 3-(tert-butylamino)-2-(2,4,5-trifluoro-3-methoxybenzoyl)acrylate

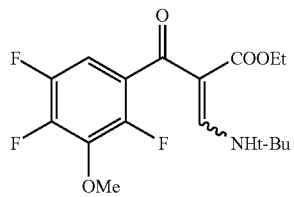

A solution of ethyl (2,4,6-trifluoro-3-methoxy benzoyl) acetate (40.05 g, 145 mmol), Ac$_2$O (80 mL, 846 mmol) and triethyl orthoformate (48.0 mL, 289 mmol) was heated at 120° C. for 3 h. The mixture was concentrated in vacuo and dried under high vacuum. The crude product was dissolved in anhydrous tolene (400 mL) and tert-butylamine (18.0 mL, 171 mmol) was added very slowly at 0° C. The ration mixture was stirred at room temperature for over night, and the solvent was removed by evaporation. The crude product was purified by column chromatography (Hexane:EtOAc 10:1) to yield ethyl 3-(tert-butylamino)-2-(2,4,5-trifluoro-3-methoxybenzoyl)acrylate (42.01 g, 81%, E/Z=1/5) as a pale yellow solid.

$^1$H-NMR (400 MHz, CDCl$_3$) δ 1.06 (3H, t, J=7.3 Hz), 1.43 (9H, s), 3.95-4.10 (5H, m), 6.83-6.91 (1H×⅚, m), 6.94 (1H×⅙, m), 8.22 (1H×⅚, d, J=14.0 Hz), 8.25 (1H×⅙, d, J=14.0 Hz), 9.78 (1H×⅙, brd, J=13.5 Hz), 11.28 (1H×⅚, brd, J=13.5 Hz).

Step 2: Ethyl 1-tert-butyl-6,7-difluoro-1,4-dihydro-8-methoxy-4-oxoquinoline-3-carboxylate

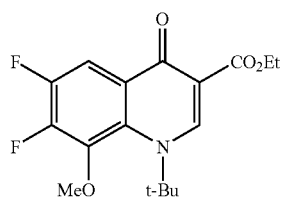

A solution of NaH (5.61 g, 140 mmol, 60% in oil) in DMF (300 mL) was cooled to 0° C. and treated dropwise with ethyl 3-(tert-butylamino)-2-(2,4,5-trifluoro-3-methoxybenzoyl)acrylate (42.02 g, 117 mmol) in DMF (100 mL). The reaction mixture was stirred at room temperature for 2 h. The reaction mixture was poured into ice water and the resulting precipitate was removed by filtration, washed with water and then dried to yield ethyl 1-tert-butyl-6,7-difluoro-1,4-dihydro-8-methoxy4-oxoquinoline-3-carboxylate (38.9 g, 98%) as a pale yellow solid.

$^1$H-NMR (400 MHz, CDCl$_3$) δ 1.40 (3H, t, J=7.3 Hz), 1.71 (9H, s), 3.95 (3H, d, J=1.8 Hz), 4.39 (2H, q, J=7.3 Hz), 7.97 (1H, t, J=8.6 Hz), 8.82 (1H, s).

Step 3: Ethyl 6,7-difluoro-1,4-dihydro-8-methoxy-5-nitro4-oxoquinoline-3-carboxylate

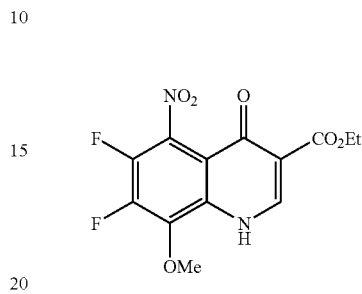

A solution of ethyl 1-tert-butyl-6,7-difluoro-1,4-dihydro-8-methoxy-4-oxoquinoline-3-carboxylate (20.0 g, 58.9 mmol) in concentrated H$_2$SO$_4$ (120 mL) was treated portionwise at 0° C. with solid KNO$_3$ (8.90 g, 88.0 mmol). After stirring at 0° C. for 1 h, the reaction mixture was poured into 500 mL of ice-water and the resulting precipitate was removed by filtration. The resulting solid washed with EtOH, dried to yield ethyl 6,7-difluoro-1,4-dihydro-8-methoxy-5-nitro-4-oxoquinoline-3-carboxylate (12.77 g, 66%) as a pale yellow solid.

$^1$H-NMR (400 MHz, DMSO-d$_6$) δ 1.27 (3H, t, J=7.3 Hz), 4.16-4.30 (5H, m), 8.40 (1H, d, J=6.1 Hz), 12.59 (1H, brd, J=6.1 Hz).

Step 4: Ethyl 5-amino-6,7-difluoro-1,4-dihydro-8-methoxy-4-oxoquinoline-3-carboxylate

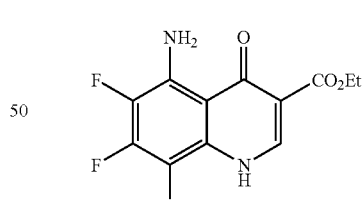

A solution of ethyl 6,7-difluoro-1,4-dihydro-8-methoxy-5-nitro-4-oxoquinoline-3-carboxylate (1.50 g, 4.57 mmol) and 10% Pd/C (40.5 mg) in DMF (20 mL) was stirred under hydrogen atmosphere at room temprature for 14 h. The catalyst was removed by filtration over Celite and the filtrate was concentrated in vacuo. The resulting solid was recrystallized by EtOH, and dried to yield ethyl 5-amino-6,7-difluoro-1,4-dihydro-8-methoxy-4-oxoquinoline-3-carboxylate (735 mg, 54%) as a pale brown solid.

¹H-NMR (400 MHz, DMSO-d₆) δ 1.26 (3H, t, J=7.3 Hz), 3.85 (3H, s), 4.18 (2H, q, J=7.3 Hz), 7.47 (2H, brs), 8.20 (1H, s), 11.80 (1H, brs).

Step 5: 5-Amino-6,7-difluoro-1,4-dihydro-8-methoxy-4-oxoquinoline-3-carboxylic acid

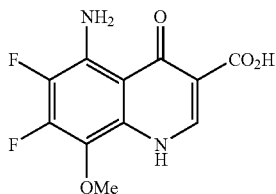

A solution of ethyl 5-amino-6,7-difluoro-1,4-dihydro-8-methoxy-4-oxoquinoline-3-carboxylate (689 mg, 2.31 mmol) in a mixture of AcOH—H₂O—H₂SO₄ (6:3:1 v/v, 10 mL) was heated at 100° C. for 4 h. The reaction mixture was poured into ice water and the resulting precipitate was removed by filtration, washed with ethanol, and then dried to yield 5-amino-6,7-difluoro-1,4-dihydro-8-methoxy-4-oxoquinoline-3-carboxylic acid (580 mg, 93%) as a pale yellow solid.

¹H-NMR (400 MHz, DMSO-d₆) δ 3.89 (3H, s), 7.36 (2H, brs), 8.45 (1H, s), 12.76 (1H, brs), 14.72 (1H, s).

Step 6: 5-Amino-6-fluoro-1,4-dihydro-8-methoxy-4-oxo-7-[2-(2-pyridylamino)ethylamino]quinoline-3-carboxylic acid

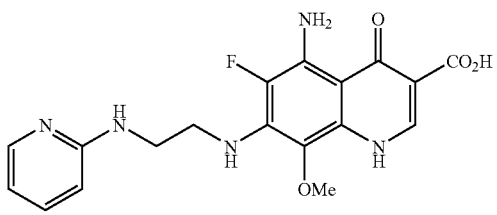

A solution of 5-amino-6,7-difluoro-1,4-dihydro-8-methoxy-4-oxoquinoline-3-carboxylic acid (400 mg, 1.48 mmol), N-2-pyridyl-1,2-ethanediamine (406 mg, 2.96 mmol) and triethylamine (0.410 mL, 2.94 mmol) in DMSO (2 mL) was stirred at 100° C. After 8 h, to the solution was added N-2-pyridyl-1,2-ethanediamine (102 mg, 0.744 mmol) and triethylamine (0.200 mL, 1.43 mmol) and stirred at 100° C. for another 8 h. The reaction mixture was poured into ice water and the resulting precipitate was removed by filtration, washed with ethanol. The resulting solid recrystallized by CH₃CN, and dried to yield 5-amino-6-fluoro-1,4-dihydro-8-methoxy-4-oxo-7-[2-(2-pyridylamino)ethylamino]quinoline-3-carboxylic acid (132 mg, 23%) as a pale yellow solid.

¹H-NMR (400 MHz, DMSO-d₆) δ 3.47 (2H, q, J=5.5 Hz), 3.56-3.64 (5H, m), 6.25-6.34 (1H, m), 6.44-6.51 (2H, m), 6.72 (1H, t, J=5.5 Hz), 6.88 (2H, brs), 7.32-7.38 (1H, m), 7.96 (1H, dd, J=5.5, 1.2 Hz), 8.28 (1H, s), 12.08 (1H, brs), 15.31 (1H, s).

HRESIMS (+): 388.14213(Calcd for $C_{18}H_{19}FN_5O_4$, 388.14211).

Example 21

5-Amino-1-benzyl-6-fluoro-1,4-dihydro-8-methoxy-4-oxo-7-[2-(2-pyridylamino)ethylamino]quinoline-3-carboxylic acid Step 1: Ethyl 1-benzyl-6,7-difluoro-1,4-dihydro-8-methoxy-5-nitro-4-oxoquinoline-3-carboxylate

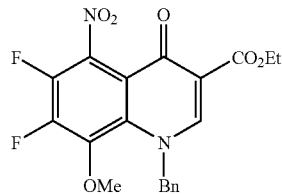

A solution of NaH (1.17 g, 29.3 mmol, 60% in oil) in DMF (50 mL) was cooled to 0° C. and treated dropwise with ethyl 6,7-difluoro-1,4-dihydro-8-methoxy-5-nitro-4-oxoquinoline-3-carboxylate (8.0 g, 24.4 mmol) in DMF (50 mL). The reaction mixture was stirred at 0° C. for 30 min and at room temperature for 30 min. To the solution was added benzyl bromide (4.4 mL, 36.9 mmol) and stirred over night. The reaction mixture was poured into ice-water and extract with CH₂Cl₂. The organic layer washed with water, brine, and then dried. The solvent was removed and the crude product was purified by column chromatography (Hexane:EtOAc 3:1 →1:1) to yield ethyl 1-benzyl-6,7-difluoro-1,4-dihydro-8-methoxy-5-nitro-4-oxoquinoline-3-carboxylate (2.74 g, 27%) as a pale yellow solid.

¹H-NMR (400 MHz, DMSO-d₆) δ 1.27 (3H, t, J=7.3 Hz), 3.74 (3H, d, J=2.4 Hz), 4.24 (2H, q, J=7.3 Hz), 5.82 (2H, s), 7.14 (2H, d, J=7.3 Hz), 7.29 (1H, t, J=7.3 Hz), 7.37 (2H, t, J=7.3 Hz), 8.81 (1H, s).

Step 2: Ethyl 5-amino-1-benzyl-6,7-difluoro-1,4-dihydro-8-methoxy-4-oxoquinoline-3-carboxylate

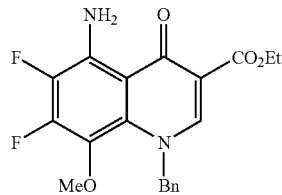

A mixture of ethyl 1-benzyl-6,7-difluoro-1,4-dihydro-8-methoxy-5-nitro-4-oxoquinoline-3-carboxylate (2.0 g, 4.78 mmol) and iron powder (2.67 g, 47.8 mmol) in AcOH (20 mL) was stirred e at 90° C. for 5 h. The catalyst was removed by filtration over Celite and the filtrate was concentrated in vacuo. The residue was diluted with water and basified with aq. NaOH. The mixture was filtrated over celite and washed with CH₂Cl₂. The resulting solution was extracted with CH₂Cl₂. The organic layer washed with water, brine, and then dried. The solvent was removed and the resulting solid washed with EtOH, dried to yield ethyl 5-amino-1-benzyl-6, 7-difluoro-1,4-dihydro-8-methoxy-4-oxoquinoline-3-carboxylate (1.12 g, 60%) as a yellow solid. M.p. 134-135° C.

$^1$H-NMR (400 MHz, DMSO-d$_6$) δ 1.27 (3H, t, J=7.3 Hz), 3.55 (3H, s), 4.19 (2H, q, J=7.3 Hz), 5.67 (2H, s), 7.05 (2H, d, J=7.3 Hz), 7.24 (1H, t, J=7.3 Hz), 7.31 (2H, t, J=7.3 Hz), 7.78 (2H, brs), 8.55 (1H, s).

Step 3: 5-Amino-1-benzyl-6,7-difluoro-1,4-dihydro-8-methoxy-4-oxoquinoline-3-carboxylic acid

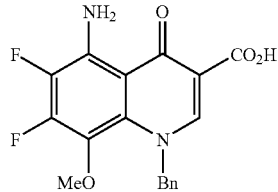

A solution of ethyl 5-amino-1-benzyl-6,7-difluoro-1,4-dihydro-8-methoxy-4-oxoquinoline-3-carboxylate (601 mg, 1.55 mmol) and 1M aq. NaOH (4.5 mL) in EtOH (10 mL) was stirred at 50° C. for 1 h. The solvent was removed and the residue was dissolved in water. The solution was acidified to pH 7 with 2M HCl and the resulting precipitate was removed by filtration, washed with water, EtOH and dried to yield 5-amino-1-benzyl-6,7-difluoro-1,4-dihydro-8-methoxy-4-oxoquinoline-3-carboxylic acid (480 mg, 85%) as a pale yellow solid.

M.p. 208-210° C.

$^1$H-NMR (400 MHz, DMSO-d$_6$) δ 3.58 (3H, s), 5.76 (2H, s), 7.06 (2H, d, J=7.3 Hz), 7.24 (1H, t, J=7.3 Hz), 7.31 (2H, t, J=7.3 Hz), 7.74 (2H, brs), 8.69 (1H, s), 14.49 (1H, brs).

Step 4: 5-Amino-1-benzyl-6-fluoro-1,4-dihydro-8-methoxy-4-oxo-7-[2-(2-pyridylamino)ethylamino]quinoline-3-carboxylic acid

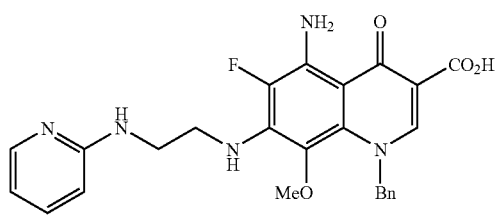

A solution of 5-amino-1-benzyl-6,7-difluoro-1,4-dihydro-8-methoxy-4-oxoquinoline-3-carboxylic acid (400 mg, 1.11 mmol), N-2-pyridyl-1,2-ethanediamine (305 mg, 2.22 mmol) and triethylamine (0.310 mL, 2.22 mmol) in DMSO (4 mL) was stirred at 100° C. After 4 h the reaction mixture was poured into ice water and the resulting precipitate was removed by filtration, washed with ethanol, and dried to yield 5-amino-1-benzyl-6-fluoro-1,4-dihydro-8-methoxy-4-oxo-7-[2-(2-pyridylamino)ethylamino]quinoline-3-carboxylic acid (285 mg, 54%) as a yellow solid.

$^1$H-NMR (400 MHz, DMSO-d$_6$) δ 3.40 (2H, q, J=5.5 Hz), 3.47 (3H, s), 3.50-3.58 (2H, m), 5.71 (2H, s), 6.37-6.45 (2H, m), 6.48 (1H, td, J=5.5, 1.2 Hz), 6.67 (1H, t, J=5.5 Hz), 7.04 (2H, dd, J=7.9, 1.2 Hz), 7.15-7.27 (5H, m), 7.32-7.39 (1H, m), 7.95 (1H, dd, J=5.5, 1.2 Hz), 8.77 (1H, s), 15.18 (1H, brs).

HRESIMS (+): 478.1880 (Calcd for C$_{25}$H$_{25}$FN$_5$O$_4$, 478.18906).

Example 22

5-Amino-6-fluoro-1,4-dihydro-8-methoxy-1-methyl-4-oxo-7-[2-(2-pyridylamino)ethylamino]quinoline-3-carboxylic acid Step 1: Ethyl 6,7-difluoro-1,4-dihydro-8-methoxy-4-oxoquinoline-3-carboxylate

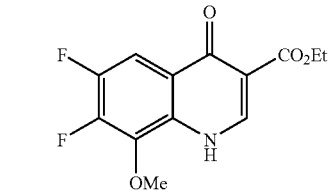

A solution of ethyl 1-tert-butyl-6,7-difluoro-1,4-dihydro-8-methoxy-4-oxoquinoline-3-carboxylate (4.00 g, 11.8 mmol) in CH$_2$Cl$_2$ (20 mL) and trifluoroacetic acid (4.0 mL) was stirred at 0° C. for 30 min. The mixture was concentrated in vacuo and poured into 500 mL of ice-water. The resulting precipitate was removed by filtration, washed with water and then dried to yield ethyl 6,7-difluoro-1,4-dihydro-8-methoxy-4-oxoquinoline-3-carboxylate (3.34 g, quant) as a colorless solid.

$^1$H-NMR (400 MHz, DMSO-d$_6$) δ1.27 (3H, t, J=7.3 Hz), 4.13 (3H, d, J=2.4 Hz), 4.22 (2H, q, J=7.3 Hz), 7.71 (1H, dd, J=11.0, 7.9 Hz), 8.38 (1H, s), 12.23 (1H, brs).

Step 2: Ethyl 1-methyl-6,7-difluoro-1,4-dihydro-8-methoxy-4-oxoquinoline-3-carboxylate

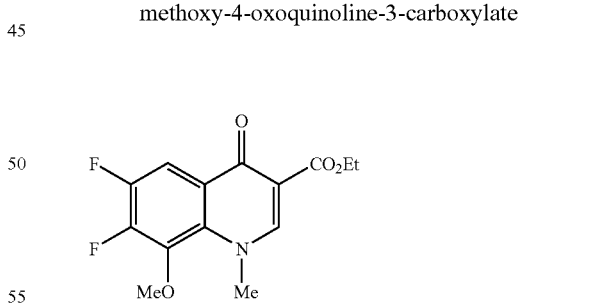

A mixture of ethyl 6,7-difluoro-1,4-dihydro-8-methoxy-4-oxoquinoline-3-carboxylate (1.00 g, 3.53 mmol), iodomethane (0.450 mL, 7.23 mmol) and K$_2$CO$_3$ (976 mg, 7.06 mmol) in DMF (15 mL) was heated at 50° C. for 1 h. The mixture was concentrated in vacuo and dried under high vacuum. The reaction mixture was poured into ice water and the resulting precipitate was removed by filtration, washed with water and then dried to yield ethyl 1-methyl-6,7-difluoro-1,4-dihydro-8-methoxy-4-oxoquinoline-3-carboxylate (845 mg, 81%) as a colorless solid.

¹H-NMR (400 MHz, DMSO-d₆) δ 1.28 (3H, t, J=7.3 Hz), 4.02 (3H, s), 4.10 (3H, s), 4.22 (2H, q, J=7.3 Hz), 7.89 (1H, dd, J=11.0, 8.6 Hz), 8.56 (1H, s).

Step 3: Ethyl 1-methyl-6,7-difluoro-1,4-dihydro-8-methoxy-5-nitro-4-oxoquinoline-3-carboxylate

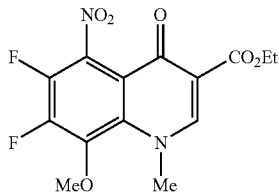

A solution of ethyl 1-methyl-6,7-difluoro-1,4-dihydro-8-methoxy-4-oxoquinoline-3-carboxylate (800 mg, 2.69 mmol) in concentrated H₂SO₄ (7 mL) was treated portionwise at 0° C. with solid KNO₃ (380 mg, 3.76 mmol). After stirring at 0° C. for 1 h, the reaction mixture was poured into ice-water and the resulting precipitate was removed by filtration. The resulting solid washed with EtOH, dried to yield ethyl 1-methyl-6,7-difluoro-1,4-dihydro-8-methoxy-5-nitro-4-oxoquinoline-3-carboxylate (765 mg, 83%) as a pale yellow solid.

¹H-NMR (400 MHz, DMSO-d₆) δ 1.26 (3H, t, J=7.3 Hz), 4.06 (3H, d, J=1.8 Hz), 4.11 (3H, s), 4.21 (2H, q, J=7.3 Hz), 8.63 (1H, s).

Step 4: Ethyl 5-amino-1-methyl-6,7-difluoro-1,4-dihydro-8-methoxy-4-oxoquinoline-3-carboxylate

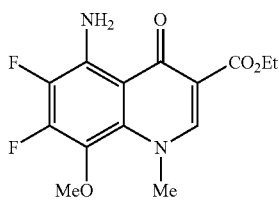

A solution of ethyl 1-methyl-6,7-difluoro-1,4-dihydro-8-methoxy-5-nitro-4-oxoquinoline-3-carboxylate (735 mg, 2.15 mmol) and iron powder (600 mg, 10.7 mmol) in AcOH (5 mL) was stirred e at 80° C. for 8 h. The catalyst was removed by filtration over Celite and the filtrate was concentrated in vacuo. The residue was diluted with water and basified with aq. NaOH. The mixture was filtrated over celite and washed with CH₂Cl₂. The resulting solution was extracted with CH₂Cl₂. The organic layer washed with water, brine, and then dried. The solvent was removed and the resulting solid washed with EtOH, dried to yield ethyl 5-amino-1-methyl-6,7-difluoro-1,4-dihydro-8-methoxy-4-oxoquinoline-3-carboxylate (215 mg, 32%) as a yellow solid.

¹H-NMR (400 MHz, DMSO-d₆) δ 1.25 (3H, t, J=7.3 Hz), 3.78 (3H, s), 3.98 (3H, s), 4.18 (2H, q, J=7.3 Hz), 7.78 (2H, brs), 8.35 (1H, s).

Step 5: 5-Amino-1-methyl-6,7-difluoro-1,4-dihydro-8-methoxy-4-oxoquinoline-3-carboxylic acid

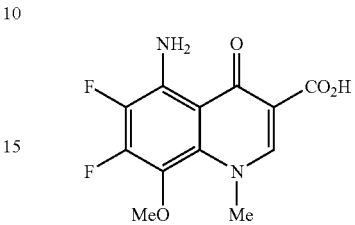

A solution of ethyl 5-amino-1-methyl-6,7-difluoro-1,4-dihydro-8-methoxy-4-oxoquinoline-3-carboxylate (203 mg, 0.650 mmol) and 1M aq. NaOH (2 mL) in EtOH (5 mL) was stirred at 50° C. for 1 h. The solvent was removed and the residue was dissolved in water. The solution was acidified to pH 7 with 2M HCl and the resulting precipitate was removed by filtration, washed with water, and dried to yield 5-amino-1-methyl-6,7-difluoro-1,4-dihydro-8-methoxy-4-oxoquinoline-3-carboxylic acid (180 mg, 97%) as a pale yellow solid.

¹H-NMR (400 MHz, DMSO-d₆) δ 3.82 (3H, s), 4.13 (3H, s), 7.68 (2H, brs), 8.70 (1H, s), 14.69 (1H, brs).

Step 6: 5-Amino-6-fluoro-1,4-dihydro-8-methoxy-1-methyl-4-oxo-7-[2-(2-pyridylamino)ethylamino]quinoline-3-carboxylic acid

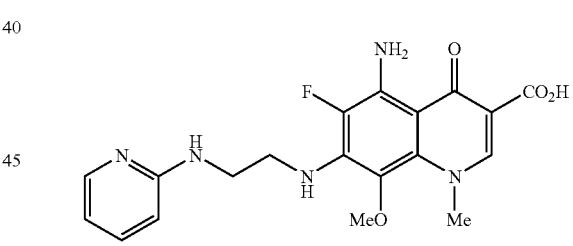

A solution 5-amino-1-methyl-6,7-difluoro-1,4-dihydro-8-methoxy-4-oxoquinoline-3-carboxylic acid (170 mg, 0.598 mmol), N-2-pyridyl-1,2-ethanediamine (123 mg, 0.897 mmol) and triethylamine (0.125 mL, 0.897 mmol) in DMSO (2 mL) was stirred at 100° C. After 4 h the reaction mixture was poured into ice water and the resulting precipitate was removed by filtration, washed with ethanol, and dried to yield 5-amino-6-fluoro-1,4-dihydro-8-methoxy-1-methyl-4-oxo-7-[2-(2-pyridylamino)ethylamino]quinoline-3-carboxylic acid (142 mg, 59%) as a pale yellow solid.

¹H-NMR (400 MHz, DMSO-d₆) δ 3.44-3.52 (5H, m), 3.56-3.66 (2H, m), 4.00 (3H, s), 6.32 (1H, s), 6.43-6.50 (2H, m), 6.71 (1H, t, J=5.8 Hz), 7.20 (2H, brs), 7.32-7.38 (1H, m), 7.96 (1H, dd, J=4.9, 1.2 Hz), 8.49 (1H, s), 15.28 (1H, brs).

HRESIMS (+): 402.15698 (Calcd for C₁₉H₂₁FN₅O₄, 402.15698).

Example 22

Ethyl 5-amino-6,8-difluoro-1,4-dihydro-4-oxo-1-(2-phenethyl)-7-[2-(2-pyridylamino)ethylamino]quinoline-2-carboxylate Step 1: Ethyl 3-pentafluorobenzoyl-2-(2-phenethylamino)acrylate

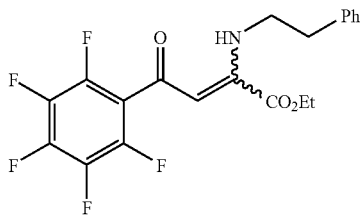

A solution of ethyl 2-hydroxy-4-oxo-4-pentafluorophenyl-but-2-enoate (4.95 g, 16.0 mmol) in toluene (50 mL) and 2-phenethylamine (2.4 mL, 19.1 mmol) was stirred at 70° C. After 1.5 h, a solution was heated at 90° C. for 3 h. The mixture was concentrated in vacuo and the crude product was purified by column chromatography (ChromatrexNH-DM2035 (Fuji Silysia Chemocal Co. Ltd.) Hexane: EtOAc 10:1→$CH_2Cl_2$: MeOH=20:1) to yield ethyl 3-pentafluorobenzoyl-2-(2-phenethylamino)acrylate (1.21 g, 18%) as a dark brown solid.

$^1$H-NMR (400 MHz, $CDCl_3$) δ 1.34 (3H, t, J=7.3 Hz), 2.97 (2H, t, J=7.3 Hz), 3.78 (2H, q, J=7.3 Hz), 4.29 (2H, q, J=7.3 Hz), 5.65 (1H, s), 7.20-7.38 (5H, m), 10.77 (1H, brs).

Step 2: Ethyl 5,6,7,8-tetrafluoro-1,4-dihydro-4-oxo-1-(2-phenethyl)quinoline-2-carboxylate

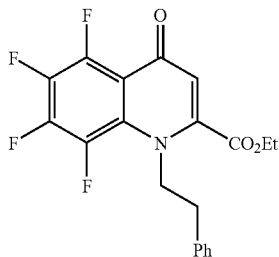

A solution of NaH (140 mg, 3.5 mmol, 60% in oil) in DMF (20 mL) was cooled to 0° C. and treated dropwise with ethyl 3-pentafluorobenzoyl-2-(2-phenethylamino)acrylate (1.20 g, 2.90 mmol) in DMF (10 mL). The reaction mixture was stirred at room temperature for 1 h. The reaction mixture was poured into ice water and acidified to pH 4 with 2M HCl. The resulting solution was extracted with EtOAc, and the organic layer washed with water, brine, and then dried. The solvent was removed and the crude product was purified by column chromatography (Hexane:EtOAc 5:1) to yield ethyl 5,6,7,8-tetrafluoro-1,4-dihydro-4-oxo-1-(2-phenethyl)quinoline-2-carboxylate (990 mg, 87%) as yellow solid.

$^1$H-NMR (400 MHz, $CDCl_3$) δ 1.38 (3H, t, J=7.3 Hz), 2.96 (2H, t, J=7.3 Hz), 4.38 (2H, q, J=7.3 Hz), 4.57 (2H, t, J=7.3 Hz), 6.44 (1H, s), 6.98 (2H, dd, J=7.9, 1.8 Hz), 7.19-7.28 (3H, m).

Step 3: Ethyl 5,6,8-trifluoro-1,4-dihydro-4-oxo-1-(2-phenethyl)-7-[2-(2-pyridylamino)ethylamino]quinoline-2-carboxylate

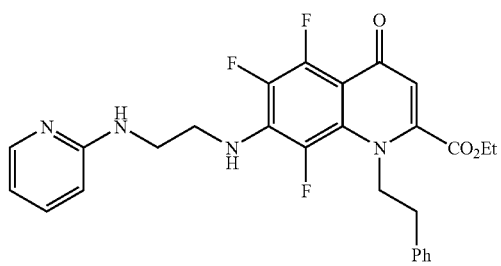

A solution ethyl 5,6,7,8-tetrafluoro-1,4-dihydro-4-oxo-1-(2-phenethyl)quinoline-2-carboxylate (987 mg, 2.51 mmol), N-2-pyridyl-1,2-ethanediamine (688 mg, 5.02 mmol) and triethylamine (1.0 mL, 7.17 mmol) in DMSO (25 mL) was stirred at 70° C. After 30 min, the reaction mixture was poured into ice water and the resulting solution was extracted with EtOAc, and the organic layer washed with water, brine, and then dried. The solvent was removed and the crude product was purified by column chromatography (Hexane:EtOAc 1:1) to yield ethyl 5,6,8-trifluoro-1,4-dihydro-4-oxo1-(2-phenethyl)-7-[2-(2-pyridylamino)ethylamino]quinoline-2-carboxylate (797 mg, 62%) as yellow solid.

$^1$H-NMR (400 MHz, $CDCl_3$) δ 1.36 (3H, t, J=7.3 Hz), 2.87 (2H, t, J=6.7 Hz), 3.70-3.84 (4H, m), 4.34 (2H, q, J=7.3 Hz), 4.44 (2H, t, J=7.3 Hz), 4.73 (1H, brs), 6.33 (1H, s), 6.46 (1H, d, J=8.6 Hz), 6.59-6.73 (2H, m), 6.94-6.99 (2H, m), 7.18-7.24 (3H, m), 7.40-7.44 (1H, m), 8.14 (1H, d, J=3.7 Hz).

Step 4: Ethyl 6,8-difluoro-1,4-dihydro-5-(4-methoxybenzylamino)-4-oxo-1-(2-phenethyl)-7-[2-(2-pyridylamino)ethylamino]quinoline-2-carboxylate

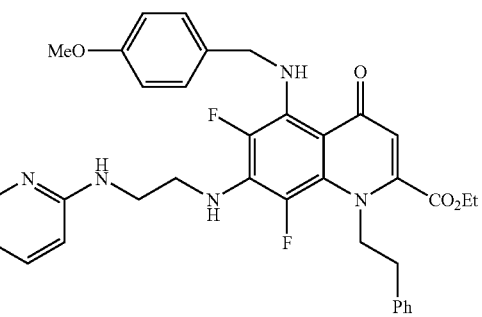

A solution of ethyl 5,6,8-trifluoro-1,4-dihydro-4-oxo-1-(2-phenethyl)-7-[2-(2-pyridylamino)ethylamino]quinoline-2-carboxylate (672 mg, 1.32 mmol) and triethylamine (0.552 mL, 3.96 mmol) and 4-methoxybenzylamine (0.512 mL, 3.95 mmol) in DMSO (12 mL) was stirred at 100° C. for 12 h. The reaction mixture was poured into water, and then extracted with EtOAc. The organic layer washed with water and brine, and dried over anhyd. $Na_2SO_4$ followed by removal of EtOAc. The crude product was purified by column chromatography (Hexane:EtOAc 1:1) to yield ethyl 6,8-difluoro-1,4-dihydro-5-(4-methoxybenzylamino)-4-oxo-1-(2-phenethyl)-7-[2-(2-pyridylamino)ethylamino]quinoline-2-carboxylate (607 mg, 73%) as a yellow solid.

$^1$H-NMR (400 MHz, CDCl$_3$) δ 1.35 (3H, t, J=7.3 Hz), 2.82 (2H, t, J=6.7 Hz), 3.57-3.65 (2H, m), 3.65-3.72 (2H, m), 3.76 (3H, s), 4.28-4.40 (4H, m), 4.53 (2H, dd, J=6.7, 3.7 Hz), 4.61 (1H, t, J=5.5 Hz), 6.24 (1H, s), 6.38 (1H, d, J=8.6 Hz), 6.60 (1H, dd, J=7.3, 4.3 Hz), 6.83 (2H, d, J=8.6 Hz), 6.96 (2H, dd, J=7.9, 1.8 Hz), 7.18-7.23 (3H, m), 7.36-7.42 (1H, m), 8.10 (1H, dd, J=4.9, 1.2 Hz), 10.13 (1H, brs).

Step 5: Ethyl 5-amino-6,8-difluoro-1,4-dihydro-4-oxo-1-(2-phenethyl)-7-[2-(2-pyridylamino)ethylamino]quinoline-2-carboxylate

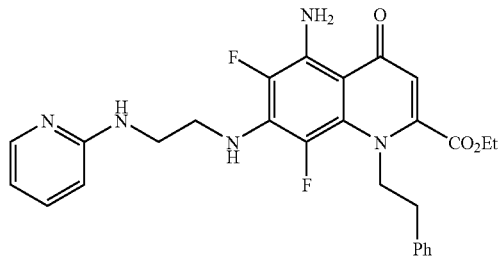

A solution of ethyl 6,8-difluoro-1,4-dihydro-5-(4-methoxybenzylamino)-4-oxo-1-(2-phenethyl)-7-[2-(2-pyridylamino)ethylamino]quinoline-2-carboxylate (583 mg, 0.929 mmol) in CH$_2$Cl$_2$ (10 mL) was cooled to 0° C. and treated dropwise with trifluoroacetic acid (2 mL). The reaction mixture was stirred at room temperature for over night. The reaction mixture was diluted with CH$_2$Cl$_2$ and washed with saturated NaHCO$_3$, brine, and dried over anhyd Na$_2$SO$_4$ followed by the removal of CH$_2$Cl$_2$. The crude product was purified by column chromatography (Hexane:EtOAc 1:1) to yield ethyl 5-amino-6,8-difluoro-1,4-dihydro-4-oxo-1-(2-phenethyl)-7-[2-(2-pyridylamino)ethylamino]quinoline-2-carboxylate (225 mg, 48%) as a yellow solid.

$^1$H-NMR (400 MHz, DMSO-d$_6$) δ 1.35 (3H, t, J=7.3 Hz), 2.88 (2H, t, J=7.3 Hz), 3.65-3.80 (4H, m), 4.34 (2H, q, J=7.3 Hz), 4.38 (2H, t, J=7.3 Hz), 4.76 (1H, brs), 5.59 (1H, brs), 6.22 (1H, s), 6.44 (1H, d, J=7.9 Hz), 6.53-6.65 (3H, m), 7.00 (2H, d, J=7.9 Hz), 7.15-7.28 (3H, m), 7.38-7.45 (1H, m), 8.10-8.13 (1H, m).

HRESIMS (+):508.21852 (Calcd for C$_{27}$H$_{28}$F$_2$N$_5$O$_3$, 508.21602).

Example 23

5-Amino-6,8-difluoro-1,4-dihydro-4-oxo-1-(2-phenethyl)-7-[2-(2-pyridylamino)ethylamino]quinoline-2-carboxylic acid

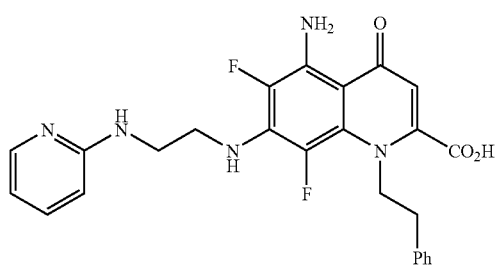

A solution of ethyl 5-amino-6,8-difluoro-1,4-dihydro-4-oxo-1-(2-phenethyl)-7-[2-(2-pyridylamino)ethylamino]quinoline-2-carboxylate (206 mg, 0.406 mmol) and 1M aq. NaOH (0.8 mL) in EtOH (8 mL) was stirred at room temperature for 3 h. The solvent was removed and the residue was dissolved in water. The solution was acidified to pH 7 with 2M HCl and the resulting precipitate was removed by filtration, washed with CH$_3$CN, and dried to yield 5-amino-6,8-difluoro-1,4-dihydro-4-oxo-1-(2-phenethyl)-7-(2-pyridylamino)ethylamino]quinoline-2-carboxylic acid (183 mg, 94%) as a yellow solid.

$^1$H-NMR (400 MHz, DMSO-d$_6$) δ 2.86 (2H, t, J=7.3 Hz), 3.49 (2H, q, J=4.9 Hz), 3.54-3.60 (2H, m), 4.28 (2H, t, J=7.3 Hz), 5.87 (1H, s), 6.25 (1H, brs), 6.47-6.56 (2H, m), 6.95 (1H, brs), 7.03 (2H, d, J=6.7 Hz), 7.12-7.27 (5H, m), 7.41 (1H, t, J=7.9 Hz), 7.93 (1H, dd, J=4.9, 1.2 Hz).

HRESIMS (+):480.18397 (Calcd for C$_{25}$H$_{24}$F$_2$N$_5$O$_3$, 480.19472).

Example 24

Ethyl 5-amino-1-cyclopropyl-6,8-difluoro-1,4-dihydro-4-oxo-7-[2-(2-pyridylamino)ethylamino]quinoline-2-carboxylate Step 1: Ethyl 2-cyclopropylamino-3-pentafluorobenzoylacrylate

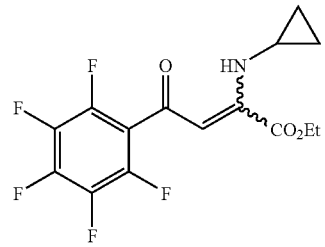

A solution of ethyl 2-hydroxy-4-oxo-4-pentafluorophenyl-but-2-enoate (3.00 g, 9.67 mmol) in toluene (50 mL) and cyclopropylamine (0.8 mL, 11.6 mmol) was stirred at 60° C. After 4 h, the mixture was concentrated in vacuo and the crude product was purified by column chromatography (Chromatrex NH-DM2035 (Fuji SislysiaChemical Co. Ltd.) Hexane:EtOAc 5:1) to yield ethyl 2-cyclopropylamino-3-pentafluorobenzoylacrylate (1.13 g, 34%) as a yellow oil.

$^1$H-NMR (400 MHz, CDCl$_3$) δ 0.65-0.92 (4H, m), 1.39 (3H, t, J=7.3 Hz), 3.05-3.15 (1H, m), 4.37 (2H, q, J=7.3 Hz), 5.61 (1H, s), 10.52 (1H, brs).

Step 2: Ethyl 1-cyclopropyl-5,6,7,8-tetrafluoro-1,4-dihydro-4-oxoquinoline-2-carboxylate

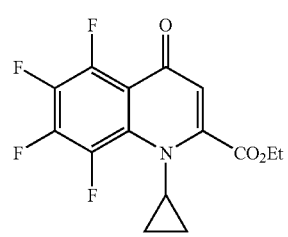

A solution of NaH (150 mg, 3.75 mmol, 60% in oil) in DMF (20 mL) was cooled to 0° C. and treated dropwise with ethyl 2-cyclopropylamino-3-pentafluorobenzoylacrylate (1.09 g, 3.12 mmol) in DMF (10 mL). The reaction mixture was stirred at room temperature for 1 h. The reaction mixture was poured into ice water and acidified to pH 4 with 2M HCl. The resulting solution was extracted with EtOAc, and the organic layer washed with water, brine, and then dried. The solvent was removed and the crude product was purified by column chromatography (Hexane:EtOAc 2:1) to yield ethyl 1-cyclopropyl-5,6,7,8-tetrafluoro-1,4-dihydro-4-oxoquinoline-2-carboxylate (714 mg, 70%) as a pale yellow solid.

$^1$H-NMR (400 MHz, CDCl$_3$) δ 0.68-0.79 (2H, m), 1.00-1.10 (2H, m), 1.45 (3H, t, J=7.3 Hz), 3.93-4.00 (1H, m), 4.45 (2H, q, J=7.3 Hz), 6.53 (1H, s).

Step 3: Ethyl 1-cyclopropyl-5,6,8-trifluoro-1,4-dihydro-4-oxo-7-[2-(2-pyridylamino)ethylamino]quinoline-2-carboxylate

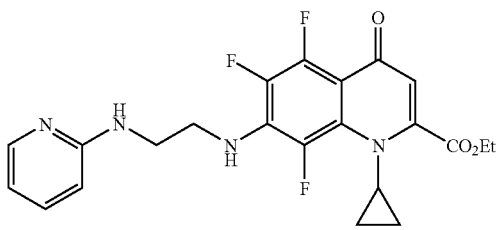

A solution ethyl 1-cyclopropyl-5,6,7,8-tetrafluoro-1,4-dihydro-4-oxoquinoline-2-carboxylate (688 mg, 2.09 mmol), N-2-pyridyl-1,2-ethanediamine (570 mg, 4.16 mmol) and triethylamine (0.87 mL, 6.24 mmol) in DMSO (20 mL) was stirred at 70° C. After 1 h, the reaction mixture was poured into ice water and the resulting solution was extracted with EtOAc, and the organic layer washed with water, brine, and then dried. The solvent was removed and the crude product was purified by column chromatography (Hexane:EtOAc 1:1) to yield ethyl 1-cyclopropyl-5,6,8-trifluoro-1,4-dihydro-4-oxo-7-[2-(2-pyridylamino)ethylamino]quinoline-2-carboxylate (773 mg, 83%) as yellow solid.

$^1$H-NMR (400 MHz, CDCl$_3$) δ 0.61-0.68 (2H, m), 0.94 (2H, q, J=6.7 Hz), 1.41 (3H, t, J=7.3 Hz), 3.67-3.75 (2H, m), 3.75-3.80 (2H, m), 3.83-3.92 (1H, m), 4.41 (2H, q, J=7.3 Hz), 4.75 (1H, t, J=5.5 Hz), 6.40-6.48 (2H, m), 6.53 (1H, brs), 6.63 (1H, dd, J=6.7, 4.9 Hz), 7.38-7.44 (1H, m), 8.12 (1H, d, J=4.9 Hz).

Step 4: Ethyl 1-cyclopropyl-6,8-difluoro-1,4-dihydro-5-(4-methoxybenzylamino)-4-oxo-7-[2-(2-pyridylamino)ethylamino]quinoline-2-carboxylate

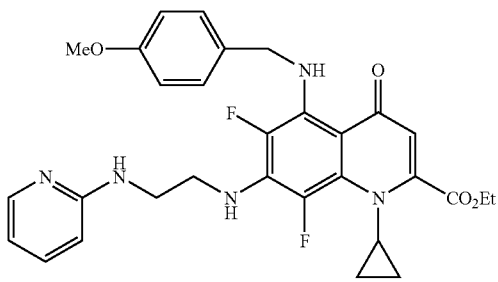

A solution of ethyl 1-cyclopropyl-5,6,8-trifluoro-1,4-dihydro-4-oxo-7-[(2-pyridylamino)ethylamino]quinoline-2-carboxylate (705 mg, 1.58 mmol) and triethylamine (0.66 mL, 4.74 mmol) and 4-methoxybenzylamine (0.600 mL, 4.62 mmol) in DMSO (15 mL) was stirred at 100° C. for 18 h. The reaction mixture was poured into water, and then extracted with EtOAc. The organic layer washed with water and brine, and dried over anhyd. Na$_2$SO$_4$ followed by the removal of EtOAc. The crude product was purified by column chromatography (Hexane:EtOAc 1:1) to yield ethyl 1-cyclopropyl-6,8-difluoro-1,4-dihydro-5-(4-methoxybenzylamino)-4-oxo-7-[2-(2-pyridylamino)ethylamino]quinoline-2-carboxylate (597 mg, 67%) as a orange amorphous solid.

$^1$H-NMR (400 MHz, CDCl$_3$) δ 0.57-0.65 (2H, m), 0.89 (2H, q, J=6.7 Hz), 1.40 (3H, t, J=7.3 Hz), 3.59 (2H, q, J=6.1 Hz), 3.64-3.70 (2H, m), 3.76 (3H, s), 3.79-3.87 (1H, m), 4.40 (2H, q, J=7.3 Hz), 4.51 (2H, dd, J=6.1, 3.7 Hz), 4.63 (1H, t, J=6.7 Hz), 5.27 (1H, brs), 6.35 (1H, s), 6.38 (1H, d, J=8.6 Hz), 6.60 (1H, dd, J=6.1, 1.2 Hz), 6.82 (2H, d, J=8.6 Hz), 7.22-7.27 (5H, m), 7.36-7.42 (1H, m), 8.07-8.11 (1H, m), 9.87 (1H, t, J=6.1 Hz).

Step 5: Ethyl 5-amino-1-cyclopropyl-6,8-difluoro-1,4-dihydro-4-oxo-7-[2-(2-pyridylamino)ethylamino]quinoline-2-carboxylate

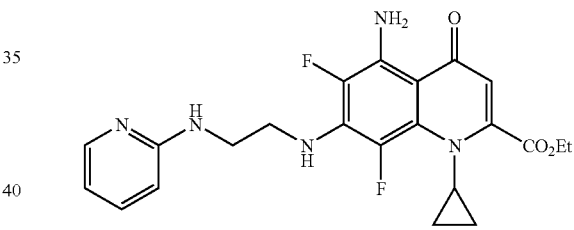

A solution of ethyl 1-cyclopropyl-6,8-difluoro-1,4-dihydro-5-(4-methoxybenzylamino)-4-oxo-7-[2-(2-pyridylamino)ethylamino]quinoline-2-carboxylate (577 mg, 1.02 mmol) in CH$_2$Cl$_2$ (10 mL) was cooled to 0° C. and treated dropwise with trifluoroacetic acid (2 mL). The reaction mixture was stirred at room temperature for over night. The reaction mixture was diluted with CH$_2$Cl$_2$ and washed with saturated NaHCO$_3$, brine, and dried over anhyd Na$_2$SO$_4$ followed by the removal of CH$_2$Cl$_2$. The crude product was purified by column chromatography (Hexane:EtOAc 1:1) to yield ethyl 5-amino-1-cyclopropyl-6,8-difluoro-1,4-dihydro-4-oxo-7-[2-(2-pyridylamino)ethylamino]quinoline-2-carboxylate (336 mg, 74%) as a orange amorphous solid.

$^1$H-NMR (400 MHz, DMSO-d$_6$) δ 0.60-0.67 (2H, m), 0.90 (2H, q, J=7.3 Hz), 1.41 (3H, t, J=7.3 Hz), 3.62-3.69 (2H, m), 3.70-3.77 (2H, m), 3.79 (1H, m), 4.41 (2H, q, J=7.3 Hz), 4.72 (1H, t, J=5.5 Hz), 5.43 (1H, brs), 6.34 (1H, s), 6.37-6.49 (3H, m), 6.57-6.64 (1H, m), 7.26 (1H, s), 8.11 (1H, d, J=4.9 Hz).

HRESIMS (+): 444.18873 (Calcd for C$_{22}$H$_{24}$F$_2$N$_5$O$_3$, 444.18472).

Example 25

5-Amino-1-cyclopropyl-6,8-difluoro-1,4-dihydro-4-oxo-7-[2-(2-pyridylamino)ethylamino]quinoline-2-carboxylic acid

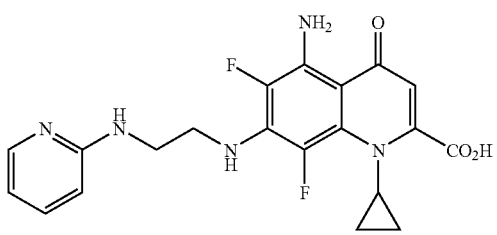

A solution of ethyl 5-amino-1-cyclopropyl-6,8-difluoro-1,4-dihydro-4-oxo-7-[2-(2-pyridylamino)ethylamino]quinoline-2-carboxylate (317 mg, 0.715 mmol) and 1M aq. NaOH (1.4 mL) in EtOH (7 mL) was stirred at room temperature for over night. The solvent was removed and the residue was dissolved in water. The solution was acidified to pH 7 with 2M HCl and the resulting precipitate was removed by filtration, washed with CH$_3$CN, and dried to yield 5-amino-1-cyclopropyl-6,8-difluoro-1,4-dihydro-4-oxo-7-[2-(2-pyridylamino)ethylamino]quinoline-2-carboxylic acid (246 mg, 83%) as a yellow solid.

$^1$H-NMR (400 MHz, DMSO-d$_6$) δ 0.55-0.63 (2H, m), 0.88 (2H, q, J=6.7 Hz), 3.46 (2H, q, J=5.5 Hz), 3.51-3.58 (2H, m), 3.65-3.75 (1H, m), 6.02 (1H, s), 6.27 (1H, brs), 6.45-6.50 (2Hm), 6.75 (1H, brs), 7.07 (2H, brs), 7.34-7.40 (1H, m), 7.94 (1H, dd, J=6.1, 1.8 Hz).

HRESIMS (+): 416.15765 (Calcd for C$_{20}$H$_{20}$F$_2$N$_5$O$_3$, 416.15342).

Example 26

5-Amino-1-cyclopropyl-6-fluoro-1,4-dihydro-8-methoxy-2-methyl-4-oxo-7-[2-(2-pyridylamino)ethylamino]quinoline-3-carboxylic acid Step 1: Ethyl 1-cyclopropyl-6,7-difluoro-1,2,3,4-tetrahydro-8-methoxy-2-methyl-5-nitro-4-oxoquinoline-3-carboxylate

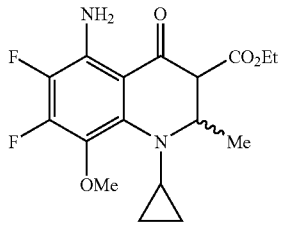

To a stirred solution of ethyl 1-cyclopropyl-6,7-difluoro-1,4-dihydro-8-methoxy-5-nitro-4-oxoquinoline-3-carboxylate (2.50 g, 6.79 mmol) and cuprous iodide (389 mg, 2.04 mmol) in THF (70 mL), 3 M methylmagnesium chloride in THF (3.40 mL, 10.2 mmol) was added under argon atmosphere at −78° C. After stirred at −78° C. for 1 h and at room temperature for 1 h, the reaction mixture was poured into ice-water (300 mL) and concentrated HCl (30 mL) was added to stirred for 30 min. The crude product was extracted with EtOAc, washed with brine, dried over MgSO$_4$ and the solvent was removed in vacuo. The crude product was purified by column chromatography (Hexane:EtOAc 20:1→5:1) to yield ethyl 1-cyclopropyl-6,7-difluoro-1,2,3,4-tetrahydro-8-methoxy-2-methyl-5-nitro-4-oxoquinoline-3-carboxylate (1.44 g, 55%) as a yellow solid.

$^1$H-NMR (400 MHz, CDCl$_3$) δ 0.47-0.51 (1H, m), 0.57-0.62 (1H, m), 0.70-0.79 (2H, m), 1.17 (3H, d, J=6.1 Hz), 1.35 (3H, t, J=7.3 Hz), 3.09-3.14 (1H, m), 3.94 (3H, d, J=1.8 Hz), 4.23-4.38 (2H, m), 4.51 (1H, q, J=6.1 Hz), 11.92 (1H, brs).

Step 2: Ethyl 1-cyclopropyl-6,7-difluoro-1,4-dihydro-8-methoxy-2-methyl-5-nitro-4-oxoquinoline-3-carboxylate

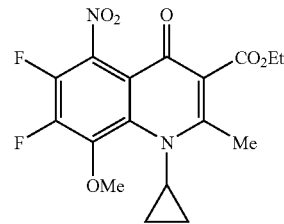

A suspension of ethyl 1-cyclopropyl-6,7-difluoro-1,2,3,4-tetrahydro-8-methoxy-2-methyl-5-nitro-4-oxoquinoline-3-carboxylate (1.42 g, 3.69 mmol) and manganese dioxide (16.1 g, 185 mmol) in CH$_2$Cl$_2$ (80 mL) was stirred at room temperature for 36 h. The catalyst was removed by filtration over Celite and the filtrate was concentrated in vacuo. The crude product was purified by column chromatography (Hexane:EtOAc 5:1→1:1) to yield ethyl 1-cyclopropyl-6,7-difluoro-1,4-dihydro-8-methoxy-2-methyl-5-nitro-4-oxoquinoline-3-carboxylate (225 mg, 16%) as a colorless solid.

$^1$H-NMR (400 MHz, CDCl$_3$) δ 0.65-0.69 (2H, m), 1.19-1.24 (2H, m), 1.35 (3H, t, J=7.3 Hz), 2.62 (3H, s), 3.64-3.69 (1H, m), 4.12 (3H, d, J=3.1 Hz), 4.34 (2H, q, J=7.3 Hz).

Step 3: Ethyl 5-amino-1-cyclopropyl-6,7-difluoro-1,4-dihydro-8-methoxy-2-methyl-4-oxoquinoline-3-carboxylate

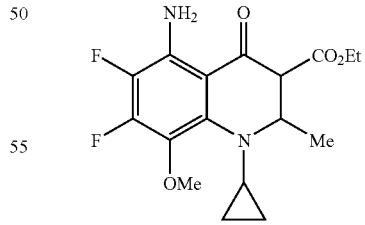

A suspension of ethyl 1-cyclopropyl-6,7-difluoro-1,4-dihydro-8-methoxy-2-methyl-5-nitro-4-oxoquinoline-3-carboxylate (200 mg, 0.523 mmol) and iron powder (175 mg, 3.14 mmol) in AcOH (5 mL) was stirred at 90° C. for 2 h. After the reaction mixture was concentrated in vacuo, the crude product was extracted with EtOAc, washed with saturated aq. NaHCO$_3$ and brine, dried over MgSO$_4$. The solvent was removed in vacuo and the residue was dried to yield ethyl 5-amino-1-cyclopropyl-6,7-difluoro-1,4-dihydro-8-methoxy-2-methyl-4-oxoquinoline-3-carboxylate (200 mg, quant.) as a yellow oil.

$^1$H-NMR (400 MHz, CDCl$_3$) δ 0.62-0.66 (2H, m), 1.11-1.17 (2H, m), 1.38 (3H, t, J=7.3 Hz), 2.55 (3H, s), 3.52-3.57 (1H, m), 3.79 (3H, s), 4.38 (2H, q, J=7.3 Hz), 6.60 (2H, brs).

Step 4: 5-Amino-1-cyclopropyl-6,7-difluoro-1,4-dihydro-8-methoxy-2-methyl-4-oxoquinoline-3-carboxylic acid

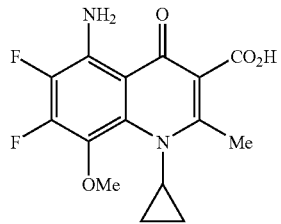

A solution of ethyl 5-amino-1-cyclopropyl-6,7-difluoro-1,4-dihydro-8-methoxy-2-methyl-4-oxoquinoline-3-carboxylate (187 mg, 0.531 mmol) and 1M aq. NaOH (1 mL) in EtOH (3 mL) was stirred at 50° C. for 1 h. After the reaction mixture was concentrated in vacuo, the residue was dissolved in water and 2M HCl was added to pH<3. The resulting precipitate was collected by filtration in vacuo, washed with water and dried to yield 5-amino-1-cyclopropyl-6,7-difluoro-1,4-dihydro-8-methoxy-2-methyl-4-oxoquinoline-3-carboxylic acid (161 mg, 93%) as a pale yellow solid.

$^1$H-NMR (400 MHz, DMSO-d$_6$) δ 0.57-0.69 (2H, m), 1.04-1.16 (2H, m), 2.94 (3H, s), 3.76 (3H, s), 3.80-3.85 (1H, m), 7.42 (2H, brs), 14.98 (1H, brs).

Step 5: 5-Amino-1-cyclopropyl-6-fluoro-1,4-dihydro-8-methoxy-2-methyl-4-oxo-7-[2-(2-pyridylamino)ethylamino]quinoline-3-carboxylic acid

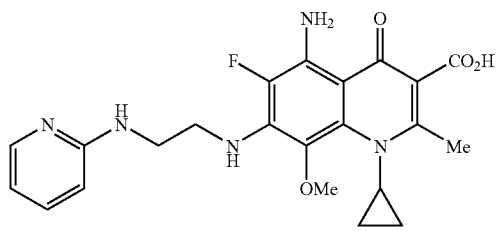

A solution of 5-amino-1-cyclopropyl-6,7-difluoro-1,4-dihydro-8-methoxy-2-methyl-4-oxoquinoline-3-carboxylic acid (140 mg, 0.432 mmol), N-2-pyridyl-1,2-ethanediamine (88.9 mg, 0.648 mmol) and triethylamine (0.0903 mL, 0.648 mmol) in DMSO (4 mL) was stirred at 100° C. for 2 h. To the reaction mixture, water and NH$_4$Cl was added to neutralize and the suspension was stirred for 30 min. The crude product was extracted with EtOAc, washed with brine, dried over MgSO$_4$ and the sovent was removed in vacuo. The crude product was purified by preparative thin layer chromatography (Hexane:EtOAc 1:4) to yield 5-amino-1-cyclopropyl-6-fluoro-1,4-dihydro-8-methoxy-2-methyl-4-oxo-7-[2-(2-pyridylamino)ethylamino]quinoline-3-carboxylic acid (79.9 mg, 42%) as a yellow amorphous solid.

$^1$H-NMR (400 MHz, DMSO-d$_6$) δ 0.39-0.70 (2H, m), 0.79-1.33 (2H, m), 2.98 (3H, s), 3.42 (3H, s), 3.45-3.50 (2H, m), 3.57-3.66 (2H, m), 3.69-3.74 (1H, m), 6.35 (1H, t, J=5.5 Hz), 6.45-6.48 (2H, m), 6.70 (1H, t, J=5.5 Hz), 6.97 (2H, brs), 7.35 (1H, td, J=7.6, 1.8 Hz), 7.95 (1H, dd, J=5.5, 1.8 Hz), 16.08 (1H, brs).

HRESIMS (+): 442.18898 (Calcd for C$_{22}$H$_{24}$FN$_5$O$_4$, 442.18906).

Example 27

5-Amino-1-cyclopropyl-6-fluoro-1,4-dihydro-8-methoxy-4-oxo-2-phenyl-7-[2-(2-pyridylamino)ethylamino]quinoline-3-carboxylic acid Step 1: Ethyl 1-cyclopropyl-6,7-difluoro-1,2,3,4-tetrahydro-8-methoxy-5-nitro-4-oxo-2-phenylquinoline-3-carboxylate

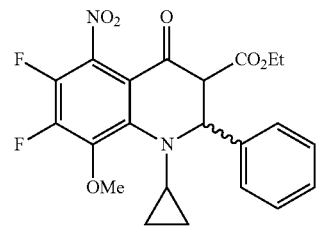

To a stirred solution of ethyl 1-cyclopropyl-6,7-difluoro-1,4-dihydro-8-methoxy-5-nitro-4-oxoquinoline-3-carboxylate (3.00 g, 8.15 mmol) and cuprous iodide (467 mg, 2.45 mmol) in THF (80 mL), 2 M phenylmagnesium bromide in THF (6.10 mL, 12.2 mmol) was added under argon atmosphere at −78° C. After stirred at −78° C. for 1 h and at room temperature for 2 h, the reaction mixture was poured into ice-water (400 mL) and concentrated HCl (40 mL) was added to stirred for 30 min. The crude product was extracted with EtOAc, washed with saturated aq. NaHCO$_3$ and brine, dried over MgSO$_4$ and the solvent was removed in vacuo. The crude product was purified by column chromatography (Hexane: EtOAc 40:1→10:1) to yield ethyl 1-cyclopropyl-6,7-difluoro-1,2,3,4-tetrahydro-8-methoxy-5-nitro-4-oxo-2-phenylquinoline-3-carboxylate (3.09 g, 85%) as a yellow solid.

$^1$H-NMR (400 MHz, CDCl$_3$) δ 0.56-0.62 (1H, m), 0.73-0.91 (3H, m), 1.26 (3H, t, J=7.3 Hz), 3.24-3.29 (1H, m), 3.69 (3H, d, J=1.2 Hz), 4.21-4.32 (2H, m), 5.53 (1H, s), 7.22-7.31 (5H, m), 12.20 (1H, brs).

Step 2: Ethyl 1-cyclopropyl-6,7-difluoro-1,4-dihydro-8-methoxy-5-nitro-4-oxo-2-phenylquinoline-3-carboxylate

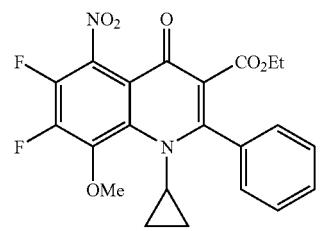

A suspension of ethyl 1-cyclopropyl-6,7-difluoro-1,2,3,4-tetrahydro-8-methoxy-5-nitro-4-oxo-2-phenylquinoline-3-carboxylate (2.60 g, 5.82 mmol) and manganese dioxide (39.0 g, 449 mmol) in CH$_2$Cl$_2$ (60 mL) was stirred at room temperature for 16 h. The catalyst was removed by filtration over Celite and the filtrate was concentrated in vacuo. The crude product was purified by column chromatography (Hexane:EtOAc 5:1→1:1) to yield ethyl 1-cyclopropyl-6,7-difluoro-1,4-dihydro-8-methoxy-5-nitro-4-oxo-2-phenylquinoline-3-carboxylate (1.05 g, 41%) as a colorless solid.

$^1$H-NMR (400 MHz, CDCl$_3$) δ 0.45-0.49 (2H, m), 0.69-0.74 (2H, m), 0.96 (3H, t, J=7.3 Hz), 3.48-3.54 (1H, m), 4.01 (2H, q, J=7.3 Hz), 4.19 (3H, d, J=3.1 Hz), 7.47-7.56 (5H, m).

Step 3: Ethyl 5-amino-1-cyclopropyl-6,7-difluoro-1,4-dihydro-8-methoxy-4-oxo-2-phenylquinoline-3-carboxylate

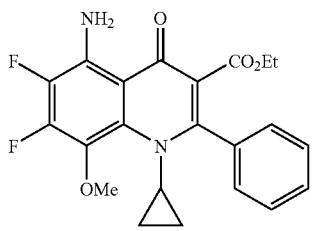

A suspension of ethyl 1-cyclopropyl-6,7-difluoro-1,4-dihydro-8-methoxy-5-nitro-4-oxo-2-phenylquinoline-3-carboxylate (1.05 g, 2.36 mmol) and iron powder (793 mg, 14.2 mmol) in AcOH (25 mL) was stirred at 90° C. for 3 h. After the reaction mixture was concentrated in vacuo, water was added and the crude product was extracted with EtOAc, washed with saturated aq. NaHCO$_3$ and brine, dried over MgSO$_4$. The solvent was removed in vacuo and the residue was dried to yield ethyl 5-amino-1-cyclopropyl-6,7-difluoro-8-methoxy-4-oxo-2-phenyl-1,4-dihydroquinoline-3-carboxylate (1.00 g, quant.) as a yellow amorphous solid.

$^1$H-NMR (400 MHz, CDCl$_3$) δ 0.41-0.45 (2H, m), 0.62-0.68 (2H, m), 0.93 (3H, t, J=7.3 Hz), 3.38-3.44 (1H, m), 3.90 (3H, s), 4.01 (2H, q, J=7.3 Hz), 6.67 (2H, brs), 7.45-7.56 (5H, m).

Step 4: 5-Amino-1-cyclopropyl-6,7-difluoro-1,4-dihydro-8-methoxy-4-oxo-2-phenylquinoline-3-carboxylic acid

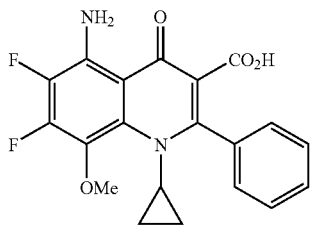

A solution of ethyl 5-amino-1-cyclopropyl-6,7-difluoro-1,4-dihydro-8-methoxy-4-oxo-2-phenylquinoline-3-carboxylate (980 mg, 2.36 nmol) and 1M aq. NaOH (5 mL) in EtOH (15 mL) was stirred at 50° C. for 24 h. After the reaction mixture was concentrated in vacuo, the residue was dissolved in water and 2M HCl was added to pH<3. The crude product was extracted with EtOAc, washed with brine, dried over MgSO$_4$ and the solvent was removed in vacuo. The crude product was purified by column chromatography (Hexane:EtOAc 5:1→1:1) to yield 5-amino-1-cyclopropyl-6,7-difluoro-1,4-dihydro-8-methoxy-4-oxo-2-phenylquinoline-3-carboxylic acid (574 mg, 63%) as a yellow amorphous solid.

$^1$H-NMR (400 MHz, DMSO-d$_6$) δ 0.39-0.48 (2H, m), 0.50-0.59 (2H, m), 3.34-3.43 (1H, m), 3.85 (3H, s), 7.44-7.63 (7H, m), 13.19 (1H, brs).

Step 5: 5-Amino-1-cyclopropyl-6-fluoro-1,4-dihydro-8-methoxy-4-oxo-2-phenyl-7-[2-(2-pyridylamino)ethylamino]quinoline-3-carboxylic acid

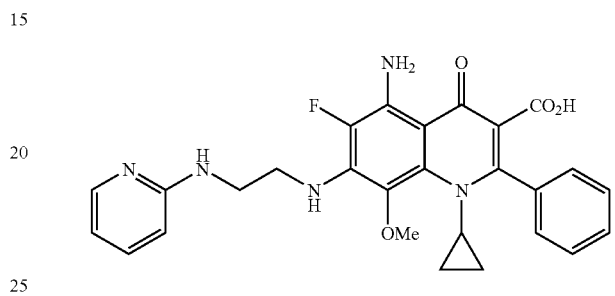

A solution of 5-amino-1-cyclopropyl-6,7-difluoro-1,4-dihydro-8-methoxy-4-oxo-2-phenylquinoline-3-carboxylic acid (550 mg, 1.42 mmol), N-2-pyridyl-1,2-ethanediamine (292 mg, 2.13 mmol) and triethylamine (0.297 mL, 2.13 mmol) in DMSO (7 mL) was stirred at 120° C. for 6 h. To the reaction mixture, water and NH$_4$Cl was added to neutralize and the suspension was stirred for 30 min. The crude product was extracted with EtOAc, washed with brine, dried over MgSO$_4$ and the solvent was removed in vacuo. The crude product was purified by column chromatography (Hexane:EtOAc 1:1→1:5) to yield 5-amino-1-cyclopropyl-6-fluoro-1,4-dihydro-8-methoxy-4-oxo-2-phenyl-7-[2-(2-pyridylamino)ethylamino]quinoline-3-carboxylic acid (356 mg, 50%) as a yellow solid.

$^1$H-NMR (400 MHz, DMSO-d$_6$) δ 0.27-0.58 (4H, m), 3.22-3.27 (1H, m), 3.47-3.50 (2H, m), 3.56 (3H, m), 3.59-3.66 (2H, m), 6.28-6.32 (1H, m), 6.44-6.49 (2H, m), 6.70 (1H, t, J=5.5 Hz), 7.03 (2H, brs), 7.33-7.37 (1H, m), 7.43-7.54 (5H, m), 7.95 (1H, dd, J=5.5, 1.8 Hz), 14.50 (1H, brs).

HRESIMS (+): 504.20407 (Calcd for C$_{27}$H$_{26}$FNSO$_4$, 504.20471).

Example 28

5-Amino-6-chloro-1-cyclopropyl-1,4-dihydro-8-methoxy-4-oxo-7-[2-(2-pyridylamino)ethylamino]quinoline-3-carboxylic acid Step 1: Ethyl 6-amino-1-cyclopropyl-7-fluoro-1,4-dihydro-8-methoxy-5-nitro-4-oxoquinoline-3-carboxylate

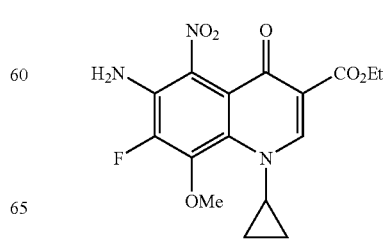

A mixture of ethyl 1-cyclopropyl-6,7-difluoro-1,4-dihydro-8-methoxy-5-nitro-4-oxoquinoline-3-carboxylate (5.00 g, 13.5 mmol) and ammonium carbonate (11.7 g, 122 mmol) in DMF (50 mL) was stirred at 90° C. for 18 h. After the reaction mixture was poured into ice-water, the crude product was extracted with $CH_2Cl_2$, washed with brine, dried over $MgSO_4$ and the solvent was removed in vacuo. The crude product washed with EtOH and dried to yield ethyl 6-amino-1-cyclopropyl-7-fluoro-1,4-dihydro-8-methoxy-5-nitro-4-oxoquinoline-3-carboxylate (2.55 g, 52%) as a yellow solid.

$^1$H-NMR (400 MHz, $CDCl_3$) δ 0.98-1.02 (2H, m), 1.16-1.21 (2H, m), 1.37 (3H, t, J=7.3 Hz), 3.95-4.00 (1H, m), 4.08 (3H, d, J=2.4 Hz), 4.36 (2H, q, J=7.3 Hz), 4.48 (2H, brs), 8.53 (1H, s).

Step 2: Ethyl 6-chloro-1-cyclopropyl-7-fluoro-1,4-dihydro-8-methoxy-5-nitro-4-oxoquinoline-3-carboxylate

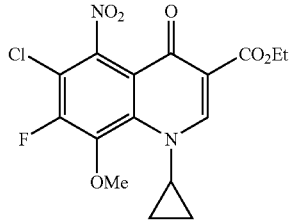

To a mixture of tert-butyl nitrite (0.244 mL, 2.06 mmol) and copper (II) chloride (388 mg, 2.74 mmol) in $CH_3CN$ (7 mL), ethyl 6-amino-1-cyclopropyl-7-fluoro-1,4-dihydro-8-methoxy-5-nitro-4-oxoquinoline-3-carboxylate (500 mg, 1.37 mmol) was added and the mixture was stirred at ice-cooling for 1 h and at room temperature for 4 h. After water was added to the reaction mixture, the crude product was extracted with $CH_2Cl_2$, washed successively with 2M HCl, saturated aq. $NaHCO_3$ and brine, dried over $MgSO_4$ and the solvent was removed in vacuo. The residue was dried to yield ethyl 6-chloro-1-cyclopropyl-7-fluoro-1,4-dihydro-8-methoxy-5-nitro-4-oxoquinoline-3-carboxylate (520 mg, 99%) as a pale yellow solid.

$^1$H-NMR (400 MHz, $CDCl_3$) δ1.01-1.07 (2H, m), 1.21-1.26 (2H, m), 1.37 (3H, t, J=7.3 Hz), 4.01-4.07 (1H, m), 4.13 (3H, d, J=2.4 Hz), 4.35 (2H, q, J=7.3 Hz), 8.60 (1H, s).

Step 3: Ethyl 5-amino-6-chloro-1-cyclopropyl-7-fluoro-1,4-dihydro-8-methoxy-4-oxoquinoline-3-carboxylate

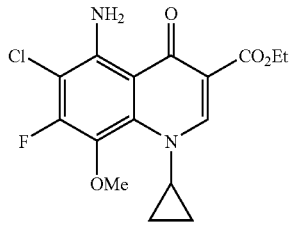

A mixture of ethyl 6-chloro-1-cyclopropyl-7-fluoro-1,4-dihydro-8-methoxy-5-nitro-4-oxoquinoline-3-carboxylate (240 mg, 0.624 mmol) and iron powder (209 mg, 3.74 mmol) in AcOH (10 mL) was stirred at 90° C. for 6 h. The catalyst was removed by filtration over Celite and the filtrate was concentrated in vacuo. After water was added, the crude product was extracted with EtOAc, washed successively with saturated aq. $NaHCO_3$ and brine, dried over $MgSO_4$ and the solvent was removed in vacuo. The crude product was purified by column chromatography (Chromatorex NH-DM2035 (Fuji Sylysia Chemical Co., Ltd.) Hexane:EtOAc 5:1→1:1) to yield ethyl 5-amino-6-chloro-1-cyclopropyl-7-fluoro-1,4-dihydro-8-methoxy-4-oxoquinoline-3-carboxylate (141 mg, 64%) as a colorless solid.

$^1$H-NMR (400 MHz, $CDCl_3$) δ0.92-0.96 (2H, m), 1.13-1.18 (2H, m), 1.39 (3H, t, J=7.3 Hz), 3.83 (3H, s), 3.90-3.96 (1H, m), 4.38 (2H, q, J=7.3 Hz), 8.46 (1H, s).

Step 4: 5-Amino-6-chloro-1-cyclopropyl-7-fluoro-1,4-dihydro-8-methoxy-4-oxoquinoline-3-carboxylic acid

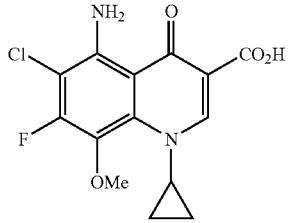

A mixture of ethyl 5-amino-6-chloro-1-cyclopropyl-7-fluoro-1,4-dihydro-8-methoxy-4-oxoquinoline-3-carboxylate (236 mg, 0.665 mmol) and 1M aq. NaOH (1.06 mL, 1.06 mmol) in EtOH (3 mL) was stirred at 50° C. for 1 h. To the reaction mixture, ice-water and 2M HCl was added to pH<3 and the resulting precipitate was collected by filtration in vacuo, washed with water and dried to yield 5-amino-6-chloro-1-cyclopropyl-7-fluoro-1,4-dihydro-8-methoxy-4-oxoquinoline-3-carboxylic acid (204 mg, 94%) as a pale yellow solid.

$^1$H-NMR (400 MHz, DMSO-$d_6$) δ0.99-1.03 (2H, m), 1.06-1.13 (2H, m), 3.80 (3H, s), 4.09-4.14 (1H, m), 8.62 (1H, s), 14.45 (1H, s).

Step 5: 5-Amino-6-chloro-1-cyclopropyl-1,4-dihydro-8-methoxy-4-oxo-7-[2-(2-pyridylamino)ethylamino]quinoline-3-carboxylic acid

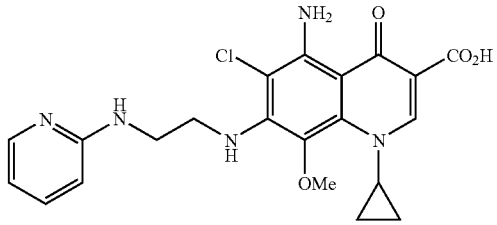

A solution of 5-amino-6-chloro-1-cyclopropyl-7-fluoro-1,4-dihydro-8-methoxy-4-oxoquinoline-3-carboxylic acid (180 mg, 0.551 mmol), N-2-pyridyl-1,2-ethanediamine (113 mg, 0.827 mmol) and triethylamine (0.115 mL, 0.827 mmol) in DMSO (5 mL) was stirred at 100° C. for 8 h. After the reaction mixture was poured into ice-water, AcOH was added to pH<3 and the resulting precipitate was collected by filtration in vacuo, washed successibly with water and hot EtOH, dried to yield 5-amino-6-chloro-1-cyclopropyl-1,4-dihydro-8-methoxy-4-oxo-7-[2-(2-pyridylamino)ethylamino]quinoline-3-carboxylic acid (179 mg, 73%) as a pale yellow solid.

$^1$H-NMR (400 MHz, DMSO-d$_6$) δ 0.80-0.91 (2H, m), 0.97-1.05 (2H, m), 3.45 (3H, s), 3.48-3.52 (2H, m), 3.65-3.69 (2H, m), 3.99-4.04 (1H, m), 6.15 (1H, t, J=5.5 Hz), 6.46-6.64 (2H, m), 7.38-7.52 (2H, m), 7.94 (1H, dd, J=5.5, 1.2 Hz), 8.51 (1H, s), 15.04 (1H, s).

HRESIMS (+): 444.14458 (Calcd for $C_{21}H_{22}ClN_5O_4$, 444.14386).

Example 29

5-Amino-1-cyclopropyl-6-fluoro-1,4-dihydro-4-oxo-7-[2-(2-pyridylamino)ethylamino]quinoline-3-carboxylic acid

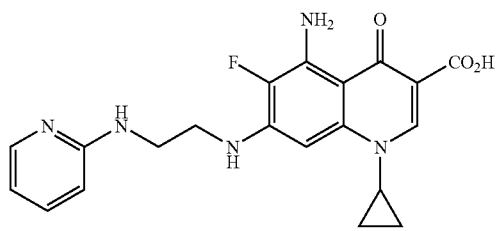

A solution of 5-amino-1-cyclopropyl-6,7-difluoro-4-oxo-1,4-dihydroquinoline-3-carboxylic acid (300 mg, 1.07 mmol), N-2-pyridyl-1,2-ethanediamine (221 mg, 1.61 mmol) and triethylamine (0.224 mL, 1.61 mmol) in DMSO (5 mL) was stirred at 100° C. for 3 h. After the reaction mixture was cooled to room temperature, 10% aq. NH$_4$Cl was added to neutralize and the suspension was stirred for 30 min. The resulting precipitate was collected by filtration in vacuo, washed with water and hot EtOH, dried to yield 5-amino-1-cyclopropyl-6-fluoro-1,4-dihydro-4-oxo-7-[2-(2-pyridylamino)ethylamino]quinoline-3-carboxylic acid (385 mg, 91%) as a colorless solid.

$^1$H-NMR (400 MHz, DMSO-d$_6$) δ 0.99-1.07 (2H, m), 1.16-1.21 (2H, m), 3.39-3.43 (3H, m), 3.48-3.53 (2H, m), 6.45-6.49 (3H, m), 6.79 (1H, t, J=5.5 Hz), 6.93-7.00 (1H, m), 7.11 (2H, brs), 7.36 (1H, td, J=6.7, 1.8 Hz), 7.93 (1H, d, J=4.3 Hz), 8.39 (1H, s), 15.46 (1H, s).

HRESIMS (+): 398.16310 (Calcd for $C_{20}H_{20}FN_5O_3$, 398.16284).

Example 30

5-Amino-1-cyclopropyl-6-fluoro-1,4-dihydro-8-isopropoxy-4-oxo-7-[2-(2-pyridylamino)ethylamino]quinoline-3-carboxylic acid Step 1: Ethyl 1-cyclopropyl-6,7-difluoro-1,4-dihydro-8-hydroxy-4-oxoquinoline-3-carboxylate

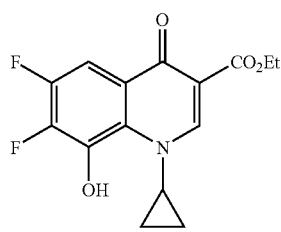

A solution of ethyl 8-(benzyloxy)-1-cyclopropyl-6,7-difluoro-1,4-dihydro-4-oxoquinoline-3-carboxylate (3.00 g, 7.51 mmol) in THF (60 mL)-EtOH (10 mL) was hydrogenated under atmospheric pressure over 10% Pd/C (300 mg) at room temperature for 2 h. The catalyst was removed by filtration over Celite and the filtrate was concentrated in vacuo. The crude product washed with Hexane and dried to yield ethyl 1-cyclopropyl-6,7-difluoro-1,4-dihydro-8-hydroxy-4-oxoquinoline-3-carboxylate (1.10 g, 47%) as a colorless solid.

$^1$H-NMR (400 MHz, DMSO-d$_6$) δ 1.02-1.11 (4H, m), 1.27 (3H, t, J=7.3 Hz), 4.14-4.24 (3H, m), 4.37 (1H, brs), 7.53 (1H, dd, J=10.4, 8.6 Hz), 8.48 (1H, s).

Step 2: Ethyl 1-cyclopropyl-6,7-difluoro-1,4-dihydro-8-isopropoxy-4-oxo-1,4-dihydroquinoline-3-carboxylate

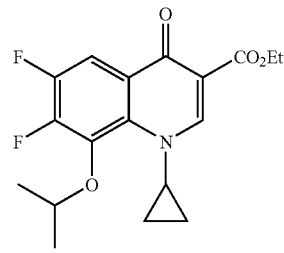

A solution of ethyl 1-cyclopropyl-6,7-difluoro-1,4-dihydro-8-hydroxy-4-oxoquinoline-3-carboxylate (1.10 g, 3.56 mmol), 2-Iodopropane (0.534 mL, 5.34 mmol) and K$_2$CO$_3$ (738 mg, 5.34 mmol) in DMF (10 mL) was stirred at room temperature for 1 h and at 70° C. for 3 h. After cooled to room temperature, the reaction mixture was poured into ice-water and the resulting precipitate was collected by filtration, washed with water and dried to yield ethyl 1-cyclopropyl-6,7-difluoro-1,4-dihydro-8-isopropoxy-4-oxoquinoline-3-carboxylate (611 mg, 49%) as a colorless solid.

$^1$H-NMR (400 MHz, DMSO-d$_6$) δ 0.94-0.98 (2H, m), 1.06-1.11 (2H, m), 1.25-1.30 (9H, m), 4.03-4.08 (1H, m), 4.22 (2H, q, J=7.3 Hz), 4.54-4.60 (1H, m), 7.82 (1H, dd, J=10.4, 8.6 Hz), 8.53 (1H, s).

Step 3: Ethyl 1-cyclopropyl-6,7-difluoro-1,4-dihydro-8-hydroxy-5-nitro-4-oxoquinoline-3-carboxylate

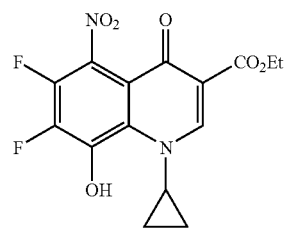

A solution of ethyl 1-cyclopropyl-6,7-difluoro-1,4-dihydro-8-isopropoxy-4-oxoquinoline-3-carboxylate (600 mg, 1.71 mmol) in concentrated H$_2$SO$_4$ (5 mL) was treated portionwise with solid KNO$_3$ (242 mg, 2.39 mmol) at 0° C. After stirred at 0° C. for 30 min and at room temperature for 1 h, the reaction mixture was poured into ice-water and the resulting precipitate was collected by filtration, washed with water and dried to yield ethyl 1-cyclopropyl-6,7-difluoro-1,4-dihydro-8-hydroxy-5-nitro-4-oxoquinoline-3-carboxylate (393 mg, 65%) as a pale brown solid.

$^1$H-NMR (400 MHz, DMSO-d$_6$) δ 1.02-1.10 (4H, m), 1.25 (3H, t, J=7.3 Hz), 4.16-4.25 (3H, m), 8.52 (1H, s).

Step 4: Ethyl 1-cyclopropyl-6,7-difluoro-1,4-dihydro-8-isopropoxy-5-nitro-4-oxoquinoline-3-carboxylate

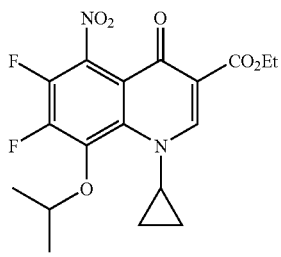

A solution of ethyl 1-cyclopropyl-6,7-difluoro-1,4-dihydro-8-hydroxy-5-nitro-4-oxoquinoline-3-carboxylate (393 mg, 1.11 mmol), 2-Iodopropane (0.167 mL, 1.67 mmol) and K$_2$CO$_3$ (231 mg, 1.67 mmol) in DMF (5 mL) was stirred at 80° C. for 5 h. After the reaction mixture was poured into ice-water, the crude product was extracted with CH$_2$Cl$_2$, washed with 1M HCl, saturated aq. NaHCO$_3$ and brine, dried over MgSO$_4$ and the solvent was removed in vacuo. The crude product washed with hot EtOH and dried to yield ethyl 1-cyclopropyl-6,7-difluoro-1,4-dihydro-8-isopropoxy-5-nitro-4-oxoquinoline-3-carboxylate (237 mg, 54%) as a pale yellow solid.

$^1$H-NMR (400 MHz, CDCl$_3$) δ 0.93-0.98 (2H, m), 1.17-1.22 (2H, m), 1.33-1.42 (9H, m), 3.99-4.04 (1H, m), 4.37 (2H, q, J=7.3 Hz), 4.70-4.76 (1H, m), 8.61 (1H, s).

Step 5: Ethyl 5-amino-1-cyclopropyl-6,7-difluoro-1,4-dihydro-8-isopropoxy-4-oxoquinoline-3-carboxylate

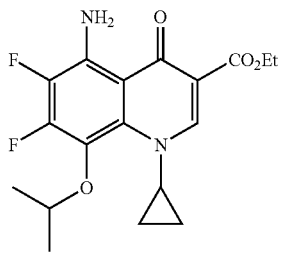

A suspension of ethyl 1-cyclopropyl-6,7-difluoro-1,4-dihydro-8-isopropoxy-5-nitro-4-oxoquinoline-3-carboxylate (222 mg, 0.560 mmol) and iron powder (188 mg, 3.36 mmol) in AcOH (6 mL) was stirred at 90° C. for 5 h. After water was added, the reaction mixture was stirred for 30 min. The crude product was extracted with EtOAc, washed with saturated aq. NaHCO$_3$ and brine, dried over MgSO$_4$ and the solvent was removed in vacuo. The crude product was purified by column chromatography (Hexane:EtOAc 5:1→1:1) to yield ethyl 5-amino-1-cyclopropyl-6,7-difluoro-1,4-dihydro-8-isopropoxy-4-oxoquinoline-3-carboxylate (141 mg, 69%) as a pale yellow solid.

$^1$H-NMR (400 MHz, CDCl$_3$) δ 0.83-0.87 (2H, m), 1.08-1.13 (2H, m), 1.25 (6H, d, J=6.1 Hz), 1.39 (3H, t, J=7.3 Hz), 3.89-3.95 (1H, m), 4.21-4.27 (1H, m), 4.38 (2H, q, J=7.3 Hz), 6.85 (2H, brs), 8.45 (1H, s).

Step 6: 5-Amino-1-cyclopropyl-6,7-difluoro-1,4-dihydro-8-isopropoxy-4-oxoquinoline-3-carboxylic acid

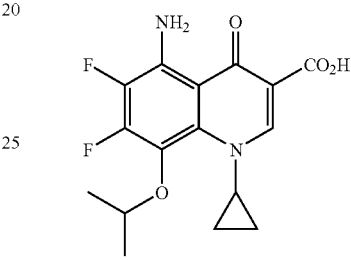

A solution of ethyl 5-amino-1-cyclopropyl-6,7-difluoro-1,4-dihydro-8-isopropoxy-4-oxoquinoline-3-carboxylate (125 mg, 0.341 mmol) and 1M aq. NaOH (0.5 mL) in EtOH (1.5 mL) was stirred at 50° C. for 1 h. After 2M HCl was added to the reaction mixture to pH<3, the crude product was extracted with EtOAc, washed with brine, dried over MgSO$_4$ and the solvent was removed in vacuo. The residue was dried in vacuo to yield 5-amino-1-cyclopropyl-6,7-difluoro-1,4-dihydro-8-isopropoxy-4-oxoquinoline-3-carboxylic acid (113 mg, 98%) as a yellow solid.

$^1$H-NMR (400 MHz, DMSO-d$_6$) δ 0.88-0.92 (2H, m), 1.03-1.08 (2H, m), 1.19 (6H, d, J=6.1 Hz), 4.07-4.12 (1H, m), 4.18-4.24 (1H, m), 7.59 (2H, brs), 8.61 (1H, s), 14.49 (1H, brs).

Step 7: 5-Amino-1-cyclopropyl-6-fluoro-1,4-dihydro-8-isopropoxy-4-oxo-7-[2-(2-pyridylamino)ethylamino]quinoline-3-carboxylic acid

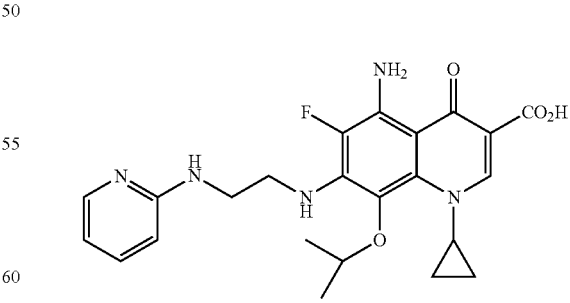

A solution of 5-amino-1-cyclopropyl-6,7-difluoro-1,4-dihydro-8-isopropoxy-4-oxoquinoline-3-carboxylic acid (100 mg, 0.296 mmol), N-2-pyridyl-1,2-ethanediamine (60.9 mg, 0.444 mmol) and triethylamine (0.0619 mL, 0.444 mmol) in DMSO (3 mL) was stirred at 100° C. for 8 h. After the reaction mixture was poured into ice-water, NH₄Cl was added and stirred for 30 min. The resulting precipitate was collected by filtration in vacuo and washed with water. The crude product was purified by preparative thin layer chromatography (Hexane:EtOAc 1:4) to yield 5-amino-1-cyclopropyl-6-fluoro-1,4-dihydro-8-isopropoxy-4-oxo-7-[2-(2-pyridylamino)ethylamino]quinoline-3-carboxylic acid (80.6 mg, 60%) as a pale yellow amorphous solid.

¹H-NMR (400 MHz, DMSO-d₆) δ 0.72-0.92 (2H, m), 0.96-1.11 (2H, m), 1.15 (6H, d, J=6.1 Hz), 3.54-3.58 (2H, m), 3.65-3.72 (2H, m), 4.02-4.12 (2H, m), 6.06-6.12 (1H, m), 6.53-6.56 (2H, m), 6.75 (1H, t, J=5.5 Hz), 7.17 (2H, brs), 7.43 (1H, td, J=7.9, 1.8 Hz), 8.02 (1H, dd, J=5.5, 1.8 Hz), 8.51 (1H, s), 15.20 (1H, brs).

HRESIMS (+): 456.20433 (Calcd for C₂₃H₂₆FN₅O₄, 456.20471).

Example 31

10-Amino-11-fluoro-2,3,4,5-tetrahydro-9-oxo-12-[2-(2-pyridylamino)ethylamino]-9H-pyrido[1,2,3-fg]-1,6-benzoxazocine-8-carboxylic acid Step 1: Ethyl 3-(4-hydroxybutylamino)-2-(2,3,4,5-tetrafluorobenzoyl)acrylate

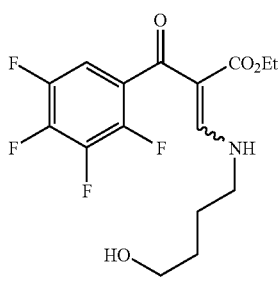

A mixture of ethyl 2,3,4,5-tetrafluorobenzoylacetate (2.64 g, 10.0 mmol), Ac₂O (2.36 mL, 25.0 mmol) and triethyl orthoformate (2.49 mL, 15.0 mmol) was stirred at 130° C. for 3 h. The mixture was concentrated in vacuo and dried under high vacuum. The crude product was dissolved in EtOH (50 mL) and 4-amino-1-butanol (0.972 mL, 10.5 mmol) was added. After stirred at room temperature for 17 h, the mixture was concentrated in vacuo and the crude product was purified by column chromatography (Hexane:EtOAc 2:1→1:2) to yield ethyl 3-(4-hydroxybutylamino)-2-(2,3,4,5-tetrafluorobenzoyl)acrylate (3.53 g, 97%) as a pale yellow solid.

¹H-NMR (400 MHz, CDCl₃) δ0.96 (3H×⅕, t, J=7.3 Hz), 1.10 (3H×⅘, t, J=7.3 Hz), 1.39-1.49 (1H, m), 1.65-1.71 (2H, m), 1.76-1.86 (2H, m), 3.49-3.55 (2H, m), 3.69-3.78 (2H, m), 4.02 (2H×⅕, q, J=7.3 Hz), 4.06 (2H×⅘, q, J=7.3 Hz), 6.94-7.01 (1H×⅘, m), 7.06-7.26 (1H×⅕, m), 8.10-8.15 (1H, m), 9.49-9.66 (1H×⅕, m), 10.87-11.07 (1H×⅘, m).

Step 2: Ethyl 11,12-difluoro-2,3,4,5-tetrahydro-9-oxo-9H-pyrido[1,2,3-fg]-1,6-benzoxazocine-8-carboxylate

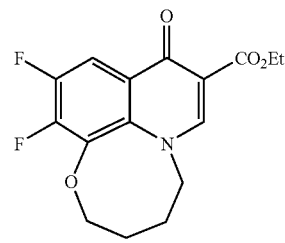

A mixture of ethyl 3-(4-hydroxybutylamino)-2-(2,3,4,5-tetrafluorobenzoyl)acrylate (3.00 g, 8.26 mmol) and K₂CO₃ (2.39 g, 17.3 mmol) in DMF (40 mL) was stirred at reflux for 3 h. After the reaction mixture was poured into 1 M HCl, EtOAc was added and the mixture was stirred for 30 min. The resulting precipitate was removed by filtration in vacuo, the organic layer washed with saturated aq. NaHCO₃ and brine, dried over MgSO₄ and the solvent was removed in vacuo. The crude product was purified by column chromatography (Hexane: EtOAc 1:1→EtOAc) to yield ethyl 11,12-difluoro-2,3,4,5-tetrahydro-9-oxo-9H-pyrido[1,2,3-fg]1,6-benzoxazocine-8-carboxylate (457 mg, 17%) as a pale yellow solid.

¹H-NMR (400 MHz, DMSO-d₆) δ 1.27 (3H, t, J=7.3 Hz), 1.51-1.68 (2H, m), 1.93-2.19 (2H, m), 4.06-4.19 (1H, m), 4.22 (2H, q, J=7.3 Hz), 4.26-4.40 (1H, m), 4.42-4.62 (1H, m), 5.04-5.23 (1H, m), 7.92 (1H, dd, J=10.4, 8.6 Hz), 8.57 (1H, s).

Step 3: Ethyl 11,12-difluoro-2,3,4,5-tetrahydro-10-nitro-9-oxo-9H-pyrido[1,2,3-fg]-1,6-benzoxazocine-8-carboxylate

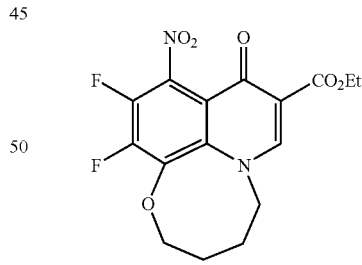

A solution of ethyl 11,12-difluoro-2,3,4,5-tetrahydro-9-oxo-9H-pyrido[1,2,3-fg]-1,6-benzoxazocine-8-carboxylate (450 mg, 1.39 mmol) in concentrated H₂SO₄ (7 mL) was treated portion wise at 0° C. with solid KNO₃ (197 mg, 1.95 mmol). After stirring at room temperature for 50 h, the reaction mixture was poured into ice-water and the resulting precipitate was collected by filtration, washed with water and dried to yield ethyl 11,12-difluoro-2,3,4,5-tetrahydro-10-nitro-9-oxo-9H-pyrido[1,2,3-fg]-1,6-benzoxazocine-8-carboxylate (327 mg, 64%) as a colorless solid.

$^1$H-NMR (400 MHz, DMSO-d$_6$) δ 1.26 (3H, t, J=7.3 Hz), 1.58-1.69 (2H, m), 1.93-2.20 (2H, m), 4.16-4.27 (3H, m), 4.31-4.45 (1H, m), 4.48-4.66 (1H, m), 5.00-5.27 (1H, m), 8.65 (1H, s).

Step 4: Ethyl 10-amino-11,12-difluoro-2,3,4,5-tetrahydro-9-oxo-9H-pyrido[1,2,3-fg]-1,6-benzoxazocine-8-carboxylate

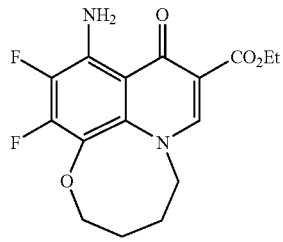

A suspension of ethyl 11,12-difluoro-2,3,4,5-tetrahydro-10-nitro-9-oxo-9H-pyrido[1,2,3-fg]-1,6-benzoxazocine-8-carboxylate (310 mg, 0.842 mmol) and iron powder (282 mg, 5.05 mmol) in AcOH (8 mL) was stirred at 90° C. for 3 h. After the reaction mixture was concentrated in vacuo, 1M HCl was added and the mixture was stirred for 30 min. The crude product was extracted with EtOAc, washed with saturated aq. NaHCO$_3$ and brine, dried over MgSO$_4$ and the solvent was removed in vacuo. The residue was dried to yield ethyl 10-amino-11,12-difluoro-2,3,4,5-tetrahydro-9-oxo-9H-pyrido[1,2,3-fg]-1,6-benzoxazocine-8-carboxylate (239 mg, 84%) as a yellow solid.

$^1$H-NMR (400 MHz, DMSO-d$_6$) δ 1.26 (3H, t, J=7.3 Hz), 1.52-1.62 (2H, m), 1.87-2.01 (1H, m), 2.02-2.16 (1H, m), 3.90-3.98 (1H, m), 4.12-4.24 (3H, m), 4.28-4.40 (1H, m), 5.07-5.19 (1H, m), 7.56-8.02 (2H, m), 8.36 (1H, s).

Step 5: 10-Amino-11,12-difluoro-2,3,4,5-tetrahydro-9-oxo-9H-pyrido[1,2,3-fg]-1,6-benzoxazocine-8-carboxylic acid

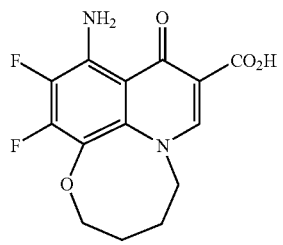

A mixture of ethyl 10-amino-11,12-difluoro-2,3,4,5-tetrahydro-9-oxo-9H-pyrido[1,2,3-fg]-1,6-benzoxazocine-8-carboxylate (220 mg, 0650 mmol) and 1M aq. NaOH (2 mL) in EtOH (4 mL) was stirred at 50° C. for 3 h. After the reaction mixture was concentrated in vacuo, the residue was dissolved in water and 2M HCl was added to pH<3. The resulting precipitate was collected by filtration in vacuo, washed with water and dried to yield 10-amino-11,12-difluoro-2,3,4,5-tetrahydro-9-oxo-9H-pyrido[1,2,3-fg]-1,6-benzoxazocine-8-carboxylic acid (189 mg, 94%) as a pale yellow solid.

$^1$H-NMR (400 MHz, DMSO-d$_6$) δ 1.52-1.64 (2H, m), 1.92-2.04 (1H, m), 2.06-2.19 (1H, m), 3.91-4.03 (1H, m), 4.32-4.47 (2H, m), 5.18-5.30 (1H, m), 7.70 (2H, brs), 8.74 (1H, s), 14.72 (1H, brs).

Step 6: 10-Amino-11-fluoro-2,3,4,5-tetrahydro-9-oxo-12-[2-(2-pyridylamino)ethylamino]-9H-pyrido[1,2,3-fg]-1,6-benzoxazocine-8-carboxylic acid

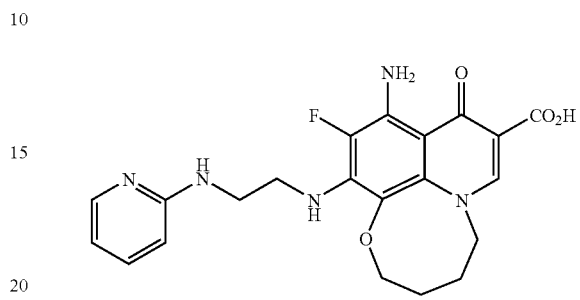

A solution of 10-amino-11,12-difluoro-2,3,4,5-tetrahydro-9-oxo-9H-pyrido[1,2,3-fg]-1,6-benzoxazocine-8-carboxylic acid (170 mg, 0.548 mmol), N-2-pyridyl-1,2-ethanediamine (113 mg, 0.822 mmol) and triethylamine (0.115 mL, 0.822 mmol) in DMSO (5 mL) was stirred at 100° C. for 8 h. The reaction mixture was poured into saturated aq. NH$_4$Cl and stirred for 30 min. The resulting precipitate was collected by filtration, washed with water, and dissolved in CH$_2$Cl$_2$-EtOH (3:1). After the unsolble precipitate was removed by filtration, the filtrate was concentrated in vacuo and the resulting precipitate was collected by filtration, washed with EtOH and dried to yield 10-amino-11-fluoro-2,3,4,5-tetrahydro-9-oxo-12-[2-(2-pyridylamino)ethylamino]-9H-pyrido[1,2,3-fg]-1,6-benzoxazocine-8-carboxylic acid (179 mg, 76%) as a pale yellow solid.

$^1$H-NMR (400 MHz, DMSO-d$_6$) δ 1.41-1.55 (2H, m), 1.92-2.03 (1H, m), 2.03-2.16 (1H, m), 3.44-3.48 (2H, m), 3.55-3.65 (2H, m), 3.71-3.79 (1H, m), 4.08-4.15 (1H, m), 4.23 (1H, dd, J=14.1, 6.7 Hz), 5.16 (1H, td, J=12.8, 3.7 Hz), 6.25-6.32 (1H, m), 6.44-6.48 (2H, m), 6.69 (1H, t, J=5.5 Hz), 7.21 (2H, brs), 7.35 (1H, td, J=6.7, 1.8 Hz), 7.95 (1H, dd, J=4.9, 1.2 Hz), 8.48 (1H, s), 15.33 (1H, brs).

HRESIMS (+): 428.17779 (Calcd for C$_{21}$H$_{22}$FN$_5$O$_4$, 428.17341).

Example 32

5-Amino-6-fluoro-1,4-dihydro-4-oxo-1-(2-phenylethyl)-7-[2-(2-pyridylamino)ethylamino]3-quinolinecarboxylic Acid Step 1: Ethyl 5,6,7-trifluoro-4-hydroxy-3-quinolinecarboxylate

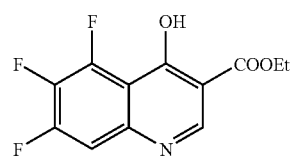

A mixture of 3,4,5-trifluoroaniline (5.00 g, 34.0 mmol) and diethyl ethoxymethylenemalnate (5.00 mL, 34.0 mmol) was stirred at 120° C. for 1 h. After cooling, diisopropyl ether was added to the reaction mixture and the resulting precipitates were collected by filtration to give diethyl [[(3,4,5-trifluorophenyl)amino]methylene]malonate (8.02 g, 74%) as a white powder. A mixture of diethyl [[(3,4,5-trifluorophenyl)amino]methylene]malonate (7.83 g, 23.1 mmol) and diphenyl ether (20 mL) was stirred at 250° C. for 1 h. After cooling, the resulting precipitates were collected by filtration. The filtered precipitates were suspended in hexane, and then filtered to give ethyl 5,6,7-trifluoro-4-hydroxy-3-quinolinecarboxylate (6.27 g, 94%) as a pale yellow powder.

$^1$H NMR (400 MHz, DMSO-$d_6$) δ 1.26 (3H, t, J=7.3 Hz,), 4.20 (2H, q, J=7.3 Hz), 7.42-7.46 (1H, m), 8.52 (1H, s), 12.4 (1H, brs).

Step 2: Ethyl 5,6,7-trifluoro-1,4-dihydro-4-oxo-1-(2-phenylethyl)-3-quinolinecarboxylate

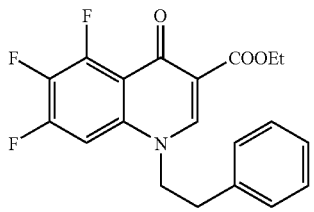

A mixture of ethyl 5,6,7-trifluoro-4-hydroxy-3-quinolinecarboxylate (2.00 g, 7.37 mmol), $K_2CO_3$ (3.06 g, 22.1 mmo) and 2-phenylethyl bromide (1.50 mL, 11.1 mmol) in DMF (16 mL) was stirred at 90° C. for 27 h and concentrated in vacuo. After dilution of the residue with CHCl$_3$, the mixture washed with water, dried over anhydrous Na$_2$SO$_4$, filtered, and concentrated in vacuo. Flash chromatography of the residue (EtOAc: MeOH 10:1) gave ethyl 5,6,7-trifluoro-1,4-dihydro-4-oxo-1-(2-phenylethyl)-3-quinolinecarboxylate (913 mg, 33%) as a pale yellow powder.

$^1$H NMR (400 MHz, CDCl$_3$) δ 1.35 (3H, t, J=7.3 Hz), 3.13 (2H, t, J=7.3 Hz), 4.28-4.35 (4H, m), 7.02 (1H, ddd, J=11.6, 6.1, 2.4 Hz), 7.06-7.08 (2H, m), 7.27-7.34 (3H, m), 8.02 (1H, s).

Step 3: Ethyl 5-benzylamino-6,7-difluoro-1,4-dihydro-4-oxo-1-(2-phenylethyl)-3-quinolinecarboxylate

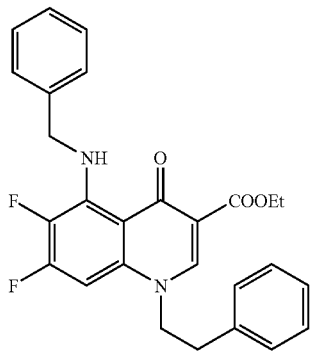

A suspension of ethyl 5,6,7-trifluoro-1,4-dihydro-4-oxo-1-(2-phenylethyl)-3-quinolinecarboxylate (891 mg, 2.37 mmol), benzylamine (285 μL, 2.61 mmol), and triethylamine (991 μL, 7.11 mmol) in toluene (16 mL) was heated at 100° C. for 1.5 h, heated under reflux for 1 h and concentrated in vacuo. After dilution of the residue with CHCl$_3$, the mixture washed with water, dried over anhydrous Na$_2$SO$_4$, filtered, and then concentrated in vacuo. Recrystallization of the residue from EtOH gave ethyl 5-benzylamino-6,7-drifluoro-1,4-dihydro-4-oxo-1-(2-phenylethyl)-3-quinolinecarboxylate (941 mg, 86%) as a pale yellow powder.

$^1$H NMR (400 MHz, CDCl$_3$) δ 1.31 (3H, t, J=7.3 Hz), 3.11 (2H, t, J=7.3 Hz), 4.20 (2H, t, J=7.3 Hz), 4.29 (2H, q, J=7.3 Hz), 6.30 (1H, dd, J=12.2, 6.1 Hz), 7.07-7.10 (2H, m), 7.22-7.39 (10H, m), 7.88 (1H, s), 11.2 (1H, brs).

Step 4: Ethyl 5-amino-6,7-difluoro-1,4-dihydro-4-oxo-1-(2-phenylethyl)-3-quinolinecarboxylate

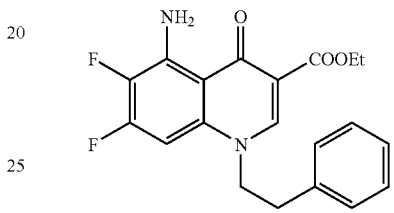

To a suspension of ethyl 5-benzylamino-6,7-difluoro-1,4-dihydro-4-oxo-1-(2-phenylethyl)-3-quinolinecarboxylate (700 mg, 1.51 mmol) in a mixture of EtOH (2 mL) and AcOH (2 mL), was added 10% Pd—C (70.0 mg), the whole mixture was stirred at room temperature for 4 h under H$_2$ atmosphere (1 atm). After insoluble materials were filtered off, the filtrate was concentrated in vacuo. To a solution of the residue in AcOH (2 mL), a suspension of 10% Pd—C (70 mg) in AcOH (2 mL) was added, the whole mixture was stirred at room temperature for 4 h under H$_2$ atmosphere (1 atm). After insoluble materials were filtered off and washed with DMF, the combined filtrate and washing was concentrated in vacuo. Trituration of the residue with EtOH gave ethyl 5-amino-6,7-difluoro-1,4-dihydro-4-oxo-1-(2-phenylethyl)-3-quinolinecarboxylate (499 mg, 89%) as pale brown powder.

$^1$H NMR (400 MHz, CDCl$_3$) δ 1.33 (3H, t, J=7.3 Hz), 3.12 (3H, t, J=7.3 Hz), 4.22 (2H, t, J=7.3 Hz), 4.31 (2H, q, J=7.3 Hz), 6.35 (1H, dd, J=12.2, 6.1 Hz), 7.08-7.10 (2H, m), 7.26-7.34 (3H, m), 7.93 (1H, s).

Step 5: 5-Amino-6,7-difluoro-1,4-dihydro-4-oxo-1-(2-phenylethyl)-3-quinolinecarboxylic acid

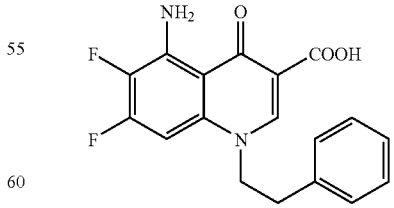

To a suspension of 5-amino-6,7-difluoro-1,4-dihydro-4-oxo-1-(2-phenylethyl)-3-quinolinecarboxylate (458 mg, 1.21 mmol) in a mixture of AcOH (1.8 mL) and water (1.5 mL), was added H$_2$SO$_4$ (0.3 mL), the whole mixture was heated under reflux for 1 h. The reaction mixture was poured into ice-water and the resulting precipitates were collected by filtration. The filtered precipitates were suspended in water, filtered, and dried in vacuo to give 5-amino-6,7-difluoro-1,4-dihydro-4-oxo-1-(2-phenylethyl)-3-quinolinecarboxylic acid (401 mg, 95%) as a pale yellow powder.

$^1$H NMR (400 MHz, DMSO-$d_6$) δ 3.05 (2H, t, J=7.3 Hz), 4.63 (2H, t, J=7.3 Hz), 7.10-7.21 (4H, m), 7.24-7.27 (2H, m), 7.87 (2H, br), 8.52 (1H, s), 14.6 (1H, s).

Step 6: 5-Amino-6-fluoro-1,4-dihydro-4-oxo-1-(2-phenylethyl)-7-[2-(2-pyridylamino)ethylamino]-3-quinolinecarboxylic acid

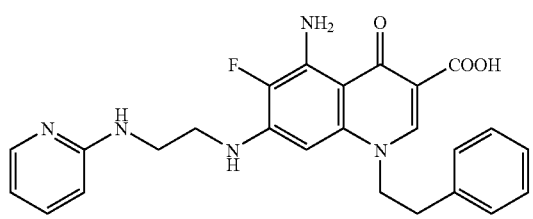

A suspension of 5-amino-6,7-difluoro-1,4-dihydro-4-oxo-1-(2-phenylethyl)-3-quinolinecarboxylic acid (101 mg, 0.292 mmol), 2-(2-pyridylamino)ethylamine (60.2 mg, 0.436 mmol), and triethylamine (60.7 μL, 0.435 mmol) in DMSO (1.5 mL) was stirred at 100° C. for 3 h. The reaction mixture was poured into ice-water and the resulting precipitates were collected by filtration. Recrystallization of the filtered precipitates from $CH_2Cl_2$-EtOH gave 5-amino-6-fluoro-1,4-dihydro-4-oxo-1-(2-phenylethyl)-7-[2-(2-pyridylamino)ethylamino]-3-quinolinecarboxylic acid (103 mg, 76%) as a pale brown powder.

$^1$H NMR (400 MHz, DMSO-$d_6$) δ 3.04 (2H, t, J=7.3 Hz), 3.44-3.54 (4H, m), 4.53 (2H, t, J=7.3 Hz), 6.19 (1H, d, J=6.7 Hz), 6.43-6.48 (2H, m), 6.78 (1H, t, J=6.1 Hz), 6.94 (1H, br), 7.11-7.24 (7H, m), 7.33-7.37 (1H, m), 7.91 (1H, dd, J=5.5, 1.2 Hz), 8.34 (1H, s), 15.4 (1H, s).

HREIMS (+): 464.19140 (calcd for $C_{25}H_{25}FN_5O_3$, 462.14414).

Example 33

(3S)-8-Amino-9-fluoro-2,3-dihydro-7-oxo-3-phenylmethyl-10-[2-(2-pyridylamino)ethylamino]-7H-pyrido[1,2,3-de]-1,4-benzoxazine-6-carboxylic Acid Step 1: Ethyl 3-[(2S)-1-hydroxy-3-phenylprop-2-ylamino]-2-(2,3,4,5,6-pentafluorobenzoyl)acrylate

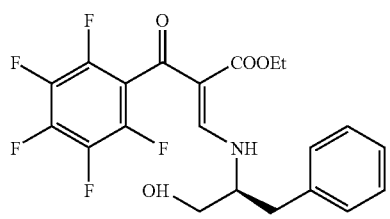

A mixture of ethyl (2,3,4,5,6-pentafluorobenzoyl)acetate (2.01 g, 7.09 mmol), triethyl orthoformate (2.40 mL, 14.4 mmol), and acetic anhydride (2.0 mL) was heated under reflux for 4.5 h and concentrated in vacuo. To a solution of the residue in toluene (10 mL), was added a solution of L-phenylalaninol (1.18 g, 7.80 mmol) in toluene (10 mL) dropwise under cooling with ice, the whole mixture was allowed to stand for 2 days and concentrated in vacuo. Flash chromatography of the residue (henxane:EtOAc 1:1) gave ethyl 3-[(2S)-1-hydroxy-3-phenylprop-2-ylamino]-2-(2,3,4,5,6-pentafluorobenzoyl)acrylate (2.13 g, 67%) as a yellow oil.

$^1$H NMR (400 MHz, CDCl$_3$) δ 1.08 (3H, t, J=7.0 Hz), 1.80 (1H, t, J=4.9 Hz), 2.92-3.08 (2H, m), 3.68-4.04 (5H, m), 7.18-7.20 (2H, m), 7.29-7.36 (3H, m), 7.96 (1H, d, J=14.1 Hz), 11.1 (1H, br).

$[α]_D^{25}$ −195° (c 0.708, CHCl$_3$).

Step 2: Ethyl (3S)-8,9,10-Trifluoro-2,3-dihydro-7-oxo-3-phenylmethyl-7H-pyrido[1,2,3-de]-1,4-benzoxazine-6-carboxylate

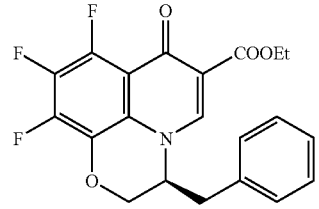

To a suspension of NaH (60% dispersion in mineral oil, 397 mg, 9.92 mmol) in DMF (20 mL), was added solution of ethyl 3-[(2S)-1-hydroxy-3-phenylprop-2-ylamino]-2-(2,3,4,5,6-pentafluorobenzoyl)acrylate (2.00 g, 4.51 mmol) in DMF (5 mL), the whole mixture was stirred at 90° C. for 3 h and concentrated in vacuo. After addition of water to the residue, the resulting precipitetes were collected by filtration. The filtered precipitetes were suspended in water, filtered, and dried in vacuo. Trituration of the precipitates with $CH_2Cl_2$-EtOH gave ethyl (3S)-8,9,10-trifluoro-2,3-dihydro-7-oxo-3-phenylmethyl-7H-pyrido[1,2,3-de]-1,4-enzoxazine-6-carboxylate (468 mg, 26%) as a pale yellow powder.

$^1$H NMR (400 MHz, CDCl$_3$) δ 1.33 (3H, t, J=7.3 Hz), 3.04-3.17 (2H, m), 4.25-4.33 (4H, m), 4.58 (1H, d, J=10.4 Hz), 7.09-7.11 (2H, m), 7.28-7.37 (3H, m), 7.79 (1H, s).

$[α]_D^{26}$ −181° (c 0.704, CHCl$_3$).

Step 3: Ethyl (3S)-8-Benzylamino-9,10-difluoro-2,3-dihydro-7-oxo-3-phenylmethyl-7H-pyrido[1,2,3-de]-1,4-benzoxazine-6-carboxylate

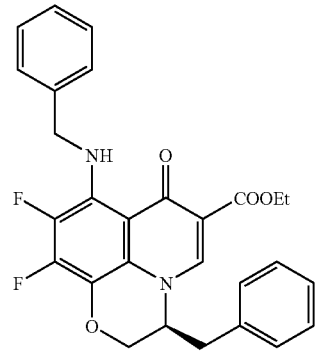

A mixture of ethyl (3S)-8,9,10-trifluoro-2,3-dihydro-7-oxo-3-phenylmethyl-7H-pyrido[1,2,3-de]-1,4-benzoxazine-6-carboxylate (400 mg, 0.992 mmol), benzylamine (119 μL, 1.09 mmol), and triethylamine (415 μL, 2.98 mmol) in toluene (8 mL) was heated under reflux for 48 h and concentrated in vacuo. Flash chromatography of the residue (EtOAc) gave ethyl (3S)-8-benzylamino-9,10-drifluoro-2,3-dihydro-7-oxo-3-phenylmethyl-7H-pyrido[1,2,3-de]-1,4-benzoxazine-6-carboxylate (305 mg, 63%) as a yellow amorphous product.

$^1$H NMR (400 MHz, CDCl$_3$) δ 1.30 (3H, t, J=7.3 Hz), 3.02-3.14 (2H, m), 4.10-4.32 (4H, m), 4.44 (1H, d, J=12.2 Hz), 4.65 (2H, dd, J=6.7, 3.7 Hz), 7.09-7.11 (2H, m), 7.21-7.39 (8H, m), 7.67 (1H, s), 10.3 (1H, br).

[α]$_D^{26}$ −160° (c 0.753, CHCl$_3$).

Step 4: Ethyl (3S)-8-Amino-9,10-difluoro-2,3-dihydro-7-oxo-3-phenylmethyl-7H-pyrido[1,2,3-de]-1,4-benzoxazine-6-carboxylate

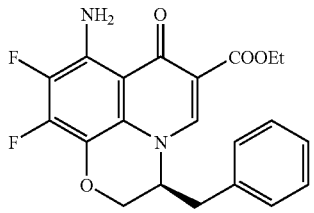

To a suspension of ethyl (3S)-8-benzylamino-9,10-drifluoro-2,3-dihydro-7-oxo-3-phenylmethyl-7H-pyrido[1,2,3-de]-1,4-benzoxazine-6-carboxylate (253 mg, 0.515 mmol) in a mixture of EtOH (2 mL) and AcOH (2 mL), was added 10% Pd—C (25.0 mg), the whole mixture was stirred at room temperature for 4 h under H$_2$ atmosphere (1 atm). After insoluble materials were filtered off, the filtrate was concentrated in vacuo. To a solution of the residue in a mixture of EtOH (1 mL) and AcOH (1 mL), a suspension of 10% Pd—C (28.0 mg) in a mixture of EtOH (1 mL) and AcOH (1 mL) was added, the whole mixture was stirred at room temperature for 4 h under H$_2$ atmosphere (1 atm). After insoluble materials were filtered off and washed with DMF, the combined filtrate and washing was concentrated in vacuo. Trituration of the residue with EtOH gave ethyl (3S)-8-Amino-9,10-difluoro-7-oxo-3-phenylmethyl-7H-pyrido[1,2,3-de]-1,4-benzoxazine-6-carboxylate (124 mg, 60%) as pale brown powder.

$^1$H NMR (400 MHz, CDCl$_3$) δ 1.32 (3H, t, J=7.3 Hz), 3.04-3.16 (2H, m), 4.13-4.49 (5H, m), 6.65 (2H, br), 7.10-7.12 (2H, m), 7.29-7.36 (3H, m), 7.71 (1H, s).

[α]$_D^{26}$ −224° (c 0.701, CHCl$_3$).

Step 5: (3S)-8-Amino-9,10-difluoro-2,3-dihydro-7-oxo-3-phenylmethyl-7H-pyrido[1,2,3-de]-1,4-benzoxazine-6-carboxylic Acid

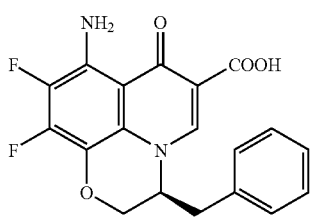

To a suspension of ethyl (3S)-8-amino-9,10-difluoro-2,3-dihydro-7-oxo-3-phenylmethyl-7H-pyrido[1,2,3-de]-1,4-benzoxazine-6-carboxylate (100 mg, 0.250 mmol) in a mixture of AcOH (0.6 mL) and water (0.5 mL), was added H$_2$SO$_4$ (0.1 mL), the whole mixture was heated under reflux for 3 h. The reaction mixture was poured into ice-water and the resulting precipitates were collected by filtration. The filtered precipitates were suspended in water, filtered, and dried in vacuo to give (3S)-8-amino-9,10-difluoro-2,3-dihydro-7-oxo-3-phenylmethyl-7H-pyrido[1,2,3-de]-1,4-benzoxazine-6-carboxylic acid (88.0 mg, 95%) as a yellow powder.

$^1$H NMR (400 MHz, DMSO-d$_6$) δ 2.99 (1H, dd, J=13.4, 8.6 Hz), 3.10 (2H, dd, J=13.4, 7.3 Hz), 4.22 (1H, dd, J=11.6, 2.4 Hz), 4.46 (1H, d, J=11.0 Hz), 4.98 (1H, t, J=7.9 Hz), 7.15-7.31 (5H, m), 8.33 (1H, s), 14.6 (1H, s).

[α]$_D^{26}$ −204° (c 0.310, CHCl$_3$).

Step 6: (3S)-8-Amino-9-fluoro-2,3-dihydro-7-oxo-3-phenylmethyl-10-[2-(2-pyridylamino)ethylamino]-7H-pyrido[1,2,3-de]-1,4-benzoxazine-6-carboxylic Acid

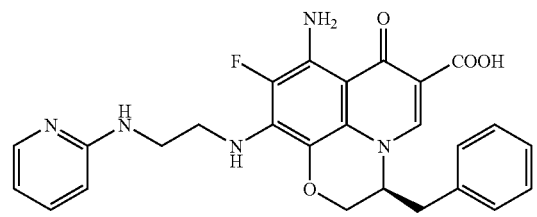

A mixture of (3S)-8-Amino-9,10-difluoro-2,3-dihydro-7-oxo-3-phenylmethyl-7H-pyrido[1,2,3-de]-1,4-benzoxazine-6-carboxylic acid (76.9 mg, 0.207 mmol), 2-(2-pyridylamino)ethylamine (41.8 mg, 0.303 mmol), and triethylamine (42.1 μL, 0.302 mmol) in DMSO (1.5 mL) was stirred at 100° C. for 3 h. The reaction mixture was poured into ice-water and the resulting precipitates were collected by filtration. Recrystallization of the filtered precipitates from CH$_2$Cl$_2$-EtOH gave (3S)-8-amino-9-fluoro-2,3-dihydro-7-oxo-3-phenylmethyl-10-[2-(2-pyridylamino)ethylamino]-7H-pyrido[1,2,3-de]-1,4-benzoxazine-6-carboxylic acid (55.4 mg, 55%) as a yellow powder.

$^1$H NMR (400 MHz, CDCl$_3$) δ 2.98-3.09 (2H, m), 3.71 (2H, br), 3.82 (2H, br), 3.97 (1H, d, J=11.0 Hz), 4.20 (1H, t, J=7.9 Hz), 4.33 (1H, d, J=11.0 Hz), 4.71 (1H, br), 5.75 (1H, br), 6.25 (2H, br), 6.44 (1H, d, J=7.9 Hz), 6.60 (1H, dd, J=6.7, 5.5 Hz), 7.11 (2H, d, J=6.7 Hz), 7.31-7.43 (4H, m), 8.07 (1H, s), 8.69 (1H, dd, J=5.5, 1.5 Hz), 15.1 (1H, s).

HRESIMS (+): 490.19342 (calcd for C$_{26}$H$_{25}$FN$_5$O$_4$, 490.18906).

[α]$_D^{27}$ −204° (c 0.313, CHCl$_3$).

Example 34

(3R)-8-Amino-9-fluoro-3-fluoromethyl-2,3-dihydro-7-oxo-10-[2-(2-pyridylamino)ethylamino]-7H-pyrido[1,2,3-de]-1,4-benzoxazine-6-carboxylic Acid Step 1: Ethyl (3R)-9,10-Difluoro-3-fluoromethyl-2,3-dihydro-8-nitro-7-oxo-7H-pyrido[1,2,3-de]-1,4-benzoxazine-6-carboxylate

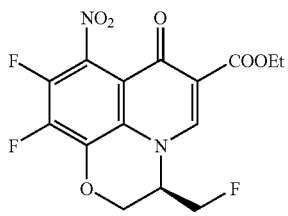

To a solution of ethyl (3R)-9,10-difluoro-3-fluoromethyl-2,3-dihydro-7-oxo-7H-pyrido[1,2,3-de]-1,4-benzoxazine-6-carboxylate (500 mg, 1.53 mmol) in $H_2SO_4$ (5.0 mL), was added $KNO_3$ (216 mg, 2.14 mmol) under cooling with ice, the whole mixture was stirred under cooling with ice for 2 h. The reaction mixture was poured into ice-water and the resulting precipitates were collected by filtration. The filtered precipitates were washed with water, and dried in vacuo to give ethyl (3R)-9,10-difluoro-3-fluoromethyl-2,3-dihydro-8-nitro-7-oxo-7H-pyrido[1,2,3-de]-1,4-benzoxazine-6-carboxylate (453 mg, 80%) as a pale brown powder.

$^1$H NMR (400 MHz, DMSO-$d_6$) δ 1.27 (3H, t, J=7.3 Hz), 4.18-4.29 (2H, m), 4.53-4.58 (1H, m), 4.67-4.96 (3H, m), 5.15-5.23 (1H, m), 8.73 (1H, s).

Step 2: Ethyl (3R)-8-amino-9,10-difluoro-3-fluoromethyl-2,3-dihydro-7-oxo-7H-pyrido[1,2,3-de]-1,4-benzoxazine-6-carboxylate

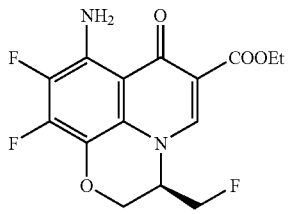

To a solution of ethyl (3R)-9,10-difluoro-3-fluoromethyl-8-nitro-7-oxo-7H-pyrido[1,2,3-de]-1,4-benzoxazine-6-carboxylate (357 mg, 0.959 mmol) in DMF (10 mL), was added 10% Pd—C (44.5 mg), the whole mixture was stirred at room temperature for 10 h under $H_2$ atmosphere (1 atm). After insoluble materials were filtered off, the filtrate was concentrated in vacuo. Trituration of the residue with EtOH (5 mL) at 50° C. gave ethyl (3R)-8-amino-9,10-difluoro-3-fluoromethyl-2,3-dihydro-7-oxo-7H-pyrido[1,2,3-de]-1,4-benzoxazine-6-carboxylate (286 mg, 87%) as a brown powder.

$^1$H NMR (400 MHz, DMSO-$d_6$) δ 1.26 (3H, t, J=7.3 Hz), 4.14-4.26 (3H, m), 4.54-4.98 (4H, m), 7.38 (2H, br), 8.43 (1H, s).

Step 3: (3R)-8-Amino-9,10-difluoro-3-fluoromethyl-2,3-dihydro-7-oxo-7H-pyrido[1,2,3-de]-1,4-benzoxazine-6-carboxylic Acid

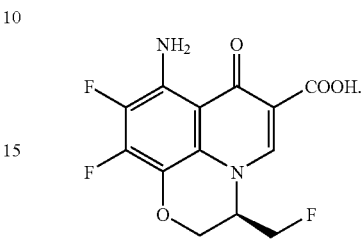

A suspension of ethyl (3R)-8-amino-9,10-difluoro-3-fluoromethyl-2,3-dihydro-7-oxo-7H-pyrido[1,2,3-de]-1,4-benzoxazine-6-carboxylate (270 mg, 0.789 mmol) in a mixture of $H_2SO_4$—$H_2O$—AcOH (1:5:6, 3 mL) was heated under reflux for 1 h. The reaction mixture was poured into ice-water and the resulting precipitates were collected by filtration. The filtered precipitates were washed with water, and dried in vacuo to give (3R)-8-amino-9,10-difluoro-3-fluoromethyl-2,3-dihydro-7-oxo-7H-pyrido[1,2,3-de]-1,4-benzoxazine-6-carboxylic acid (237 mg, 96%) as a yellow powder.

$^1$H NMR (400 MHz, DMSO-$d_6$) δ 4.27-4.32 (1H, m), 4.58-5.19 (4H, m), 7.31 (2H, br), 8.80 (1H, s), 14.6 (1H, s).

Step 4: (3R)-8-Amino-9-fluoro-3-fluoromethyl-2,3-dihydro-7-oxo-10-[2-(2-pyridylamino)ethylamino]-7H-pyrido[1,2,3-de]-1,4-benzoxazine-6-carboxylic Acid

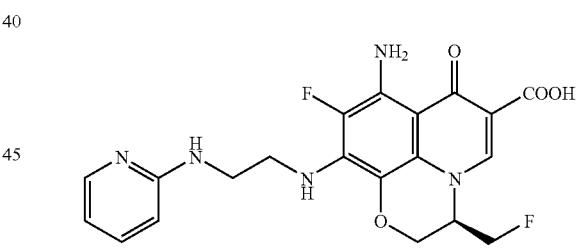

A mixture of (3R)-8-amino-9,10-difluoro-3-fluoromethyl-2,3-dihydro-7-oxo-7H-pyrido[1,2,3-de]-1,4-benzoxazine-6-carboxylic acid (200 mg, 0.636 mmol), 2-(2-pyridylamino)ethylamine (131 mg, 0.955 mmol), and triethylamine (0.13 mL, 0.933 mmol) in DMSO (2.0 mL) was stirred at 120° C. for 2.5 h. After dilution of the reaction mixture with 10% MeOH in $CHCl_3$, the whole mixture washed with water and the washing was extracted with 10% MeOH in $CHCl_3$ three times. The combined the organic layer and the extracts washed with water, dried over anhydrous $Na_2SO_4$, filtered, and concentrated in vacuo. Flash chromatography of the residue (10% MeOH in $CHCl_3$) gave (3R)-8-amino-9-fluoro-3-fluoromethyl-2,3-dihydro-7-oxo-10-[2-(2-pyridylamino)ethylamino]-7H-pyrido[1,2,3-de]-1,4-benzoxazine-6-carboxylic acid (184 mg, 67%) as a yellow powder.

$^1$H NMR (400 MHz, DMSO-$d_6$) δ 3.42-3.46 (2H, m), 3.57-3.64 (2H, m), 4.09-4.14 (1H, m), 4.50-5.03 (4H, m), 6.36 (1H, br), 6.44-6.48 (2H, m), 6.70 (1H, t, J=5.5 Hz), 6.88 (2H, br), 7.33-7.37 (1H, m), 7.94-7.95 (1H, m), 8.54 (1H, s), 15.2 (1H, s).
[α]$_D^{27}$ −86.3° (c 0.501, DMSO).

Example 35

5-Amino-6-fluoro-1,4-dihydro-4-oxo-1-(tetrahydropyran-4-yl)-7-[2-(2-pyridylamino)ethylamino]-3-quinolinecarboxylic Acid Step 1: 4-(3,4,5-Trifluorophenyl)aminotetrahydropyran

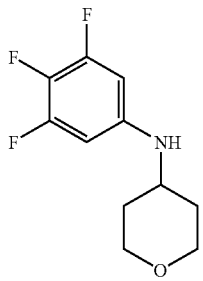

To a mixture of 3,4,5-trifluoroaniline (3.70 g, 25.1 mmol), tetrahydro-4H-pyran-4-one (2.52 g, 25.1 mmol), and benzoic acid (3.07 g, 25.1 mmol), was added sodium NaBH$_4$ (0.95 g, 25.1 mmol), the whole mixture was stirred at room temperature for 1.5 h. After quenching with the reaction mixture with 1 M aq. NaOH under cooling with ice, the whole mixture was extracted with Et$_2$O. The extract was washed with brine, dried over anhydrous Na$_2$SO$_4$, filtered, and concentrated in vacuo. Flash chromatography of the residue (hexane:EtOAc=3:2) gave 4-(3,4,5-trifluorophenyl)aminotetrahydropyran (2.40 g, 41%) as a white powder.
$^1$H NMR (400 MHz, CDCl$_3$) δ 1.41-1.51 (2H, m), 1.98-2.02 (2H, m), 3.32-3.39 (1H, m), 3.50 (2H, dt, J=11.6, 2.4 Hz), 3.57 (1H, br), 4.00 (2H, dt, J=11.6, 3.1 Hz), 6.11-6.19 (2H, m).

Step 2: Diethyl [[N-(3,4,5-trifluorophenyl)-N-(tetrahydropyran-4-yl)amino]methylene]malonate

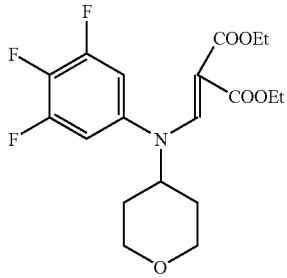

A mixture of 4-(3,4,5-trifluorophenyl)aminotetrahydropyran (500 mg, 2.16 mmol) and diethyl ethoxymethylenemalonate (0.32 mL, 2.16 mmol) was stirred at 120° C. for 24 h. Flash chromatography of the reaction mixture (hexane:EtOAc 2:3) gave diethyl [[N-(3,4,5-trifluorophenyl)-N-(tetrahydropyran-4-yl)amino]methylene]malonate (429 mg, 49%) as a pale yellow oil.

$^1$H NMR (400 MHz, CDCl$_3$) δ 1.14 (3H, t, J=7.3 Hz), 1.24 (3H, t, J=7.3 Hz), 1.73-1.91 (4H, m), 3.39 (2H, dt, J=11.6, 1.8 Hz), 3.58-3.66 (1H, m), 3.72 (2H, q, J=7.3 Hz), 4.05 (2H, dd, J=11.6, 4.3 Hz), 4.17 (2H, q, J=7.3 Hz), 6.77-6.86 (2H, m), 7.62 (1H, s).

Step 3: Ethyl 5,6,7-trifluoro-1,4-dihydro-4-oxo-1-(tetrahydropyran-4-yl)-3-quinolinecarboxylate

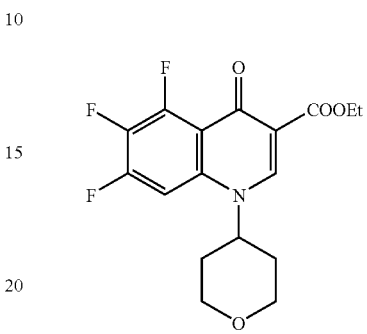

To a mixture of phosphorous pentaoxide (2.95 g, 20.8 mmol) and phosphoric acid (5.91 g, 41.6 mmol), was added diethyl [[N-(3,4,5-trifluorophenyl)-N-(tetrahydropyan-4-yl)amino]methylene]malonate (405 mg, 1.01 mmol) was added at 135° C., the whole mixture was stirred at 140° C. for 30 min. The reaction mixture was poured into water and the whole mixture was extracted with CHCl$_3$ (4×5 mL), and then 10% MeOH in CHCl$_3$ (2×5 mL). The combined extracts washed with brine, dried over anhydrous Na$_2$SO$_4$, filtered, and concentrated in vacuo. Flash chromatography of the residue (EtOAc: MeOH 10:1) gave ethyl 5,6,7-trifluoro-1,4-dihydro-4-oxo-1-(tetrahydropyran-4-yl)-3-quinolinecarboxylate (110 mg 38%) as a white powder.
$^1$H NMR (400 MHz, CDCl$_3$) δ 1.41 (3H, t, J=7.3 Hz), 2.05-2.20 (4H, m), 3.65 (2H, dt, J=11.6, 1.8 Hz), 4.24 (2H, dd, J=11.6, 4.3 Hz), 4.36-4.46 (3H, m), 7.16 (1H, dd, J=11.6, 6.1, 1.8 Hz), 8.54 (1H, s).

Step 4: Ethyl 5-benzylamino-6,7-difluoro-1,4-dihydro-4-oxo-1-(tetrahydropyran-4-yl)-3-quinolinecarboxylate

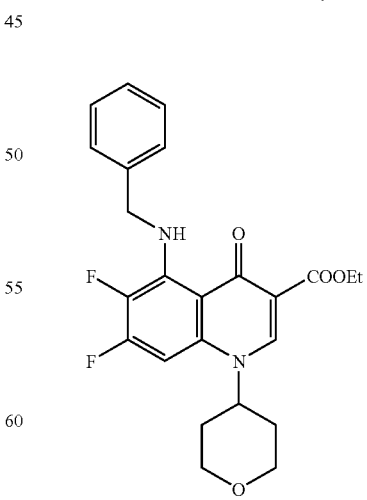

A suspension of 5,6,7-trifluoro-1,4-dihydro-4-oxo-1-(tetrahydropyran-4-yl)-3-quinolinecarboxylate (95.0 mg, 0.267 mmol), benzylamine (0.032 mL, 0.292 mmol) and triethylamine (0.11 mL, 0.789 mmol) in toluene (2 mL) was heated at 100° C. for 2 h. The reaction mixture was poured into water and the whole mixture was extracted with CHCl₃ two times. The combined extracts was dried over anhydrous Na₂SO₄, filtered, and then concentrated in vacuo. Flash chromatography of the residue (hexane: EtOAc=1:1) gave ethyl 5-benzylamino-6,7-difluoro-1,4-dihydro-4-oxo-1-(tetrahydropyran-4-yl)-3-quinolinecarboxylate (117 mg, 99%) as a pale yellow powder.

¹H NMR (400 MHz, CDCl₃) δ 1.39 (3H, t, J=7.3 Hz), 2.05-2.10 (4H, m), 3.59-3.65 (2H, m), 4.19-4.23 (2H, m), 4.31-4.42 (3H, m), 4.71-4.74 (2H, m), 6.34 (1H, dd, J=12.8, 6.1), 7.21-7.38 (5H, m), 8.43 (1H, s), 11.2 (1H, br).

Step 5: Ethyl 5-amino-6,7-difluoro-1,4-dihydro-4-oxo-1-(tetrahydropyran-4-yl)-3-quinolinecarboxylate

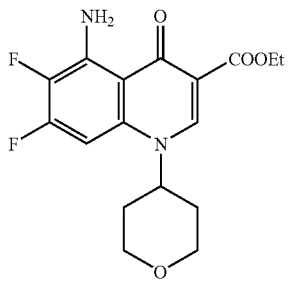

To a suspension of ethyl 5-benzylamino-6,7-difluoro-1,4-dihydro-4-oxo-1-(tetrahydropyran-4-yl)-3-quinolinecarboxylate (112 mg, 0.252 mmol) in AcOH (5 mL), was added 10% Pd—C (11.2 mg), the whole mixture was stirred at room temperature for 4 h under H₂ atmosphere (1 atm). After insoluble materials were filtered off, the filtrate was concentrated in vacuo. Flash chromatography of the residue (EtOAc) gave ethyl 5-amino-6,7-difluoro-1,4-dihydro-4-oxo-1-(tetrahydropyran-4-yl)-3-quinolinecarboxylate (76.5 mg, 86%) as pale yellow powder.

¹H NMR (400 MHz, CDCl₃) δ 1.41 (3H, t, J=7.3 Hz), 2.05-2.12 (4H, m), 3.60-3.66 (2H, m), 4.20-4.43 (3H, m), 6.40 (1H, dd, J=12.8, 6.1 Hz), 8.48 (1H, s).

Step 6: 5-Amino-6,7-difluoro-1,4-dihydro-4-oxo-1-(tetrahydropyran-4-yl)-3-quinolinecarboxylic Acid

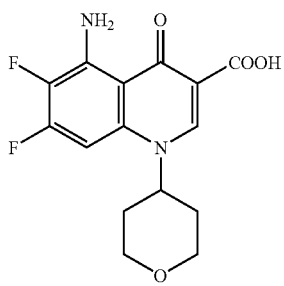

A suspension of ethyl 5-amino-6,7-difluoro-1,4-dihydro-4-oxo-1-(tetrahydropyran-4-yl)-3-quinolinecarboxylate (70.0 mg, 0.199 mmol) in a mixture of H₂SO₄/H₂O/AcOH (1:5:6, 3 mL) was heated under reflux for 1 h. The reaction mixture was poured into ice-water and the resulting precipitates were collected by filtration. The filtered precipitates were washed with water, and dried in vacuo to give 5-amino-6,7-difluoro-1,4-dihydro-4-oxo-1-(tetrahydropyran-4-yl)-3-quinolinecarboxylic acid (51.8 mg, 80%) as a yellow powder.

¹H NMR (400 MHz, DMSO-d₆) δ 1.94-2.01 (4H, m), 3.62-3.68 (2H, m), 3.96-3.99 (2H, m), 4.83-4.91 (1H, m), 7.32 (1H, dd, J=13.5, 6.1 Hz), 8.65 (1H, s), 14.7 (1H, s).

Step 7: 5-Amino-6-fluoro-1,4-dihydro-4-oxo-1-(tetrahydropyran-4-yl)-7-[2-(2-pyridylamino)ethylamino]-3-quinolinecarboxylic Acid

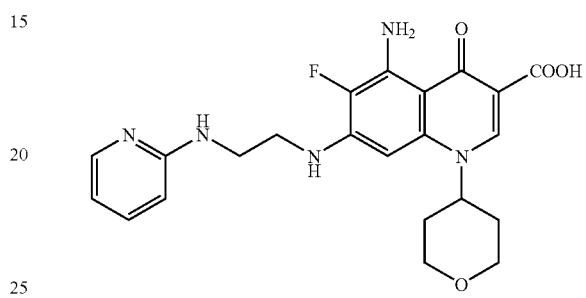

A mixture of 5-amino-6,7-difluoro-1,4-dihydro-4-oxo-1-(tetrahydropyran-4-yl)-3-quinolinecarboxylic acid (45.0 mg, 0.139 mmol), 2-(2-pyridylamino)ethylamine (29.0 mg, 0.211 mmol), and triethylamine (0.029 mL, 0.209 mmol) in DMSO (1.0 mL) was stirred at 120° C. for 3 h. After dilution of the reaction mixture with 10% MeOH in CHCl₃, the whole mixture washed with water, and the washing was extracted with 10% MeOH in CHCl₃ two times. The combined the organic layer and the extracts washed with water, dried over anhydrous Na₂SO₄, filtered, and concentrated in vacuo. Flash chromatography of the residue (10% MeOH in CHCl₃) gave 5-Amino-6-fluoro-1,4-dihydro-4-oxo-1-(tetrahydropyran-4-yl)-7-[2-(2-pyridylamino)ethylamino]-3-quinolinecarboxylic Acid (54.0 mg, 88%) as a white powder.

¹H NMR (400 MHz, DMSO-d₆) δ 1.88-2.02 (4H, m), 3.40-3.60 (6H, m), 3.94-3.98 (2H, m), 4.71-4.78 (1H, m), 6.18 (1H, d, J=6.7 Hz), 6.46-6.51 (2H, m), 6.75 (1H, t, J=6.1 Hz), 6.94 (1H, br), 7.20 (1H, br), 7.34-7.38 (1H, m), 7.98-7.99 (1H, m), 8.47 (1H, s), 15.5 (1H, s).

MS (ESI⁺) m/z 442 (M⁺+H).

Example 36

Preparation of (S)-8-amino-9,10-difluoro-3-methyl-7-oxo-3,7-dihydro-2H-[1,4]oxazino[2,3,4-ij]quinoline-6-carboxamide

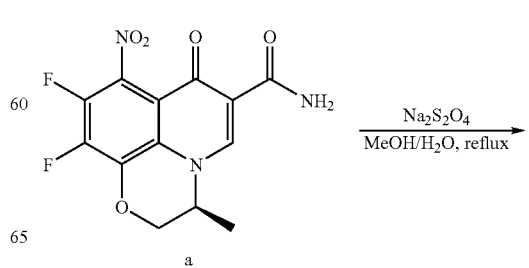

a

-continued

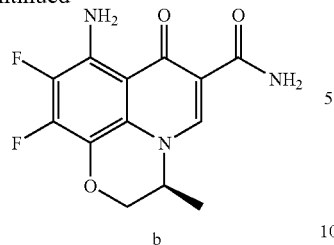

b

To a suspension of a (1 g, 3.07 mmole) in a mixture of water/methanol v/v (15 ml/15 ml) was added 8 equivalents of sodium hydrosulfite (Na2S2O4, 24.6 mmol, 4.3 g). The suspension was refluxed for 5-8 h until all starting material has disappeared. Upon completion, the reaction mixture was cooled to room temperature and 50 ml of water were added. After 20 minutes, the light yellow solid b was collected by filtration and washed with water. The solid was dried under vacuum to give 725 mg (80% yield) of B (95% pure) that is used without further purification in the next step.

Several other compounds were prepared using synthetic procedures similar to those described in Examples above or routine modifications thereof. Exempary compounds with their biological activity data are listed in Tables 1 and 2. The low resolution mass spectroscopy data for certain compounds is provided below:

I. 7-(3-(1H-imidazol-1-yl)propylamino)-5-amino-6,
8-difluoro-1-phenethylquiolin-4(1H)-one

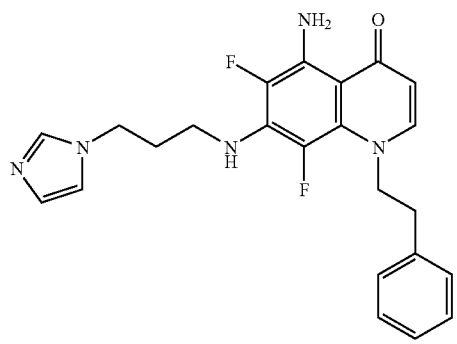

MS (EP) m/z: 424 (M$^+$+1). (Calcd. for $C_{23}H_{23}F_2N_5O$, 423.19)

II. 5-amino-1-cyclopropyl-6-fluoro-8-methoxy-7-(2-(naphthalen-1-ylamino)ethylamino)-4-oxo-1,4-dihydroquinoline-3-carboxylic acid

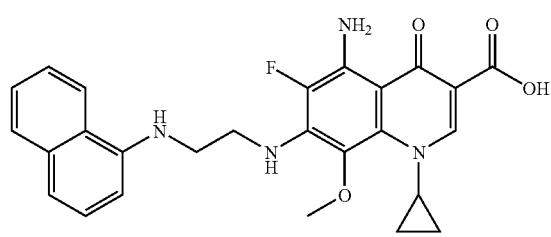

MS (EP) m/z: 477 (M$^+$+1). (Calcd. for $C_{26}H_{25}FN_4O_4$, 476.5)

III. 5-amino-1-cyclopropyl-6-fluoro-8-methoxy-4-oxo-7-(2-(pyridin-2-ylamino)ethylamino)-1,4-dihydroquinoline-3-carboxylic acid

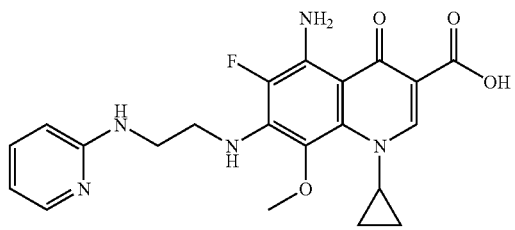

MS (EP) m/z: 428 (M$^+$+1). (Calcd. for $C_{21}H_{22}FN_5O_4$, 427.4)

IV. 8-amino-9-fluoro-3,3-dimethyl-7-oxo-10-(2-(pyridin-2-ylamino)ethylamino)-3,7-dihydro-2H-[1,4]oxazino[2,3,4-ij]quinoline-6-carboxylic acid

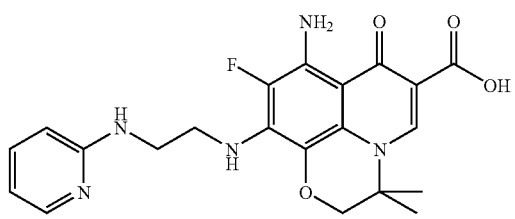

MS (EP) m/z: 428 (M$^+$+1). (Calcd. for $C_{21}H_{22}FN_5O_4$, 427.43)

V. (S)-8-amino-9-fluoro-3-methyl-7-oxo-10-(2-(pyridin-2-ylamino)ethylamino)-3,7-dihydro-2H-[1,4]oxazino[2,3,4-ij]quinoline-6-carboxylic acid

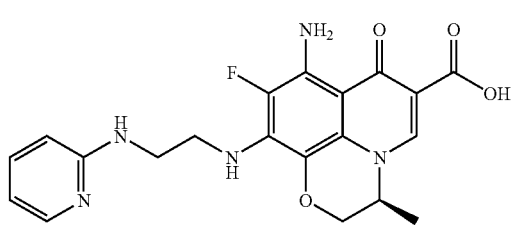

MS (EP) m/z: 414 (M$^+$+1). (Calcd. for $C_{20}H_{20}FN_5O_4$, 413.15)

VI. (R)-8-amino-9-fluoro-3-methyl-7-oxo-10-(2-(pyridin-2-ylamino)ethylamino)-3,7-dihydro-2H-[1,4]oxazino[2,3,4-ij]quinoline-6-carboxylic acid

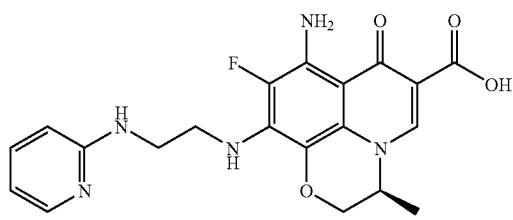

MS (EP) m/z: 414 (M⁺+1). (Calcd. for $C_{20}H_{20}FN_5O_4$, 413.40)

VII. 10-(3-(1H-imidazol-1-yl)propylamino)-8-amino-9-fluoro-3,3-dimethyl-7-oxo-3,7-dihydro-2H-[1,4]oxazino[2,3,4-ij]quinoline-6-carboxylic acid

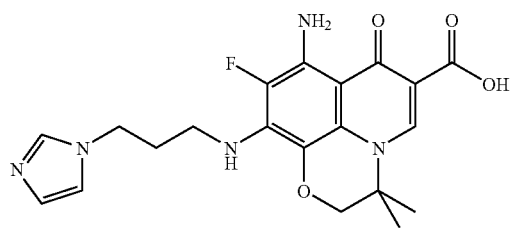

MS (EP) m/z: 416 (M⁺+1). (Calcd. for $C_{20}H_{22}FN_5O_4$, 415.40)

VIII. (S)-10-(3-(1H-benzo[d]imidazol-1-yl)propylamino)-8-amino-9-fluoro-3-isobutyl-7-oxo-3,7-dihydro-2H-[1,4]oxazino[2,3,4-ij]quinoline-6-carboxylic acid

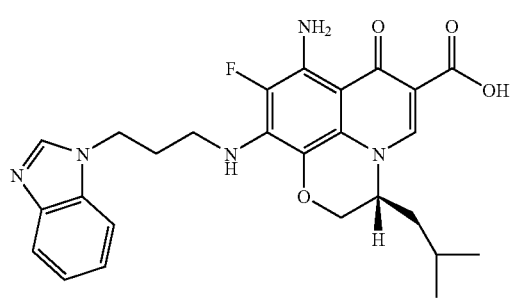

MS (EP) m/z: 494 (M⁺+1). (Calcd. for $C_{26}H_{28}FN_5O_4$, 493.21)

IX. (S)-10-(3-(1H-imidazol-1-yl)propylamino)-8-amino-9-fluoro-3-isopropyl-7-oxo-3,7-dihydro-2H-[1,4]oxazino[2,3,4-ij]quinoline-6-carboxylic acid

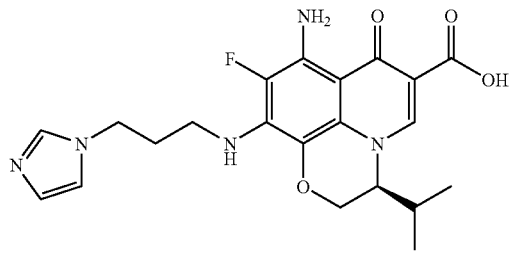

MS (EP) m/z: 430 (M⁺+1). (Calcd. for $C_{21}H_{24}FN_5O_4$, 429.44)

X. 8-amino-9-fluoro-2,2-dimethyl-7-oxo-10-(2-(pyridin-2-ylamino)ethylamino)-3,7-dihydro-2H-[1,4]oxazino[2,3,4-ij]quinoline-6-carboxylic acid

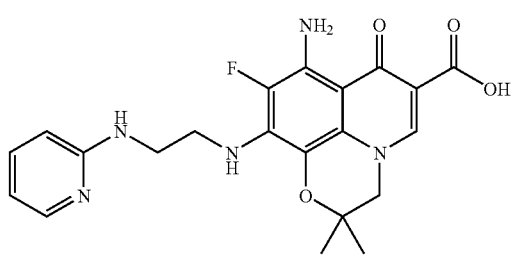

MS (EP) m/z: 428 (M⁺+1). (Calcd. for $C_{21}H_{22}FN_5O_4$, 427.17)

XI. (S)-8-amino-9-fluoro-3-isopropyl-7-oxo-10-(2-(pyridin-2-ylamino)ethylamino)-3,7-dihydro-2H-[1,4]oxazino[2,3,4-ij]quinoline-6-carboxylic acid

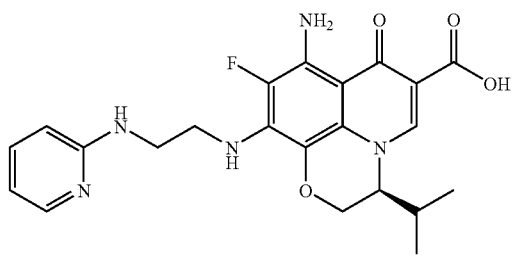

MS (EP) m/z: 442 (M⁺+1). (Calcd. for $C_{22}H_{24}FN_5O_4$, 441.18)

XII. (S)-8-amino-10-(3-(3,4-dihydroquinolin-1(2H)-yl)propylamino)-9-fluoro-3-methyl-7-oxo-3,7-dihydro-2H-[1,4]oxazino[2,3,4-ij]quinoline-6-carboxylic acid

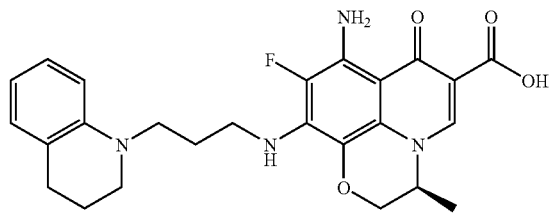

MS (EP) m/z: 467 (M$^+$+1). (Calcd. for C$_{25}$H$_{27}$FN$_4$O$_4$, 466.20)

XIII. (S)-8-amino-9-fluoro-3-methyl-7-oxo-10-(3-(pyridin-2-yl)propylamino)-3,7-dihydro-2H-[1,4]oxazino[2,3,4-ij]quinoline-6-carboxylic acid

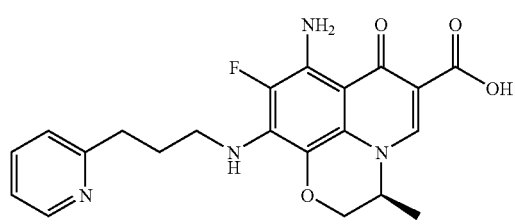

MS (EP) m/z: 413 (M$^+$+1). (Calcd. for C$_{21}$H$_{21}$FN$_4$O$_4$, 412.15)

XIV. (S)-8-amino-9-fluoro-10-(3-(4-fluorophenyl)propylamino)-3-methyl-7-oxo-3,7-dihydro-2H-[1,4]oxazino[2,3,4-ij]quinoline-6-carboxylic acid

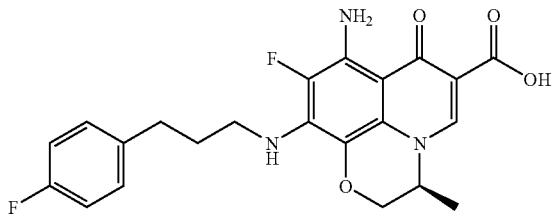

MS (EP) m/z: 430 (M$^+$+1). (Calcd. for C$_{22}$H$_{21}$F$_2$N$_3$O$_4$, 429.15)

XV. (S)-8-amino-10-(3-(ethyl(phenyl)amino)propylamino)-9-fluoro-3-methyl-7-oxo-3,7-dihydro-2H-[1,4]oxazino[2,3,4-ij]quinoline-6-carboxylic acid (AX9562)

MS (EP) m/z: 455 (M$^+$+1). (Calcd. for C$_{24}$H$_{27}$FN$_4$O$_4$, 454.20)

XIV. (S) 8-Amino-9-fluoro-2,3-dihydro-7-oxo-3-methyl-10-[3-(1-adamantanyl carboxamido)propylamino]-7H-pyrido[1,2,3-de]-1,4-benzoxazine-6-carboxylic acid

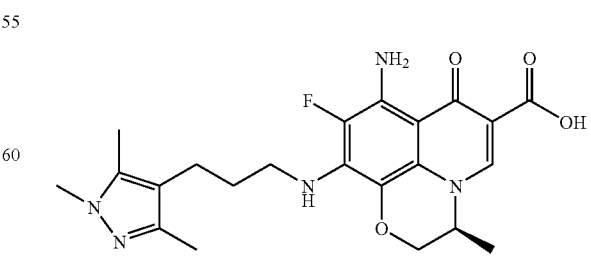

MS (EP) m/z: 513 (M$^+$+1). (Calcd. for C$_{27}$H$_{33}$FN$_4$O$_5$, 512.24)

XV. (S)-8-amino-9-fluoro-3-methyl-7-oxo-10-(3-(1,3,5-trimethyl-1H-pyrazol-4-yl)propylamino)-3,7-dihydro-2H-[1,4]oxazino[2,3,4-ij]quinoline-6-carboxylic acid MS (EP) m/z: 444 (M$^+$+1). (Calcd. for C$_{22}$H$_{26}$FN$_5$O$_4$, 443.20)

XVI. (S)-8-amino-9-fluoro-3-methyl-10-(2-(2-methylquinolin-4-ylamino)ethylamino)-7-oxo-3,7-dihydro-2H-[1,4]oxazino[2,3,4-ij]quinoline-6-carboxylic acid XIX. (S)-8-amino-9-fluoro-3-methyl-7-oxo-10-(2-(pyridin-2-ylamino)ethylamino)-3,7-dihydro-2H-[1,4]oxazino[2,3,4-ij]quinoline-6-carboxamide

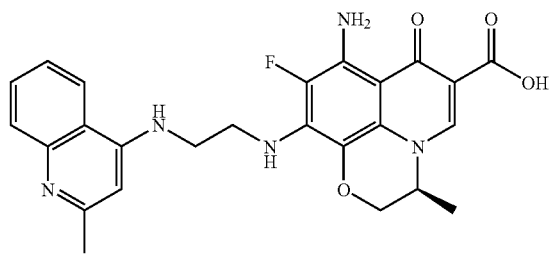

MS (EP) m/z: 478 (M$^+$+1). (Calcd. for $C_{25}H_{24}FN_5O_4$, 477.18)

MS (EP) m/z: 413 (M$^+$+1). (Calcd. for $C_{20}H_{21}FN_6O_3$, 412.17)

XVII. (S)-8-amino-9-fluoro-10-(2-(4-fluorophenoxy)ethylamino)-3-methyl-7-oxo-3,7-dihydro-2H-[1,4]oxazino[2,3,4-ij]quinoline-6-carboxylic acid XX. (S)-8-amino-9-fluoro-3-methyl-7-oxo-10-(2-(piperidin-1-ylsulfonyl)ethylamino)-3,7-dihydro-2H-[1,4]oxazino[2,3,4-ij]quinoline-6-carboxamide

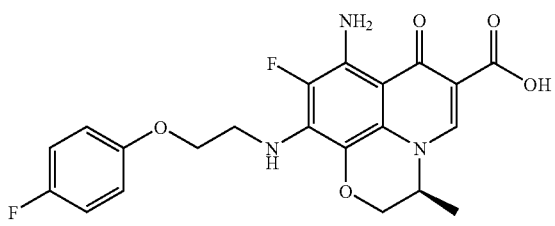

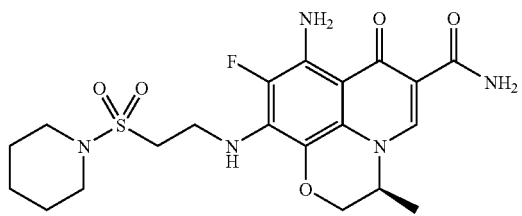

MS (EP) m/z: 432 (M$^+$+1). (Calcd. for $C_{21}H_{23}F_2N_3O_5$, 431.13)

MS (EP) m/z: 468 (M$^+$+1). (Calcd. for $C_{20}H_{26}FN_5O_5S$, 467.16)

XVIII. (S)-10-(3-(1H-imidazol-1-yl)propylamino)-8-amino-9-fluoro-3-methyl-7-oxo-3,7-dihydro-2H-[1,4]oxazino[2,3,4-ij]quinoline-6-carboxamide

XXI

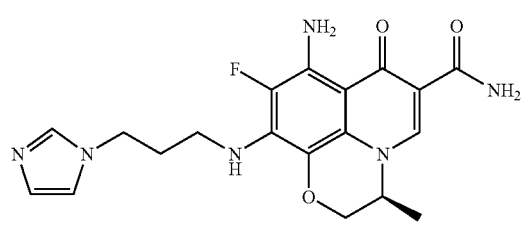

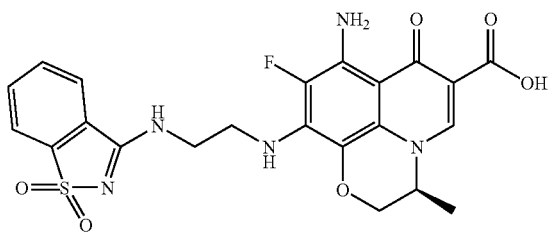

MS (EP) m/z: 401 (M$^+$+1). (Calcd. for $C_{19}H_{21}FN_6O_3$, 400.17)

MS (EP) m/z: 502 (M$^+$+1). (Calcd. for $C_{22}H_{20}FN_5O_6S$, 501.11)

XXII. (S)-10-(3-(1H-imidazol-1-yl)propylamino)-8-amino-9-fluoro-3-methyl-7-oxo-3,7-dihydro-2H-[1,4]oxazino[2,3,4-ij]quinoline-6-carbonitrile

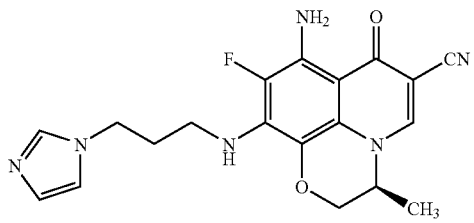

MS (EP) m/z: 383 (M$^+$+1). (Calcd. for $C_{19}H_{19}FN_6O_2$, 382.16)

XXIII. (S)-8-amino-9-fluoro-3-methyl-7-oxo-10-(3-(pyridin-2-yl)propylamino)-3,7-dihydro-2H-[1,4]oxazino[2,3,4-ij]quinoline-6-carbonitrile

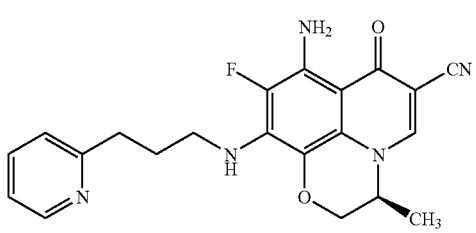

MS (EP) m/z: 394 (M$^+$+1). (Calcd. for $C_{21}H_{20}FN_5O_2$, 393.16).

Example 37

Glycogen Synthesis Activity in Hep G2 Cells

Hep G2 cells were obtained from the Japanese Collection of Research Bioresources and were grown in standard culture medium, a low-glucose Dulbecco's modified Eagle's medium (DMEM) containing 10% fetal calf serum supplemented with 100 U/mL penicillin and 100 µg/mL streptomycin, in a humidified and 5% $CO_2$ atmosphere kept at 37° C. The Hep G2 cells were harvested with 0.25% trypsin solution containing 1 mM EDTA, and were seeded on 12 well plates at 1×10$^5$ cells per well. Following a culture for 3 days, the cells were washed once with phosphate buffered saline (PBS), and were incubated with serum-free low-glucose DMEM supplemented with 100 U/mL penicillin and 100 µg/mL streptomycin. Following a culture for 3 hrs, compounds provided herein at various concentrations and 2.5 µCi/mL D-[2-$^3$H]glucose (PerkinElmer, Boston, Mass., USA) were added to the serum-free low-glucose DMEM. A vehicle control of DMSO (0.3%, final concentration) was also used. The total volume per well of the reaction medium was 1.0 mL of serum-free low-glucose DMEM. After incubation at 37° C. for 3 hrs, the medium was aspirated and cells were washed twice with PBS, and 0.25 mL of 1 N KOH containing 0.4 mg/mL carrier glycogen were added. After incubation at 37° C. for 30 min, 0.25 mL of 48.8% (w/v) KOH was added to each well for cell lysis. After incubation at 95° C. for 30 min, 1.5 mL of 95% (v/v) ethanol was added to the cell lysate. Total glycogen was precipitated overnight at −20° C. Glycogen precipitates were recovered by centrifugation at 19,000×g for 30 min at 4° C. Precipitates were washed once with 1 mL of 70% (v/v) ethanol, and were re-suspended in 0.5 mL water. [$^3$H]Glucose incorporation into glycogen was assessed using a liquid scintillation counter (Packard Instrument Co., Meriden, Conn., USA).

Example 38

Animal Study 1

Male obese hyperglycemic mice (db/db) and lean mice (C57BL/6J) were obtained from Charles River Laboratories Japan (Yokohama, Japan). All mice were given a standard diet (Clea Japan, Tokyo, Japan) and tap water ad libitum. All institutional guidelines for animal care and use were applied in this study. Test compounds were suspended in 0.3% carboxymethyl-cellulose sodium salt (CMC-Na; Sigma, St. Louis, Mo.). After fasting for 2 hr, the test compounds (100 mg/kg) were administered orally to 7-week-old db/db mice. Vehicle (0.3% CMC-Na) was administered orally to both 7-week-old db/db mice and lean mice. Blood samples were collected from tail vein using capillary tubes containing EDTA·2K at 0, 0.5, 1, 2, 4, and 6 hr after the administration. The blood samples were centrifuged at 2,500×g for 5 min and separated plasma was kept on ice and analyzed in the same day. Plasma glucose levels were determined using the glucose CII-test (Wako Pure Chemical Industries, Osaka, Japan). Results are provided in FIG. 1.

CHIR99021 is a selective inhibitor of GSK3 enzyme known in the art (see, Ring D B et al., Selective GSK-3 inhibitors potentiate insulin activation of glucose transport and utilization in vitro and in vivo. Diabetes 2003, 52(3): 588-595). FIG. 1 shows the drop in blood glucose levels for these animal experiments for compounds 6, 7 (Table I) and CHIR99021.

Example 39

Animal Study 2 (Oral Glucose Tolerance Test)

Male Crlj:CD1 (ICR) mice were obtained from Charles River Laboratries Japan (Yokohama, Japan). All mice were given a standard diet (Clea Japan, Tokyo, Japan) and tap water ad libitum. All institutional guidelines for animal care and use were applied in this study. Test compounds were suspended in 0.3% carboxymethyl-cellulose sodium salt (CMC-Na; Sigma, St. Louis, Mo.). After fasting for 15-17 hr, the test compound (300 mg/kg) or vehicle (0.3% CMC-Na) was orally administered to 7-week-old ICR mice. Glucose solution (5 g/kg) was orally administered at 30 min after test compound treatment. Blood samples were collected from tail vein using capillary tubes containing EDTA·2K before test compound treatment, and at 0, 0.5, 1, and 2 hr after glucose load. The blood samples were centrifuged at 2,500×g for 5 min and separated plasma was kept on ice and analyzed in the same day. Plasma glucose levels were determined using the glucose C II-test (Wako Pure Chemical Industries, Osaka, Japan).

The sum of plasma glucose levels at 0.5 and 1 hr after glucose load was compared to that of vehicle treatment, and results were presented as percent decrease. Results (average of % decrease of 0.5 and 1 hr after glucose load) for exemplary compounds are provided in Tables 1 and 2.

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the claimed subject matter and are encompassed by the appended claims.

What is claimed is:

1. A compound of Formula Ia:

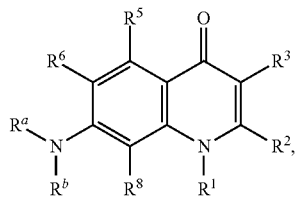

or a pharmaceutically acceptable salt thereof, wherein
$R^1$ is cycloalkyl, aryl or aralkyl;
$R^2$ is hydrogen or lower alkyl;
$R^3$ is H or —COOH;
$R^5$ is amino, optionally substituted with one or two lower alkyl groups;
$R^6$ is halo;
$R^8$ is halo or alkoxy;
$R^a$ is selected from hydrogen and lower alkyl;
$R^b$ is —$(CH_2)_n(NR^c)_mR$ or —$(CH_2)_nOR^d$;
$R^c$ is hydrogen or lower alkyl;
R is aryl, heteroaryl, —C(O)$OR^d$ or —C(O)$R^d$;
$R^d$ is alkyl, aryl, heterocyclyl, heteroaryl or cycloalkyl;
n is 0 to 6; and
m is 0 or 1, where R and $R^d$ are optionally substituted with 1, 2, 3 or 4 substituents, each independently selected from $Q^1$, where $Q^1$ is halo, hydroxy, cyano, thiocyano, selenocyano, azide, amino, nitro, alkyl, alkenyl, alkynyl, aryl or cycloalkyl.

2. The compound of claim 1, wherein $R^1$ is cycloalkyl, aryl or aralkyl;
$R^2$ is hydrogen or lower alkyl;
$R^3$ is H or COOH;
$R^5$ is amino;
$R^6$ is halo;
$R^8$ is halo or alkoxy;
$R^a$ is selected from hydrogen and lower alkyl;
$R^b$ is aralkyl, heteroaralkyl, heteroarylaminoalkyl, arylcarbonylaminoalkyl, heteroarylcarbonylaminoalkyl, alkyloxycarbonylaminoalkyl or alkoxyalkyl, where $R^b$ is optionally substituted with lower alkyl, amino or halo.

3. The compound of claim 1, wherein $R^1$ is cycloalkyl or aralkyl.

4. The compound of claim 1, wherein $R^1$ is cycloalkyl.

5. The compound of claim 1, wherein $R^1$ is cyclopropyl or cyclopentyl.

6. The compound of claim 1, wherein $R^1$ is aralkyl.

7. The compound of claim 1, wherein $R^2$ is hydrogen or methyl.

8. The compound of claim 1, wherein $R^2$ is hydrogen.

9. The compound of claim 1, wherein $R^3$ is H.

10. The compound of claim 1, wherein $R^3$ is COOH.

11. The compound of claim 1, wherein $R^5$ is amino.

12. The compound of claim 1, wherein $R^6$ and $R^8$ are halo.

13. The compound of claim 1, wherein $R^6$ and $R^8$ are each independently Cl, Br or F.

14. The compound of claim 1, wherein $R^6$ is F.

15. The compound of claim 1, wherein $R^8$ is F.

16. The compound of claim 1, wherein $R^8$ is alkoxy.

17. The compound of claim 1, wherein $R^8$ is methoxy.

18. The compound of claim 1, wherein $R^a$ is hydrogen.

19. The compound of claim 1, wherein n is 0 to 4.

20. The compound of claim 1, wherein n is 2 or 3.

21. The compound of claim 1, wherein m is 1.

22. The compound of claim 1, wherein m is 0.

23. The compound of claim 1, wherein $R^d$ is alkyl, aryl, heterocyclyl or heteroaryl.

24. The compound of claim 1, wherein $R^b$ is heteroaralkyl, heteroarylaminoalkyl, arylcarbonylaminoalkyl, heteroarylcarbonylaminoalkyl, alkyloxycarbonylaminoalkyl or alkoxyalkyl, where $R^b$ is optionally substituted with lower alkyl, amino, halo or cyano, thiocyano, selenocyano, azide.

25. The compound of claim 1, wherein $R^b$ is heteroaralkyl, where $R^b$ is optionally substituted with lower alkyl, amino, halo or cyano.

26. The compound of claim 1, wherein $R^b$ is selected from phenethyl, 4-aminophenethyl, 4-pyridinyl, 4-chlorophenethyl, 4-fluorophenethyl, phenylpropyl, pyridin-2-ylaminoethyl, 4-chlorobenzyl, 4-aminophenethyl, indol-3-ylethyl, pyrimidin-2-ylamino, 4-hydroxyphenethyl, isopropyloxypropyl, 2,4-dichlorophenethyl, 2,4-difluorophenethyl, phenylbutyl, tert-butyloxycarbonylamino, imidazolyl, isopropyloxypropyl, 4-fluorophenylcarbonylaminoethyl, pyridin-2-ylaminoethyl, 5-cyanopyridin-2-ylaminoethyl, pyridin-2-ylaminocarbonylethyl, pyridin-4-ylaminocarbonylethyl, naphthylaminoethyl, phenoxyethyl, 1-H-imidazol-1-ylethyl, 1,2,4-triazol-1-ylethyl, imidazol-1-ylpropyl and benzimidazol-1-ylethyl.

27. The compound of claim 1, wherein the compound is of Formula II:

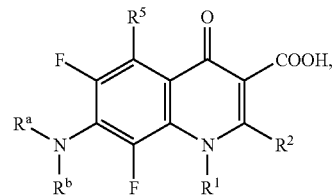

or a pharmaceutically acceptable salt thereof.

28. The compound of claim 1, wherein the compound is of Formula III:

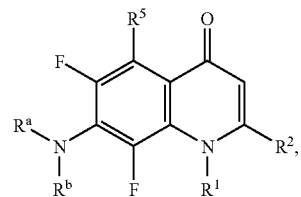

or a pharmaceutically acceptable salt thereof.

29. The compound of claim 1, wherein the compound is of Formula:

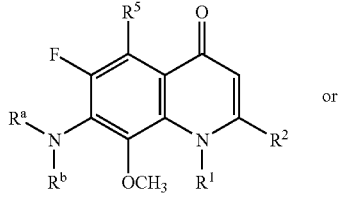

or

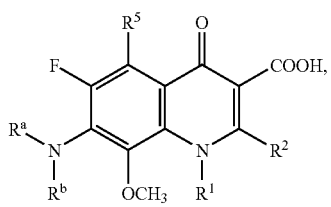

or a pharmaceutically acceptable salt thereof.

30. The compound of claim 1, wherein the compound is of Formula IV:

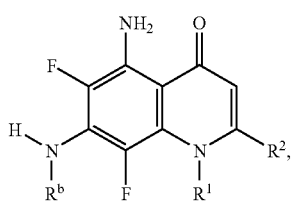

or a pharmaceutically acceptable salt thereof.

31. The compound of claim 1, wherein the compound is of Formula V:

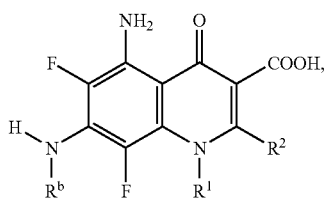

or a pharmaceutically acceptable salt thereof.

32. The compound of claim 1, wherein the compound is of Formula:

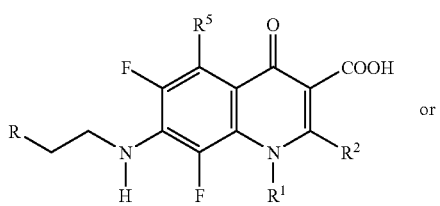

or

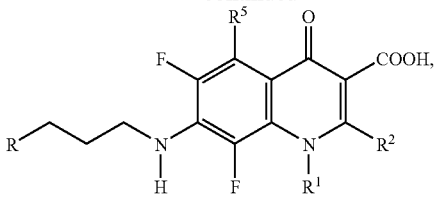

or a pharmaceutically acceptable salt thereof.

33. The compound of claim 1, wherein the compound is of Formula:

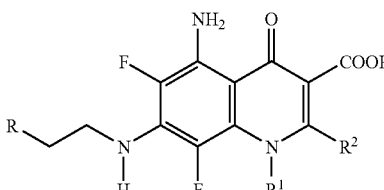

or

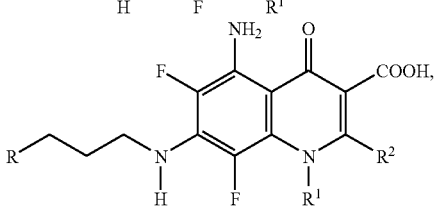

or a pharmaceutically acceptable salt thereof.

34. The compound of claim 1, wherein the compound has Formula:

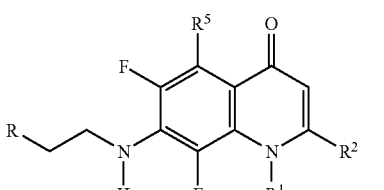

or

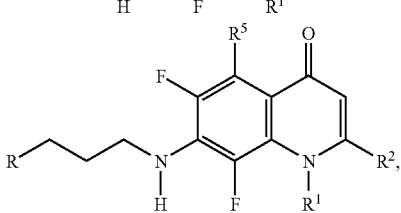

or a pharmaceutically acceptable salt thereof.

35. The compound of claim 1, wherein the compound is of Formula:

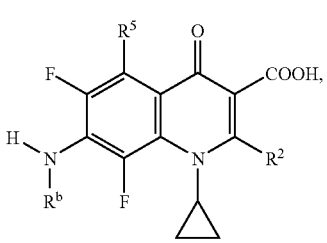

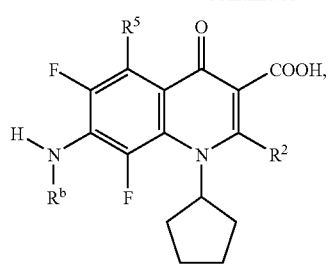
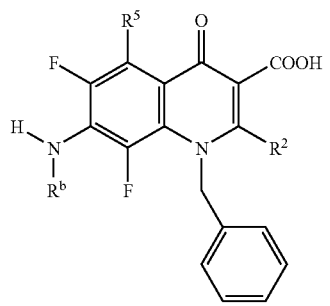
or
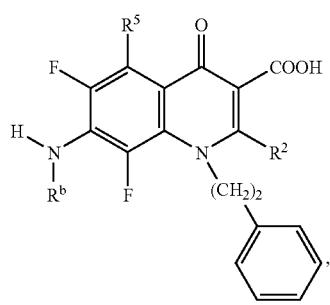
or a pharmaceutically acceptable salt thereof.
36. The compound of claim 1, wherein the compound is of Formula:
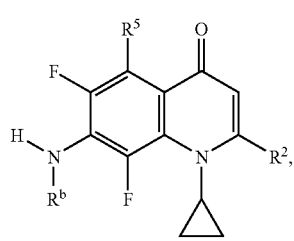
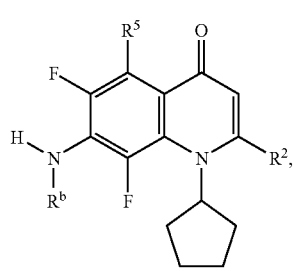
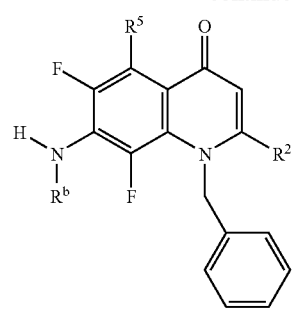
or
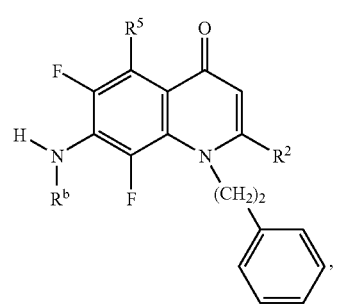
or a pharmaceutically acceptable salt thereof.
37. The compound of claim 1, wherein the compound is of Formula:
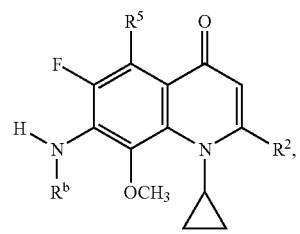
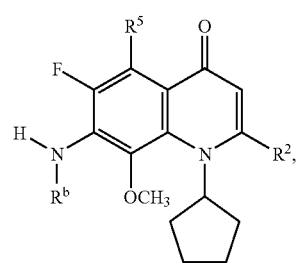
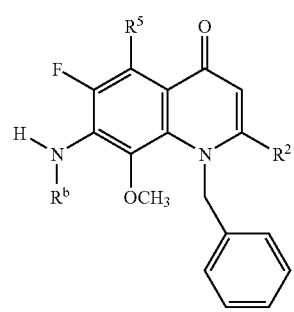
or -continued

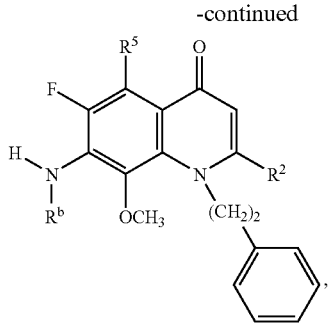

or a pharmaceutically acceptable salt thereof.

38. The compound of claim 1, wherein the compound is of Formula:

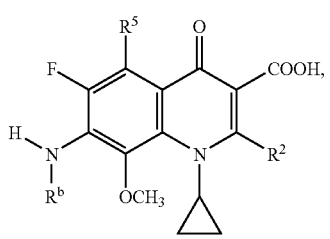

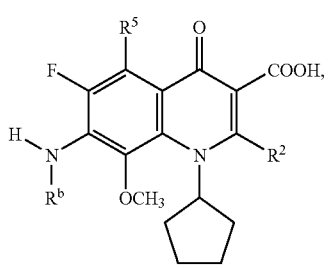

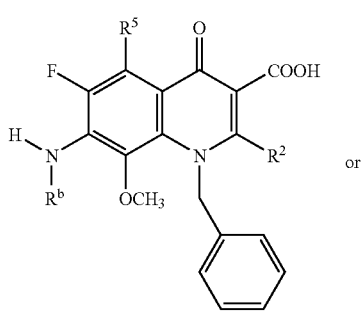 or

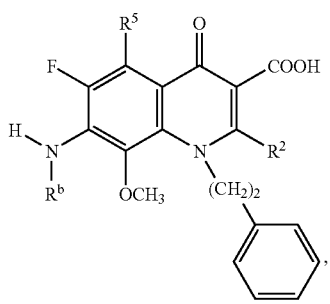

or a pharmaceutically acceptable salt thereof.

39. The compound of claim 1, wherein the compound is of Formula:

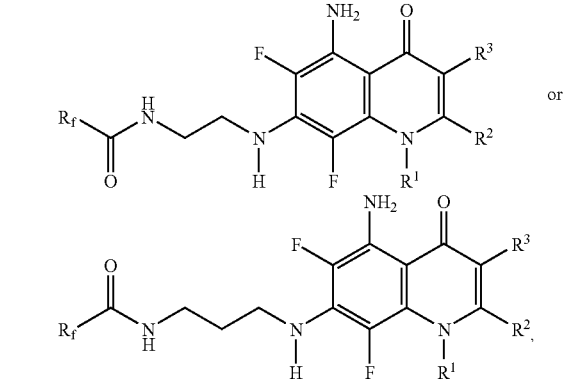

or a pharmaceutically acceptable salt thereof,
wherein $R_f$ is an optionally substituted aryl or heteroaryl, the substituents when present are selected from one or two $Q^1$ groups.

40. The compound of claim 1, wherein the compound is of Formula:

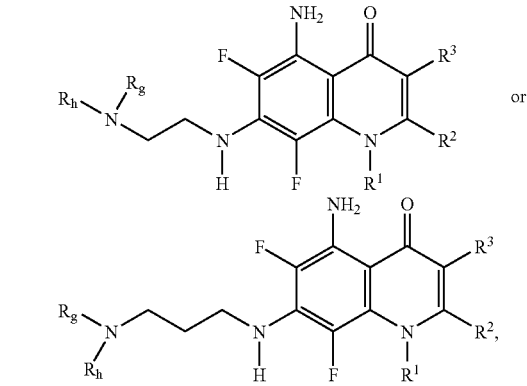

or a pharmaceutically acceptable salt thereof,
wherein $R_g$ is hydrogen or lower alkyl;
$R_h$ is aryl or heteroaryl; or
$R_g$ and $R_h$ together with the nitrogen atom on which they are substituted form an optionally substituted 4-6 membered aromatic ring, wherein the substituents when present are selected from alkyl and halo.

41. A compound of Formula:

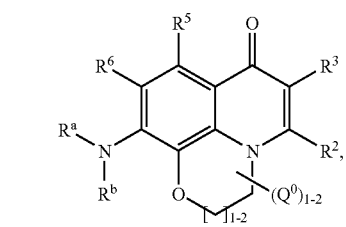

or a pharmaceutically acceptable salt thereof, wherein
$Q^0$ is halo, hydroxyl, cycloalkyl, aryl, heteroaryl, aralkyl, cyano, thiocyano, selenocyano, azide, amino, nitro, alkyl, haloalkyl, alkenyl or alkynyl;

$R^2$ is hydrogen, lower alkyl, $COOR^{2a}$ or optionally substituted aryl, wherein the substituents when present are selected from one to four $Q^1$ groups;

$R^{2a}$ is hydrogen, or lower alkyl;

$R^3$ is H, CN or $C(O)R^{3a}$;

$R^{3a}$ is OH, $NR^{3b}R^{3c}$, alkoxy, alkyl, alkenyl or alkynyl;

$R^{3b}$ is hydrogen, alkyl, alkenyl or alkynyl;

$R^{3c}$ is hydrogen, alkyl, alkenyl, alkynyl;

$R^5$ is $NR^{5a}R^{5b}$ or $SR^{5a}$;

$R^{5a}$ and $R^{5b}$ are each independently hydrogen, lower alkyl or $COR^{5c}$;

$R^{5c}$ is lower alkyl or lower haloalkyl;;

$R^6$ is halo;

$R^a$ is selected from hydrogen and lower alkyl;

$R^b$ is —$(CH_2)_n(NR^c)_mR$,
—$(CH_2)_nOR^d$,
—$(CH_2)_nS(O)_lR^d$,
—$CH(R^j)(CH_2)_n(NR^c)_mR$,
—$CH(R^j)(CH_2)_nOR^d$, or
$CH(R^j)(CH_2)_nS(O)_lR^d$;

$R^c$ is hydrogen or lower alkyl;

R is alkyl, aryl, heteroaryl, cycloalkyl, heterocyclyl, fused heterocyclylaryl, fused arylheterocyclyl, C(O)OR$^d$, C(O)R$^d$, —C(O)NR$^e$R$^e$ or —CHR$^d$R$^d$;

each $R^d$ is selected from alkyl, aryl, heteroaryl, heteroaryl, cycloalkyl, fused heterocyclylaryl and fused arylheterocyclyl;

each $R^e$ is selected from hydrogen, alkyl, aryl, heterocyclyl, heteroaryl, cycloalkyl, fused heterocyclylaryl and fused arylheterocyclyl;

$R^j$ is lower alkyl or lower haloalkyl;

n is 0 to 6;

m is 0 or 1; and l is 0 to 2, where R and $R^d$ are optionally substituted with 1 to 4 substituents, each independently selected from $Q^1$, where each $Q^1$ is halo, cyano, selenocyano, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, noalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, —$N^+R^{51}R^{52}R^{53}$, $P(R^{50})_2$, $P(=O)(R^{50})_2$, $OP(=O)(R^{50})_2$, —$NR^6OC(O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^1$ groups, which substitute atoms in a 1, 2 or 1,3 arrangement, together form —O—$(CH_2)_y$—O—, —S—$(CH_2)_y$—O— or —S—$(CH_2)_y$—S—, where y is 1 or 2; or two $Q^1$ groups, which substitute the same atom, together form alkylene; and each $Q^1$ is independently unsubstituted or substituted with one, two or three substituents, each independently selected from $Q^2$;

each $Q^2$ is independently halo, cyano, selenocyano, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, —N⁺R⁵¹R⁵²R⁵³, P(R⁵⁰)₂, OP(=O)(R⁵⁰)₂, OP(=O)(R⁵⁰)₂, —NR⁶⁰C(=O)R⁶³, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two Q² groups, which substitute atoms in a 1, 2 or 1,3 arrangement, together form —O—(CH₂)ᵧ—O—, —S—(CH₂)ᵧ—O— or —S—(CH₂)—S—, where y is 1 or 2; or two Q² groups, which substitute the same atom, together form alkylene;

R⁵⁰ is hydroxy, alkoxy, aralkoxy, alkyl, heteroaryl, heterocyclyl, aryl or —NR⁷⁰R⁷¹, where R⁷⁰ and R⁷¹ are each independently hydrogen, alkyl, aralkyl, aryl, heteroaryl, heteroaralkyl or heterocyclyl, or R⁷⁰ and R⁷¹ together form alkylene, azaalkylene, oxaalkylene or thiaalkylene;

R⁵¹, R⁵² and R⁵³ are each independently hydrogen, alkyl, aryl, aralkyl, heteroaryl, heteroaralkyl, heterocyclyl or heterocyclylalkyl;

R⁶⁰ is hydrogen, alkyl, aryl, aralkyl, heteroaryl, heteroaralkyl, heterocyclyl or heterocyclylalkyl; and R⁶³ is alkoxy, aralkoxy, alkyl, heteroaryl, heterocyclyl, aryl or —NR⁷⁰R⁷¹.

42. The compound of claim 41, wherein the compound is of Formula:

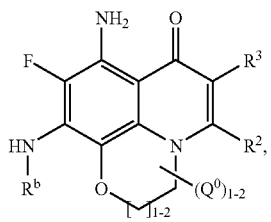

or a pharmaceutically acceptable salt thereof.

43. The compound of claim 41, wherein the compound is of Formula:

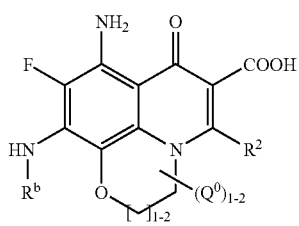

or a pharmaceutically acceptable salt thereof.

44. The compound of claim 41, wherein the compound is of Formula:

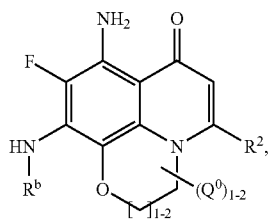

or a pharmaceutically acceptable salt thereof.

45. The compound of claim 41, wherein the compound is of Formula:

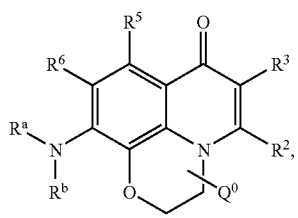

or a pharmaceutically acceptable salt thereof.

46. The compound of claim 41, wherein the compound is of Formula:

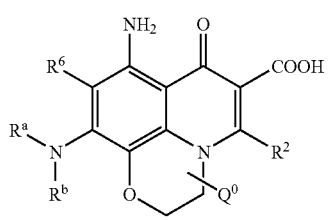

or a pharmaceutically acceptable salt thereof.

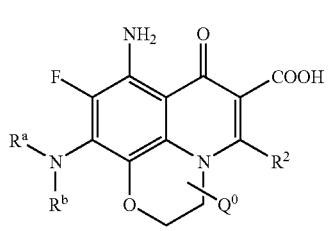

or

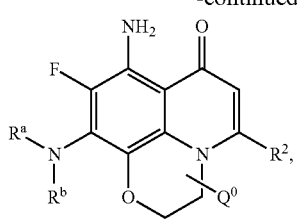
or a pharmaceutically acceptable salt thereof.
47. The compound of claim 41, wherein the compound is of Formula:
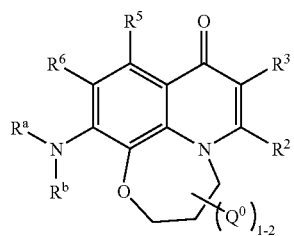
or a pharmaceutically acceptable salt thereof.
48. The compound of claim 1 selected from:
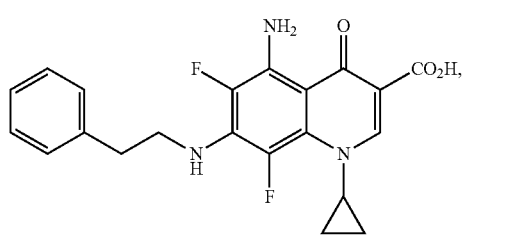
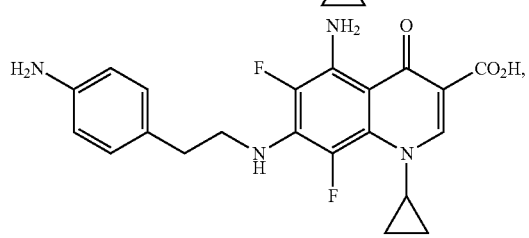
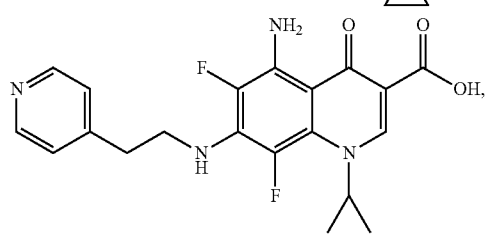
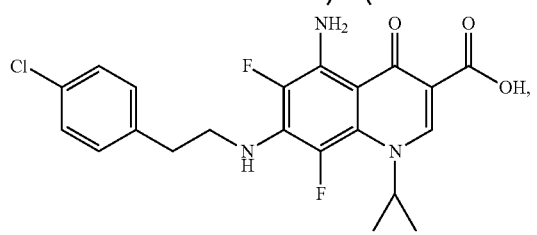
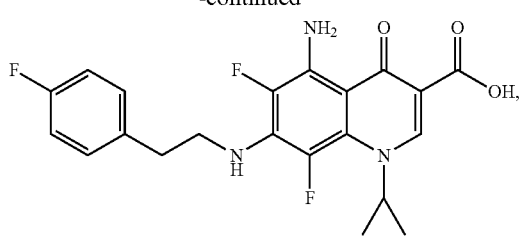
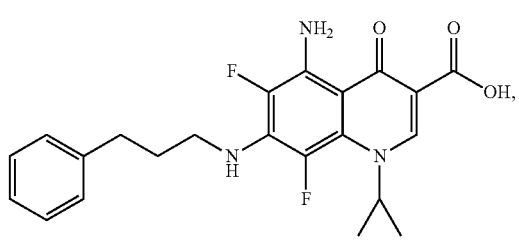
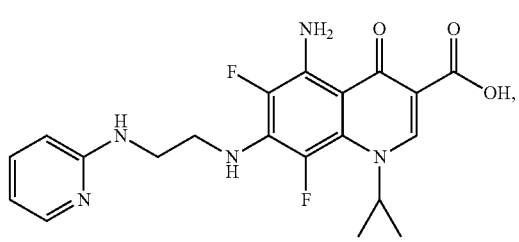
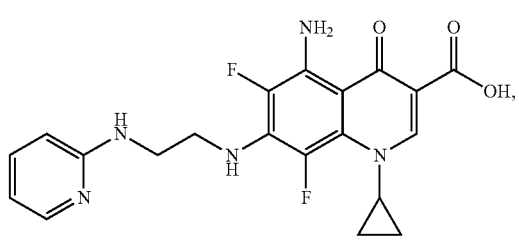
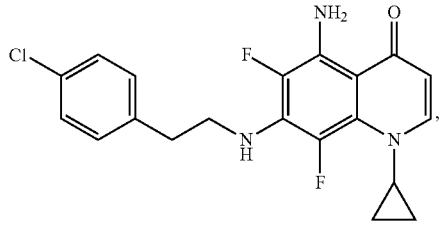
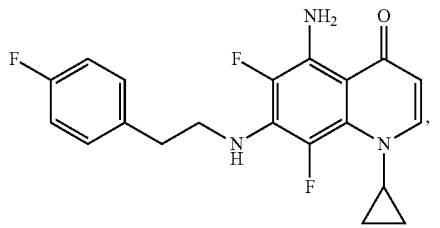
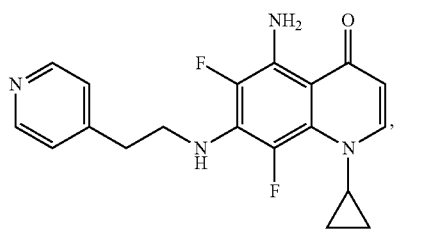

267
-continued
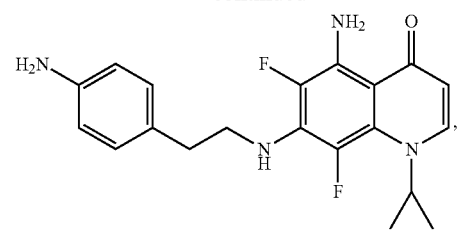
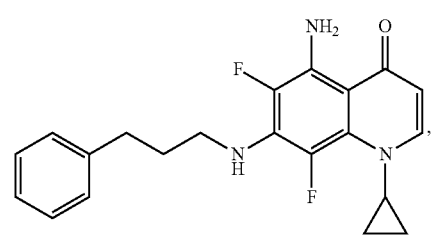
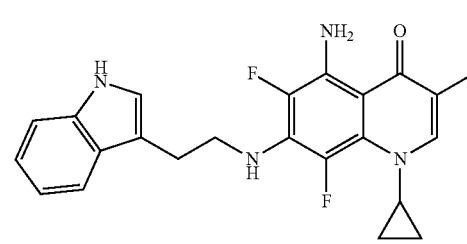
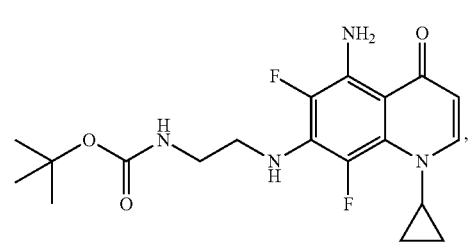
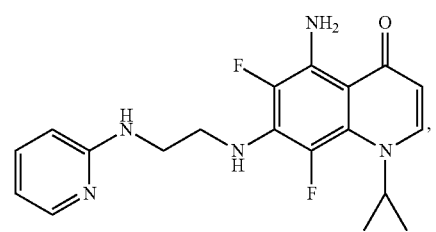
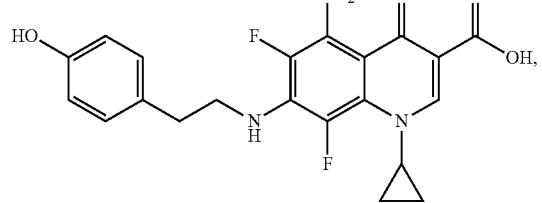
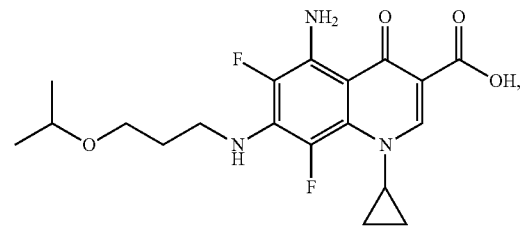
268
-continued
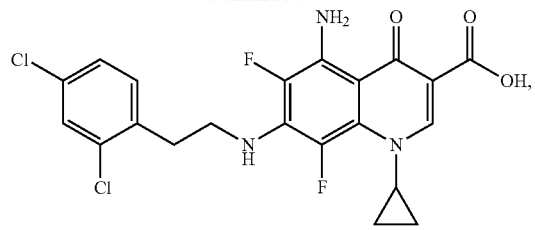
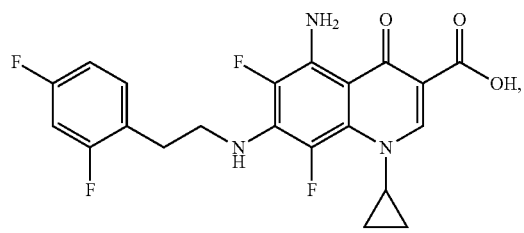
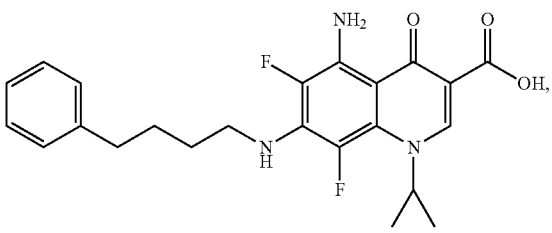
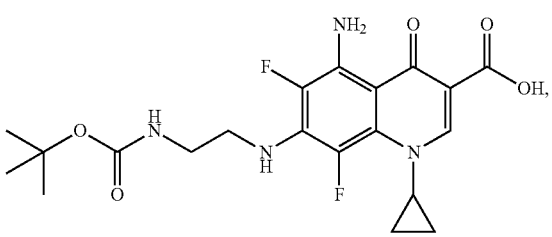
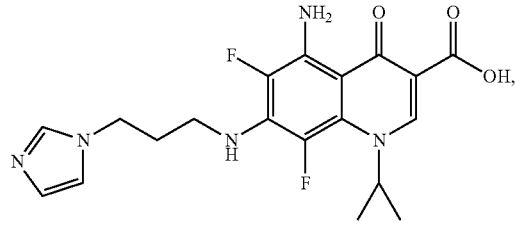
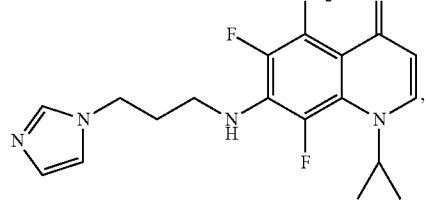
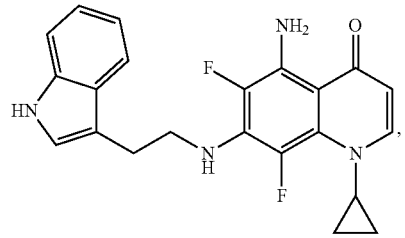

269
-continued
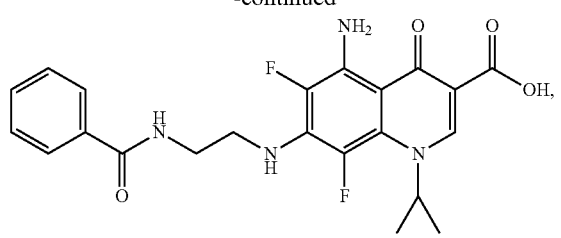
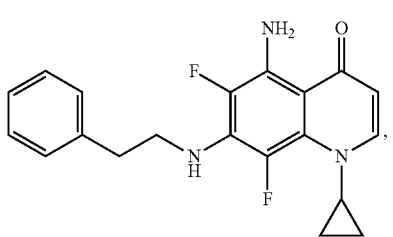
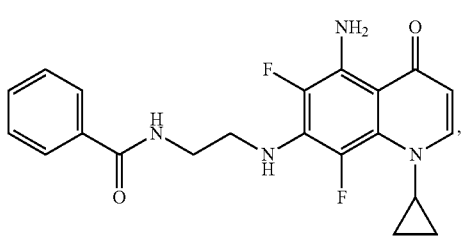
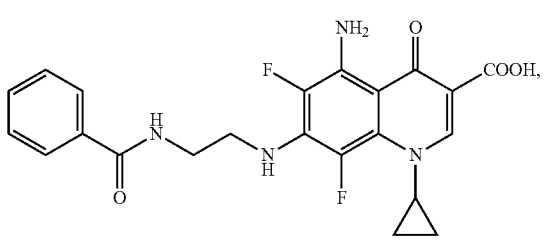
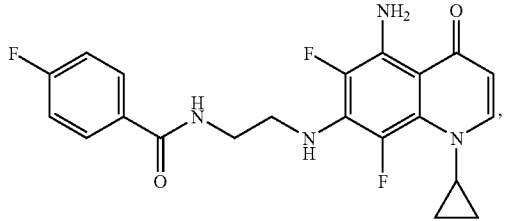
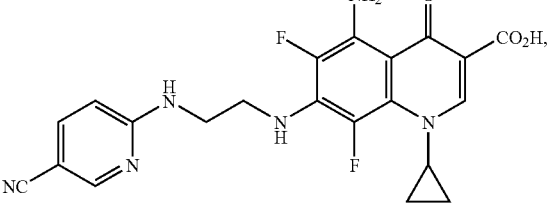
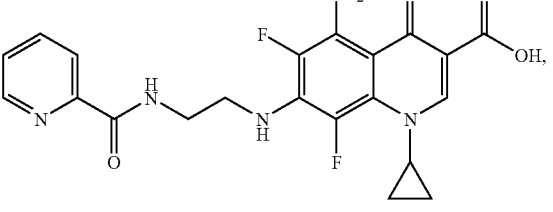
270
-continued
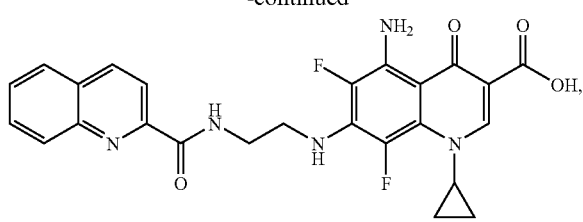
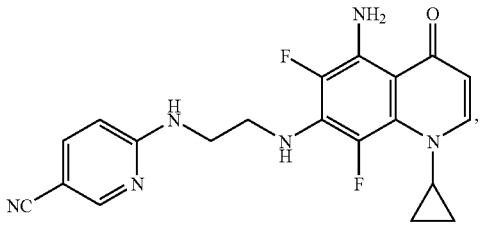
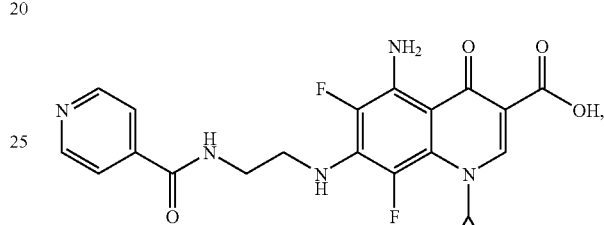
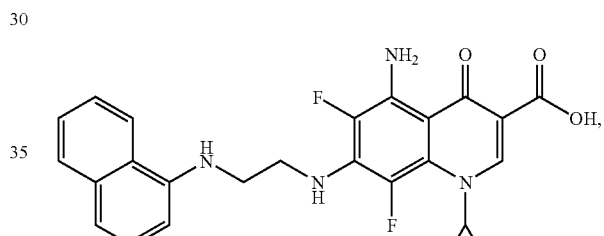
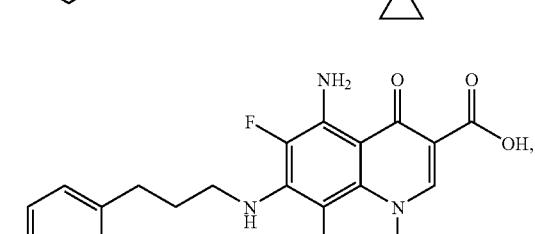
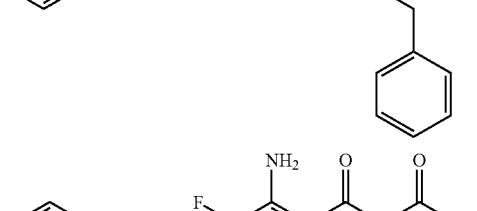
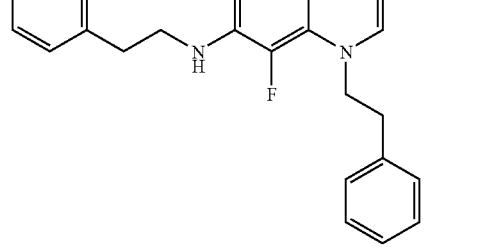

271
-continued
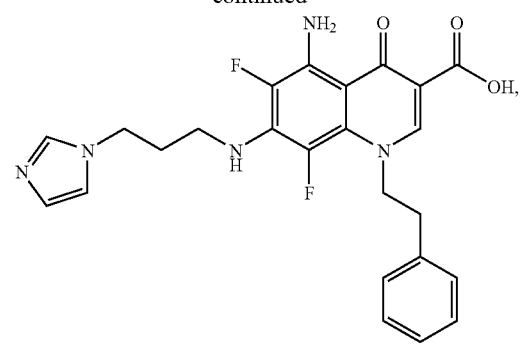
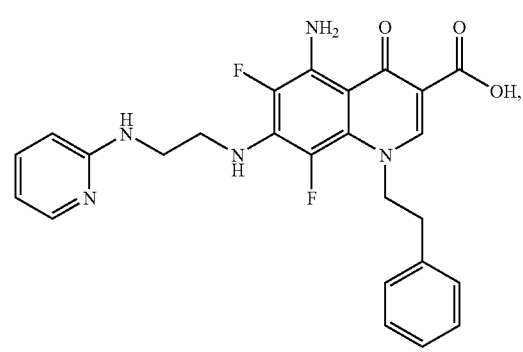
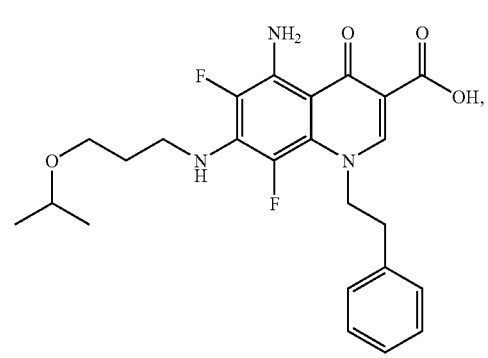
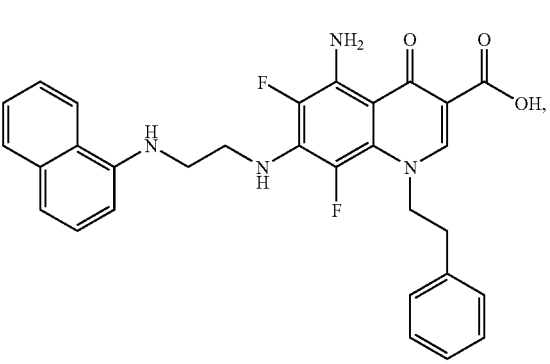
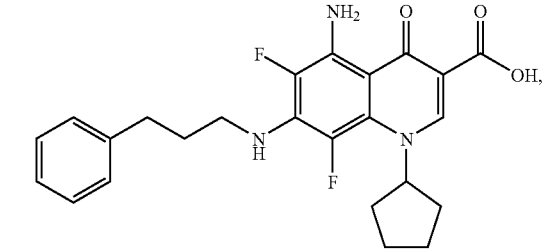
272
-continued
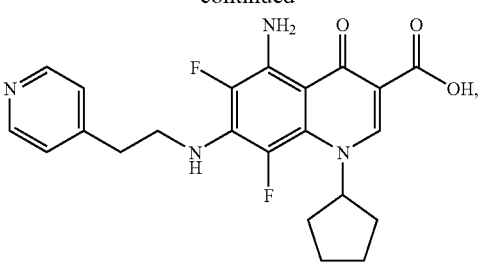
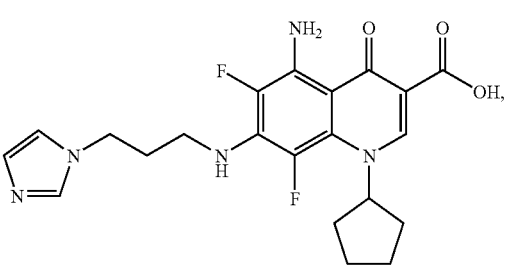
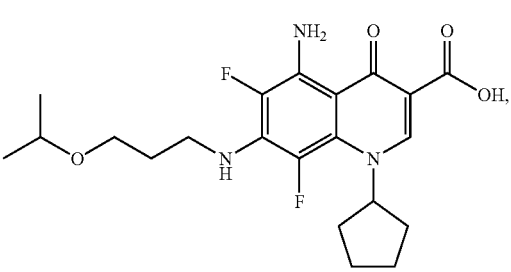
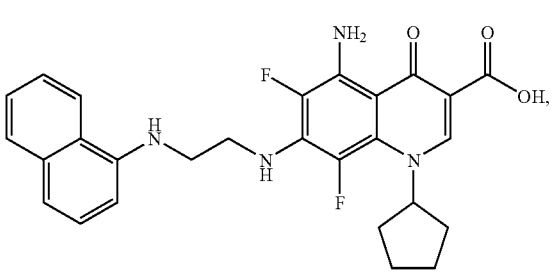
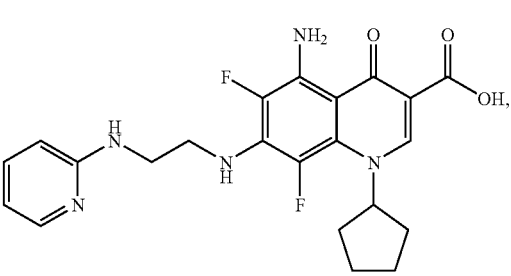
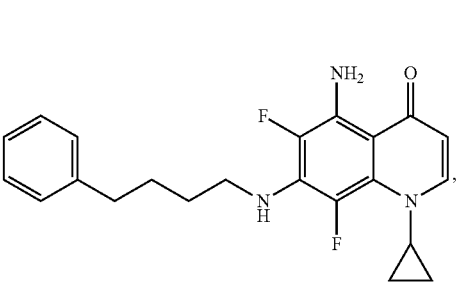

273
-continued
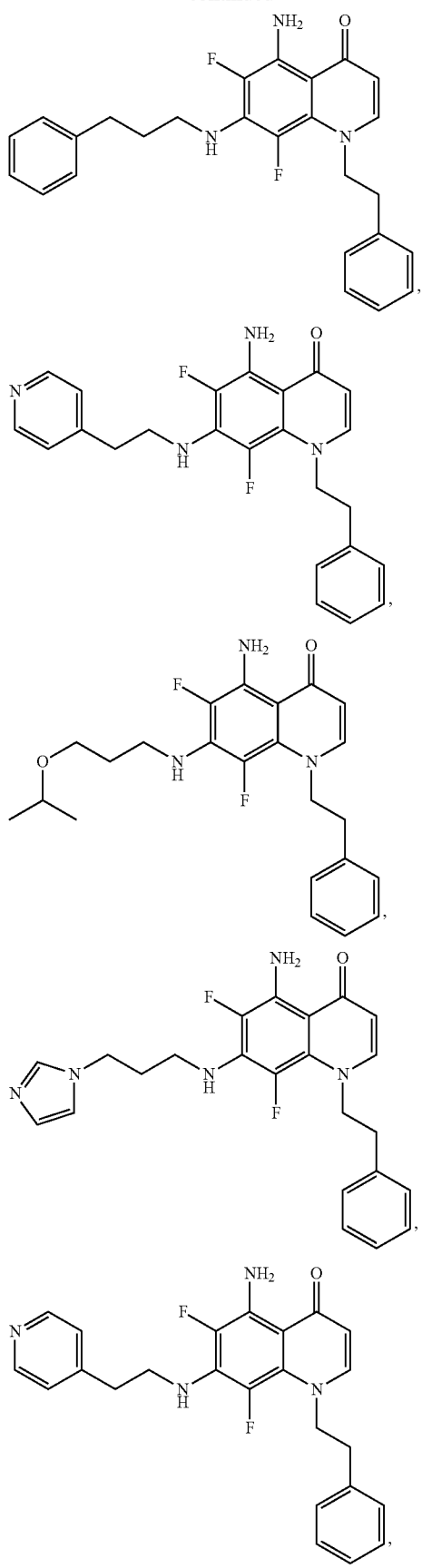
274
-continued
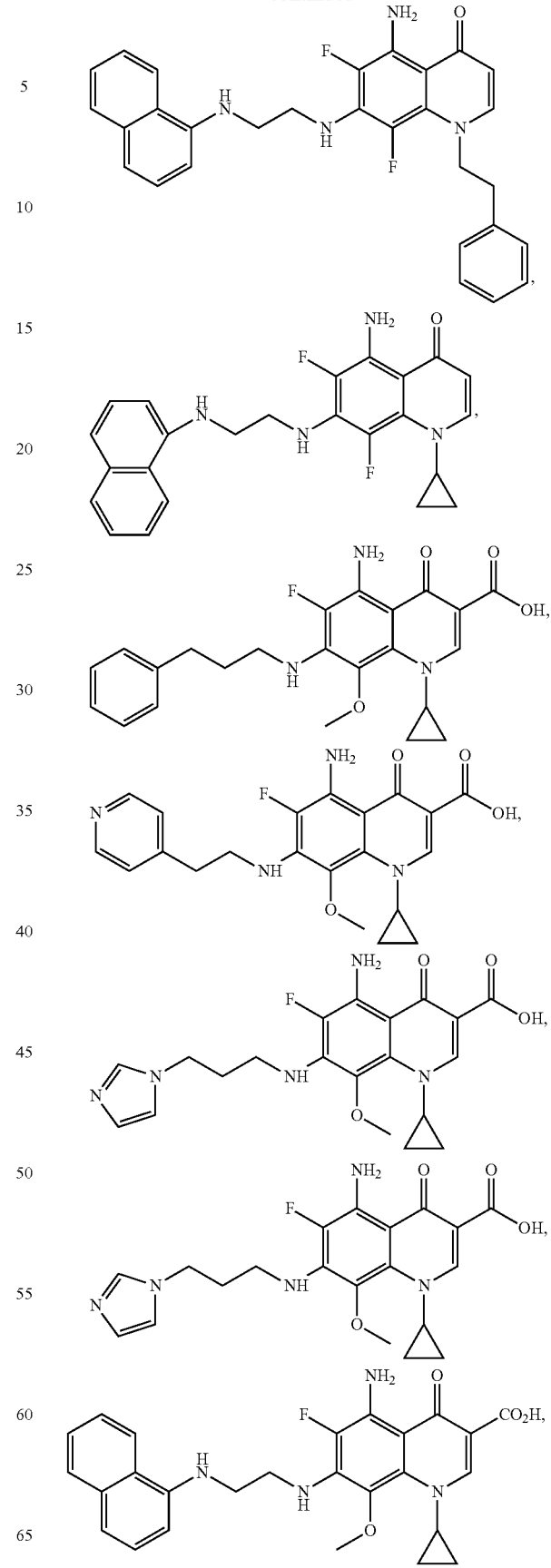

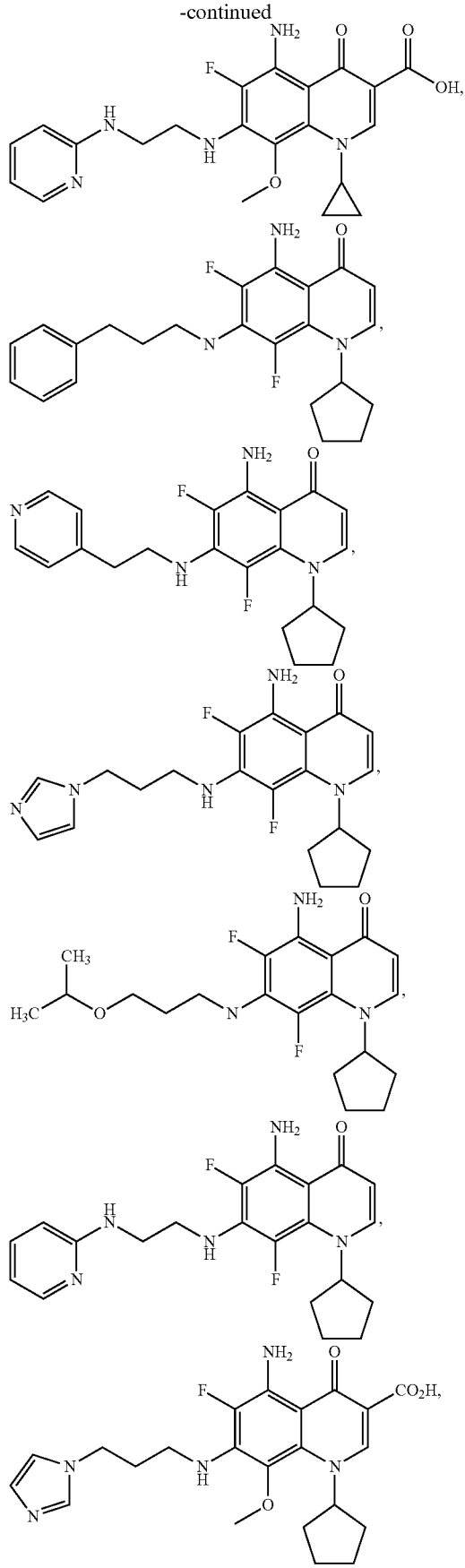
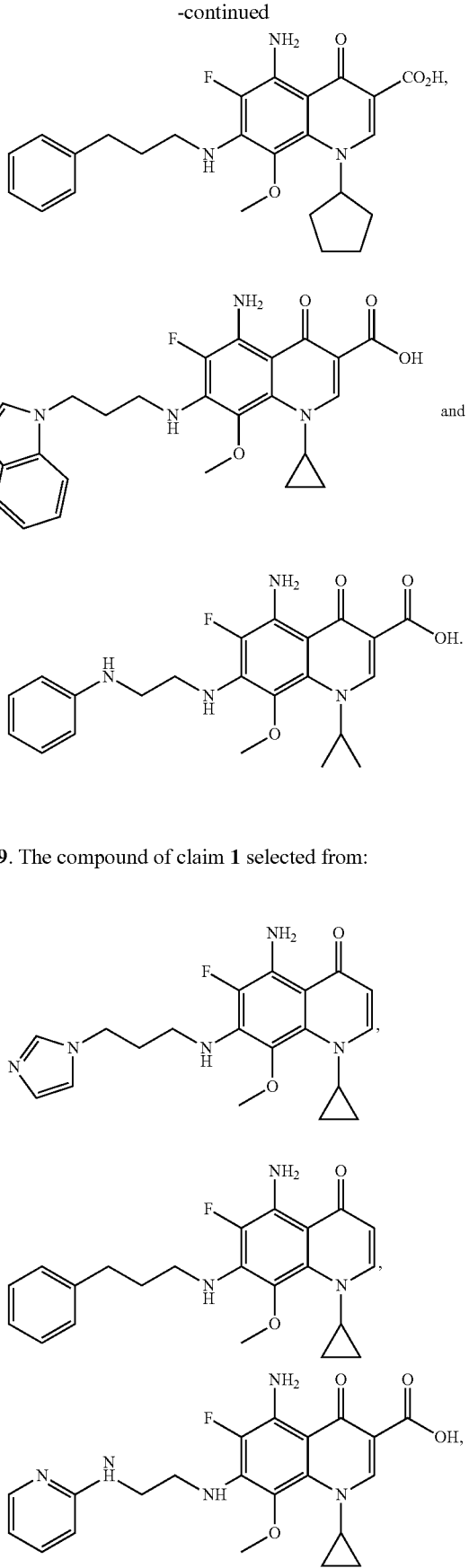
49. The compound of claim 1 selected from:

277
-continued
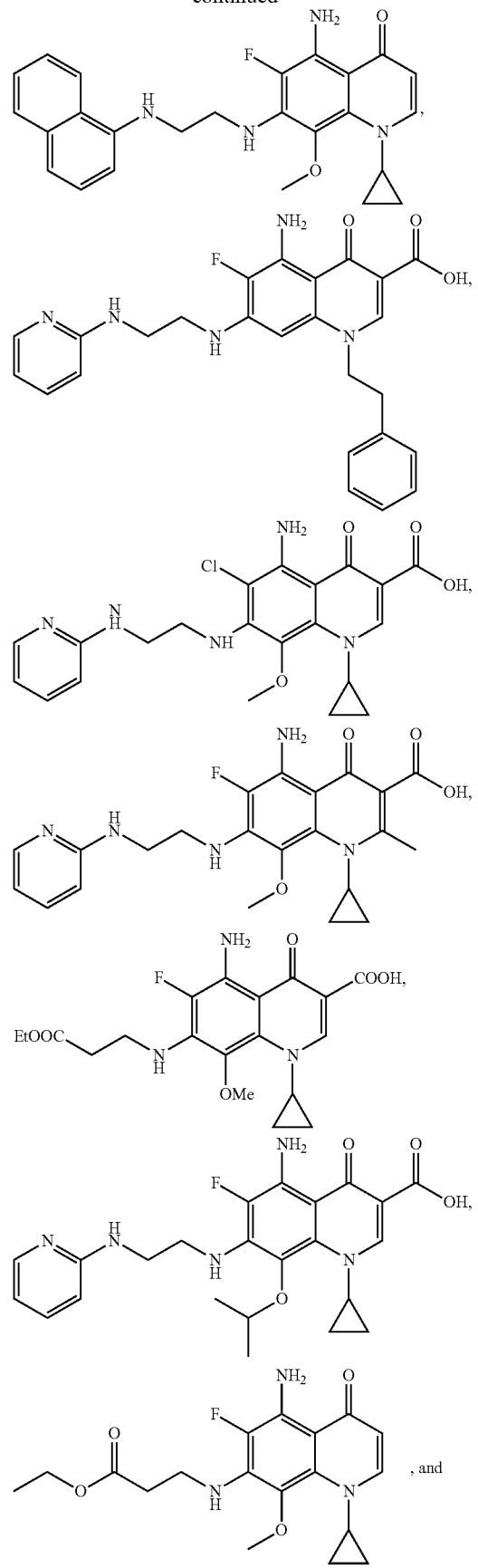
278
-continued
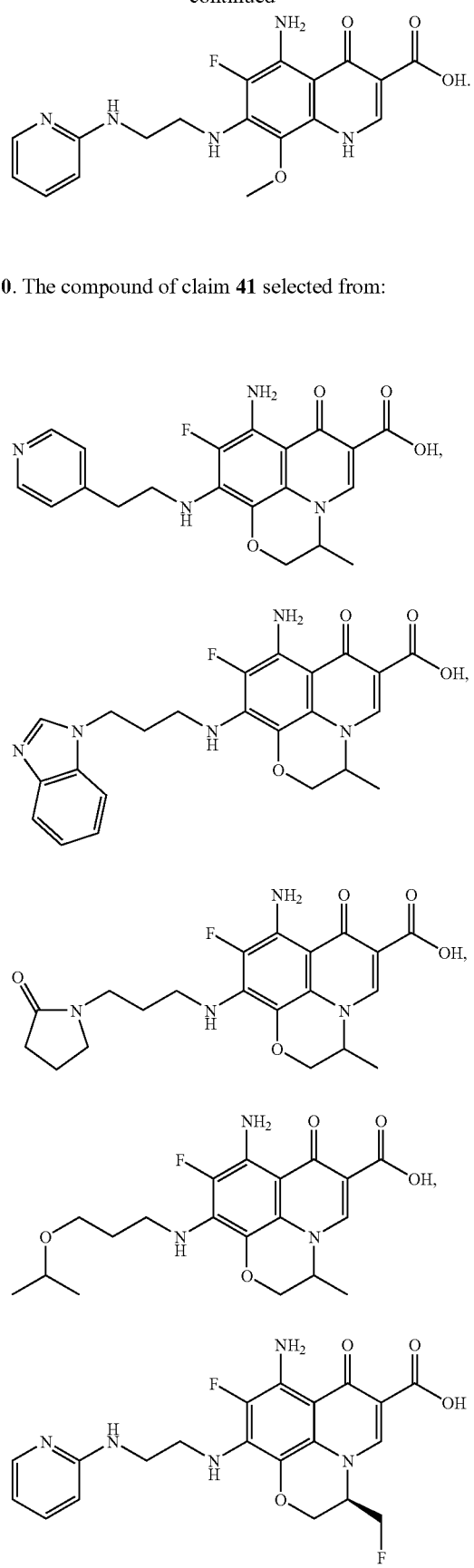
50. The compound of claim 41 selected from:

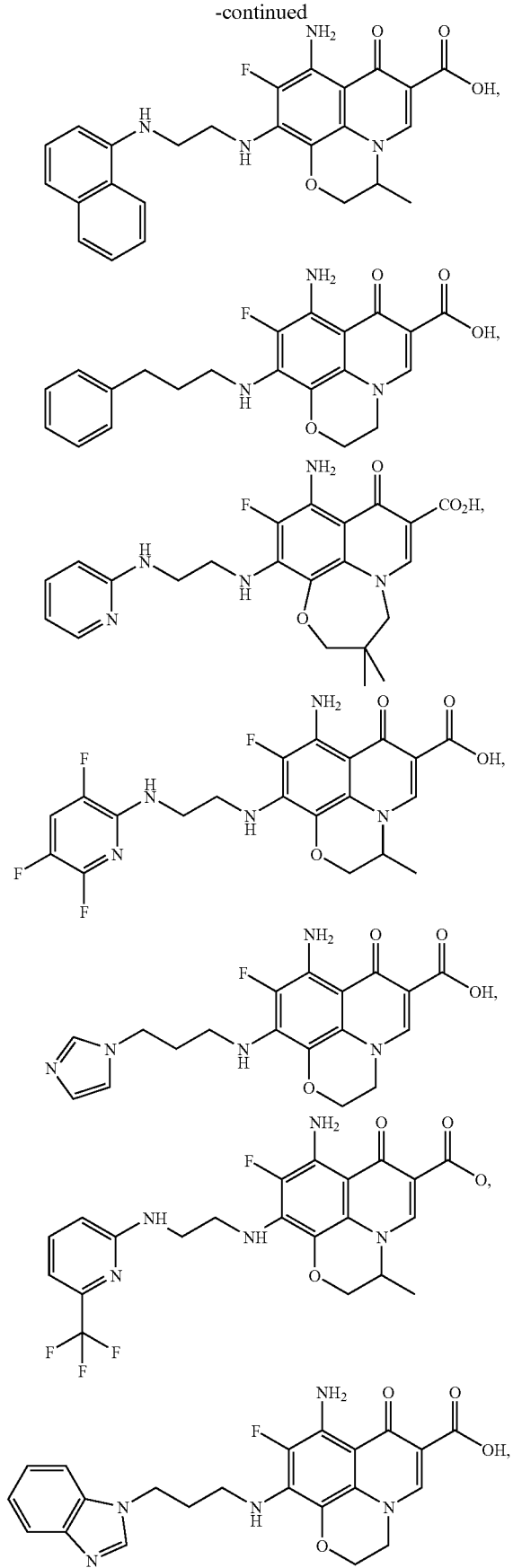
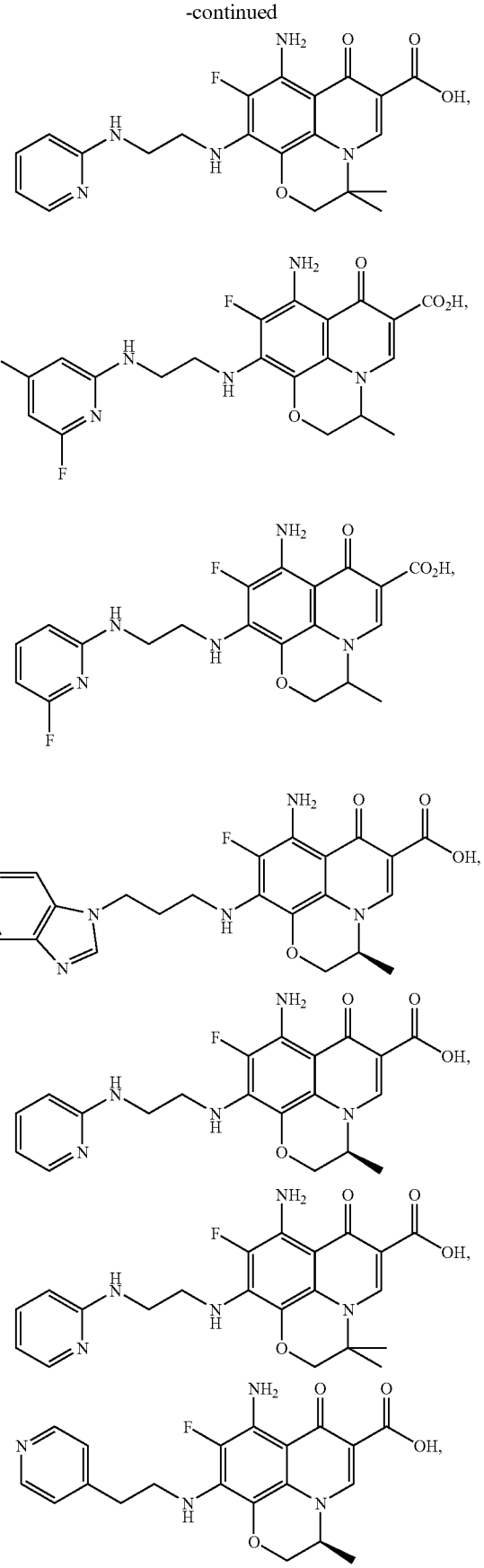

281
-continued
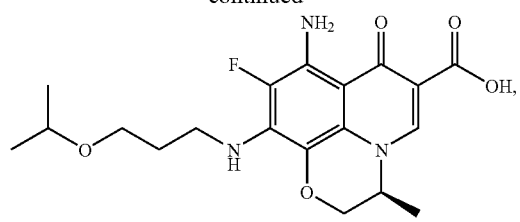
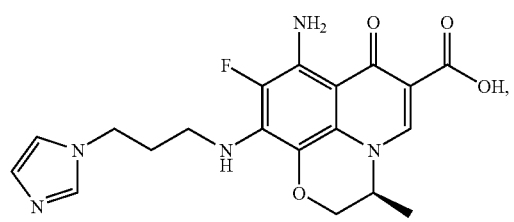
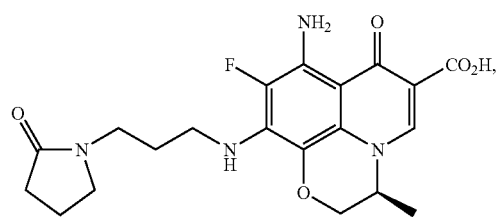
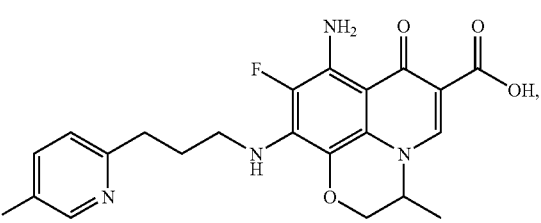
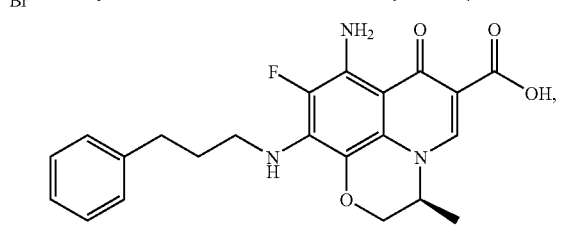
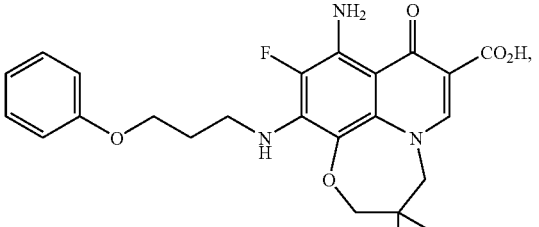
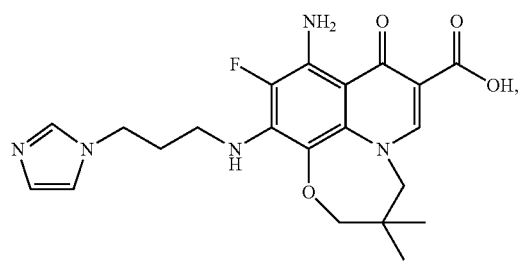
282
-continued
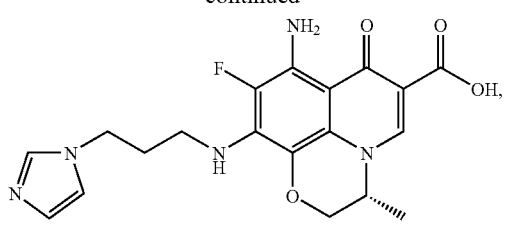
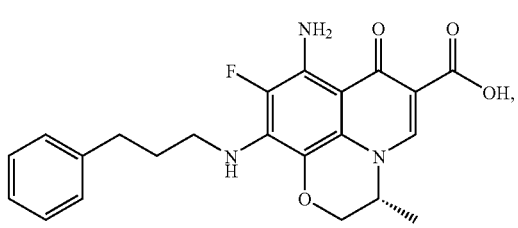
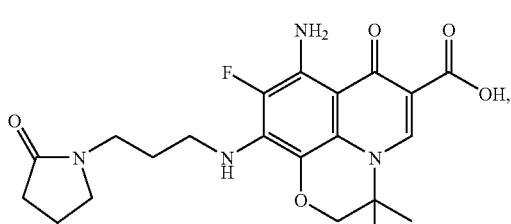
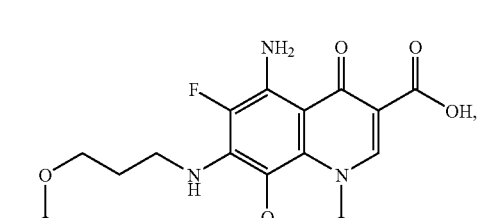
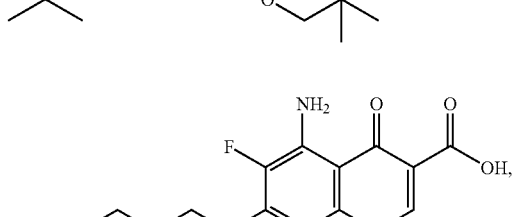
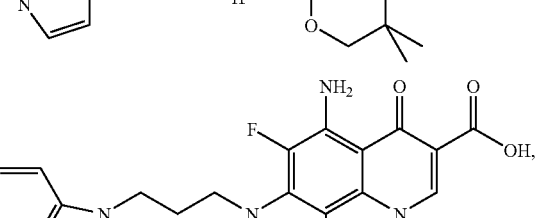
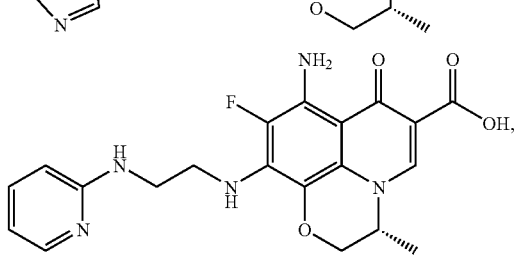

283
-continued
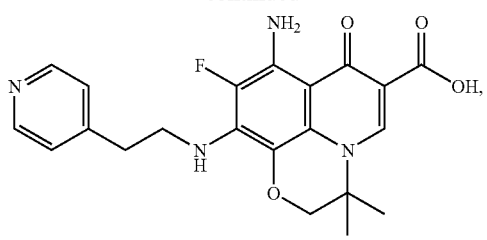
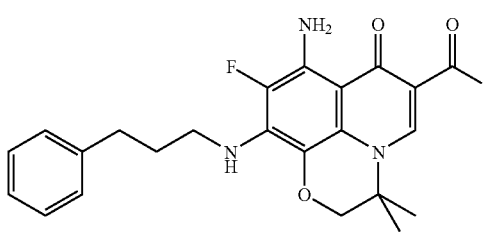
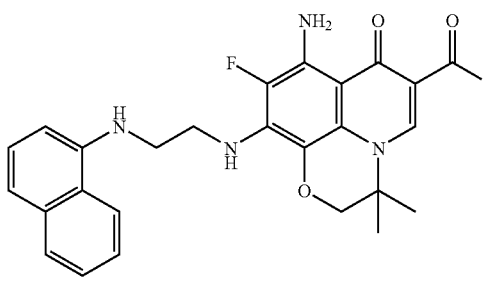
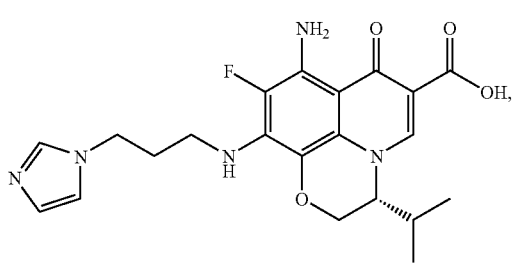
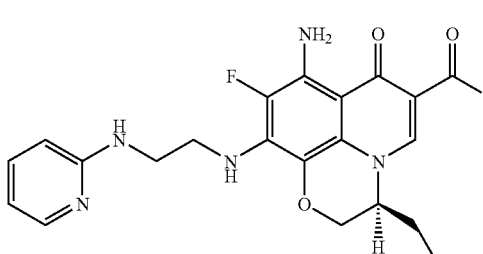
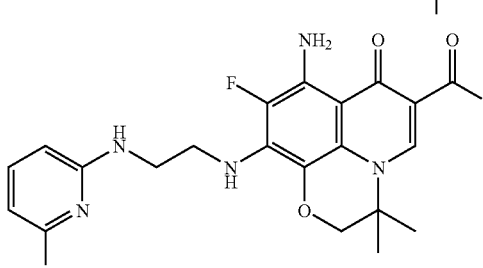
284
-continued
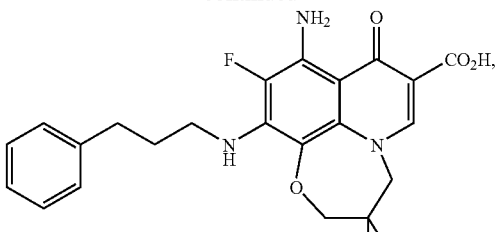
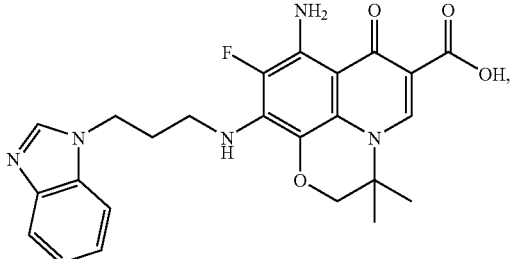
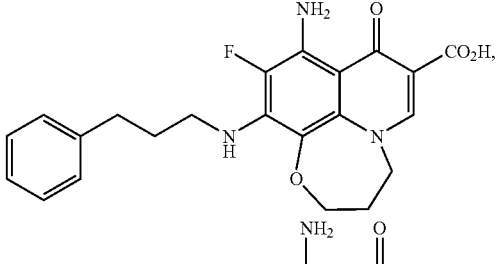
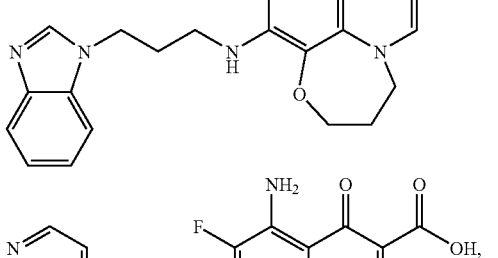
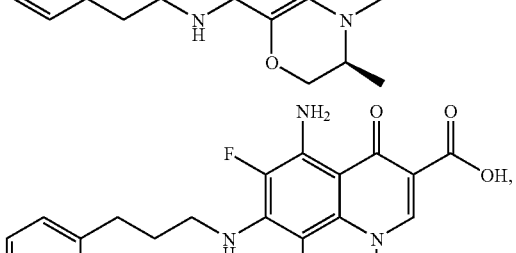
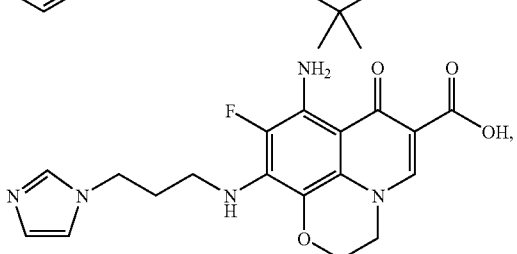

285
-continued
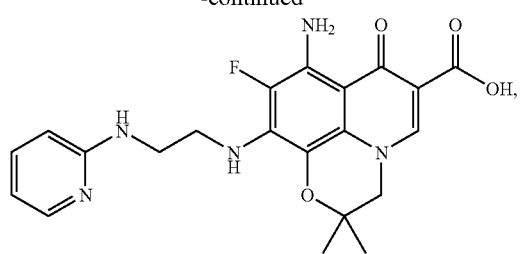
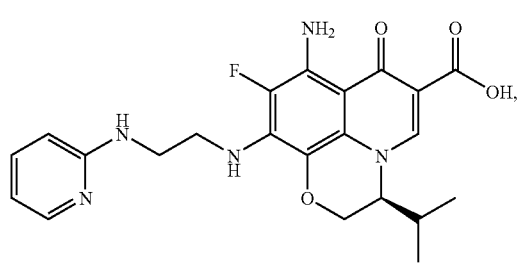
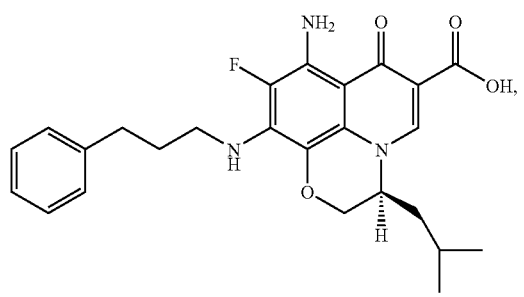
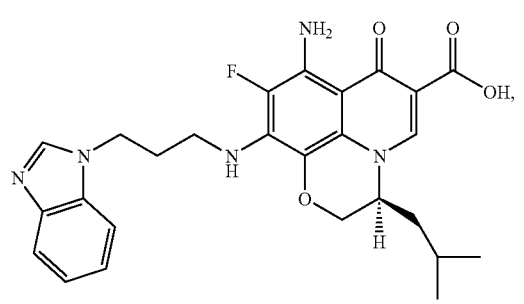
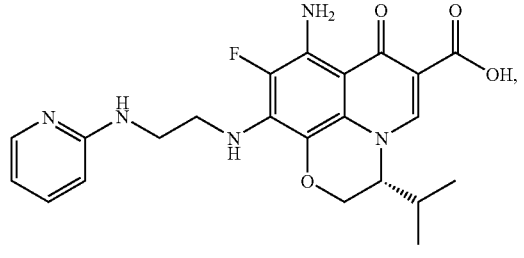
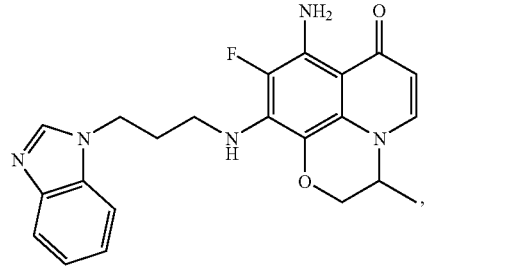
286
-continued
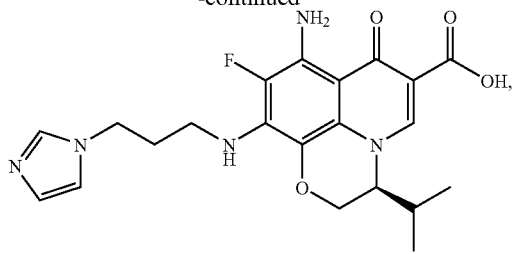
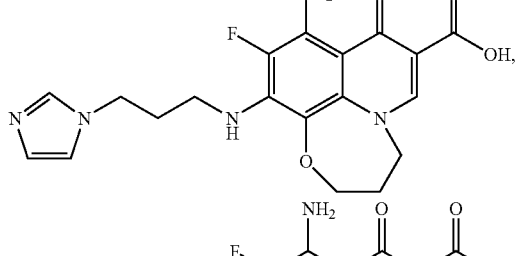
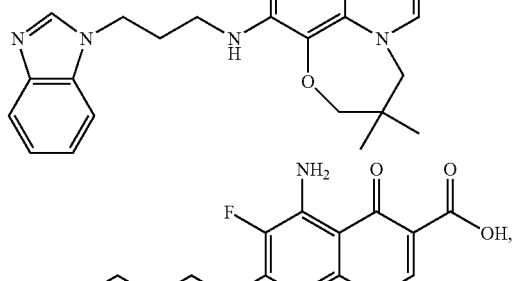
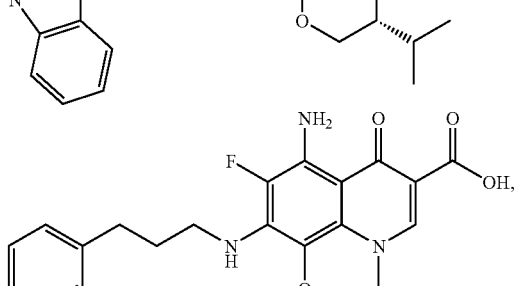
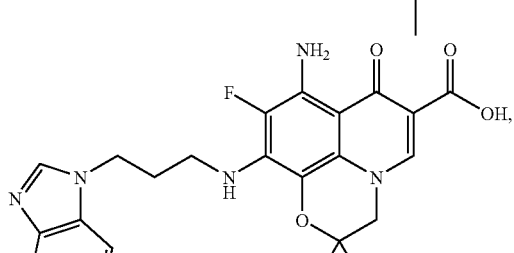
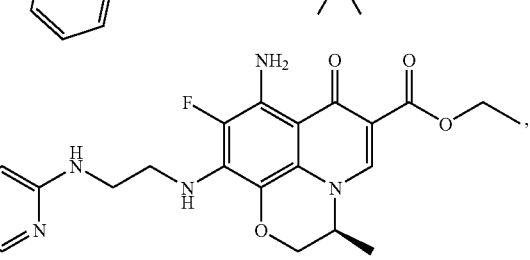

287
-continued
288
-continued
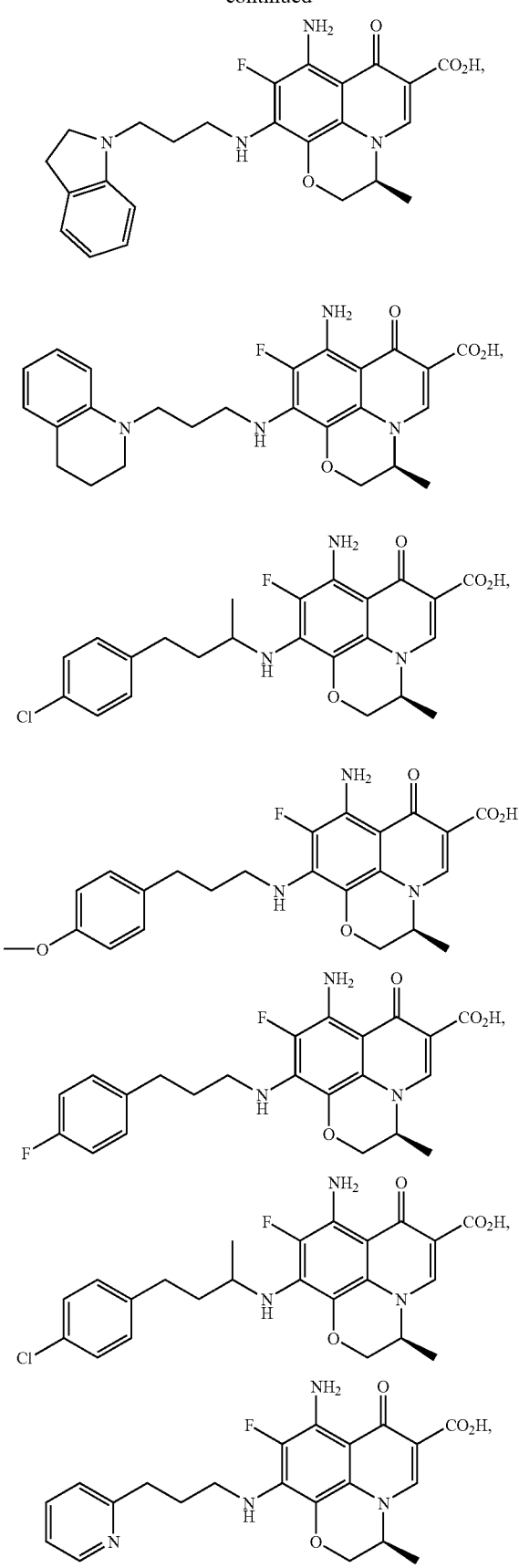
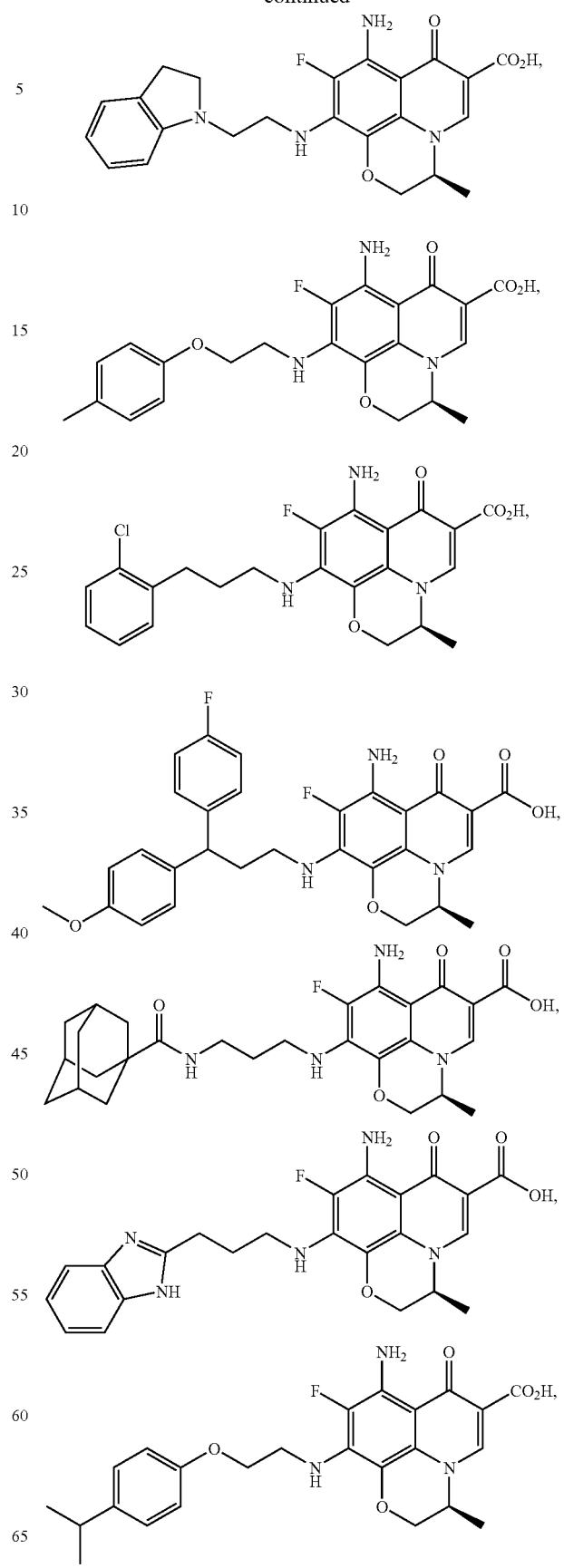

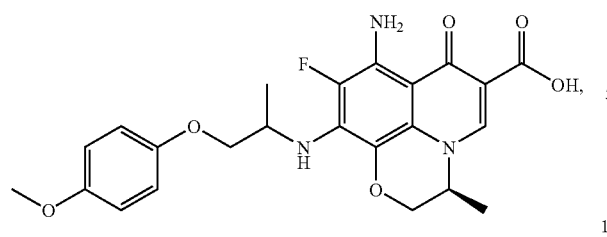
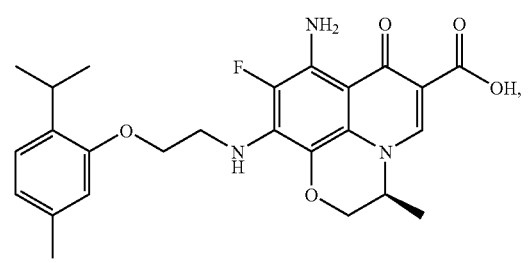
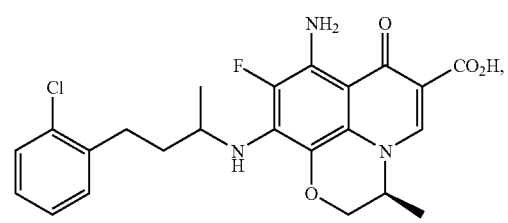
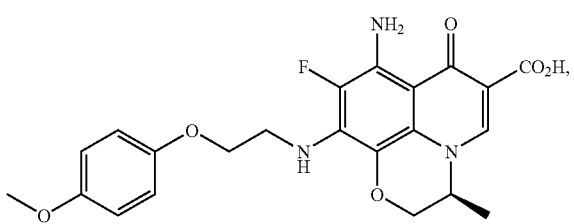
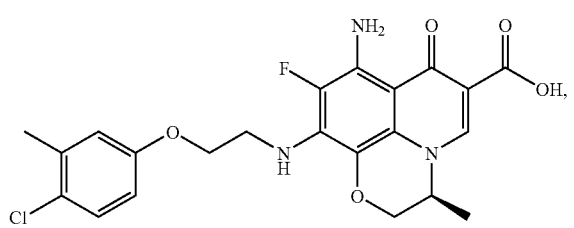
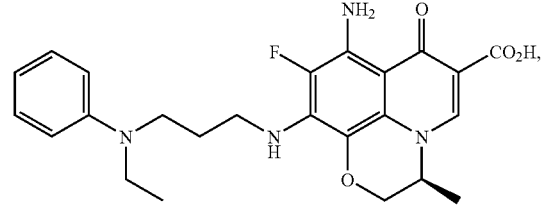
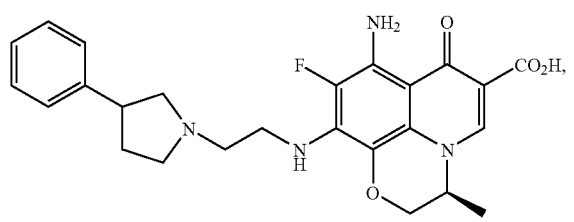
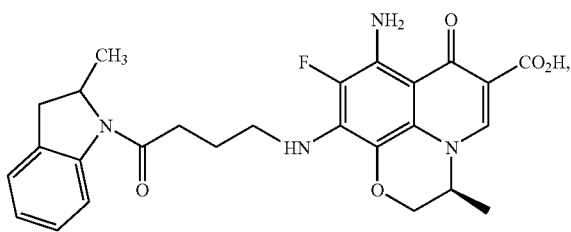
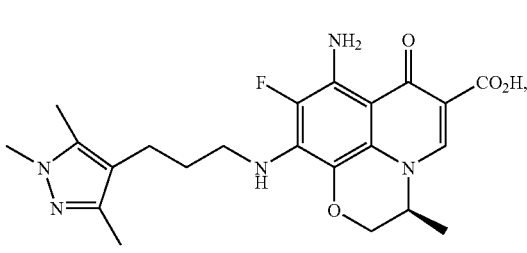
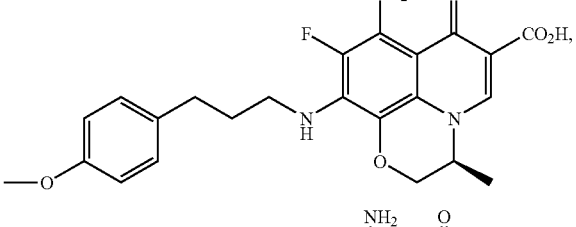
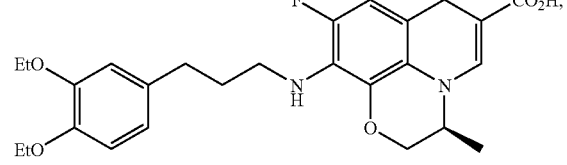
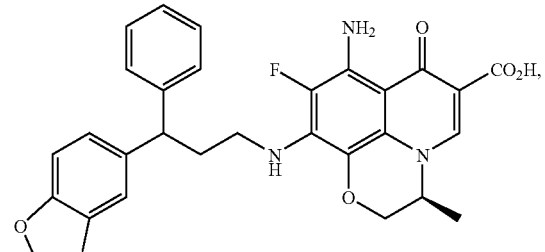
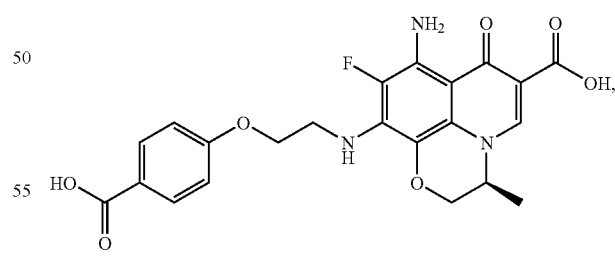
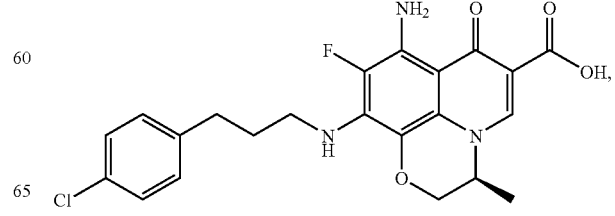

-continued
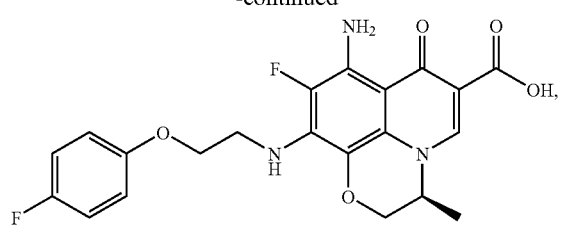
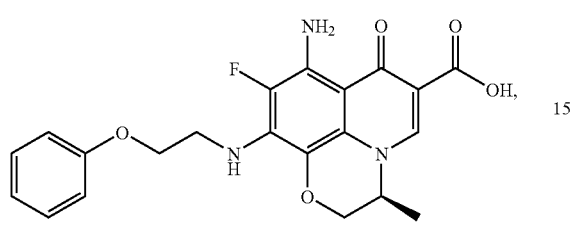
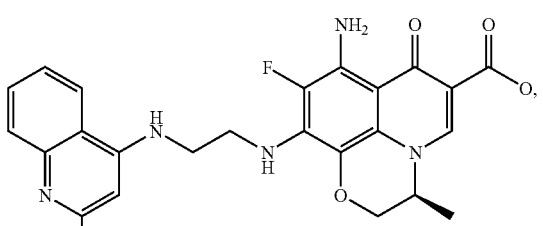
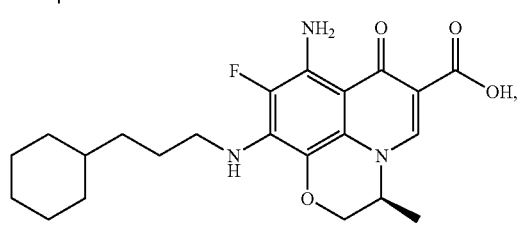
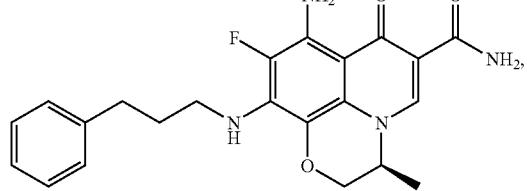
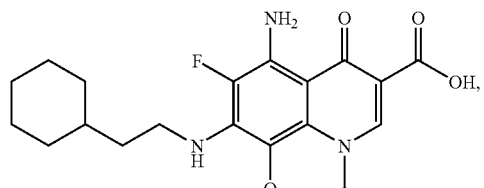
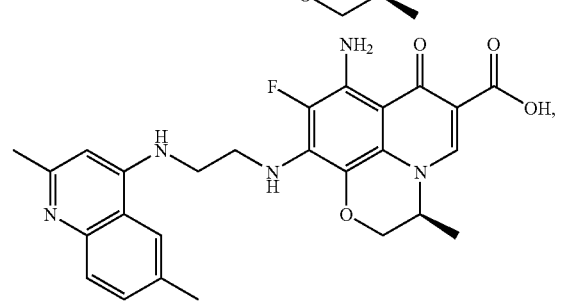
-continued
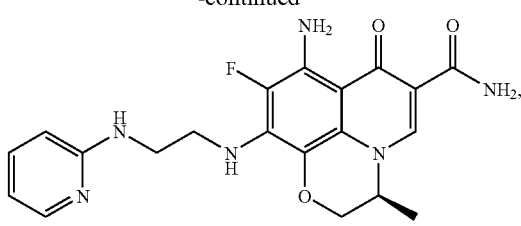
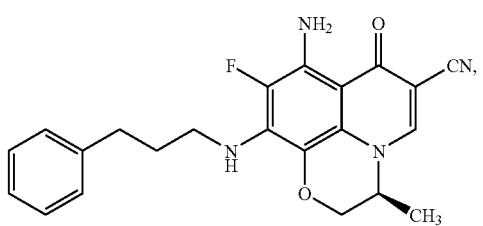
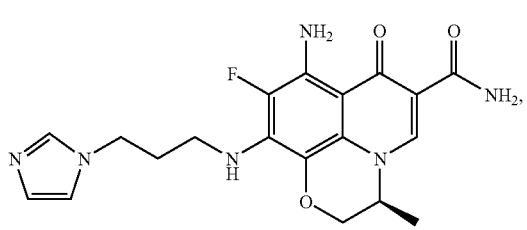
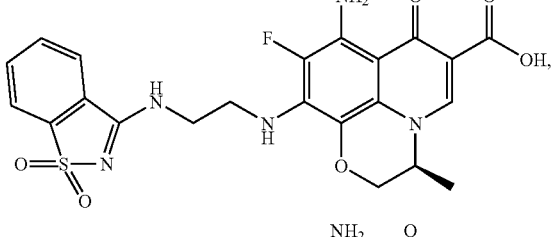
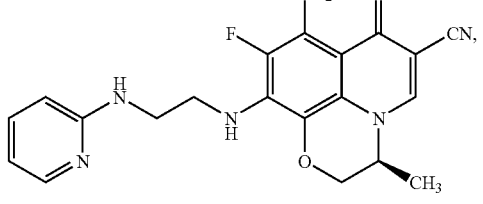
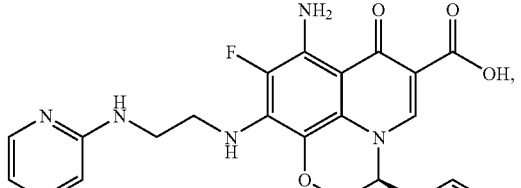
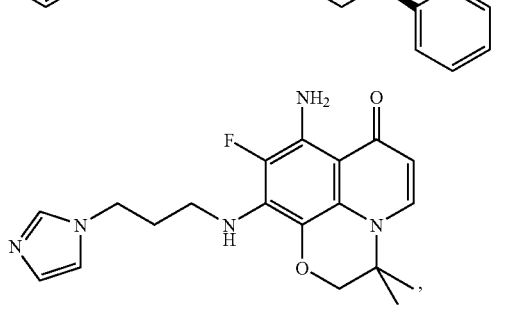

293
-continued
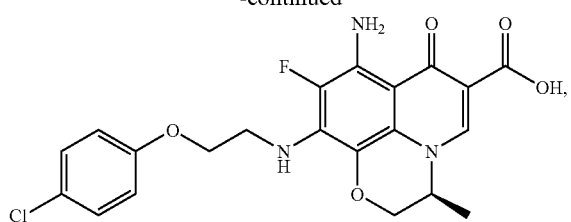
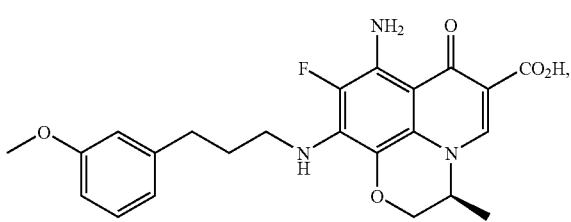
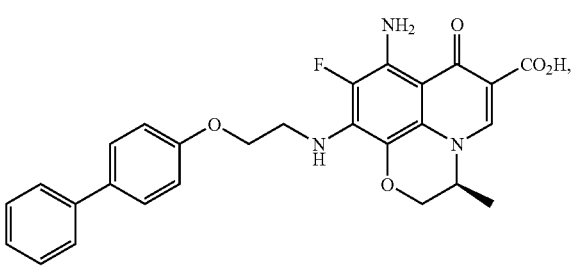
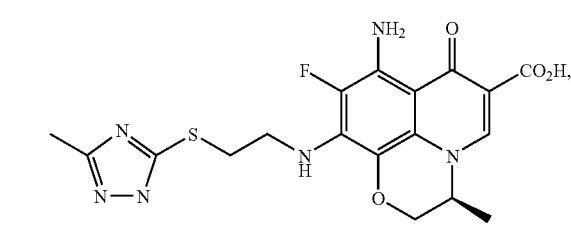
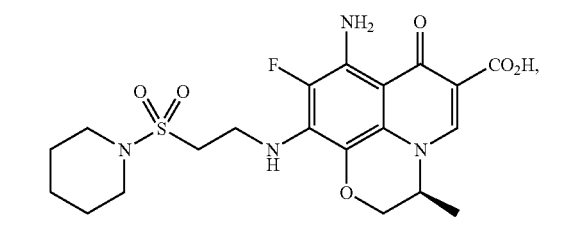
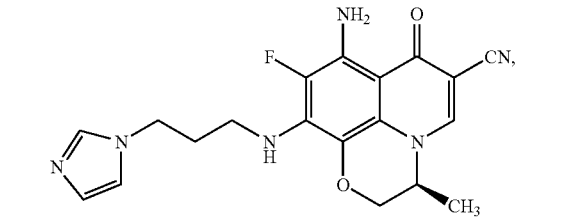
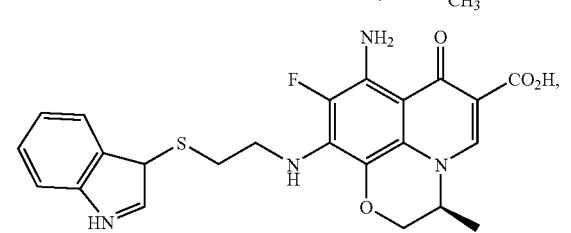
294
-continued
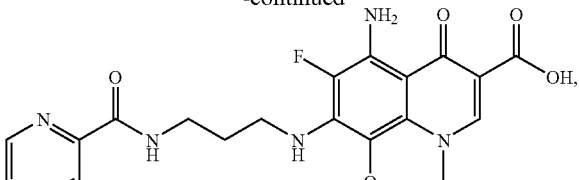
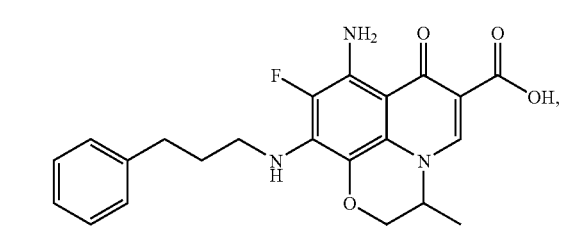
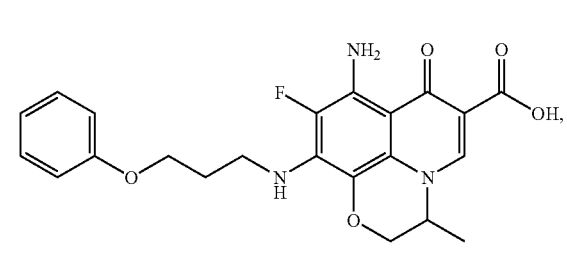
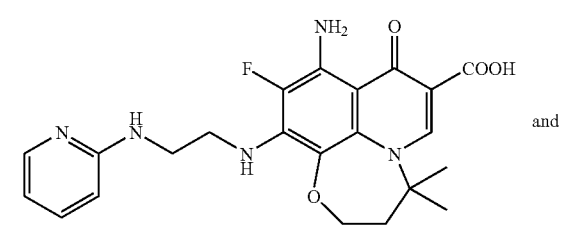
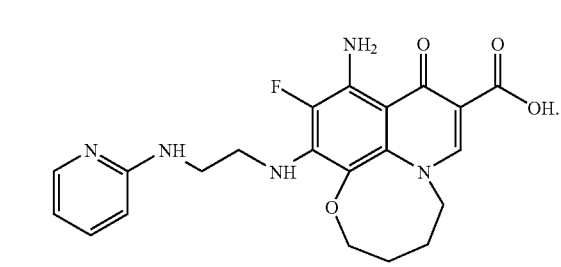
and
51. The compound of claim 1 selected from:
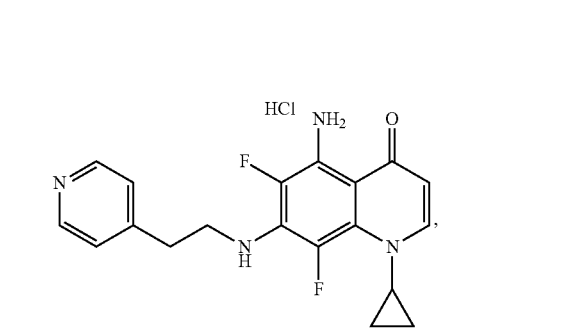

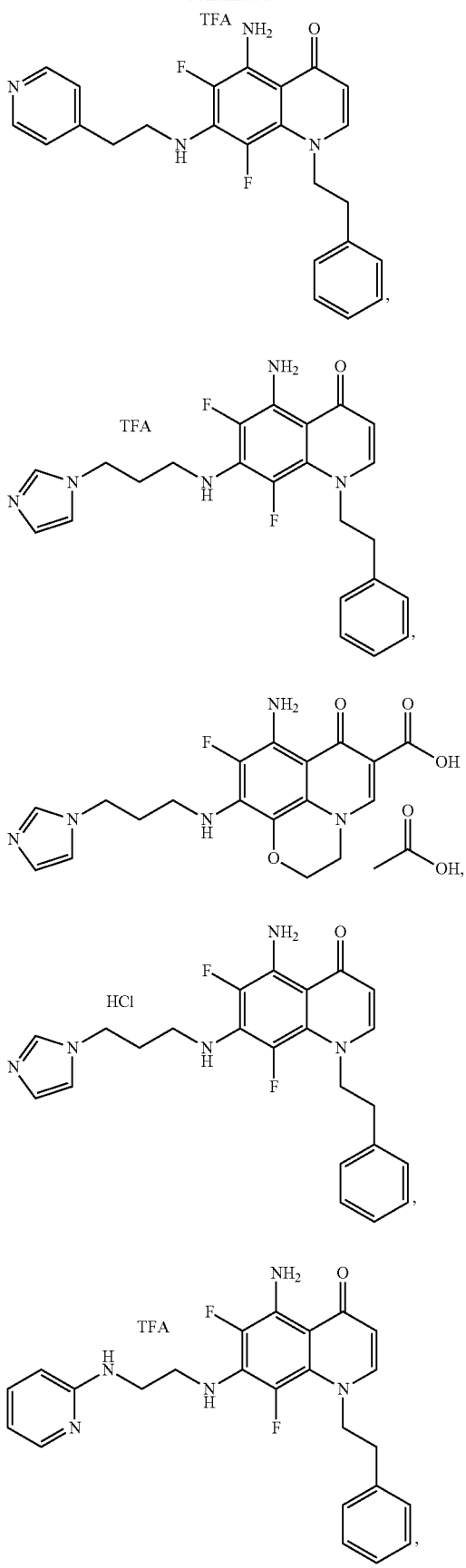

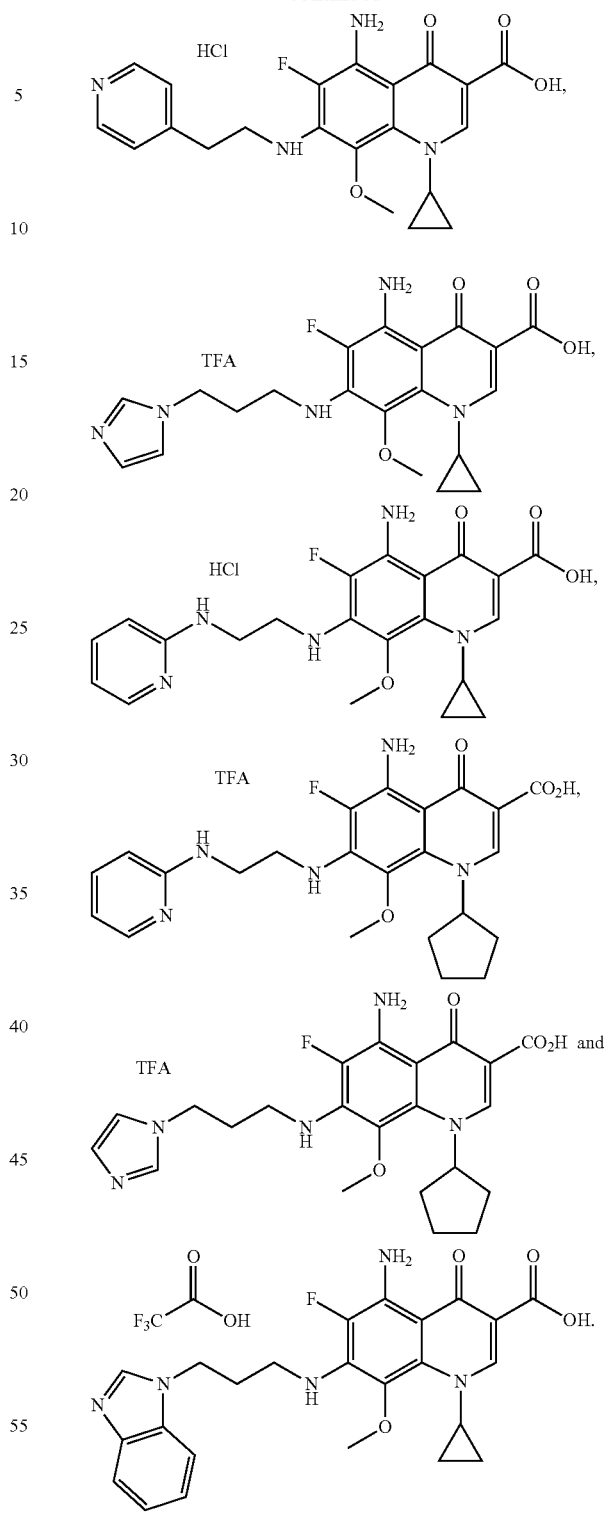

52. An article of manufacture, comprising packaging material, the compound of claim 1, or a pharmaceutically acceptable salt thereof, contained within packaging material, which is used for treatment or amelioration of diabetes, and a label that indicates that the compound or pharmaceutically acceptable salt thereof is used for treatment or amelioration of diabetes.

53. A compound of Formula Ia:

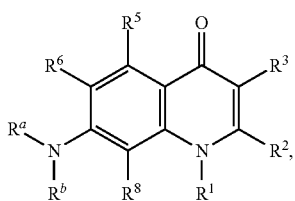

or a pharmaceutically acceptable salt thereof, wherein
$R^1$ and $R^8$ together with the atoms on which they are substituted form a 5-8 membered substituted or unsubstituted heterocyclic or heteroaryl ring containing 1-4 heteroatoms; wherein the substituents when present are selected from one or more $Q^0$;
$Q^0$ is halo, hydroxyl, cycloalkyl, aryl, heteroaryl, aralkyl, cyano, thiocyano, selenocyano, azide, amino, nitro, alkyl, haloalkyl, alkenyl or alkynyl;
$R^2$ is hydrogen, lower alkyl, $COOR^{2a}$ or optionally substituted aryl, wherein the substituents when present are selected from one to four $Q^1$ groups;
$R^{2a}$ is hydrogen, or lower alkyl;
$R^3$ is H, CN or $C(O)R^{3a}$;
$R^{3a}$ is OH, $NR^{3b}R^{3c}$, alkoxy, alkyl, alkenyl or alkynyl;
$R^{3b}$ is hydrogen, alkyl, alkenyl or alkynyl;
$R^{3c}$ is hydrogen, alkyl, alkenyl, alkynyl;
$R^5$ is $NR^{5a}R^{5b}$ or $SR^{5a}$;
$R^{5a}$ and $R^{5b}$ are each independently hydrogen, lower alkyl or $COR^{5C}$;
$R^{5C}$ is lower alkyl or lower haloalkyl;
$R^6$ is halo;
$R^a$ is selected from hydrogen and lower alkyl,
$R^b$ is —$(CH_2)_n(NR^c)_mR$,
—$(CH_2)_nOR^d$,
—$(CH_2)_nS(O)lR^d$,
—$CH(R^j)(CH_2)_n(NR^c)_mR$,
—$CH(R^j)(CH_2)_nOR^d$, or
—$CH(R^j)(CH_2)_nS(O)_lR^d$;
$R^c$ is hydrogen or lower alkyl;
R is alkyl, aryl, heteroaryl, cycloalkyl, heterocyclyl, fused heterocyclylaryl, fused arylheterocyclyl, —$C(O)OR^d$, —$C(O)R^d$, —$C(O)NR^cR^c$ or —$CHR^dR^d$;
each $R^d$ is selected from alkyl, aryl, heterocyclyl, heteroaryl, cycloalkyl, fused heterocyclylaryl and fused arylheterocyclyl;
each $R^c$ is selected from hydrogen, alkyl, aryl, heterocyclyl, heteroaryl, cycloalkyl, fused heterocyclylaryl and fused arylheterocyclyl;
$R^j$ is lower alkyl or lower haloalkyl;
n is 0 to 6;
m is 0 or 1; and
l is 0 to 2, where R and $R^d$ are optionally substituted with 1 to 4 substituents, each independently selected from $Q^1$,
where each $Q^1$ is halo, cyano, selenocyano, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N-aryl-N',N'-dialkylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, —$N^+R^{51}R^{52}R^{53}$, $P(R^{50})_2$, $P(=O)(R^{50})_2$, $OP(=O)(R^{50})_2$, —$NR^6OC(=O)R^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two $Q^1$ groups, which substitute atoms in a 1, 2 or 1,3 arrangement, together form —O—$(CH_2)_y$—O—, —S—$(CH_2)_y$—O— or —S—$(CH_2)_y$—S—, where y is 1 or 2; or two $Q^1$ groups, which substitute the same atom, together form alkylene; and
each $Q^1$ is independently unsubstituted or substituted with one, two or three substituents, each independently selected from $Q^2$;
each $Q^2$ is independently halo, cyano, selenocyano, hydroxy, oxo, thia, nitrile, nitro, formyl, mercapto, hydroxycarbonyl, hydroxycarbonylalkyl, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, heterocyclyl, heterocyclylalkyl, aryl, heteroaryl, aralkyl, aralkenyl, aralkynyl, heteroarylalkyl, trialkylsilyl, dialkylarylsilyl, alkyldiarylsilyl, triarylsilyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aralkoxycarbonyl, aralkoxycarbonylalkyl, arylcarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, heteroaryloxy, heteroaralkoxy, heterocyclyloxy, cycloalkoxy, perfluoroalkoxy, alkenyloxy, alkynyloxy, aralkoxy, alkylcarbonyloxy, arylcarbonyloxy, aralkylcarbonyloxy, alkoxycarbonyloxy, aryloxycarbonyloxy, aralkoxycarbonyloxy, aminocarbonyloxy, alkylaminocarbonyloxy, dialkylaminocarbonyloxy, alkylarylaminocarbonyloxy, diarylaminocarbonyloxy, guanidino, isothioureido, ureido, N-alkylureido, N-arylureido, N'-alkylureido, N',N'-dialkylureido, N'-alkyl-N'-arylureido, N',N'-diarylureido, N'-arylureido, N,N'-dialkylureido, N-alkyl-N'-arylureido, N-aryl-N'-alkylureido, N,N'-diarylureido, N,N',N'-trialkylureido, N,N'-dialkyl-N'-arylureido, N-alkyl-N',N'-diarylureido, N,N'-diaryl-N'-alkylureido, N,N',N'-triarylureido, amidino, alkylamidino, arylamidino, aminothiocarbonyl, alkylaminothiocarbonyl, arylaminothiocarbonyl, amino, aminoalkyl, alkylaminoalkyl, dialkylaminoalkyl, arylaminoalkyl, diarylaminoalkyl, alkylarylaminoalkyl, alkylamino, dialkylamino, haloalkylamino, arylamino, diarylamino, alkylarylamino, alkylcarbonylamino, alkoxycarbonylamino, aralkoxycarbonylamino, arylcarbonylamino, arylcarbonylaminoalkyl, aryloxycarbonylaminoalkyl, aryloxyarylcarbonylamino, aryloxycarbonylamino, alkylsulfonylamino, arylsulfonylamino, heteroarylsulfonylamino, heterocyclylsulfonylamino, heteroarylthio, azido, —N$^+$R$^{51}$R$^{52}$R$^{53}$, P(R$^{50}$)$_2$, P(=O)(R$^{50}$)$_2$, OP(=O)(R$^{50}$)$_2$, —NR$^{60}$C(=O)R$^{63}$, dialkylphosphonyl, alkylarylphosphonyl, diarylphosphonyl, hydroxyphosphonyl, alkylthio, arylthio, perfluoroalkylthio, hydroxycarbonylalkylthio, thiocyano, isothiocyano, alkylsulfinyloxy, alkylsulfonyloxy, arylsulfinyloxy, arylsulfonyloxy, hydroxysulfonyloxy, alkoxysulfonyloxy, aminosulfonyloxy, alkylaminosulfonyloxy, dialkylaminosulfonyloxy, arylaminosulfonyloxy, diarylaminosulfonyloxy, alkylarylaminosulfonyloxy, alkylsulfinyl, alkylsulfonyl, arylsulfinyl, arylsulfonyl, hydroxysulfonyl, alkoxysulfonyl, aminosulfonyl, alkylaminosulfonyl, dialkylaminosulfonyl, arylaminosulfonyl, diarylaminosulfonyl or alkylarylaminosulfonyl; or two Q$^2$ groups, which substitute atoms in a 1, 2 or 1,3 arrangement, together form —O—(CH$_2$)$_y$—O—, —S—(CH$_2$)$_y$—O— or —S—(CH$_2$)$_y$—S—, where y is 1 or 2; or two Q$^2$ groups, which substitute the same atom, together form alkylene;

R$^{50}$ is hydroxy, alkoxy, aralkoxy, alkyl, heteroaryl, heterocyclyl, aryl or —NR$^{70}$R$^{71}$, where R$^{70}$ and R$^{71}$ are each independently hydrogen, alkyl, aralkyl, aryl, heteroaryl, heteroaralkyl or heterocyclyl, or R$^{70}$ and R$^{71}$ together form alkylene, azaalkylene, oxaalkylene or thiaalkylene;

R$^{51}$, R$^{52}$ and R$^{53}$ are each independently hydrogen, alkyl, aryl, aralkyl, heteroaryl, heteroaralkyl, heterocyclyl or heterocyclylalkyl;

R$^{60}$ is hydrogen, alkyl, aryl, aralkyl, heteroaryl, heteroaralkyl, heterocyclyl or heterocyclylalkyl; and R$^{63}$ is alkoxy, aralkoxy, alkyl, heteroaryl, heterocyclyl, aryl or —NR$^{70}$R$^{71}$.

54. A pharmaceutical composition comprising a compound of claim 1 and a pharmaceutically acceptable carrier.

55. A pharmaceutical composition comprising a compound of claim 41 and a pharmaceutically acceptable carrier.

56. A pharmaceutical composition comprising a compound of claim 53 and a pharmaceutically acceptable carrier.

57. A method for treating or ameliorating diabetes comprising administering a compound of claim 1.

58. A method for treating or ameliorating diabetes comprising administering a compound of claim 41.

59. A method for treating or ameliorating diabetes comprising administering a compound of claim 53.

60. The compound of claim 41 selected from:

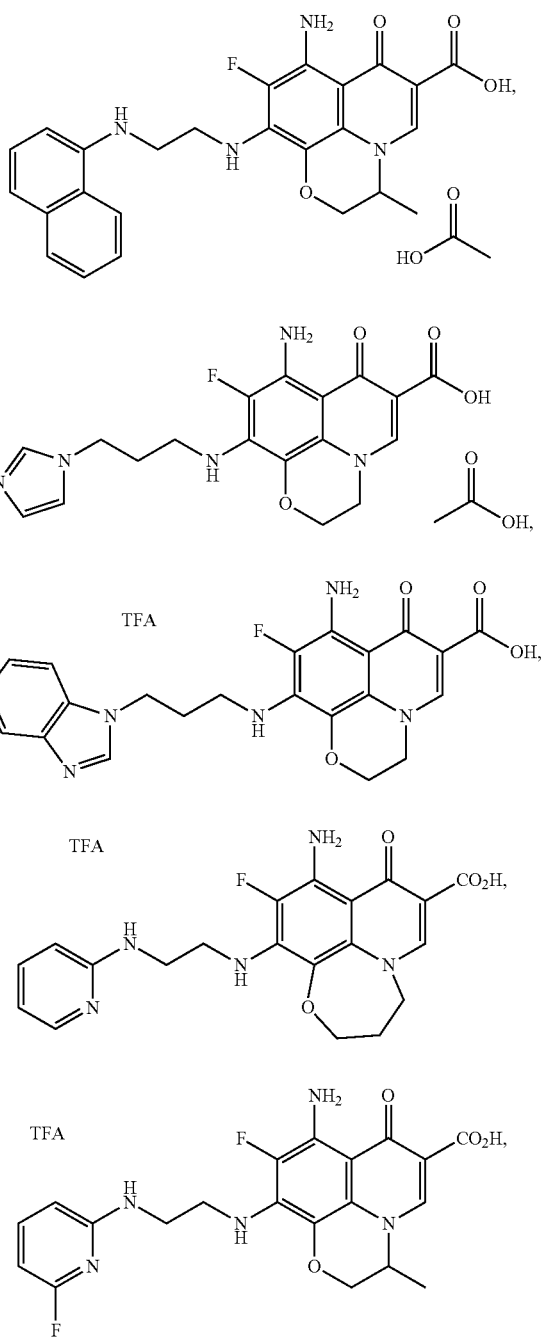

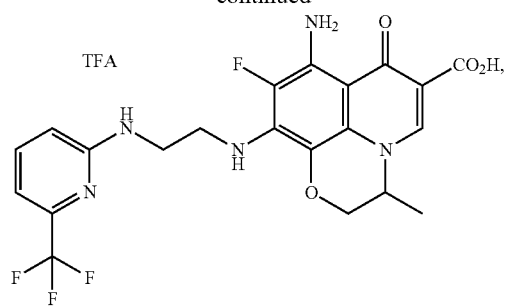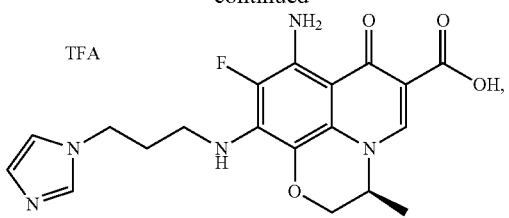

303
-continued
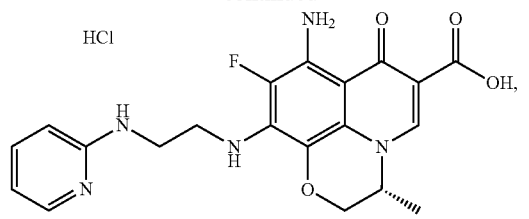
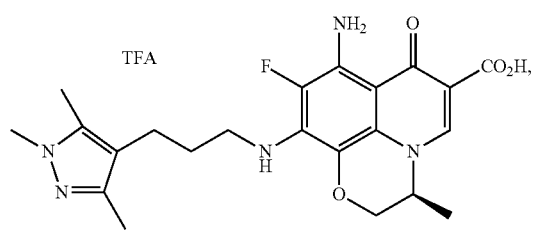
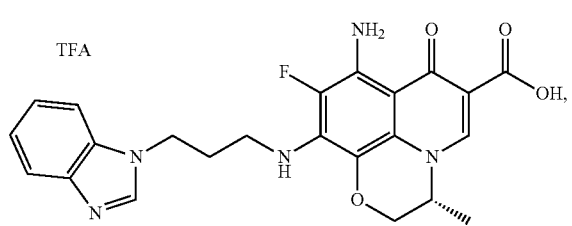
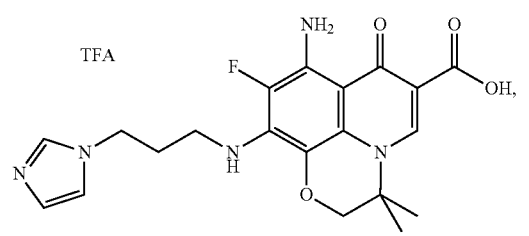
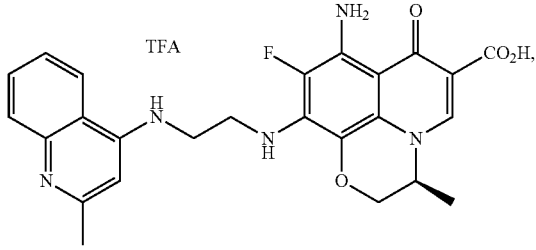
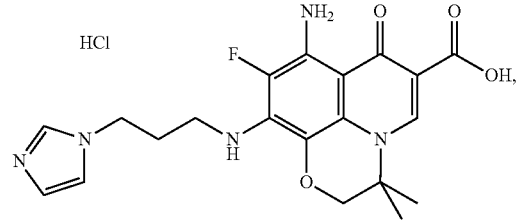
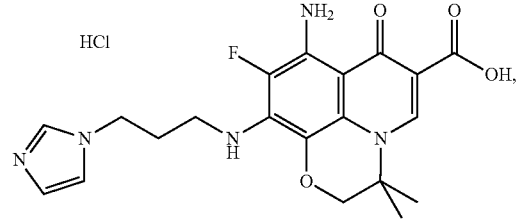
304
-continued
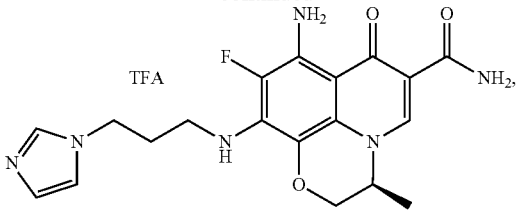
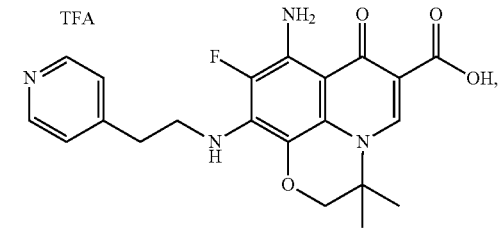
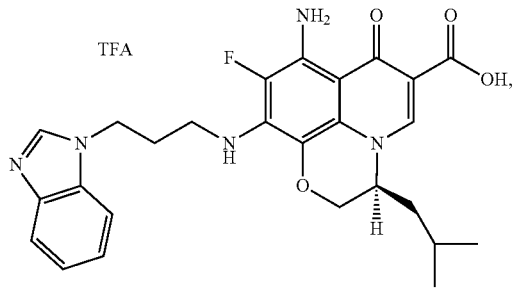
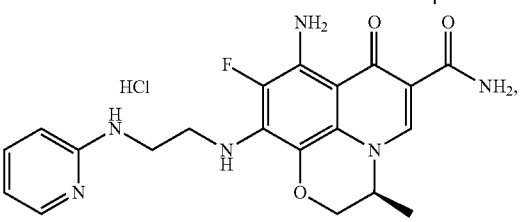
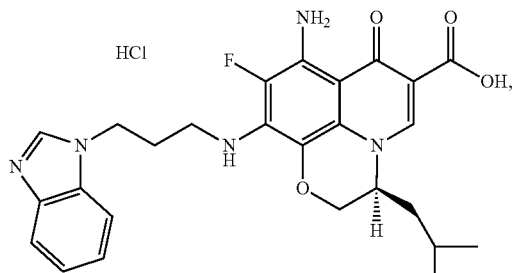
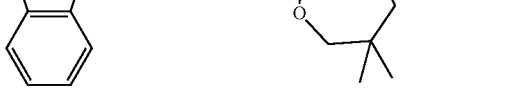
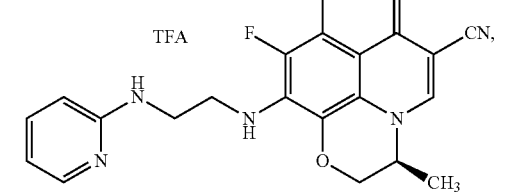

305
-continued
306
-continued
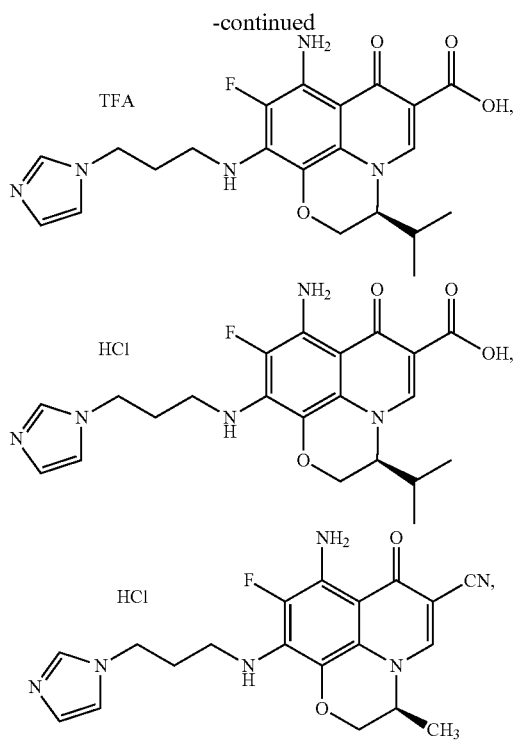
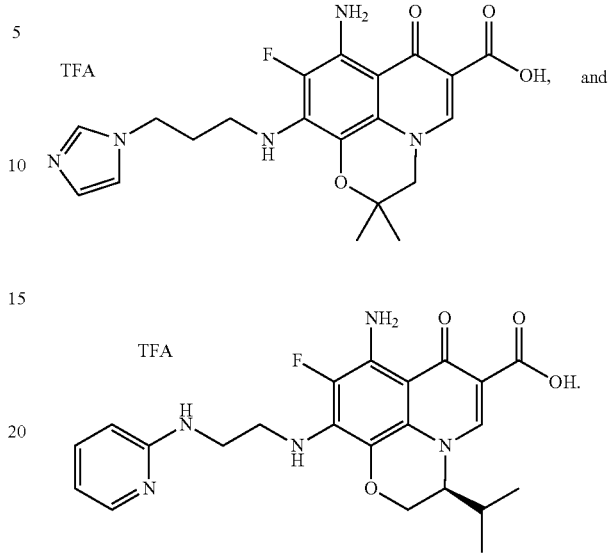
* * * * *

UNITED STATES PATENT AND TRADEMARK OFFICE
CERTIFICATE OF CORRECTION

| | |
|---|---|
| PATENT NO. | : 8,063,221 B2 |
| APPLICATION NO. | : 11/718000 |
| DATED | : November 22, 2011 |
| INVENTOR(S) | : Cociorva et al. |

It is certified that error appears in the above-identified patent and that said Letters Patent is hereby corrected as shown below:

In Claim 48, Col. 276, lines 15-25, correct the chemical structure as follows:

Replace " 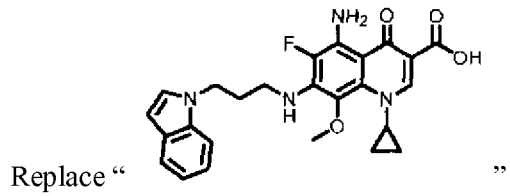 "

with -- 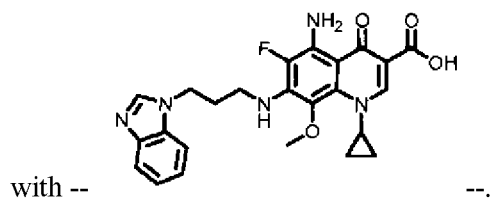 --.

Signed and Sealed this

Thirteenth Day of November, 2012

David J. Kappos
*Director of the United States Patent and Trademark Office*